(12) United States Patent
Toledo-Sherman et al.

(10) Patent No.: US 11,173,156 B2
(45) Date of Patent: Nov. 16, 2021

(54) SOLID FORMS OF A KYNURENINE-3-MONOOXYGENASE INHIBITOR

(71) Applicant: CHDI Foundation, Inc., New York, NY (US)

(72) Inventors: Leticia M. Toledo-Sherman, Santa Monica, CA (US); Celia Dominguez, Los Angeles, CA (US); Vinod Khetarpal, Ambler, PA (US); Travis Lee Houston, Lafayette, IN (US); Stephan D. Parent, West Lafayette, IN (US); Jian-xie Chen, Schenectady, NY (US); Charles H. Montgomery, Bolton, MA (US); Geetha Banda, Wilmington, NC (US)

(73) Assignee: CHDI Foundation, Inc., New York, NY (US)

( * ) Notice: Subject to any disclaimer, the term of this patent is extended or adjusted under 35 U.S.C. 154(b) by 0 days.

(21) Appl. No.: 16/898,239

(22) Filed: Jun. 10, 2020

(65) Prior Publication Data
US 2020/0397782 A1    Dec. 24, 2020

Related U.S. Application Data

(60) Provisional application No. 62/859,946, filed on Jun. 11, 2019.

(51) Int. Cl.
*A61K 31/505* (2006.01)
*C07D 239/28* (2006.01)

(52) U.S. Cl.
CPC .......... *A61K 31/505* (2013.01); *C07D 239/28* (2013.01)

(58) Field of Classification Search
None
See application file for complete search history.

(56) References Cited

U.S. PATENT DOCUMENTS

2016/0251318 A1    9/2016    Courtney et al.

FOREIGN PATENT DOCUMENTS

WO    WO-2013033085 A1 *    3/2013    ............. A61P 37/06

OTHER PUBLICATIONS

Morissette et al, Advanced Drug Delivery Reviews, vol. 56, pp. 275-300 (Year: 2004).*
International Search Report and Written Opinion, PCT/US2020/037030, dated Sep. 1, 2020, 13 pages.
Toledo-Sherman, Leticia M. et al., Development of a Series of Aryl Pyrimidine Kynurenine Monooxygenase Inhibitors as Potential Therapeutic Agents for the Treatment of Huntington's Disease, Journal of Medicinal Chemistry, vol. 58, No. 3, Jan. 15, 2015, pp. 1159-1183, XP002800093.

* cited by examiner

*Primary Examiner* — Zinna Northington Davis
(74) *Attorney, Agent, or Firm* — Sheppard Mullin Richter & Hampton LLP

(57) ABSTRACT

Forms of 6-(3-chloro-4-cyclopropoxyphenyl)pyrimidine-4-carboxylic acid (Compound I) were prepared and characterized in the solid state:

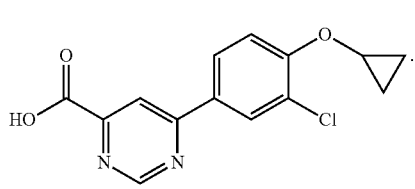

Also provided are processes of manufacture and methods of using the forms of Compound I and salts or co-crystals thereof.

10 Claims, 53 Drawing Sheets

SOLID FORMS OF A KYNURENINE-3-MONOOXYGENASE INHIBITOR

CROSS-REFERENCE TO RELATED PATENT APPLICATIONS

This application claims the benefit under 35 U.S.C. § 119(e) of U.S. Provisional Application 62/859,946, filed Jun. 11, 2019, which is hereby incorporated by reference in its entirety.

FIELD

The present disclosure relates generally to solid forms of compounds that modulate or inhibit the activity of kynurenine-3-monooxygenase (KMO) containing proteins, pharmaceutical compositions thereof, and method of making and using the forms.

BACKGROUND

There remains a need to develop effective treatments for subjects suffering from or at risk of diseases or conditions mediated, at least in part, by kynurenine-3-monooxygenase (KMO) activity. Suitable compounds for the treatment of such diseases and conditions, such as 6-(3-chloro-4-cyclopropoxyphenyl)pyrimidine-4-carboxylic acid (designated herein as Compound I or Compound I (free acid)) are disclosed in U.S. Patent App. Pub. No. 2016/0251318, the disclosure of which is hereby incorporated by reference in its entirety.

There remains a need for solid forms of Compound I or salts or co-crystals thereof that are efficacious and exhibit improved stability and solubility for the treatment of diseases mediated, at least in part, by KMO activity.

SUMMARY

Compound I is known to modulate or inhibit kynurenine-3-monooxygenase (KMO) activity and is described, for example, in U.S. Patent App. Pub. No. 2016/0251318, which is hereby incorporated by reference in its entirety. Compound I has the formula:

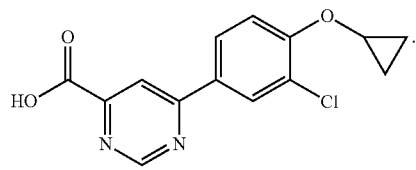

The present disclosure provides solid forms of Compound I and its salts, co-crystals, hydrates, and solvates thereof. Also described herein are processes for making the forms of Compound I, pharmaceutical compositions comprising the forms, and methods for using the forms in the treatment of diseases mediated by KMO activity.

As further described herein, the sodium salt of Compound I, and particularly Compound I sodium Form B, has been found to exhibit several benefits, including advantageous physical properties (e.g., known stoichiometry, no deliquescence, melting temperature >125° C.), and good aqueous solubility. Compound I sodium Form B was also found to be the predominant and most thermodynamically stable form at the conditions evaluated.

Accordingly, one embodiment is directed to a sodium salt of Compound I:

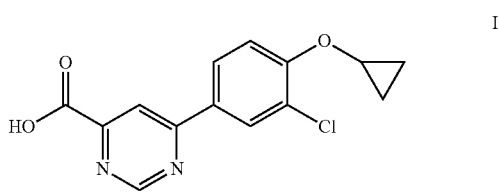 [SMILES: O=C(O)c1cc(-c2ccc(OC3CC3)c(Cl)c2)ncn1]

having a crystalline form.

In some embodiments, the sodium salt of Compound I is characterized by an X-ray powder diffractogram comprising peaks at 3.36, 8.90, and 18.30°2θ±0.2°2θ, as determined on a diffractometer using Cu-Kα radiation (Compound I Sodium Form B).

In some embodiments, Compound I Sodium Form B is further characterized by one or more peaks at 10.15, 23.93, and 26.66°2θ±0.2°2θ.

In some embodiments, Compound I Sodium Form B is characterized by a differential scanning calorimetry curve comprising an endotherm with onset at about 184° C.

Also provided herein, in one embodiment, is a pharmaceutical composition comprising one or more pharmaceutically acceptable carriers, and a therapeutically effective amount of a salt of Compound I, as described herein.

In some embodiments, the pharmaceutical compositions, as described herein, comprise at least about 50% w/w of Compound I Sodium Form B.

In some embodiments, the pharmaceutical compositions as described herein comprise a salt of Compound I, as described herein, and another therapeutic agent.

Also provided herein, in one embodiment, is a method of treating a disease or condition mediated by kynurenine 3-mono-oxygenase activity in a subject in need of such a treatment which method comprises administering to the subject a therapeutically effective amount of a salt of Compound I, as described herein, or a pharmaceutical composition, as described herein.

In some embodiments, the disease or condition treated by the methods described herein is: spinocerebellar ataxias neurodegenerative diseases, psychiatric or neurological diseases or disorders, Alzheimer's disease, Parkinson's disease, amyotrophic lateral sclerosis, Creutzfeldt-Jacob disease, trauma-induced neurodegeneration, high-pressure neurological syndrome, dystonia, olivopontocerebellar atrophy, multiple sclerosis, epilepsy, consequences of stroke, cerebral ischemia, ischemic disorders including stroke (focal ischemia), hypoxia, multi-infarct dementia, consequences of cerebral trauma or damage, damage to the spinal cord, dementia, senile dementia, AIDS-dementia complex, AIDS-induced encephalopathy, other infection related encephalopathy, viral or bacterial meningitis, infectious diseases caused by viral, bacterial and other parasites, general central nervous system (CNS) infections such as viral, bacterial or parasites, poliomyelitis, Lyme disease (Borrelia burgdorferi infection), septic shock, malaria, cancers, cancers with cerebral localization, hepatic encephalopathy, analgesia and opiate withdrawal symptoms, feeding behavior, psychiatric disorders, insomnia, depression, schizophrenia, severe deficit in working memory, severe deficit in long term memory storage, decreased cognition, severe deficit in attention, severe deficit in executive functioning, slowness in information processing, slowness in neural activity, anxiety, generalized anxiety disorders, panic anxiety, obsessive compulsive disorders, social phobia, performance anxiety, post-traumatic stress disorder, acute stress reaction, adjustment reaction, separation anxiety disorder, alcohol withdrawal anxiety, depressive disorders, disorders of the developing or aged brain, diabetes, Tourette's syndrome, Fragile X syndrome, autism spectrum disorders, disorders that cause severe and pervasive impairment in thinking, feeling, language and the ability to relate to others, mood disorders, psychological disorders characterized by abnormalities of emotional state, bipolar disorder, unipolar depression, major depression, endogenous depression, involutional depression, reactive depression, psychotic depression, depression caused by underlying medical conditions, depressive disorders, cyclothymic disorders, dysthymic disorders, mood disorders due to general medical condition, mood disorders not otherwise specified, substance-induced mood disorders, acute necrotizing pancreatitis, HIV-related disorder, AIDS (disease), analgesia, aseptic meningitis, brain disease, Gilles de la Tourette syndrome, Asperger syndrome, Rett syndrome, pervasive developmental disorders, aging-related brain disease, developmental brain disease, burnout syndrome, carbon monoxide poisoning, cardiac arrest or insufficiency, hemorrhagic shock (global brain ischemia), cataract formation and aging of the eye, central nervous system disease, cerebrovascular disease, chronic fatigue syndrome, chronic stress, cognitive disorders, convulsive disorders, variants of grand mal and petit mal epilepsy and Partial Complex Epilepsy, Diabetes mellitus, disease of the nervous system, dyskinesia, L-DOPA induced movement disorders, drug addiction, pain and cataract, drug dependence, drug withdrawal, feeding disorders, Guillain Barre-Syndrome and other neuropathies, hepatic encephalopathy, immune disease, immunity disorders and therapeutic treatment aimed at modifying biological responses (administrations of interferons or interleukins), inflammation (systemic inflammatory response syndrome), inflammatory disorders of the central and/or peripheral nervous system, injury (trauma, polytrauma), mental and behavioral disorders, metabolic disease, pain disease, inflammatory pain, neuropathic pain, migraine, allodynia, hyperalgesia pain, phantom pain, neuropathic pain related to diabetic neuropathy, multiple organ failure, near drowning, necrosis, neoplasms of the brain, neoplastic disorders including lymphomas and other malignant blood disorders, nervous system disease (high-pressure neurological syndrome), infection), nicotine addiction, alcoholism, cannabis addiction, benzodiazepine addiction, barbiturate addiction, morphine addiction, cocaine dependence, change in appetite, sleep disorders, changes in sleep pattern, lack of energy, fatigue, low self-esteem, self-reproach inappropriate guilt, frequent thoughts of death or suicide, plans or attempts to commit suicide, feelings of hopelessness and worthlessness, psychomotor agitation or retardation, diminished capacity for thinking, concentration, or decisiveness, neuroprotective agents, pain, sepsis, spinal cord disease, spinocerebellar ataxia, systemic lupus erythematosus, traumatic damage to the brain and spinal cord, traumatic brain injury, tremor syndromes and different movement disorders (dyskinesia), poor balance, bradykinesia, rigidity, tremor, change in speech, loss of facial expression, micrographia, difficulty swallowing, drooling, dementia, confusion, fear, sexual dysfunction, language impairment, impairment in decision making, violent outbursts, aggression, hallucination, apathy, impairment in abstract thinking, cardiovascular diseases, dyslipoproteinemia, dyslipidemias, cardiomegaly, atherosclerosis, myocardial infarction, congestive heart failure, coronary heart disease, hypertension, hypotension, benign hyperproliferative diseases, malignant hyperproliferative diseases, angiomas, endometriosis, obesity, Age-related Macular Degeneration, retinopathy, proliferation of ECs and smooth muscle cells that cause restenosis as a consequence of stenting in the treatment of atherosclerosis, hyperproliferative disorders involving fibroblasts cardiac remodeling and failure associated with myocardial infarction, excessive wound healing, transplant rejection, graft versus host disease, chronic kidney disease, systemic inflammatory disorders, and brain inflammatory disorders including malaria and African trypanosomiasis, stroke, or pneumococcal meningitis.

In some embodiment, the disease or condition treated by the methods, as described herein, is acute necrotizing pancreatitis, disorders of the developing or aged brain, psychiatric disorders, Alzheimer's disease, inflammation, cancer, schizophrenia, neurodegenerative disease, or transplant rejection. In some embodiments, the disease or condition comprises a neurodegenerative pathology. In some embodiments, the disease or condition is Huntington's disease. In some embodiments, the disease or condition is a Human Immunodeficiency Virus (HIV)-related disorder.

DETAILED DESCRIPTION

Figure 1:
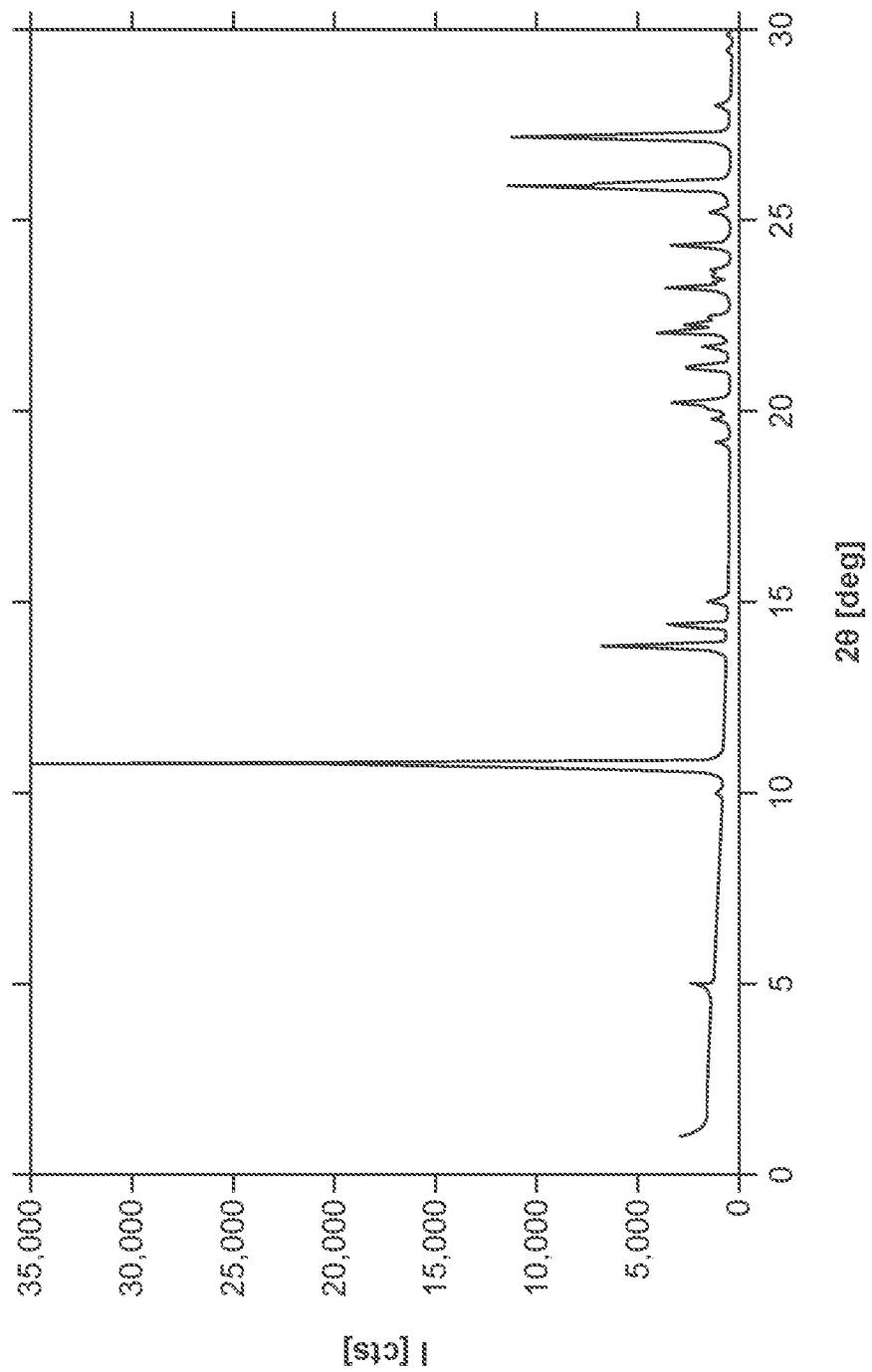
FIG. 1 is an X-ray powder diffractogram of Compound I Material A.

The compound 6-(3-chloro-4-cyclopropoxyphenyl)pyrimidine-4-carboxylic acid, designated herein as Compound I or Compound I (free acid), has the following formula:

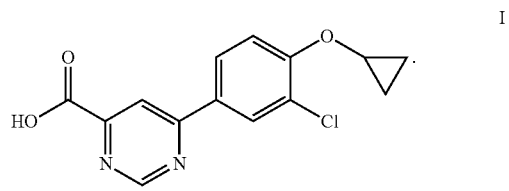 [SMILES: O=C(O)c1cc(-c2ccc(OC3CC3)c(Cl)c2)ncn1]

Compound I is a selective and potent inhibitor or modulator of KMO activity. The synthesis and methods of use thereof are described in U.S. Patent App. Pub. No. 2016/0251318, which is hereby incorporated by reference in its entirety.

The present disclosure relates to various solid forms of Compound I, and processes for making such crystalline forms.

Additional crystalline forms of salts or co-crystals of Compound I are also described herein. In some embodiments, salts or co-crystals of Compound I may have the following formula:

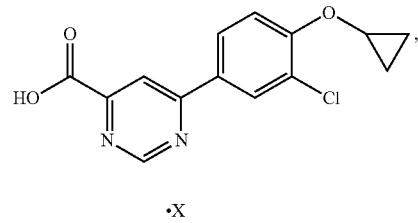

where X may be arginine, benzathine, diethanolamine, diethylamine, ethanolamine, ethylenediamine, lysine, meglumine, potassium, tromethamine, or sodium. The following exemplary salts or co-crystals of Compound I described herein include: "Compound I arginine Material A," "Compound I benzathine Form A," "Compound I diethylamine Material A," "Compound I ethanolamine Material A," "Compound I ethylenediamine Materials A+B," "Compound I lysine Material A," "Compound meglumine Material A," "Compound I potassium Material A," "Compound I tromethamine Form A," "Compound I sodium Pattern A,"

"Compound I sodium Form B," "Compound I sodium Pattern C," and "Compound I sodium Form E."

In some embodiments, salts or co-crystals of Compound I may have the formula Ia:

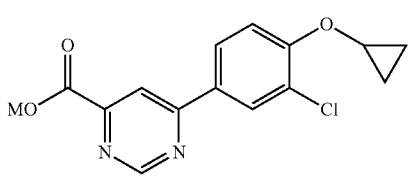

wherein M is potassium or sodium. In some embodiments, M is sodium. In all instances, reference to Compound I also refers to compounds of formula Ia. Furthermore, references to compounds described herein, compositions of this disclosure, at least one compound described herein, active compounds, and similar statements are to be interpreted as referring to Compound I, or Compound I having formula Ia, or a salt, pharmaceutically acceptable salt, deuterated analog, isotopically enriched analog, or co-crystal thereof, in any form, material, pattern, or mixture thereof in any combination, described herein.

Other forms of Compound I are further described herein, such as mesophase and amorphous forms of Compound I sodium salt.

1. Definitions

As used in the present specification, the following words and phrases are generally intended to have the meanings as set forth below, except to the extent that the context in which they are used indicates otherwise.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X".

Recitation of numeric ranges of values throughout the disclosure is intended to serve as a shorthand notation of referring individually to each separate value falling within the range inclusive of the values defining the range, and each separate value is incorporated in the specification as it were individually recited herein.

Forms of Compound I and salts/co-crystals are provided herein. In one embodiment, reference to a form of Compound I means that at least 50% to 99% (e.g., at least 50%, at least 55%, at least 60%, at least 65%, at least 70%, at least 75%, at least 80%, at least 85%, at least 90%, at least 95%, or at least 99%) of Compound I or a salt or co-crystal thereof present in a composition is in the designated form. For instance, in one embodiment, reference to Compound I sodium Form B means that at least 50%, at least 55%, at least 60%, at least 65%, at least 70%, at least 75%, at least 80%, at least 85%, at least 90%, at least 95%, or at least 99% of the Compound I sodium salt present in a composition is in Form B.

The term "solid form" refers to a type of solid-state material that includes amorphous as well as crystalline forms.

The term "crystalline form" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point).

The term "substantially crystalline" as used herein is intended to mean that greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition is in crystalline form. "Substantially crystalline" can also refer to material which has no more than about 20%, or no more than about 10%, or no more than about 5%, or no more than about 2% in the amorphous form. Likewise, the term "substantially" when qualifying any form of a compound described herein is intended to mean that greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound is present in the designated form.

The term "mesophase form" refers to a state of matter that falls between a crystal and a liquid. Such materials typically exhibit a long range order at the molecular level that is relaxed to some degree (e.g., relative to a crystal). Such materials may also have the appearance of a solid, yet the fluid properties of liquid (e.g., the material may flow like a liquid when pressed upon, rather than break and fracture as would a solid). Mesophases may further be characterized as thermotropic or lyotropic. Thermotropic mesophases are those that occur over a certain temperature range, whereas lyotropic mesophases are induced by the present of solvent and are usually formed by amphiphilic molecules. Mesophase forms may additionally be characterized by their birefringence, which is absent in amorphous solids or isotropic liquids and typically present in crystalline solids.

The term "amorphous form" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

Materials exhibiting unique X-ray powder diffraction (XRPD) patterns based at least on visual inspection of peaks in said XRPD patterns, are given a letter designation (e.g., "A," "B," etc.). The letter designation is further associated with the term "Form" (e.g., "Form B") when additional characterization data is available, including but not limited to phase purity (e.g., obtained via indexing of the XRPD pattern or single crystal structure elucidation) and chemical composition (e.g., obtained via proton nuclear magnetic resonance (NMR) spectroscopy or other analyses). In some embodiments, the letter designation associated with the terms, "Pattern," or "Material" also refers to "Form."

The term "co-crystal" refers to a molecular complex of an ionized or non-ionized form of a compound disclosed herein and one or more non-ionized co-crystal formers connected through non-covalent interactions. In some embodiments, the co-crystals disclosed herein may include a non-ionized form of Compound I (e.g., Compound I free acid) and one or more non-ionized co-crystal formers, where non-ionized Compound I and the co-crystal former(s) are connected through non-covalent interactions. In some embodiments, co-crystals disclosed herein may include an ionized form of Compound I (e.g., a salt of Compound I) and one or more non-ionized co-crystals formers, where ionized Compound I and the co-crystal former(s) are connected through non-covalent interactions. Co-crystals may additionally be present in anhydrous, solvated or hydrated forms.

The term "co-crystal former" or "co-former" refers to one or more pharmaceutically acceptable bases or pharmaceutically acceptable acids disclosed herein in association with Compound I, or any other compound disclosed herein.

Provided are also pharmaceutically acceptable salts, hydrates, and solvates, of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethyl acetate, acetic acid and ethanolamine.

The term "desolvated" refers to a Compound I form that is a solvate as described herein, and from which solvent molecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

Any formula or structure given herein, including Compound I, is also intended to represent unlabeled forms as well as isotopically labeled forms of the compounds. Isotopically labeled compounds have structures depicted by the formulae given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$, $^{35}$, $^{36}$Cl and $^{125}$I. Various isotopically labeled compounds of the present disclosure, for example those into which isotopes such as $^3$H, $^{13}$C and $^{14}$C are incorporated, may be prepared. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen" the position is understood to have hydrogen at its natural abundance isotopic composition. For example, its natural abundance at the Earth's surface. Accordingly, in the compounds of this disclosure any atom specifically designated as a deuterium (D) is meant to represent deuterium.

The phrase "substantially as shown in Figure" as applied to DSC thermograms is meant to include a variation of ±3 Celsius, and as applied to thermogravimetric analysis (TGA) is meant to include a variation of ±2% in weight loss.

In addition, abbreviations as used herein have respective meanings as follows:

| | |
|---|---|
| ACN (MeCN) | Acetonitrile |
| DCM | Dichloromethane |
| BuOH | Butanol |
| DMF | Dimethylformamide |
| DMSO | Dimethylsulfoxide |
| DSC | Differential scanning calorimetry |
| DVS | Dynamic vapor sorption |
| EtOAc | Ethyl acetate |
| EtOH | Ethanol |
| HFIPA | Hexafluoroisopropanol |
| HPLC | High pressure liquid chromatography |
| IPA | Isopropanol |
| IPAc | Isopropyl acetate |
| MEK | Methyl ethyl ketone |
| MeOH | Methanol |
| 2-meTHF | 2-Methyltetrahydrofuran |
| MIK | Methyl isopropyl ketone |
| MTBE | Methyl tert-butyl ether |
| NMP | N-methyl-2-pyrrolidinone |
| NMR | Nuclear magnetic resonance spectroscopy |
| PEG | Polyethylene glycol |
| RH | Relative humidity |
| RT | Room temperature |
| TFE | 2,2,2-Trifluoroethanol |
| TGA | Thermogravimetric analysis |
| THF | Tetrahydrofuran |
| TLC | Thin layer chromatography |
| XRPD | X-ray powder diffraction |

2. Forms of Compound I

As described generally above, the present disclosure provides solid forms of Compound I and salts/co-crystals thereof. Additional forms (including mesophase and amorphous forms) are also discussed further herein. Solid forms of Compound I (free acid), the solid forms of salts/co-crystals of Compound I, and other forms (e.g., mesophase or amorphous forms) of Compound I (free acid) and salts/co-crystals thereof, are collectively referred to herein as "forms of Compound I."

Crystalline salts that have a known stoichiometry, are not deliquescent, exhibit a melting temperature >125° C., and exhibit suitable aqueous solubility are advantageous for many applications. Additional criteria for consideration include yield, crystalline quality, phase purity, and evidence of disproportionation in water. Several forms of the salts of Compound I were forms were found to exhibit suitable aqueous solubility, yet poor physical properties such as: Compound I Arginine Material A (low yield, atypical stoichiometric ratio); Compound I ethylenediamine Materials A+B (disordered XRPD spectrum, multiple crystalline phases, disproportionates in water); Compound I meglumine Material A (phase impurity, undesirable thermal behavior); and Compound I potassium Material A (disordered XRPD pattern, undesirable thermal behavior, mesophasic). Moreover, other forms were found to exhibit good physical properties, but poor low aqueous solubility, such as: Compound I benzathine Form A; Compound I ethanolamine Material A; and Compound I lysine material A.

In contrast, several solid forms of the salts of Compound I were found to exhibit both good physical properties (e.g., known stoichiometry, no deliquescence, melting temperature >125° C.) and desirable aqueous solubility, such as Compound I diethanolamine Form A; Compound I diethylamine Material; and Compound I sodium Form B; and Compound I tromethamine Form A. Moreover, Compound I sodium Form B was found to be the predominant and most thermodynamically stable form at the conditions evaluated (see Examples).

a. Compound I Material A

The present disclosure provides, in one embodiment, a crystalline form of 6-(3-chloro-4-cyclopropoxyphenyl)pyrimidine-4-carboxylic acid (Compound I Material A) characterized by an X-ray powder diffractogram comprising the following peaks 10.79, 25.92, and 27.18 θ2θ±0.2°2θ, as determined on a diffractometer using Cu-Kα radiation (1.54 Å). In one embodiment, the diffractogram of Compound I Material A further comprises one or more peaks at: 13.85, 22.08, and 24.34°2θ±0.2°2θ.

In one embodiment, Compound I Material A is characterized by an X-ray powder diffractogram comprising at least two of the following peaks: 4.98, 9.99, 10.79, 13.85, 14.42, 15.03, 19.22, 19.81, 20.23, 21.15, 21.70, 22.08, 22.28, 22.47, 23.26, 23.56, 23.69, 24.34, 25.22, 25.92, 27.18, 28.04, 29.45, and 29.86°2θ±0.2°2θ. In one embodiment, Compound I Material A is characterized by an X-ray powder diffractogram comprising at least four of the following peaks: 4.98, 9.99, 10.79, 13.85, 14.42, 15.03, 19.22, 19.81, 20.23, 21.15, 21.70, 22.08, 22.28, 22.47, 23.26, 23.56, 23.69, 24.34, 25.22, 25.92, 27.18, 28.04, 29.45, and 29.86°2θ. In one embodiment, Compound I Material A is characterized by an X-ray powder diffractogram comprising at least six of the following peaks: 4.98, 9.99, 10.79, 13.85, 14.42, 15.03, 19.22, 19.81, 20.23, 21.15, 21.70, 22.08, 22.28, 22.47, 23.26, 23.56, 23.69, 24.34, 25.22, 25.92, 27.18, 28.04, 29.45, and 29.86°2θ±0.2°2θ. In one embodiment, Compound I Material A is characterized by an X-ray powder diffractogram comprising at least eight of the following peaks: 4.98, 9.99, 10.79, 13.85, 14.42, 15.03, 19.22, 19.81, 20.23, 21.15, 21.70, 22.08, 22.28, 22.47, 23.26, 23.56, 23.69, 24.34, 25.22, 25.92, 27.18, 28.04, 29.45, and 29.86°2θ±0.2°2θ. In one embodiment Compound I Material A is characterized by an X-ray powder diffractogram comprising each of the following peaks: 4.98, 9.99, 10.79, 13.85, 14.42, 15.03, 19.22, 19.81, 20.23, 21.15, 21.70, 22.08, 22.28, 22.47, 23.26, 23.56, 23.69, 24.34, 25.22, 25.92, 27.18, 28.04, 29.45, and 29.86°2θ±0.2°2θ. In one embodiment, Compound I Material A is characterized by the full X-ray powder diffractogram as substantially shown in FIG. 1.

In one embodiment, Compound I Material A is characterized by a differential scanning calorimetry (DSC) curve that comprises an endotherm with onset at about 172° C. In one embodiment, the DSC curve of Compound I Material A comprises additional endotherms with peaks at about 118° C. and about 152° C., as well as an exotherm with a peak at about 156° C. In one embodiment, Compound I Material A is characterized by the full DSC curve as substantially shown in FIG. 2.

In one embodiment, Compound I Material A is characterized by a thermogravimetric analysis (TGA) thermogram showing a weight loss of about 4.3% up to about 100° C. In one embodiment, Compound I Material A is characterized by the full TGA thermogram as substantially shown in FIG. 3.

In one embodiment, Compound I Material A is characterized as a monohydrate.

The present disclosure also provides at least one process for making Compound I Material A. In one embodiment, Compound I Material A may be prepared from an aqueous solution comprising Compound I sodium Pattern A and HCl. In one embodiment, the process for making Compound I Material A is as described in the Examples provided herein.

b. Compound I Material B

The present disclosure provides, in one embodiment, a crystalline form of 6-(3-chloro-4-cyclopropoxyphenyl)pyrimidine-4-carboxylic acid (Compound I Material B) characterized by an X-ray powder diffractogram comprising the following peaks 9.42, 12.28, and 27.03°2θ±0.2°2θ, as determined on a diffractometer using Cu-Kα radiation (1.54 Å). In one embodiment, the diffractogram of Compound I Material B further comprises one or more peaks at: 11.65, 13.05, and 17.69°2θ±0.2°2θ.

In one embodiment, Compound I Material B is characterized by an X-ray powder diffractogram comprising at least two of the following peaks: 5.27, 7.83, 9.14, 9.42, 10.08, 10.60, 11.65, 12.28, 13.05, 15.44, 16.16, 16.65, 17.17, 17.69, 18.17, 19.14, 19.48, 20.29, 21.37, 22.40, 23.45, 23.80, 25.27, 25.60, 26.30, and 27.03°2θ±0.2°2θ. In one embodiment, Compound I Material B is characterized by an X-ray powder diffractogram comprising at least four of the following peaks: 5.27, 7.83, 9.14, 9.42, 10.08, 10.60, 11.65, 12.28, 13.05, 15.44, 16.16, 16.65, 17.17, 17.69, 18.17, 19.14, 19.48, 20.29, 21.37, 22.40, 23.45, 23.80, 25.27, 25.60, 26.30, and 27.03°2θ±0.2°2θ±0.2°2θ. In one embodiment, Compound I Material B is characterized by an X-ray powder diffractogram comprising at least six of the following peaks: 5.27, 7.83, 9.14, 9.42, 10.08, 10.60, 11.65, 12.28, 13.05, 15.44, 16.16, 16.65, 17.17, 17.69, 18.17, 19.14, 19.48, 20.29, 21.37, 22.40, 23.45, 23.80, 25.27, 25.60, 26.30, and 27.03°2θ±0.2°2θ±0.2°2θ. In one embodiment, Compound I Material B is characterized by an X-ray powder diffractogram comprising at least eight of the following peaks: 5.27, 7.83, 9.14, 9.42, 10.08, 10.60, 11.65, 12.28, 13.05, 15.44, 16.16, 16.65, 17.17, 17.69, 18.17, 19.14, 19.48, 20.29, 21.37, 22.40, 23.45, 23.80, 25.27, 25.60, 26.30, and 27.03°2θ±0.2°2θ±0.2°2θ. In one embodiment Compound I Material B is characterized by an X-ray powder diffractogram comprising each of the following peaks: 5.27, 7.83, 9.14, 9.42, 10.08, 10.60, 11.65, 12.28, 13.05, 15.44, 16.16, 16.65, 17.17, 17.69, 18.17, 19.14, 19.48, 20.29, 21.37, 22.40, 23.45, 23.80, 25.27, 25.60, 26.30, and 27.03°2θ±0.2°2θ±0.2°2θ. In one embodiment, Compound I Material B is characterized by the full X-ray powder diffractogram as substantially shown in FIG. 4A.

The present disclosure also provides at least one process for making Compound I Material B. In one embodiment, Compound I Material B may be isolated from a diethyl ether filtrate involved in the method to extract, using ethyl acetate, Compound I free acid from an aqueous solution comprising Compound I sodium Pattern A and HCl. In one embodiment, the process for making Compound I Material B is as described in the Examples provided herein.

c. Compound I Material C

The present disclosure provides, in one embodiment, a crystalline form of 6-(3-chloro-4-cyclopropoxyphenyl)pyrimidine-4-carboxylic acid (Compound I Material D) characterized by an X-ray powder diffractogram comprising the following peaks 3.40, 6.88, and 11.99°2θ±0.2°2θ, as determined on a diffractometer using Cu-Kα radiation (1.54 Å). In one embodiment, the diffractogram of Compound I Material C further comprises one or more peaks at: 10.37, 15.09, and 24.26°2θ±0.2°2θ.

In one embodiment, Compound I Material C is characterized by an X-ray powder diffractogram comprising at least two of the following peaks: 3.40, 5.92, 6.88, 9.12, 10.37, 11.99, 13.90, 15.09, 15.98, 18.30, 19.29, 21.21, 22.87, 24.26, and 25.74°2θ±0.2°2θ. In one embodiment, Compound I Material C is characterized by an X-ray powder diffractogram comprising at least four of the following peaks: 3.40, 5.92, 6.88, 9.12, 10.37, 11.99, 13.90, 15.09, 15.98, 18.30, 19.29, 21.21, 22.87, 24.26, and 25.74°2θ±0.2°2θ. In one embodiment, Compound I Material C is characterized by an X-ray powder diffractogram comprising at least six of the following peaks: 3.40, 5.92, 6.88, 9.12, 10.37, 11.99, 13.90, 15.09, 15.98, 18.30, 19.29, 21.21, 22.87, 24.26, and 25.74°2θ±0.2°2θ. In one embodiment, Compound I Material C is characterized by an X-ray powder diffractogram comprising at least eight of the following peaks: 3.40, 5.92, 6.88, 9.12, 10.37, 11.99, 13.90, 15.09, 15.98, 18.30, 19.29, 21.21, 22.87, 24.26, and 25.74°2θ±0.2°2θ. In one embodiment Compound I Material C is characterized by an X-ray powder diffractogram comprising each of the following peaks: 3.40, 5.92, 6.88, 9.12, 10.37, 11.99, 13.90, 15.09, 15.98, 18.30, 19.29, 21.21, 22.87, 24.26, and 25.74°2θ±0.2°2θ. In one embodiment, Compound I Material C is characterized by the full X-ray powder diffractogram as substantially shown in FIG. 4B.

The present disclosure also provides at least one process for making Compound I Material C. In one embodiment, Compound I Material C may be evaporated from a diethyl ether filtrate involved in the method to extract, using ethyl acetate, Compound I free acid from an aqueous solution comprising Compound I sodium Pattern A and HCl. In one embodiment, the process for making Compound I Material C is as described in the Examples provided herein.

d. Compound I Material D

The present disclosure provides, in one embodiment, a crystalline form of 6-(3-chloro-4-cyclopropoxyphenyl)pyrimidine-4-carboxylic acid (Compound I Material D) characterized by an X-ray powder diffractogram comprising the following peaks 10.42, 23.80, and 26.59°2θ±0.2°2θ, as determined on a diffractometer using Cu-Kα radiation (1.54 Å). In one embodiment, the diffractogram of Compound I Material D further comprises one or more peaks at: 4.87, 13.66, and 21.39°2θ±0.2°2θ.

In one embodiment, Compound I Material D is characterized by an X-ray powder diffractogram comprising at least two of the following peaks: 4.87, 10.42, 13.66, 14.11, 14.67, 14.91, 17.35, 17.51, 18.49, 19.21, 19.61, 20.25, 21.10, 21.39, 21.70, 21.94, 22.28, 22.79, 22.98, 23.34, 23.80, 24.58, 25.10, 25.41, 26.59, 27.07, 27.56, 28.11, 28.44, 29.73, and 29.94°2θ±0.2°2θ. In one embodiment, Compound I Material D is characterized by an X-ray powder diffractogram comprising at least four of the following peaks: 4.87, 10.42, 13.66, 14.11, 14.67, 14.91, 17.35, 17.51, 18.49, 19.21, 19.61, 20.25, 21.10, 21.39, 21.70, 21.94, 22.28, 22.79, 22.98, 23.34, 23.80, 24.58, 25.10, 25.41, 26.59, 27.07, 27.56, 28.11, 28.44, 29.73, and 29.94°2θ±0.2°2θ. In one embodiment, Compound I Material D is characterized by an X-ray powder diffractogram comprising at least six of the following peaks 4.87, 10.42, 13.66, 14.11, 14.67, 14.91, 17.35, 17.51, 18.49, 19.21, 19.61, 20.25, 21.10, 21.39, 21.70, 21.94, 22.28, 22.79, 22.98, 23.34, 23.80, 24.58, 25.10, 25.41, 26.59, 27.07, 27.56, 28.11, 28.44, 29.73, and 29.94°2θ±0.2°2θ. In one embodiment, Compound I Material D is characterized by an X-ray powder diffractogram comprising at least eight of the following peaks: 4.87, 10.42, 13.66, 14.11, 14.67, 14.91, 17.35, 17.51, 18.49, 19.21, 19.61, 20.25, 21.10, 21.39, 21.70, 21.94, 22.28, 22.79, 22.98, 23.34, 23.80, 24.58, 25.10, 25.41, 26.59, 27.07, 27.56, 28.11, 28.44, 29.73, and 29.94°2θ±0.2°2θ. In one embodiment Compound I Material D is characterized by an X-ray powder diffractogram comprising each of the following peaks: 4.87, 10.42, 13.66, 14.11, 14.67, 14.91, 17.35, 17.51, 18.49, 19.21, 19.61, 20.25, 21.10, 21.39, 21.70, 21.94, 22.28, 22.79, 22.98, 23.34, 23.80, 24.58, 25.10, 25.41, 26.59, 27.07, 27.56, 28.11, 28.44, 29.73, and 29.94°2θ±0.2°2θ. In one embodiment, Compound I Material D is characterized by the full X-ray powder diffractogram as substantially shown in FIGS. 5, 6A.

In one embodiment, Compound I Material D is characterized as a dihydrate.

The present disclosure also provides at least one process for making Compound I Material D. In one embodiment, Compound I Material D may be prepared from an aqueous solution comprising Compound I sodium Pattern A and HCl. In one embodiment, Compound I Material D may be prepared from an aqueous solution comprising Compound I sodium Pattern B and HCl. In one embodiment, the process for making Compound I Material D is as described in the Examples provided herein.

e. Compound I Material E

The present disclosure provides, in one embodiment, a crystalline form of 6-(3-chloro-4-cyclopropoxyphenyl)pyrimidine-4-carboxylic acid (Compound I Material E) characterized by an X-ray powder diffractogram comprising the following peaks 4.31, 5.42, and 13.21°2θ±0.2°2θ, as determined on a diffractometer using Cu-Kα radiation (1.54 Å). In one embodiment, the diffractogram of Compound I Material E further comprises one or more peaks at: 8.65, 11.46, and 15.40°2θ±0.2°2θ.

In one embodiment, Compound I Material E is characterized by an X-ray powder diffractogram comprising at least two of the following peaks: 3.29, 4.31, 4.98, 5.42, 8.19, 8.65, 9.01, 9.99, 10.22, 10.89, 11.46, 11.93, 12.46, 13.21, 14.10, 14.57, 15.03, 15.40, 16.74, 17.38, 17.67, 18.08, 18.74, 19.19, 19.60, 20.16, 21.15, 21.94, 23.05, 24.01, 25.17, and 25.99°2θ±0.2°2θ. In one embodiment, Compound I Material E is characterized by an X-ray powder diffractogram comprising at least four of the following peaks: 3.29, 4.31, 4.98, 5.42, 8.19, 8.65, 9.01, 9.99, 10.22, 10.89, 11.46, 11.93, 12.46, 13.21, 14.10, 14.57, 15.03, 15.40, 16.74, 17.38, 17.67, 18.08, 18.74, 19.19, 19.60, 20.16, 21.15, 21.94, 23.05, 24.01, 25.17, and 25.99°2θ±0.2°2θ. In one embodiment, Compound I Material E is characterized by an X-ray powder diffractogram comprising at least six of the following peaks: 3.29, 4.31, 4.98, 5.42, 8.19, 8.65, 9.01, 9.99, 10.22, 10.89, 11.46, 11.93, 12.46, 13.21, 14.10, 14.57, 15.03, 15.40, 16.74, 17.38, 17.67, 18.08, 18.74, 19.19, 19.60, 20.16, 21.15, 21.94, 23.05, 24.01, 25.17, and 25.99°2θ±0.2°2θ. In one embodiment, Compound I Material E is characterized by an X-ray powder diffractogram comprising at least eight of the following peaks: 3.29, 4.31, 4.98, 5.42, 8.19, 8.65, 9.01, 9.99, 10.22, 10.89, 11.46, 11.93, 12.46, 13.21, 14.10, 14.57, 15.03, 15.40, 16.74, 17.38, 17.67, 18.08, 18.74, 19.19, 19.60, 20.16, 21.15, 21.94, 23.05, 24.01, 25.17, and 25.99°2θ±0.2°2θ. In one embodiment Compound I Material E is characterized by an X-ray powder diffractogram comprising each of the following peaks: 3.29, 4.31, 4.98, 5.42, 8.19, 8.65, 9.01, 9.99, 10.22, 10.89, 11.46, 11.93, 12.46, 13.21, 14.10, 14.57, 15.03, 15.40, 16.74, 17.38, 17.67, 18.08, 18.74, 19.19, 19.60, 20.16, 21.15, 21.94, 23.05, 24.01, 25.17, and 25.99°2θ±0.2°2θ. In one embodiment, Compound I Material E is characterized by the full X-ray powder diffractogram as substantially shown in FIG. 6D.

The present disclosure also provides at least one process for making Compound I Material E. In one embodiment, this process comprises contacting Compound I sodium Pattern A with an aqueous solution comprising and HCl, whereby the resulting solids were rinsed with water, dried, and reheated above about 150° C. to form Compound I Material E. In one embodiment, the process for making Compound I Material E is as described in the Examples provided herein.

f. Compound I Material F

The present disclosure provides, in one embodiment, a crystalline form of 6-(3-chloro-4-cyclopropoxyphenyl)pyrimidine-4-carboxylic acid (Compound I Material F) characterized by an X-ray powder diffractogram comprising the following peaks 11.97, 12.53, and 26.75°2θ±0.2°2θ, as determined on a diffractometer using Cu-Kα radiation (1.54 Å). In one embodiment, the diffractogram of Compound I Material F further comprises one or more peaks at: 12.17, 21.34, and 26.65°2θ±0.2°2θ.

In one embodiment, Compound I Material F is characterized by an X-ray powder diffractogram comprising at least two of the following peaks: 5.77, 6.08, 9.23, 11.97, 12.17, 15.53, 13.37, 13.94, 14.12, 14.69, 15.64, 16.27, 16.47, 16.73, 16.92, 17.32, 17.56, 18.07, 18.44, 20.99, 21.34, 24.85, 25.32, 26.29, 26.65, and 26.75°2θ±0.2°2θ. In one embodiment, Compound I Material F is characterized by an X-ray powder diffractogram comprising at least four of the following peaks: 5.77, 6.08, 9.23, 11.97, 12.17, 15.53, 13.37, 13.94, 14.12, 14.69, 15.64, 16.27, 16.47, 16.73, 16.92, 17.32, 17.56, 18.07, 18.44, 20.99, 21.34, 24.85, 25.32, 26.29, 26.65, and 26.75°2θ±0.2°2θ. In one embodiment, Compound I Material F is characterized by an X-ray powder diffractogram comprising at least six of the following peaks: 5.77, 6.08, 9.23, 11.97, 12.17, 15.53, 13.37, 13.94, 14.12, 14.69, 15.64, 16.27, 16.47, 16.73, 16.92, 17.32, 17.56, 18.07, 18.44, 20.99, 21.34, 24.85, 25.32, 26.29, 26.65, and 26.75°2θ±0.2°2θ. In one embodiment, Compound I Material F is characterized by an X-ray powder diffractogram comprising at least eight of the following peaks: 5.77, 6.08, 9.23, 11.97, 12.17, 15.53, 13.37, 13.94, 14.12, 14.69, 15.64, 16.27, 16.47, 16.73, 16.92, 17.32, 17.56, 18.07, 18.44, 20.99, 21.34, 24.85, 25.32, 26.29, 26.65, and 26.75°2θ±0.2°2θ. In one embodiment Compound I Material F is characterized by an X-ray powder diffractogram comprising each of the following peaks: 5.77, 6.08, 9.23, 11.97, 12.17, 15.53, 13.37, 13.94, 14.12, 14.69, 15.64, 16.27, 16.47, 16.73, 16.92, 17.32, 17.56, 18.07, 18.44, 20.99, 21.34, 24.85, 25.32, 26.29, 26.65, and 26.75°2θ±0.2°2θ.

In one embodiment Compound I Material F may be present as a mixture with Compound I Material A. In one embodiment, Compound I Material F is characterized by the full X-ray powder diffractogram as substantially shown in FIG. 6C. An X-ray powder diffractogram of Compound I Material A is provided in FIG. 6B for reference.

In one embodiment, Compound I Material F is characterized as a dihydrate.

The present disclosure also provides at least one process for making Compound I Material F. In one embodiment, Compound I Material F may be prepared by contacting Compound I sodium Pattern A with an aqueous solution comprising and HCl, and heating the resulting solution above about 83° C. under vacuum. In one embodiment, Compound I Material F may be prepared by treating an aqueous solution of Compound I sodium Form B with activated carbon, adding HCl to the solution, and filtering, rinsing and drying the resulting solids. In one embodiment, the process for making Compound I Material F is as described in the Examples provided herein.

g. Compound I Arginine Material A

The present disclosure provides, in one embodiment, a crystalline form of 6-(3-chloro-4-cyclopropoxyphenyl)pyrimidine-4-carboxylic acid (Compound I arginine Material A) characterized by an X-ray powder diffractogram comprising the following peaks 3.75, 19.25, and 22.86°2θ±0.2°2θ, as determined on a diffractometer using Cu-Kα radiation (1.54 Å). In one embodiment, the diffractogram of Compound I arginine Material A further comprises one or more peaks at: 12.35, 14.81, and 24.88°2θ±0.2°2θ.

In one embodiment, Compound I arginine Material A is characterized by an X-ray powder diffractogram comprising at least two of the following peaks: 3.75, 10.33, 10.74, 11.24, 12.35, 13.07, 14.81, 16.18, 17.74, 19.25, 19.63, 20.04, 20.78, 21.56, 22.13, 22.86, 23.68, 24.16, 24.88, and 25.63°2θ±0.2020. In one embodiment, Compound I arginine Material A is characterized by an X-ray powder diffractogram comprising at least four of the following peaks: 3.75, 10.33, 10.74, 11.24, 12.35, 13.07, 14.81, 16.18, 17.74, 19.25, 19.63, 20.04, 20.78, 21.56, 22.13, 22.86, 23.68, 24.16, 24.88, and 25.63°2θ±0.2°2θ. In one embodiment, Compound I arginine Material A is characterized by an X-ray powder diffractogram comprising at least six of the following peaks: 3.75, 10.33, 10.74, 11.24, 12.35, 13.07, 14.81, 16.18, 17.74, 19.25, 19.63, 20.04, 20.78, 21.56, 22.13, 22.86, 23.68, 24.16, 24.88, and 25.63°2θ±0.2°2θ. In one embodiment, Compound I arginine Material A is characterized by an X-ray powder diffractogram comprising at least eight of the following peaks: 3.75, 10.33, 10.74, 11.24, 12.35, 13.07, 14.81, 16.18, 17.74, 19.25, 19.63, 20.04, 20.78, 21.56, 22.13, 22.86, 23.68, 24.16, 24.88, and 25.63°2θ±0.2°2θ. In one embodiment Compound I arginine Material A is characterized by an X-ray powder diffractogram comprising each of the following peaks: 3.75, 10.33, 10.74, 11.24, 12.35, 13.07, 14.81, 16.18, 17.74, 19.25, 19.63, 20.04, 20.78, 21.56, 22.13, 22.86, 23.68, 24.16, 24.88, and 25.63°2θ±0.2°2θ. In one embodiment, Compound I arginine Material A is characterized by the full X-ray powder diffractogram as substantially shown in FIG. 7A.

In one embodiment, Compound I arginine Material A is characterized by a 2:3 ratio of Compound I to arginine.

The present disclosure also provides at least one process for making Compound I arginine Material A. In one embodiment, Compound I arginine Material A may be prepared by combining Compound I free acid Material A+F (e.g., a combination of Compound I Material A and Compound I Material F as described herein) in acetonitrile with arginine in water, and further treating the solution with acetonitrile. In one embodiment, the process for making Compound I arginine Material A is as described in the Examples provided herein.

h. Compound I Benzathine Material A

The present disclosure provides, in one embodiment, a crystalline form of 6-(3-chloro-4-cyclopropoxyphenyl)pyrimidine-4-carboxylic acid (Compound I benzathine Form A) characterized by an X-ray powder diffractogram comprising the following peaks 10.07, 19.04, and 24.58°2θ±0.2°2θ, as determined on a diffractometer using Cu-Kα radiation (1.54 Å). In one embodiment, the diffractogram of Compound I benzathine Form A further comprises one or more peaks at: 15.43, 15.87, and 22.11°2θ±0.2°2θ.

In one embodiment, Compound I benzathine Form A is characterized by an X-ray powder diffractogram comprising at least two of the following peaks: 4.74, 9.54, 10.07, 12.07, 12.26, 14.35, 15.43, 15.87, 16.63, 17.58, 17.87, 19.04, 19.32, 19.60, 20.36, 20.58, 21.25, 21.66, 21.82, 22.11, 22.61, 23.42, 23.93, 24.24, 24.58, 24.88, 25.22, 25.77, 25.99, 26.42, 26.64, 27.42, 27.86, 28.24, and 28.50°2θ±0.2°2θ. In one embodiment, Compound I benzathine Form A is characterized by an X-ray powder diffractogram comprising at least four of the following peaks: 4.74, 9.54, 10.07, 12.07, 12.26, 14.35, 15.43, 15.87, 16.63, 17.58, 17.87, 19.04, 19.32, 19.60, 20.36, 20.58, 21.25, 21.66, 21.82, 22.11, 22.61, 23.42, 23.93, 24.24, 24.58, 24.88, 25.22, 25.77, 25.99, 26.42, 26.64, 27.42, 27.86, 28.24, and 28.50°2θ±0.2°2θ. In one embodiment, Compound I benzathine Form A is characterized by an X-ray powder diffractogram comprising at least six of the following peaks: 4.74, 9.54, 10.07, 12.07, 12.26, 14.35, 15.43, 15.87, 16.63, 17.58, 17.87, 19.04, 19.32, 19.60, 20.36, 20.58, 21.25, 21.66, 21.82, 22.11, 22.61, 23.42, 23.93, 24.24, 24.58, 24.88, 25.22, 25.77, 25.99, 26.42, 26.64, 27.42, 27.86, 28.24, and 28.50°2θ±0.2°2θ. In one embodiment, Compound I benzathine Form A is characterized by an X-ray powder diffractogram comprising at least eight of the following peaks: 44.74, 9.54, 10.07, 12.07, 12.26, 14.35, 15.43, 15.87, 16.63, 17.58, 17.87, 19.04, 19.32, 19.60, 20.36, 20.58, 21.25, 21.66, 21.82, 22.11, 22.61, 23.42, 23.93, 24.24, 24.58, 24.88, 25.22, 25.77, 25.99, 26.42, 26.64, 27.42, 27.86, 28.24, and 28.50°2θ±0.2°2θ. In one embodiment Compound I benzathine Form A is characterized by an X-ray powder diffractogram comprising each of the following peaks: 4.74, 9.54, 10.07, 12.07, 12.26, 14.35, 15.43, 15.87, 16.63, 17.58, 17.87, 19.04, 19.32, 19.60, 20.36, 20.58, 21.25, 21.66, 21.82, 22.11, 22.61, 23.42, 23.93, 24.24, 24.58, 24.88, 25.22, 25.77, 25.99, 26.42, 26.64, 27.42, 27.86, 28.24, and 28.50°2θ±0.2°2θ. In one embodiment, Compound I benzathine Form A is characterized by the full X-ray powder diffractogram as substantially shown in FIG. 8.

In one embodiment, Compound I benzathine Form A is characterized by a differential scanning calorimetry (DSC) curve that comprises an endotherm with onset at about 195° C. In one embodiment, the DSC curve of Compound I benzathine Form A comprises an additional endotherm with a peak at about 65° C. In one embodiment, Compound I benzathine Form A is characterized by the full DSC curve as substantially shown in FIG. 9.

In one embodiment, Compound I benzathine Form A is characterized by a thermogravimetric analysis (TGA) thermogram showing a weight loss of about 1.8% up to about 195° C. In one embodiment, Compound I benzathine Form A is characterized by the full TGA thermogram as substantially shown in FIG. 10.

In one embodiment, Compound I benzathine Form A is characterized by a 2:1 ratio of Compound I to benzathine.

The present disclosure also provides at least one process for making Compound I benzathine Material A. In one embodiment, Compound I benzathine Material A may be prepared by combining Compound I free acid Materials A+F in methanol with benzathine, and evaporating Compound I benzathine Material A therefrom. In one embodiment, Compound I benzathine Material A may be prepared by combining Compound I free acid in acetonitrile with benzathine. In one embodiment, the process for making Compound I benzathine Form A is as described in the Examples provided herein.

i. Compound I Diethanolamine Form A

The present disclosure provides, in one embodiment, a crystalline form of 6-(3-chloro-4-cyclopropoxyphenyl)pyrimidine-4-carboxylic acid (Compound I diethanolamine Form A) characterized by an X-ray powder diffractogram comprising the following peaks 11.90, 21.25, and 23.96°2θ±0.2°2θ, as determined on a diffractometer using Cu-Kα radiation (1.54 Å). In one embodiment, the diffractogram of Compound I diethanolamine Form A further comprises one or more peaks at: 12.71, 15.18, and 22.47°2θ±0.2°2θ.

In one embodiment, Compound I diethanolamine Form A is characterized by an X-ray powder diffractogram comprising at least two of the following peaks: 11.90, 12.23, 12.71, 13.03, 13.41, 15.18, 15.78, 16.10, 16.86, 17.25, 18.80, 19.13, 19.56, 20.07, 20.38, 21.25, 21.71, 22.47, 22.73, 23.04, 23.35, 23.49, 23.96, 24.23, 24.61, 25.61, 25.87, 26.25, 26.40, 26.69, 26.93, 27.61, 28.75, 29.42, and 29.80°2θ±0.2°2θ. In one embodiment, Compound I diethanolamine Form A is characterized by an X-ray powder diffractogram comprising at least four of the following peaks: 11.90, 12.23, 12.71, 13.03, 13.41, 15.18, 15.78, 16.10, 16.86, 17.25, 18.80, 19.13, 19.56, 20.07, 20.38, 21.25, 21.71, 22.47, 22.73, 23.04, 23.35, 23.49, 23.96, 24.23, 24.61, 25.61, 25.87, 26.25, 26.40, 26.69, 26.93, 27.61, 28.75, 29.42, and 29.80°2θ±0.2°2θ. In one embodiment, Compound I diethanolamine Form A is characterized by an X-ray powder diffractogram comprising at least six of the following peaks: 11.90, 12.23, 12.71, 13.03, 13.41, 15.18, 15.78, 16.10, 16.86, 17.25, 18.80, 19.13, 19.56, 20.07, 20.38, 21.25, 21.71, 22.47, 22.73, 23.04, 23.35, 23.49, 23.96, 24.23, 24.61, 25.61, 25.87, 26.25, 26.40, 26.69, 26.93, 27.61, 28.75, 29.42, and 29.80°2θ±0.2°2θ. In one embodiment, Compound I diethanolamine Form A is characterized by an X-ray powder diffractogram comprising at least eight of the following peaks: 11.90, 12.23, 12.71, 13.03, 13.41, 15.18, 15.78, 16.10, 16.86, 17.25, 18.80, 19.13, 19.56, 20.07, 20.38, 21.25, 21.71, 22.47, 22.73, 23.04, 23.35, 23.49, 23.96, 24.23, 24.61, 25.61, 25.87, 26.25, 26.40, 26.69, 26.93, 27.61, 28.75, 29.42, and 29.80°2θ±0.2°2θ. In one embodiment Compound I diethanolamine Form A is characterized by an X-ray powder diffractogram comprising each of the following peaks: 11.90, 12.23, 12.71, 13.03, 13.41, 15.18, 15.78, 16.10, 16.86, 17.25, 18.80, 19.13, 19.56, 20.07, 20.38, 21.25, 21.71, 22.47, 22.73, 23.04, 23.35, 23.49, 23.96, 24.23, 24.61, 25.61, 25.87, 26.25, 26.40, 26.69, 26.93, 27.61, 28.75, 29.42, and 29.80°2θ±0.2°2θ. In one embodiment, Compound I diethanolamine Form A is characterized by the full X-ray powder diffractogram as substantially shown in FIG. 11.

In one embodiment, Compound I diethanolamine Form A is characterized by a differential scanning calorimetry (DSC) curve that comprises an endotherm with onset at about 149° C. In one embodiment, Compound I diethanolamine Form A is characterized by the full DSC curve as substantially shown in FIG. 12.

In one embodiment, Compound I diethanolamine Form A is characterized by a thermogravimetric analysis (TGA) thermogram showing a weight loss of about 0.7% up to about 150° C. In one embodiment, Compound I diethanolamine Form A is characterized by the full TGA thermogram as substantially shown in FIG. 13.

Figure 14:
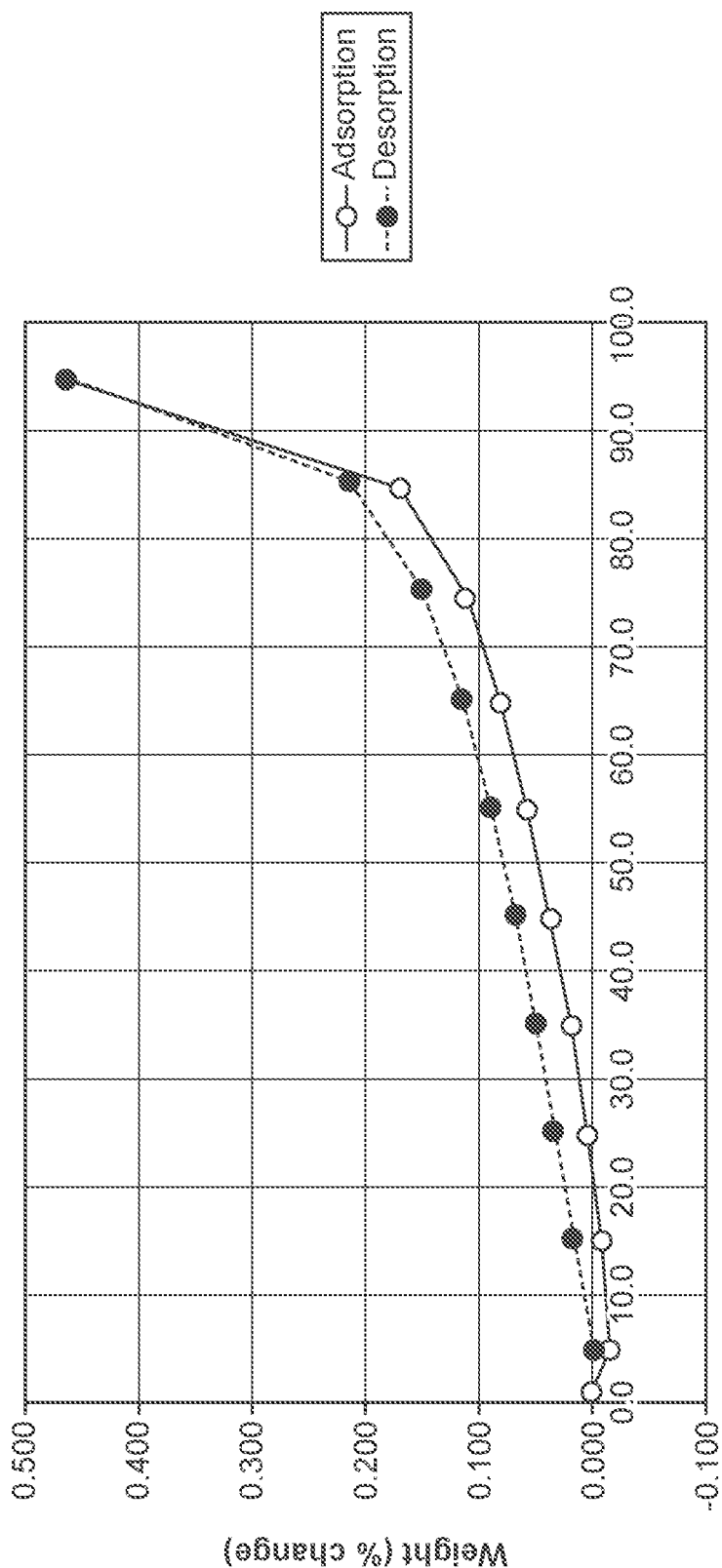
FIG. 14 is a dynamic vapor sorption curve (DVS) of Compound I diethanolamine Form A.

In one embodiment, Compound I diethanolamine Form A is characterized by a dynamic vapor sorption (DVS) analysis showing a weight loss of about 0.2% upon equilibration at about 5% RH; about a 0.48% weight gain from about 5 to about 95% RH; and about a 0.47% weight loss from about 95% to about 5% RH. In one embodiment, Compound I diethanolamine is characterized by the full DVS curve as shown in FIG. 14.

In one embodiment, Compound I diethanolamine Form A is characterized by a 1:1 ratio of Compound I to diethanolamine.

The present disclosure also provides at least one process for making Compound I diethanolamine Form A. In one embodiment, Compound I diethanolamine Form A may be prepared by combining Compound I free acid Materials A+F in acetonitrile with diethanolamine. In one embodiment, the process for making Compound I diethanolamine Form A is as described in the Examples provided herein.

j. Compound I Diethylamine Material A

The present disclosure provides, in one embodiment, a crystalline form of 6-(3-chloro-4-cyclopropoxyphenyl)pyrimidine-4-carboxylic acid (Compound I diethylamine Material A) characterized by an X-ray powder diffractogram comprising the following peaks 6.21, 11.30, and 13.25°2θ±0.2°2θ, as determined on a diffractometer using Cu-Kα radiation (1.54 Å). In one embodiment, the diffractogram of Compound I diethylamine Material A further comprises one or more peaks at: 7.98, 21.89, and 24.57°2θ±0.2°2θ.

In one embodiment, Compound I diethylamine Material A is characterized by an X-ray powder diffractogram comprising at least two of the following peaks: 6.21, 7.98, 8.81, 11.30, 11.56, 12.45, 12.85, 13.25, 13.57, 14.29, 14.53, 15.61, 15.93, 16.50, 16.80, 17.93, 18.18, 18.74, 18.98, 19.54, 20.23, 20.80, 21.25, 21.66, 21.89, 22.28, 22.81, 23.04, 23.25, 23.44, 23.70, 23.83, 24.12, 24.57, 25.13, 25.88, 26.07, 26.51, 27.35, 27.54, 28.42, 28.86, 29.11 and 29.50°2θ±0.2°2θ. In one embodiment, Compound I diethylamine Material A is characterized by an X-ray powder diffractogram comprising at least four of the following peaks: 6.21, 7.98, 8.81, 11.30, 11.56, 12.45, 12.85, 13.25, 13.57, 14.29, 14.53, 15.61, 15.93, 16.50, 16.80, 17.93, 18.18, 18.74, 18.98, 19.54, 20.23, 20.80, 21.25, 21.66, 21.89, 22.28, 22.81, 23.04, 23.25, 23.44, 23.70, 23.83, 24.12, 24.57, 25.13, 25.88, 26.07, 26.51, 27.35, 27.54, 28.42, 28.86, 29.11 and 29.50°2θ±0.2°2θ. In one embodiment, Compound I diethylamine Material A is characterized by an X-ray powder diffractogram comprising at least six of the following peaks 6.21, 7.98, 8.81, 11.30, 11.56, 12.45, 12.85, 13.25, 13.57, 14.29, 14.53, 15.61, 15.93, 16.50, 16.80, 17.93, 18.18, 18.74, 18.98, 19.54, 20.23, 20.80, 21.25, 21.66, 21.89, 22.28, 22.81, 23.04, 23.25, 23.44, 23.70, 23.83, 24.12, 24.57, 25.13, 25.88, 26.07, 26.51, 27.35, 27.54, 28.42, 28.86, 29.11 and 29.50°2θ±0.2°2θ. In one embodiment, Compound I diethylamine Material A is characterized by an X-ray powder diffractogram comprising at least eight of the following peaks: 6.21, 7.98, 8.81, 11.30, 11.56, 12.45, 12.85, 13.25, 13.57, 14.29, 14.53, 15.61, 15.93, 16.50, 16.80, 17.93, 18.18, 18.74, 18.98, 19.54, 20.23, 20.80, 21.25, 21.66, 21.89, 22.28, 22.81, 23.04, 23.25, 23.44, 23.70, 23.83, 24.12, 24.57, 25.13, 25.88, 26.07, 26.51, 27.35, 27.54, 28.42, 28.86, 29.11 and 29.50°2θ±0.2°2θ. In one embodiment Compound I diethylamine Material A is characterized by an X-ray powder diffractogram comprising each of the following peaks: 6.21, 7.98, 8.81, 11.30, 11.56, 12.45, 12.85, 13.25, 13.57, 14.29, 14.53, 15.61, 15.93, 16.50, 16.80, 17.93, 18.18, 18.74, 18.98, 19.54, 20.23, 20.80, 21.25, 21.66, 21.89, 22.28, 22.81, 23.04, 23.25, 23.44, 23.70, 23.83, 24.12, 24.57, 25.13, 25.88, 26.07, 26.51, 27.35, 27.54, 28.42, 28.86, 29.11 and 29.50°2θ±0.2°2θ. In one embodiment, Compound I diethylamine Material A is characterized by the full X-ray powder diffractogram as substantially shown in FIG. 7B.

In one embodiment, Compound I diethylamine Material A is characterized by a differential scanning calorimetry (DSC) curve that comprises an endotherm with onset at about 176° C. In one embodiment, the DSC curve of Compound I diethylamine Material A comprises an additional endotherm with a peak at about 105° C. In one embodiment, Compound I diethylamine Material A is characterized by the full DSC curve as substantially shown in FIG. 15.

In one embodiment, Compound I diethylamine Material A is characterized by a thermogravimetric analysis (TGA) thermogram showing a weight loss of about 1.2% up to about 150° C. In one embodiment, Compound I diethylamine Material A is characterized by the full TGA thermogram as substantially shown in FIG. 16.

Figure 17:
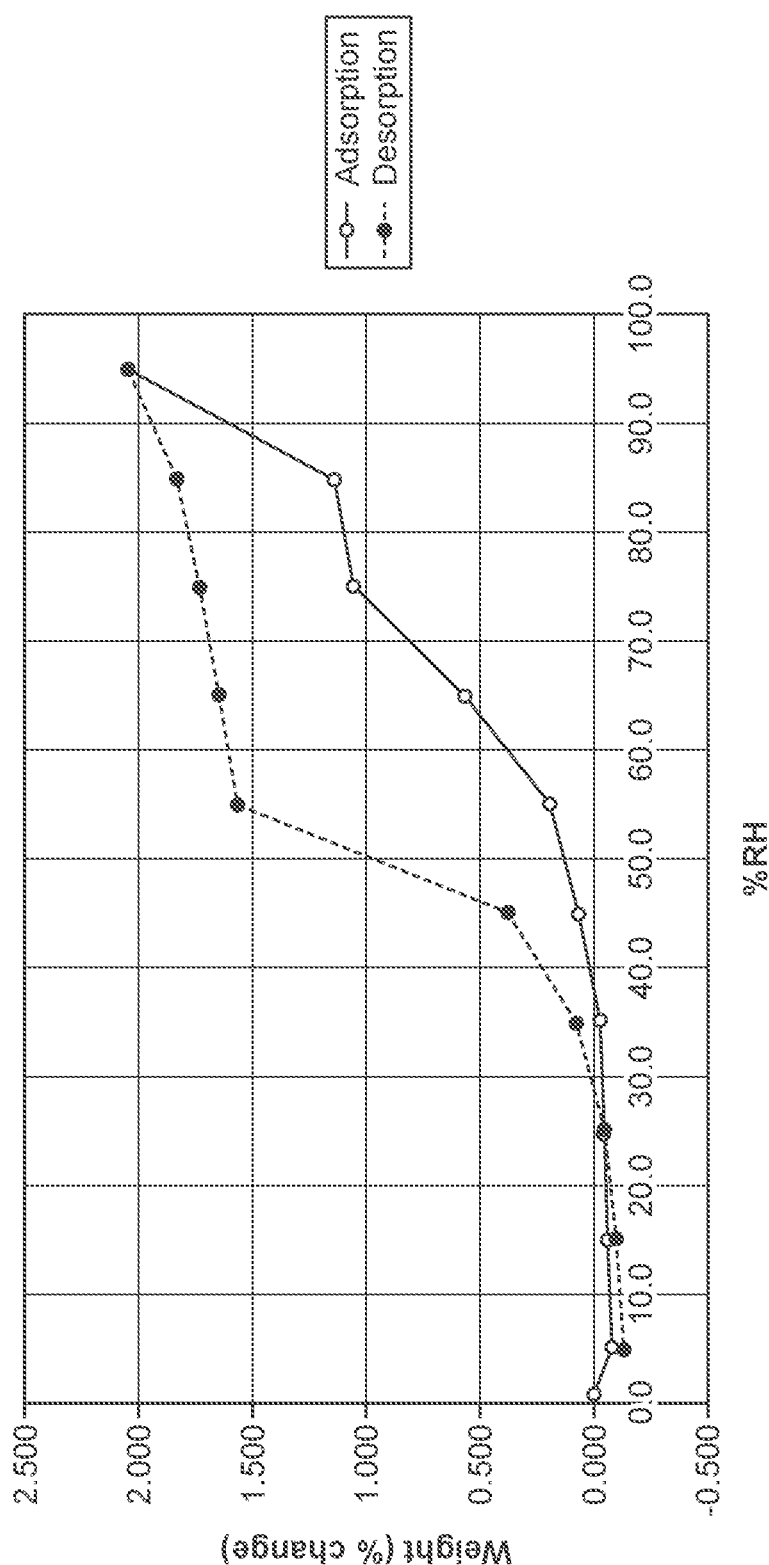
FIG. 17 is a dynamic vapor sorption (DVS) curve of Compound I diethylamine Material A.

In one embodiment, Compound I diethylamine Material A is characterized by a dynamic vapor sorption (DVS) analysis showing a weight loss of about 0.08% upon equilibration at about 5% RH; about a 2.12% weight gain from about 5 to about 95% RH; and about a 1.92% weight loss from about 95% to about 5% RH. In one embodiment, Compound I diethylamine Material A is characterized by the full DVS curve as substantially shown in FIG. 17.

In one embodiment, Compound I diethylamine Material A is characterized by a 1:1 ratio of Compound I to diethylamine.

The present disclosure also provides at least one process for making Compound I diethylamine Material A. In one embodiment, Compound I diethylamine Material A may be prepared by combining Compound I free acid Materials A+F in acetonitrile with diethylamine. In one embodiment, the process for making Compound I diethylamine Material A is as described in the Examples provided herein.

k. Compound I Ethanolamine Material A

The present disclosure provides, in one embodiment, a crystalline form of 6-(3-chloro-4-cyclopropoxyphenyl)pyrimidine-4-carboxylic acid (Compound I ethanolamine Material A) characterized by an X-ray powder diffractogram comprising the following peaks 12.86, 21.14, and 24.95°2θ±0.2°2θ, as determined on a diffractometer using Cu-Kα radiation (1.54 Å). In one embodiment, the diffractogram of Compound I ethanolamine Material A further comprises one or more peaks at: 10.27, 20.36, and 22.40°2θ±0.2°2θ.

In one embodiment, Compound I ethanolamine Material A is characterized by an X-ray powder diffractogram comprising at least two of the following peaks: 3.90, 10.27, 11.72, 12.86, 14.20, 15.69, 15.98, 17.28, 18.95, 20.36, 20.67, 21.14, 21.65, 22.40, 22.61, 23.82, 24.06, 24.95, 25.98, 26.46, 26.99, 27.24, 28.26, 29.03, 29.46, and 29.96°2θ±0.2°2θ. In one embodiment, Compound I ethanolamine Material A is characterized by an X-ray powder diffractogram comprising at least four of the following peaks: 3.90, 10.27, 11.72, 12.86, 14.20, 15.69, 15.98, 17.28, 18.95, 20.36, 20.67, 21.14, 21.65, 22.40, 22.61, 23.82, 24.06, 24.95, 25.98, 26.46, 26.99, 27.24, 28.26, 29.03, 29.46, and 29.96°2θ±0.2°2θ. In one embodiment, Compound I ethanolamine Material A is characterized by an X-ray powder diffractogram comprising at least six of the following peaks 3.90, 10.27, 11.72, 12.86, 14.20, 15.69, 15.98, 17.28, 18.95, 20.36, 20.67, 21.14, 21.65, 22.40, 22.61, 23.82, 24.06, 24.95, 25.98, 26.46, 26.99, 27.24, 28.26, 29.03, 29.46, and 29.96°2θ±0.2°2θ. In one embodiment, Compound I ethanolamine Material A is characterized by an X-ray powder diffractogram comprising at least eight of the following peaks: 33.90, 10.27, 11.72, 12.86, 14.20, 15.69, 15.98, 17.28, 18.95, 20.36, 20.67, 21.14, 21.65, 22.40, 22.61, 23.82, 24.06, 24.95, 25.98, 26.46, 26.99, 27.24, 28.26, 29.03, 29.46, and 29.96°2θ±0.2°2θ. In one embodiment Compound I ethanolamine Material A is characterized by an X-ray powder diffractogram comprising each of the following peaks: 3.90, 10.27, 11.72, 12.86, 14.20, 15.69, 15.98, 17.28, 18.95, 20.36, 20.67, 21.14, 21.65, 22.40, 22.61, 23.82, 24.06, 24.95, 25.98, 26.46, 26.99, 27.24, 28.26, 29.03, 29.46, and 29.96°2θ±0.2°2θ. In one embodiment, Compound I ethanolamine Material A is characterized by the full X-ray powder diffractogram as substantially shown in FIG. 7C.

In one embodiment, Compound I ethanolamine Material A is characterized by a differential scanning calorimetry (DSC) curve that comprises an endotherm with onset at about 201° C. In one embodiment, Compound I ethanolamine Material A is characterized by the full DSC curve as substantially shown in FIG. 18.

In one embodiment, Compound I ethanolamine Material A is characterized by a thermogravimetric analysis (TGA) thermogram showing a weight loss of about 0.39% up to about 170° C. In one embodiment, Compound I ethanolamine Material A is characterized by the full TGA thermogram as substantially shown in FIG. 19.

In one embodiment, Compound I ethanolamine Material A is characterized by a 1:1 ratio of Compound I to ethanolamine.

The present disclosure also provides at least one process for making Compound I ethanolamine Material A. In one embodiment, Compound I ethanolamine Material A may be prepared by combining Compound I free acid Materials A+F in methyl ethyl ketone with ethanolamine, and further treating the solution with ethyl acetate. In one embodiment, the process for making Compound I ethanolamine Material A is as described in the Examples provided herein.

l. Compound I Ethylenediamine Materials A+B

The present disclosure provides, in one embodiment, a crystalline form of 6-(3-chloro-4-cyclopropoxyphenyl)pyrimidine-4-carboxylic acid (Compound I ethylenediamine Materials A+B) characterized by an X-ray powder diffractogram comprising the following peaks 13.03, 17.85, and 25.40°2θ±0.2°2θ, as determined on a diffractometer using Cu-Kα radiation (1.54 Å). In one embodiment, the diffractogram of Compound I ethylenediamine Materials A+B further comprises one or more peaks at: 14.00, 21.27, and 23.22°2θ±0.2°2θ.

In one embodiment, Compound I ethylenediamine Materials A+B is characterized by an X-ray powder diffractogram comprising at least two of the following peaks: 13.03, 14.00, 14.71, 16.40, 17.85, 19.13, 19.96, 21.27, 23.22, 25.40, 26.28, 26.68, 27.34, 27.73, and 29.94°2θ±0.2°2θ. In one embodiment, Compound I ethylenediamine Materials A+B is characterized by an X-ray powder diffractogram comprising at least four of the following peaks: 13.03, 14.00, 14.71, 16.40, 17.85, 19.13, 19.96, 21.27, 23.22, 25.40, 26.28, 26.68, 27.34, 27.73, and 29.94°2θ±0.2°2θ. In one embodiment, Compound I ethylenediamine Materials A+B is characterized by an X-ray powder diffractogram comprising at least six of the following peaks: 13.03, 14.00, 14.71, 16.40, 17.85, 19.13, 19.96, 21.27, 23.22, 25.40, 26.28, 26.68, 27.34, 27.73, and 29.94°2θ±0.2°2θ. In one embodiment, Compound I ethylenediamine Materials A+B is characterized by an X-ray powder diffractogram comprising at least eight of the following peaks 13.03, 14.00, 14.71, 16.40, 17.85, 19.13, 19.96, 21.27, 23.22, 25.40, 26.28, 26.68, 27.34, 27.73, and 29.94°2θ±0.2°2θ. In one embodiment Compound I ethylenediamine Materials A+B is characterized by an X-ray powder diffractogram comprising each of the following peaks: 13.03, 14.00, 14.71, 16.40, 17.85, 19.13, 19.96, 21.27, 23.22, 25.40, 26.28, 26.68, 27.34, 27.73, and 29.94°2θ±0.2°2θ. In one embodiment, Compound I ethylenediamine Materials A+B is characterized by the full X-ray powder diffractogram as substantially shown in FIG. 7D.

In one embodiment, Compound I ethylenediamine Materials A+B comprises a mixture of crystalline phases.

In one embodiment, Compound I ethylenediamine Materials A+B is characterized by a differential scanning calorimetry (DSC) curve that comprises an endotherm with onset at about 239° C. In one embodiment, the DSC curve of Compound I ethylenediamine Materials A+B comprises an additional endotherm with a peak at about 187° C. In one embodiment, Compound I ethylenediamine Materials A+B is characterized by the full DSC curve as substantially shown in FIG. 20.

In one embodiment, Compound I ethylenediamine Materials A+B is characterized by a thermogravimetric analysis (TGA) thermogram showing a weight loss of about 0.7% up to about 200° C. In one embodiment, Compound I ethylenediamine Materials A+B is characterized by the full TGA thermogram as substantially shown in FIG. 21.

The present disclosure also provides at least one process for making Compound I ethylenediamine Materials A+B. In one embodiment, Compound I ethylenediamine Materials A+B may be prepared by combining Compound I free acid in acetonitrile with ethylenediamine. In one embodiment, Compound I ethylenediamine Materials A+B may be prepared by combining Compound I free acid Materials A+F in methyl ethyl ketone with ethylenediamine, and further treating the solution with ethyl acetate. In one embodiment, the process for making Compound I ethylenediamine Materials A+B is as described in the Examples provided herein.

m. Compound I Lysine Material A

The present disclosure provides, in one embodiment, a crystalline form of 6-(3-chloro-4-cyclopropoxyphenyl)pyrimidine-4-carboxylic acid (Compound I lysine Material A) characterized by an X-ray powder diffractogram comprising the following peaks 12.09, 23.82, and 26.00°2θ±0.2°2θ, as determined on a diffractometer using Cu-Kα radiation (1.54 Å). In one embodiment, the diffractogram of Compound I lysine Material A further comprises one or more peaks at: 14.83, 20.43, and 22.45°2θ±0.2°2θ.

In one embodiment, Compound I lysine Material A is characterized by an X-ray powder diffractogram comprising at least two of the following peaks: 10.20, 11.33, 11.52, 12.09, 13.00, 13.59, 14.83, 15.98, 17.33, 17.49, 17.93, 18.83, 19.26, 20.43, 20.84, 21.42, 22.25, 22.45, 22.78, 23.17, 23.48, 23.82, 24.21, 24.65, 25.09, 26.00, 26.57, 27.27, 27.55, 28.02, 29.09, 29.49, 29.76, and 29.90°2θ±0.2°2θ. In one embodiment, Compound I lysine Material A is characterized by an X-ray powder diffractogram comprising at least four of the following peaks: 10.20, 11.33, 11.52, 12.09, 13.00, 13.59, 14.83, 15.98, 17.33, 17.49, 17.93, 18.83, 19.26, 20.43, 20.84, 21.42, 22.25, 22.45, 22.78, 23.17, 23.48, 23.82, 24.21, 24.65, 25.09, 26.00, 26.57, 27.27, 27.55, 28.02, 29.09, 29.49, 29.76, and 29.90°2θ±0.2°2θ. In one embodiment, Compound I lysine Material A is characterized by an X-ray powder diffractogram comprising at least six of the following peaks: 10.20, 11.33, 11.52, 12.09, 13.00, 13.59, 14.83, 15.98, 17.33, 17.49, 17.93, 18.83, 19.26, 20.43, 20.84, 21.42, 22.25, 22.45, 22.78, 23.17, 23.48, 23.82, 24.21, 24.65, 25.09, 26.00, 26.57, 27.27, 27.55, 28.02, 29.09, 29.49, 29.76, and 29.90°2θ±0.2°2θ. In one embodiment, Compound I lysine Material A is characterized by an X-ray powder diffractogram comprising at least eight of the following peaks: 10.20, 11.33, 11.52, 12.09, 13.00, 13.59, 14.83, 15.98, 17.33, 17.49, 17.93, 18.83, 19.26, 20.43, 20.84, 21.42, 22.25, 22.45, 22.78, 23.17, 23.48, 23.82, 24.21, 24.65, 25.09, 26.00, 26.57, 27.27, 27.55, 28.02, 29.09, 29.49, 29.76, and 29.90°2θ±0.2°2θ. In one embodiment Compound I lysine Material A is characterized by an X-ray powder diffractogram comprising each of the following peaks: 10.20, 11.33, 11.52, 12.09, 13.00, 13.59, 14.83, 15.98, 17.33, 17.49, 17.93, 18.83, 19.26, 20.43, 20.84, 21.42, 22.25, 22.45, 22.78, 23.17, 23.48, 23.82, 24.21, 24.65, 25.09, 26.00, 26.57, 27.27, 27.55, 28.02, 29.09, 29.49, 29.76, and 29.90°2θ±0.2°2θ. In one embodiment, Compound I lysine Material A is characterized by the full X-ray powder diffractogram as substantially shown in FIG. 7E.

In one embodiment, Compound I lysine Material A is characterized by a differential scanning calorimetry (DSC) curve that comprises an endotherm with onset at about 189° C. In one embodiment, the DSC curve of Compound I lysine Material A comprises an additional endotherm with onset at about 143° C., and an exotherm with a peak at about 167° C. In one embodiment, Compound I lysine Material A is characterized by the full DSC curve as substantially shown in FIG. 22.

In one embodiment, Compound I lysine Material A is characterized by a thermogravimetric analysis (TGA) thermogram showing a weight loss of about 5.2% up to about 175° C. In one embodiment, Compound I lysine Material A is characterized by the full TGA thermogram as substantially shown in FIG. 23.

In one embodiment, Compound I lysine Material A is characterized by a 1:1 ratio of Compound I to lysine.

The present disclosure also provides at least one process for making Compound I lysine Material A. In one embodiment, Compound I lysine Material A may be prepared by combining Compound I free acid Materials A+F in acetonitrile with lysine in water. In one embodiment, the process for making Compound I lysine Material A is as described in the Examples provided herein.

n. Compound I Meglumine Material A

The present disclosure provides, in one embodiment, a crystalline form of 6-(3-chloro-4-cyclopropoxyphenyl)pyrimidine-4-carboxylic acid (Compound I meglumine Material A) characterized by an X-ray powder diffractogram comprising the following peaks 3.27, 9.14, and 18.38°2θ±0.2°2θ, as determined on a diffractometer using Cu-Kα radiation (1.54 Å). In one embodiment, the diffractogram of Compound I meglumine Material A further comprises one or more peaks at: 10.26, 22.23, and 25.25°2θ±0.2°2θ.

In one embodiment, Compound I meglumine Material A is characterized by an X-ray powder diffractogram comprising at least two of the following peaks: 2.64, 3.27, 9.14, 9.91, 10.26, 13.63, 14.65, 17.72, 18.09, 18.38, 18.90, 20.40, 22.23, 22.68, 23.21, 24.53, and 25.25°2θ±0.2°2θ. In one embodiment, Compound I meglumine Material A is characterized by an X-ray powder diffractogram comprising at least four of the following peaks: 2.64, 3.27, 9.14, 9.91, 10.26, 13.63, 14.65, 17.72, 18.09, 18.38, 18.90, 20.40, 22.23, 22.68, 23.21, 24.53, and 25.25°2θ±0.2°2θ. In one embodiment, Compound I meglumine Material A is characterized by an X-ray powder diffractogram comprising at least six of the following peaks: 2.64, 3.27, 9.14, 9.91, 10.26, 13.63, 14.65, 17.72, 18.09, 18.38, 18.90, 20.40, 22.23, 22.68, 23.21, 24.53, and 25.25°2θ±0.2°2θ. In one embodiment, Compound I meglumine Material A is characterized by an X-ray powder diffractogram comprising at least eight of the following peaks: 2.64, 3.27, 9.14, 9.91, 10.26, 13.63, 14.65, 17.72, 18.09, 18.38, 18.90, 20.40, 22.23, 22.68, 23.21, 24.53, and 25.25°2θ±0.2°2θ. In one embodiment Compound I meglumine Material A is characterized by an X-ray powder diffractogram comprising each of the following peaks: 2.64, 3.27, 9.14, 9.91, 10.26, 13.63, 14.65, 17.72, 18.09, 18.38, 18.90, 20.40, 22.23, 22.68, 23.21, 24.53, and 25.25°2θ±0.2°2θ. In one embodiment, Compound I meglumine Material A is characterized by the full X-ray powder diffractogram as substantially shown in FIG. 7F.

In one embodiment, Compound I meglumine Material A is characterized by a differential scanning calorimetry (DSC) curve that comprises an endotherm with a peak at about 116° C. In one embodiment, the DSC curve of Compound I meglumine Material A comprises an additional endotherm with a peak at about 73° C. In one embodiment, Compound I meglumine Material A is characterized by the full DSC curve as substantially shown in FIG. 24.

In one embodiment, Compound I meglumine Material A is characterized by a thermogravimetric analysis (TGA) thermogram showing a weight loss of about 2.3% up to about 190° C. In one embodiment, Compound I meglumine Material A is characterized by the full TGA thermogram as substantially shown in FIG. 25.

In one embodiment, Compound I meglumine Material A is characterized by a 1:1.75 ratio of Compound I to meglumine.

The present disclosure also provides at least one process for making Compound I meglumine Material A. In one embodiment, Compound I meglumine Material A may be prepared by combining Compound I free acid Materials A+F in acetonitrile with meglumine in acetonitrile. In one embodiment, the process for making Compound I meglumine Material A is as described in the Examples provided herein.

o. Compound I Potassium Material A

The present disclosure provides, in one embodiment, a crystalline form of 6-(3-chloro-4-cyclopropoxyphenyl)pyrimidine-4-carboxylic acid (Compound I potassium Material A) characterized by an X-ray powder diffractogram comprising the following peaks 3.22, 9.71, and 24.13°2θ±0.2°2θ, as determined on a diffractometer using Cu-Kα radiation (1.54 Å). In one embodiment, the diffractogram of Compound I potassium Material A further comprises one or more peaks at: 13.05, 18.18, and 26.66°2θ±0.2°2θ.

In one embodiment, Compound I potassium Material A is characterized by an X-ray powder diffractogram comprising at least two of the following peaks: 3.22, 8.70, 9.71, 10.20, 10.81, 12.49, 13.05, 14.98, 16.59, 17.46, 18.18, 20.51, 21.66, 24.13, 24.84, 25.56, 26.66, 27.42, and 30.15°2θ±0.2°2θ. In one embodiment, Compound I potassium Material A is characterized by an X-ray powder diffractogram comprising at least four of the following peaks: 3.22, 8.70, 9.71, 10.20, 10.81, 12.49, 13.05, 14.98, 16.59, 17.46, 18.18, 20.51, 21.66, 24.13, 24.84, 25.56, 26.66, 27.42, and 30.15°2θ±0.2°2θ. In one embodiment, Compound I potassium Material A is characterized by an X-ray powder diffractogram comprising at least six of the following peaks: 3.22, 8.70, 9.71, 10.20, 10.81, 12.49, 13.05, 14.98, 16.59, 17.46, 18.18, 20.51, 21.66, 24.13, 24.84, 25.56, 26.66, 27.42, and 30.15°2θ±0.2°2θ. In one embodiment, Compound I potassium Material A is characterized by an X-ray powder diffractogram comprising at least eight of the following peaks: 33.22, 8.70, 9.71, 10.20, 10.81, 12.49, 13.05, 14.98, 16.59, 17.46, 18.18, 20.51, 21.66, 24.13, 24.84, 25.56, 26.66, 27.42, and 30.15°2θ±0.2°2θ. In one embodiment Compound I potassium Material A is characterized by an X-ray powder diffractogram comprising each of the following peaks: 3.22, 8.70, 9.71, 10.20, 10.81, 12.49, 13.05, 14.98, 16.59, 17.46, 18.18, 20.51, 21.66, 24.13, 24.84, 25.56, 26.66, 27.42, and 30.15°2θ±0.2°2θ. In one embodiment, Compound I potassium Material A is characterized by the full X-ray powder diffractogram as substantially shown in FIG. 7G.

In one embodiment, Compound I potassium Material A is characterized by a differential scanning calorimetry (DSC) curve that comprises an endotherm with a peak at about 175° C. In one embodiment, the DSC curve of Compound I potassium Material A comprises an additional endotherm with a peak at about 137° C. In one embodiment, Compound I potassium Material A is characterized by the full DSC curve as substantially shown in FIG. 26.

In one embodiment, Compound I potassium Material A is characterized by a thermogravimetric analysis (TGA) thermogram showing a weight loss of about 2.3% up to about 175° C. In one embodiment, Compound I potassium Material A is characterized by the full TGA thermogram as substantially shown in FIG. 27.

The present disclosure also provides at least one process for making Compound I potassium Material A. In one embodiment, Compound I potassium Material A may be prepared by contacting Compound I free acid Materials A+F in acetonitrile with potassium rinsed with heptane. In one embodiment, the process for making Compound I potassium Material A is as described in the Examples provided herein.

p. Compound I Tromethamine Form A

The present disclosure provides, in one embodiment, a crystalline form of 6-(3-chloro-4-cyclopropoxyphenyl)pyrimidine-4-carboxylic acid (Compound I tromethamine Form A) characterized by an X-ray powder diffractogram comprising the following peaks 16.38, 19.49, and 23.98°2θ±0.2°2θ, as determined on a diffractometer using Cu-Kα radiation (1.54 Å). In one embodiment, the diffractogram of Compound I tromethamine Form A further comprises one or more peaks at: 18.78, 25.75, and 30.32°2θ±0.2°2θ.

In one embodiment, Compound I tromethamine Form A is characterized by an X-ray powder diffractogram comprising at least two of the following peaks: 3.95, 12.76, 12.91, 13.37, 15.06, 16.00, 16.38, 16.98, 17.79, 18.78, 19.49, 19.92, 20.49, 20.99, 21.20, 21.84, 22.10, 22.59, 22.84, 23.98, 24.82, 25.22, 25.49, 25.75, 26.01, 26.40, 26.96, 28.00, 28.43, 29.11, 29.34, 30.09, and 30.32°2θ±0.2°2θ. In one embodiment, Compound I tromethamine Form A is characterized by an X-ray powder diffractogram comprising at least four of the following peaks: 0.95, 12.76, 12.91, 13.37, 15.06, 16.00, 16.38, 16.98, 17.79, 18.78, 19.49, 19.92, 20.49, 20.99, 21.20, 21.84, 22.10, 22.59, 22.84, 23.98, 24.82, 25.22, 25.49, 25.75, 26.01, 26.40, 26.96, 28.00, 28.43, 29.11, 29.34, 30.09, and 30.32°2θ±0.2°2θ. In one embodiment, Compound I tromethamine Form A is characterized by an X-ray powder diffractogram comprising at least six of the following peaks: 0.95, 12.76, 12.91, 13.37, 15.06, 16.00, 16.38, 16.98, 17.79, 18.78, 19.49, 19.92, 20.49, 20.99, 21.20, 21.84, 22.10, 22.59, 22.84, 23.98, 24.82, 25.22, 25.49, 25.75, 26.01, 26.40, 26.96, 28.00, 28.43, 29.11, 29.34, 30.09, and 30.32°2θ±0.2°2θ. In one embodiment, Compound I tromethamine Form A is characterized by an X-ray powder diffractogram comprising at least eight of the following peaks: 3.95, 12.76, 12.91, 13.37, 15.06, 16.00, 16.38, 16.98, 17.79, 18.78, 19.49, 19.92, 20.49, 20.99, 21.20, 21.84, 22.10, 22.59, 22.84, 23.98, 24.82, 25.22, 25.49, 25.75, 26.01, 26.40, 26.96, 28.00, 28.43, 29.11, 29.34, 30.09, and 30.32°2θ±0.2°2θ. In one embodiment Compound I tromethamine Form A is characterized by an X-ray powder diffractogram comprising each of the following peaks: 0.95, 12.76, 12.91, 13.37, 15.06, 16.00, 16.38, 16.98, 17.79, 18.78, 19.49, 19.92, 20.49, 20.99, 21.20, 21.84, 22.10, 22.59, 22.84, 23.98, 24.82, 25.22, 25.49, 25.75, 26.01, 26.40, 26.96, 28.00, 28.43, 29.11, 29.34, 30.09, and 30.32°2θ±0.2°2θ. In one embodiment, Compound I tromethamine Form A is characterized by the full X-ray powder diffractogram as substantially shown in FIG. 28.

In one embodiment, Compound I tromethamine Form A is characterized by a differential scanning calorimetry (DSC) curve that comprises an endotherm onset at about 183° C. In one embodiment, the DSC curve of Compound I tromethamine Form A comprises an additional endotherm with onset at about 139° C. In one embodiment, Compound tromethamine Form A is characterized by the full DSC curve as substantially shown in FIG. 29.

In one embodiment, Compound I tromethamine Form A is characterized by a thermogravimetric analysis (TGA) thermogram showing a weight loss of about 0.6% up to about 180° C. In one embodiment, Compound I tromethamine Form A is characterized by the full TGA thermogram as substantially shown in FIG. 30.

Figure 31:
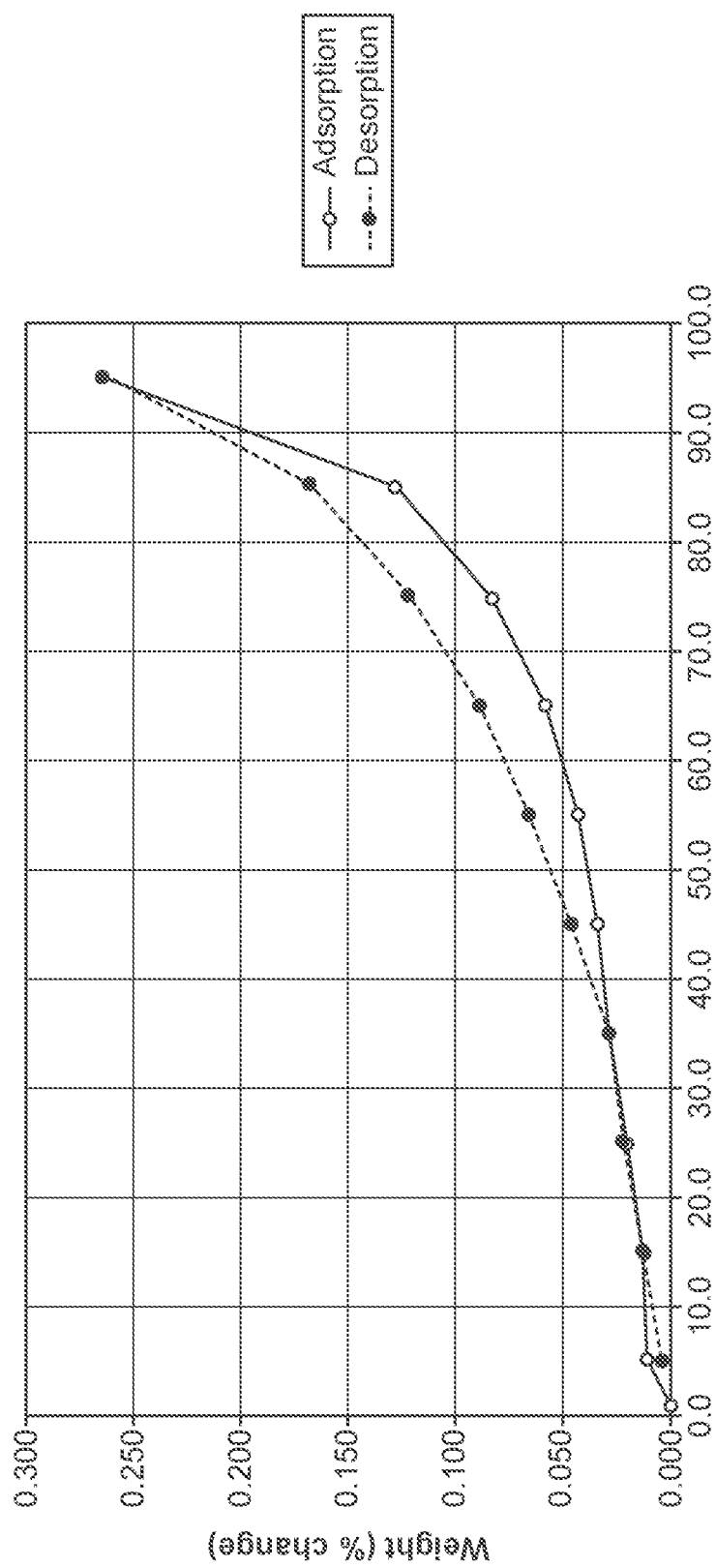
FIG. 31 is a dynamic vapor sorption (DVS) curve of Compound I tromethamine Form A.

In one embodiment, Compound I tromethamine Form A is characterized by a dynamic vapor sorption (DVS) analysis showing a weight loss of about 0.01% upon equilibration at about 5% RH; about a 0.25% weight gain from about 5 to about 95% RH; and about a 0.26% weight loss from about 95% to about 5% RH. In one embodiment, Compound I tromethamine Form A is characterized by the full DVS curve as substantially shown in FIG. 31.

In one embodiment, Compound I tromethamine Form A is characterized by a 1:1 ratio of Compound I to tromethamine.

The present disclosure also provides at least one process for making Compound I tromethamine Form A. In one embodiment, Compound I tromethamine Form A may be prepared by combining Compound I free acid Materials A+F in acetonitrile with tromethamine in acetonitrile/methanol. In one embodiment, the process for making Compound I tromethamine Form A is as described in the Examples provided herein.

q. Compound I Sodium Pattern A

The present disclosure provides, in one embodiment, a crystalline form of 6-(3-chloro-4-cyclopropoxyphenyl)pyrimidine-4-carboxylic acid (Compound I sodium Pattern A) characterized by an X-ray powder diffractogram comprising the following peaks 3.35, 10.11, and 13.31°2θ±0.2°2θ, as determined on a diffractometer using Cu-Kα radiation (1.54 Å). In one embodiment, the diffractogram of Compound I sodium Pattern A further comprises one or more peaks at: 11.79, 24.94, and 25.76°2θ±0.2°2θ.

In one embodiment, Compound I sodium Pattern A is characterized by an X-ray powder diffractogram comprising at least two of the following peaks: 3.35, 6.73, 10.11, 11.79, 12.11, 13.31, 13.87, 15.19, 24.94, and 25.76°2θ±0.2°2θ. In one embodiment, Compound I sodium Pattern A is characterized by an X-ray powder diffractogram comprising at least four of the following peaks: 3.35, 6.73, 10.11, 11.79, 12.11, 13.31, 13.87, 15.19, 24.94, and 25.76°2θ±0.2°2θ. In one embodiment, Compound I sodium Pattern A is characterized by an X-ray powder diffractogram comprising at least six of the following peaks: 3.35, 6.73, 10.11, 11.79, 12.11, 13.31, 13.87, 15.19, 24.94, and 25.76°2θ±0.2°2θ. In one embodiment, Compound I sodium Pattern A is characterized by an X-ray powder diffractogram comprising at least eight of the following peaks: 3.35, 6.73, 10.11, 11.79, 12.11, 13.31, 13.87, 15.19, 24.94, and 25.76°2θ±0.2°2θ. In one embodiment Compound I sodium Pattern A is characterized by an X-ray powder diffractogram comprising each of the following peaks: 33.35, 6.73, 10.11, 11.79, 12.11, 13.31, 13.87, 15.19, 24.94, and 25.76°2θ±0.2°2θ. In one embodiment, Compound I sodium Pattern A is characterized by the full X-ray powder diffractogram as substantially shown in FIG. 32.

In one embodiment, Compound I sodium Pattern A is characterized by a differential scanning calorimetry (DSC) curve that comprises an endotherm with onset at about 152° C. In one embodiment, Compound sodium Pattern A is characterized by the full DSC curve as substantially shown in FIG. 33.

In one embodiment, Compound I sodium Pattern A is characterized by a thermogravimetric analysis (TGA) thermogram showing a weight loss of about 2.2% up at about 40-170° C., followed by onset of decomposition at about 204.5° C. In one embodiment, Compound I sodium Pattern A is characterized by the full TGA thermogram as substantially shown in FIG. 34.

In one embodiment, Compound I sodium Pattern A is characterized by a dynamic vapor sorption (DVS) analysis showing weight gains of about 4.9% at 60% RH and about 21.2% at 90% RH. In one embodiment, Compound sodium Pattern A is characterized by the full DVS curve as substantially shown in FIG. 35.

In one embodiment Compound I sodium Pattern A is characterized as an anhydrate form.

In one embodiment, Compound I sodium Pattern A may convert to Compound I sodium Form B when triturated in acetone or isopropanol. In one embodiment, Compound I sodium Pattern A may convert to Compound I sodium Form E in solvent systems comprises high water activity.

The present disclosure also provides at least one process for making Compound I sodium Pattern A. In one embodiment, Compound I sodium Pattern A may be prepared by cooling a solution comprising Compound I sodium Form B and water from about 100° C. In one embodiment, the process for making Compound I sodium Pattern A is as described in the Examples provided herein.

r. Compound I Sodium Form B

The present disclosure provides, in one embodiment, a crystalline form of 6-(3-chloro-4-cyclopropoxyphenyl)pyrimidine-4-carboxylic acid (Compound I sodium Form B) characterized by an X-ray powder diffractogram comprising the following peaks 3.36, 8.90, and 18.30°2θ±0.2°2θ, as determined on a diffractometer using Cu-Kα radiation (1.54 Å). In one embodiment, the diffractogram of Compound I sodium Form B further comprises one or more peaks at: 10.15, 23.93, and 26.66°2θ±0.2°2θ.

Figure 36:
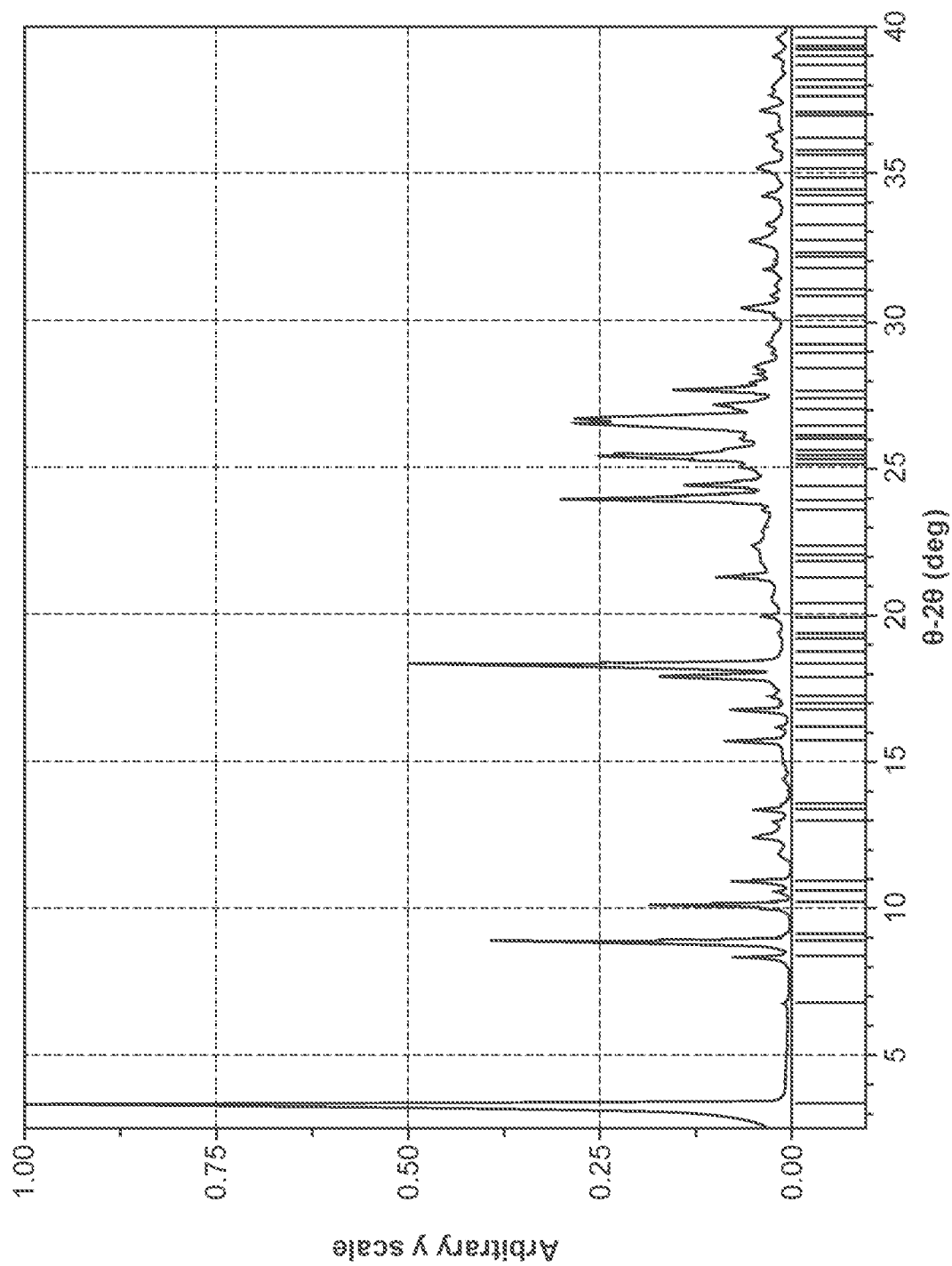
FIG. 36 is an X-ray powder diffractogram of Compound I sodium Form B.

In one embodiment, Compound I sodium Form B is characterized by the full X-ray powder diffractogram as substantially shown in FIG. 36.

In one embodiment, Compound I sodium Form B is characterized by a differential scanning calorimetry (DSC) curve that comprises an endotherm onset at about 184° C. In one embodiment, the DSC curve of Compound I sodium Form B comprises an additional endotherm with a peak at about 95° C. In one embodiment, Compound sodium Form B is characterized by the full DSC curve as substantially shown in FIG. 37.

In one embodiment, Compound I sodium Form B is characterized by a differential scanning calorimetry (DSC) curve that comprises an endotherm with a peak at about 199° C.

In one embodiment, Compound I sodium Form B is characterized by a thermogravimetric analysis (TGA) thermogram showing a weight loss of about 2.3% up to about 190° C. In one embodiment, Compound sodium Form B is characterized by the full TGA thermogram as substantially shown in FIG. 38.

Figure 39:
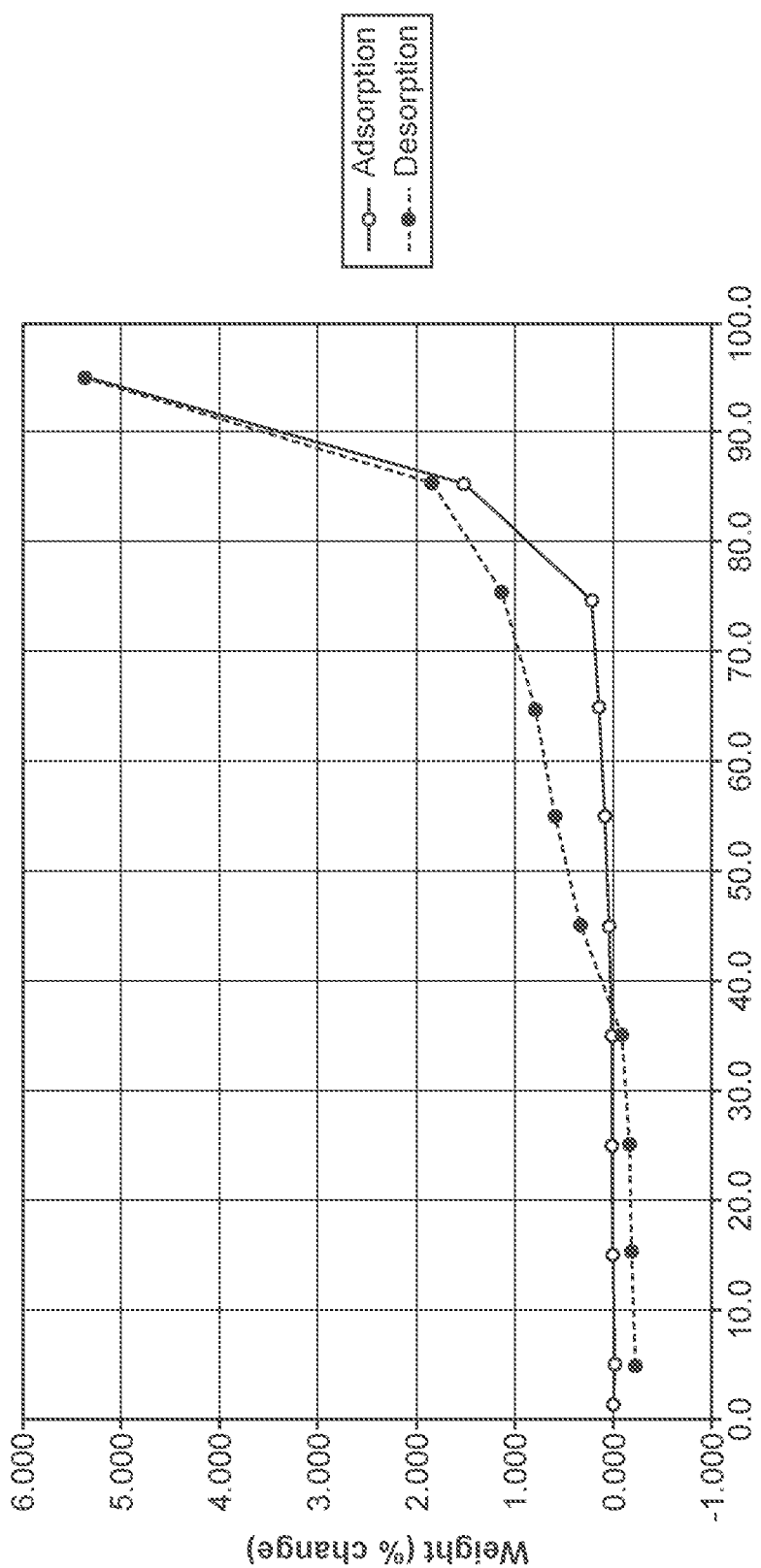
FIG. 39 is an dynamic vapor sorption (DVS) curve of Compound I sodium Form B.

In one embodiment, Compound I sodium Form B is characterized by a dynamic vapor sorption (DVS) analysis showing a weight loss of about 0.03% at about 5% RH; about a 5.39% weight gain from about 5 to about 95% RH; and about a 5.14% weight loss from about 95% to about 5% RH. In one embodiment, Compound sodium Form B is characterized by the full DVS curve as substantially shown in FIG. 39.

In one embodiment, Compound I sodium Form B is characterized as a anhydrate form.

The present disclosure also provides at least one process for making Compound I sodium Form B. In one embodiment, Compound I sodium Form B may be prepared by combining Compound I Material D in acetonitrile with sodium in water. In one embodiment, Compound I sodium Form B may be prepared by combining Compound I Material F with $Na_2CO_3$ in DMF. In one Compound I sodium Form B may be prepared by combining sodium Form A with various anti-solvents (e.g., dimethyl sulfoxide, water, methanol, ethanol, isopropyl alcohol, acetonitrile, ethyl acetate, acetone, methyl ethyl ketone, dichloromethane, toluene, or methyl tert-butyl ether). In one embodiment, the process for making Compound I sodium Form B is as described in the Examples provided herein.

s. Compound I Sodium Pattern C

The present disclosure provides, in one embodiment, a crystalline form of 6-(3-chloro-4-cyclopropoxyphenyl)pyrimidine-4-carboxylic acid (Compound I sodium Pattern C) characterized by an X-ray powder diffractogram comprising the following peaks 3.31, 11.89, and 25.75°2θ±0.2°2θ, as determined on a diffractometer using Cu-Kα radiation (1.54 Å). In one embodiment, the diffractogram of Compound I sodium Pattern C further comprises one or more peaks at: 13.45, 24.98, and 26.65°2θ±0.2°2θ.

In one embodiment, Compound I sodium Pattern C is characterized by an X-ray powder diffractogram comprising at least two of the following peaks: 3.01, 3.31, 3.94, 4.98, 6.08, 6.67, 7.94, 9.16, 10.04, 11.89, 12.24, 13.09, 13.45, 13.86, 14.89, 15.31, 16.21, 17.76, 20.98, 23.18, 24.56, 24.98, 25.75, 26.65, and 27.70°2θ±0.2°2θ. In one embodiment, Compound I sodium Pattern C is characterized by an X-ray powder diffractogram comprising at least four of the following peaks: 3.01, 3.31, 3.94, 4.98, 6.08, 6.67, 7.94, 9.16, 10.04, 11.89, 12.24, 13.09, 13.45, 13.86, 14.89, 15.31, 16.21, 17.76, 20.98, 23.18, 24.56, 24.98, 25.75, 26.65, and 27.70°2θ±0.2°2θ. In one embodiment, Compound I sodium Pattern C is characterized by an X-ray powder diffractogram comprising at least six of the following peaks: 3.01, 3.31, 3.94, 4.98, 6.08, 6.67, 7.94, 9.16, 10.04, 11.89, 12.24, 13.09, 13.45, 13.86, 14.89, 15.31, 16.21, 17.76, 20.98, 23.18, 24.56, 24.98, 25.75, 26.65, and 27.70°2θ±0.2°2θ. In one embodiment, Compound I sodium Pattern C is characterized by an X-ray powder diffractogram comprising at least eight of the following peaks: 3.01, 3.31, 3.94, 4.98, 6.08, 6.67, 7.94, 9.16, 10.04, 11.89, 12.24, 13.09, 13.45, 13.86, 14.89, 15.31, 16.21, 17.76, 20.98, 23.18, 24.56, 24.98, 25.75, 26.65, and 27.70°2θ±0.2°2θ. In one embodiment, Compound I sodium Pattern C is characterized by an X-ray powder diffractogram comprising each of the following peaks: 3.01, 3.31, 3.94, 4.98, 6.08, 6.67, 7.94, 9.16, 10.04, 11.89, 12.24, 13.09, 13.45, 13.86, 14.89, 15.31, 16.21, 17.76, 20.98, 23.18, 24.56, 24.98, 25.75, 26.65, and 27.70°2θ±0.2°2θ. In one embodiment, Compound I sodium Pattern C is characterized by the full X-ray powder diffractogram as substantially shown in FIG. 40C.

In one embodiment, Compound I sodium Pattern C is characterized by a differential scanning calorimetry (DSC) curve that comprises an endotherm with a peak at about 166° C. In one embodiment, the DSC curve of Compound I sodium Pattern C comprises additional endotherms with peaks at about 84° C. and 292° C. In one embodiment, Compound I sodium Pattern C is characterized by the full DSC curve as substantially shown in FIG. 41.

In one embodiment, Compound I sodium Pattern C is characterized by a thermogravimetric analysis (TGA) thermogram showing a weight loss of about 2.08% before about 200° C. In one embodiment, Compound sodium Pattern C is characterized by the full TGA thermogram as substantially shown in FIG. 42.

In one embodiment, Compound I sodium Pattern C is characterized by a dynamic vapor sorption (DVS) analysis showing weight gains of about 1.9% at 60% RH, and about 8.4% at 90% RH. In one embodiment, Compound sodium Pattern C is characterized by the full DVS curve as substantially shown in FIG. 43.

In one embodiment, Compound I sodium Pattern C is characterized as a methanol solvate.

In one embodiment, Compound I sodium Pattern C may convert to Compound I sodium Form B when triturated in acetone or isopropanol. In one embodiment, Compound I sodium Pattern C may convert to Compound I sodium Form E in solvent systems comprises high water activity.

The present disclosure also provides at least one process for making Compound I sodium Pattern C. In one embodiment, Compound I sodium Pattern C may be isolated from a solution comprising Compound I sodium Form B and methanol. In one embodiment, the process for making Compound I sodium Pattern C is as described in the Examples provided herein.

t. Compound I Sodium Pattern D

The present disclosure provides, in one embodiment, a crystalline form of 6-(3-chloro-4-cyclopropoxyphenyl)pyrimidine-4-carboxylic acid (Compound I sodium Pattern D) characterized by an X-ray powder diffractogram comprising the following peaks 3.05, 5.75, and 13.09°2θ±0.2°2θ, as determined on a diffractometer using Cu-Kα radiation (1.54 Å). In one embodiment, the diffractogram of Compound I sodium Pattern D further comprises one or more peaks at: 3.52, 5.55, and 14.00°2θ±0.2°2θ.

In one embodiment, Compound I sodium Pattern D is characterized by an X-ray powder diffractogram comprising at least two of the following peaks: 3.05, 3.52, 3.87, 4.05, 4.39, 4.69, 4.93, 5.11, 5.55, 5.75, 5.93, 6.48, 6.98, 7.72, 8.12, 8.67, 9.11, 9.65, 9.83, 10.32, 10.47, 10.95, 11.83, 12.01, 12.52, 12.68, 13.09, 14.00, 14.08, 14.59, 15.13, 15.99, 17.96, 19.82, 19.93, 20.89, 21.80, 24.43, 26.15, 27.53, 27.83, and 28.12°2θ±0.2°2θ. In one embodiment, Compound I sodium Pattern D is characterized by an X-ray powder diffractogram comprising at least four of the following peaks: 3.05, 3.52, 3.87, 4.05, 4.39, 4.69, 4.93, 5.11, 5.55, 5.75, 5.93, 6.48, 6.98, 7.72, 8.12, 8.67, 9.11, 9.65, 9.83, 10.32, 10.47, 10.95, 11.83, 12.01, 12.52, 12.68, 13.09, 14.00, 14.08, 14.59, 15.13, 15.99, 17.96, 19.82, 19.93, 20.89, 21.80, 24.43, 26.15, 27.53, 27.83, and 28.12°2θ±0.2°2θ. In one embodiment, Compound I sodium Pattern D is characterized by an X-ray powder diffractogram comprising at least six of the following peaks: 3.05, 3.52, 3.87, 4.05, 4.39, 4.69, 4.93, 5.11, 5.55, 5.75, 5.93, 6.48, 6.98, 7.72, 8.12, 8.67, 9.11, 9.65, 9.83, 10.32, 10.47, 10.95, 11.83, 12.01, 12.52, 12.68, 13.09, 14.00, 14.08, 14.59, 15.13, 15.99, 17.96, 19.82, 19.93, 20.89, 21.80, 24.43, 26.15, 27.53, 27.83, and 28.12°2θ±0.2°2θ. In one embodiment, Compound I sodium Pattern D is characterized by an X-ray powder diffractogram comprising at least eight of the following peaks: 3.05, 3.52, 3.87, 4.05, 4.39, 4.69, 4.93, 5.11, 5.55, 5.75, 5.93, 6.48, 6.98, 7.72, 8.12, 8.67, 9.11, 9.65, 9.83, 10.32, 10.47, 10.95, 11.83, 12.01, 12.52, 12.68, 13.09, 14.00, 14.08, 14.59, 15.13, 15.99, 17.96, 19.82, 19.93, 20.89, 21.80, 24.43, 26.15, 27.53, 27.83, and 28.12°2θ±0.2°2θ. In one embodiment Compound I sodium Pattern D is characterized by an X-ray powder diffractogram comprising each of the following peaks: 3.05, 3.52, 3.87, 4.05, 4.39, 4.69, 4.93, 5.11, 5.55, 5.75, 5.93, 6.48, 6.98, 7.72, 8.12, 8.67, 9.11, 9.65, 9.83, 10.32, 10.47, 10.95, 11.83, 12.01, 12.52, 12.68, 13.09, 14.00, 14.08, 14.59, 15.13, 15.99, 17.96, 19.82, 19.93, 20.89, 21.80, 24.43, 26.15, 27.53, 27.83, and 28.12°2θ±0.2°2θ. In one embodiment, Compound I sodium Pattern D is characterized by the full X-ray powder diffractogram as substantially shown in FIG. 44.

In one embodiment, Compound I sodium Pattern D is characterized by a differential scanning calorimetry (DSC) curve that comprises an endotherm with a peak at about 139° C. In one embodiment, the DSC curve of Compound I sodium Pattern D comprises additional endotherms with peaks at about 191° C. and 289° C., and an exotherm with a peak at about 164° C. In one embodiment, Compound I sodium Pattern D is characterized by the full DSC curve as substantially shown in FIG. 45.

In one embodiment, Compound I sodium Pattern D is characterized by a thermogravimetric analysis (TGA) thermogram showing a weight loss of about 2.5% before about 160° C. In one embodiment, Compound sodium Pattern D is characterized by the full TGA thermogram as substantially shown in FIG. 46.

In one embodiment, Compound I sodium Pattern D is characterized as either an ethanol inclusion complex.

In one embodiment, Compound I sodium Pattern D may convert to Compound I sodium Form B in acetone or isopropanol. In one embodiment, Compound I sodium Pattern D may convert to Compound I sodium Form E in solvent systems comprises high water activity.

The present disclosure also provides at least one process for making Compound I sodium Pattern C. In one embodiment, Compound I sodium Pattern D may be isolated from a solution comprising compound I sodium Pattern A and ethanol. In one embodiment, the process for making Compound I sodium Pattern D is as described in the Examples provided herein.

u. Compound I Sodium Form E

The present disclosure provides, in one embodiment, a crystalline form of 6-(3-chloro-4-cyclopropoxyphenyl)pyrimidine-4-carboxylic acid (Compound I sodium Form E) characterized by an X-ray powder diffractogram comprising the following peaks 3.25, 11.47, and 26.51°2θ±0.2°2θ, as determined on a diffractometer using Cu-Kα radiation (1.54 Å). In one embodiment, the diffractogram of Compound I sodium Form E further comprises one or more peaks at: 9.80, 12.58, and 24.52°2θ±0.2°2θ.

In one embodiment, Compound I sodium Form E is characterized by an X-ray powder diffractogram comprising at least two of the following peaks: 3.25, 6.51, 9.80, 11.47, 11.96, 12.58, 13.09, 13.46, 14.36, 15.54, 17.96, 19.69, 20.61, 21.98, 22.64, 23.12, 24.09, 24.52, 26.03, 26.51, 27.37, 27.93, 28.34, and 29.73°2θ±0.2°2θ. In one embodiment, Compound I sodium Form E is characterized by an X-ray powder diffractogram comprising at least four of the following peaks: 3.25, 6.51, 9.80, 11.47, 11.96, 12.58, 13.09, 13.46, 14.36, 15.54, 17.96, 19.69, 20.61, 21.98, 22.64, 23.12, 24.09, 24.52, 26.03, 26.51, 27.37, 27.93, 28.34, and 29.73°2θ±0.2°2θ. In one embodiment, Compound I sodium Form E is characterized by an X-ray powder diffractogram comprising at least six of the following peaks: 3.25, 6.51, 9.80, 11.47, 11.96, 12.58, 13.09, 13.46, 14.36, 15.54, 17.96, 19.69, 20.61, 21.98, 22.64, 23.12, 24.09, 24.52, 26.03, 26.51, 27.37, 27.93, 28.34, and 29.73°2θ±0.2°2θ. In one embodiment, Compound I sodium Form E is characterized by an X-ray powder diffractogram comprising at least eight of the following peaks: 3.25, 6.51, 9.80, 11.47, 11.96, 12.58, 13.09, 13.46, 14.36, 15.54, 17.96, 19.69, 20.61, 21.98, 22.64, 23.12, 24.09, 24.52, 26.03, 26.51, 27.37, 27.93, 28.34, and 29.73°2θ±0.2°2θ. In one embodiment Compound I sodium Form E is characterized by an X-ray powder diffractogram comprising each of the following peaks: 3.25, 6.51, 9.80, 11.47, 11.96, 12.58, 13.09, 13.46, 14.36, 15.54, 17.96, 19.69, 20.61, 21.98, 22.64, 23.12, 24.09, 24.52, 26.03, 26.51, 27.37, 27.93, 28.34, and 29.73°2θ±0.2°2θ. In one embodiment, Compound I sodium Form E is characterized by the full X-ray powder diffractogram as substantially shown in FIG. 47.

In one embodiment, Compound I sodium Form E is characterized by a differential scanning calorimetry (DSC) curve that comprises an endotherm with a peak at about 132° C. In one embodiment, the DSC curve of Compound I sodium Form E comprises additional endotherms with peaks at about 77° C. and 297° C., and an exotherm with a peak at about 164° C. In one embodiment, Compound I sodium Form E is characterized by the full DSC curve as substantially shown in FIG. 48.

In one embodiment, Compound I sodium Form E is characterized by a thermogravimetric analysis (TGA) thermogram showing a weight loss of about 2.5% before about 80° C., and about 1.2% before about 130° C. In one embodiment, Compound sodium Form E is characterized by the full TGA thermogram as substantially shown in FIG. 49.

In one embodiment, Compound I sodium Form E is characterized as a hydrate.

In one embodiment, Compound I sodium Form E may convert to Compound I sodium Pattern A upon dehydration thereof under certain conditions, as set forth, e.g., in the Examples. In one embodiment, Compound I sodium Form E may convert to Compound I sodium Pattern A upon air drying or exposure to vacuum at ambient temperatures.

The present disclosure also provides at least one process for making Compound I sodium Form E. In one embodiment, Compound I sodium Form E may be isolated from a solution comprising Compound I sodium Form B, sodium, and various solvents or solvent systems (e.g., water, acetone/water, ethanol/water, or isopropyl alcohol/water). In one embodiment, the process for making Compound I sodium Form E is as described in the Examples provided herein.

v. Compound I Sodium Pattern F

The present disclosure provides, in one embodiment, a crystalline form of 6-(3-chloro-4-cyclopropoxyphenyl)pyrimidine-4-carboxylic acid (Compound I sodium Pattern F) characterized by an X-ray powder diffractogram comprising the following peaks 12.67, 25.02, and 28.10°2θ±0.2°2θ, as determined on a diffractometer using Cu-Kα radiation (1.54 Å). In one embodiment, the diffractogram of Compound I sodium Pattern F further comprises one or more peaks at: 3.01, 9.04, and 17.80°2θ±0.2°2θ.

In one embodiment, Compound I sodium Pattern F is characterized by an X-ray powder diffractogram comprising at least two of the following peaks: 3.01, 9.04, 12.08, 12.38, 12.67, 12.80, 13.94, 15.14, 15.52, 17.80, 18.68, 21.23, 21.55, 22.47, 22.89, 23.08, 24.39, 25.02, 25.85, 26.16, 26.86, 28.10, and 28.65°2θ±0.2°2θ. In one embodiment, Compound I sodium Pattern F is characterized by an X-ray powder diffractogram comprising at least four of the following peaks: 3.01, 9.04, 12.08, 12.38, 12.67, 12.80, 13.94, 15.14, 15.52, 17.80, 18.68, 21.23, 21.55, 22.47, 22.89, 23.08, 24.39, 25.02, 25.85, 26.16, 26.86, 28.10, and 28.65°2θ±0.2°2θ. In one embodiment, Compound I sodium Pattern F is characterized by an X-ray powder diffractogram comprising at least six of the following peaks: 3.01, 9.04, 12.08, 12.38, 12.67, 12.80, 13.94, 15.14, 15.52, 17.80, 18.68, 21.23, 21.55, 22.47, 22.89, 23.08, 24.39, 25.02, 25.85, 26.16, 26.86, 28.10, and 28.65°2θ±0.2°2θ. In one embodiment, Compound I sodium Pattern F is characterized by an X-ray powder diffractogram comprising at least eight of the following peaks: 3.01, 9.04, 12.08, 12.38, 12.67, 12.80, 13.94, 15.14, 15.52, 17.80, 18.68, 21.23, 21.55, 22.47, 22.89, 23.08, 24.39, 25.02, 25.85, 26.16, 26.86, 28.10, and 28.65°2θ±0.2°2θ. In one embodiment Compound I sodium Pattern F is characterized by an X-ray powder diffractogram comprising each of the following peaks: 3.01, 9.04, 12.08, 12.38, 12.67, 12.80, 13.94, 15.14, 15.52, 17.80, 18.68, 21.23, 21.55, 22.47, 22.89, 23.08, 24.39, 25.02, 25.85, 26.16, 26.86, 28.10, and 28.65°2θ±0.2°2θ. In one embodiment, Compound I sodium Pattern F is characterized by the full X-ray powder diffractogram as substantially shown in FIG. 50.

In one embodiment, Compound I sodium Pattern F is characterized as an ethanol solvate.

In one embodiment, Compound I sodium Pattern F may be disordered, and thus not stable, upon exposure to vacuum at ambient conditions.

The present disclosure also provides at least one process for making Compound I sodium Pattern F. In one embodiment, Compound I sodium Pattern F may be isolated from a solution comprising Compound I sodium Form B, sodium, and a water/ethanol solvent system. In one embodiment, the process for making Compound I sodium Pattern F is as described in the Examples provided herein.

w. Compound I Sodium Mesophase Patterns A-C

The present disclosure provides, in one embodiment, a form of 6-(3-chloro-4-cyclopropoxyphenyl)pyrimidine-4-carboxylic acid (Compound I sodium mesophase Pattern A) characterized by an X-ray powder diffractogram as substantially shown in FIG. 51A. The present disclosure also provides, in one embodiment, a form of 6-(3-chloro-4-cyclopropoxyphenyl)pyrimidine-4-carboxylic acid (Compound I sodium mesophase Pattern B) characterized by an X-ray powder diffractogram as substantially shown in FIG. 51B. The present disclosure further provides, in one embodiment, a form of 6-(3-chloro-4-cyclopropoxyphenyl)pyrimidine-4-carboxylic acid (Compound I sodium mesophase Pattern C) characterized by an X-ray powder diffractogram as substantially shown in FIG. 51C.

The present disclosure also provides at least one process for making Compound I sodium mesophase Patterns A-C. In one embodiment, Compound I sodium mesophase A may be prepared via evaporation from a solution comprising Compound I sodium Form B and hexafluoroisopropyl alcohol. In one embodiment, Compound I sodium mesophase B may be isolated from a slurry comprising Compound I sodium Form B and hexafluoroisopropyl alcohol. In one embodiment, Compound I sodium mesophase A may isolated from a slurry comprising Compound I sodium Form B and TFE. In one embodiment, the process for making Compound I sodium mesophase Patterns A-C is as described in the Examples provided herein.

x. Compound I Sodium Amorphous

Figure 52:
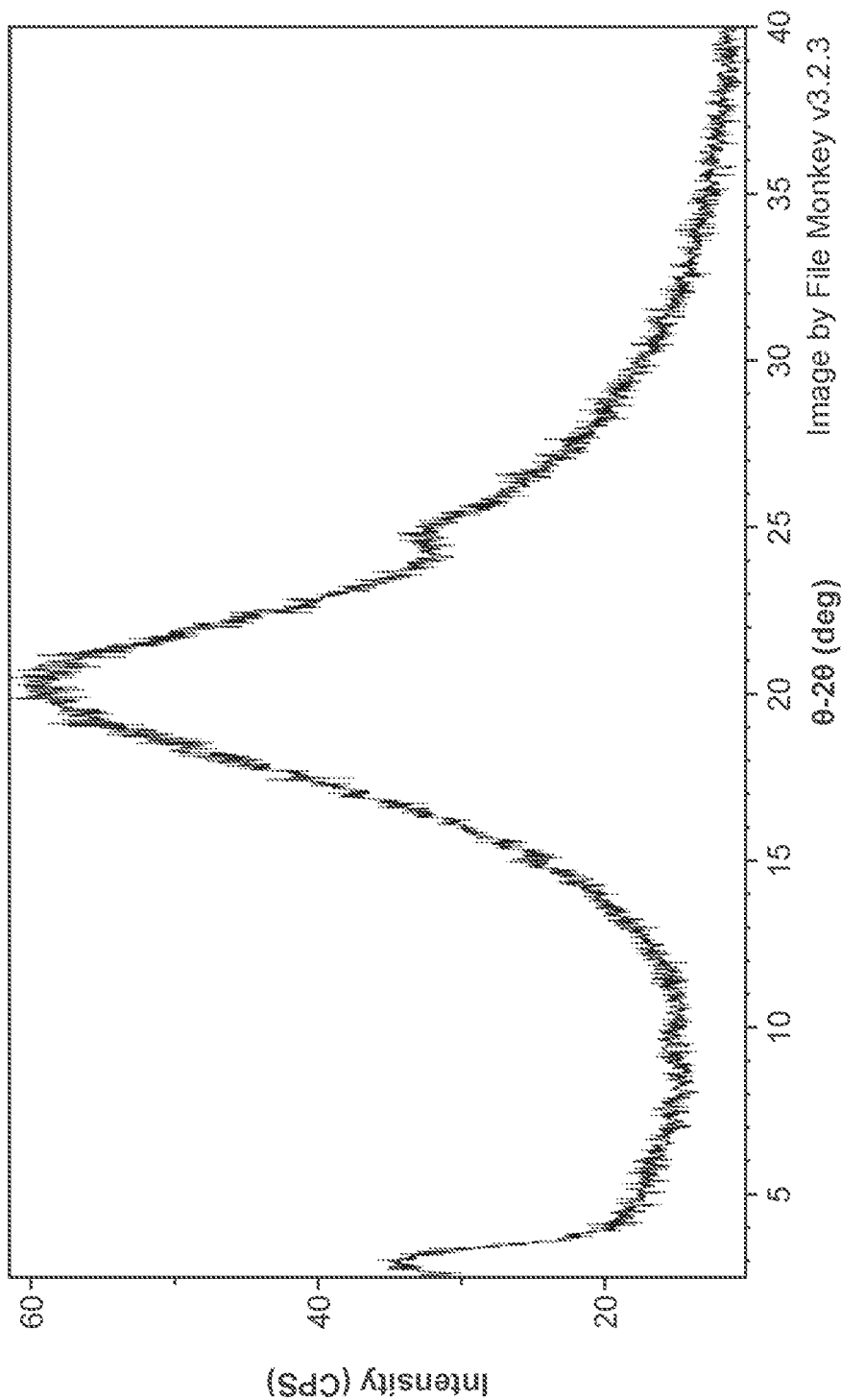
FIG. 52 is an X-ray powder diffractogram of Compound I sodium amorphous.

The present disclosure provides, in one embodiment, a form of 6-(3-chloro-4-cyclopropoxyphenyl)pyrimidine-4-carboxylic acid (Compound I sodium amorphous) characterized by an X-ray powder diffractogram as substantially shown in FIG. 52.

In one embodiment, Compound I sodium amorphous may convert to Compound I sodium Form B when heated to about 150° C.

The present disclosure also provides at least one process for making Compound I sodium amorphous. In one embodiment, Compound I sodium amorphous may be prepared via lyophilizing a solution comprising dimethyl sulfoxide and water. In one embodiment, the process for making Compound I amorphous is as described in the Examples provided herein.

3. Pharmaceutical Compositions and Modes of Administration

The forms of Compound I as described herein may be administered in a pharmaceutical composition. Thus, the present disclosure provides pharmaceutical compositions comprising one or more of the forms of Compound I or of a salt/co-crystal thereof as described herein and one or more pharmaceutically acceptable vehicles such as carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G.S. Banker & C.T. Rhodes, Eds.). The pharmaceutical compositions may be administered alone or in combination with other therapeutic agents.

Some embodiments are directed to pharmaceutical compositions comprising a form of Compound I as described herein. In one embodiment a pharmaceutical composition comprises Compound I, wherein at least 75% of Compound I is in a form as described herein. In one embodiment, a pharmaceutical composition comprises Compound I, wherein at least 75% of Compound I is Compound I Material A. In one embodiment, a pharmaceutical composition comprises Compound I, wherein at least 75% of Compound I is Compound I Material B. In one embodiment, a pharmaceutical composition comprises Compound I, wherein at least 75% of Compound I is Compound I Material C. In one embodiment, a pharmaceutical composition comprises Compound I, wherein at least 75% of Compound I is Compound I Material D. In one embodiment, a pharmaceutical composition comprises Compound I, wherein at least 75% of Compound I is Compound I Material E. In one embodiment, a pharmaceutical composition comprises Compound I, wherein at least 75% of Compound I is Compound I Material F.

In one embodiment a pharmaceutical composition comprises Compound I, wherein at least 80% of Compound I is in a form as described herein. In one embodiment, a pharmaceutical composition comprises Compound I, wherein at least 80% of Compound I is Compound I Material A. In one embodiment, a pharmaceutical composition comprises Compound I, wherein at least 80% of Compound I is Compound I Material B. In one embodiment, a pharmaceutical composition comprises Compound I, wherein at least 80% of Compound I is Compound I Material C. In one embodiment, a pharmaceutical composition comprises Compound I, wherein at least 80% of Compound I is Compound I Material D. In one embodiment, a pharmaceutical composition comprises Compound I, wherein at least 80% of Compound I is Compound I Material E. In one embodiment, a pharmaceutical composition comprises Compound I, wherein at least 80% of Compound I is Compound I Material F.

In one embodiment a pharmaceutical composition comprises Compound I, wherein at least 85% of Compound I is in a form as described herein. In one embodiment, a pharmaceutical composition comprises Compound I, wherein at least 85% of Compound I is Compound I Material A. In one embodiment, a pharmaceutical composition comprises Compound I, wherein at least 85% of Compound I is Compound I Material B. In one embodiment, a pharmaceutical composition comprises Compound I, wherein at least 85% of Compound I is Compound I Material C. In one embodiment, a pharmaceutical composition comprises Compound I, wherein at least 85% of Compound I is Compound I Material D. In one embodiment, a pharmaceutical composition comprises Compound I, wherein at least 85% of Compound I is Compound I Material E. In one embodiment, a pharmaceutical composition comprises Compound I, wherein at least 85% of Compound I is Compound I Material F.

In one embodiment a pharmaceutical composition comprises Compound I, wherein at least 90% of Compound I is in a form as described herein. In one embodiment, a pharmaceutical composition comprises Compound I, wherein at least 90% of Compound I is Compound I Material A. In one embodiment, a pharmaceutical composition comprises Compound I, wherein at least 90% of Compound I is Compound I Material B. In one embodiment, a pharmaceutical composition comprises Compound I, wherein at least 90% of Compound I is Compound I Material C. In one embodiment, a pharmaceutical composition comprises Compound I, wherein at least 90% of Compound I is Compound I Material D. In one embodiment, a pharmaceutical composition comprises Compound I, wherein at least 90% of Compound I is Compound I Material E. In one embodiment, a pharmaceutical composition comprises Compound I, wherein at least 90% of Compound I is Compound I Material F.

In one embodiment a pharmaceutical composition comprises Compound I, wherein at least 95% of Compound I is in a form as described herein. In one embodiment, a pharmaceutical composition comprises Compound I, wherein at least 95% of Compound I is Compound I Material A. In one embodiment, a pharmaceutical composition comprises Compound I, wherein at least 95% of Compound I is Compound I Material B. In one embodiment, a pharmaceutical composition comprises Compound I, wherein at least 95% of Compound I is Compound I Material C. In one embodiment, a pharmaceutical composition comprises Compound I, wherein at least 95% of Compound I is Compound I Material D. In one embodiment, a pharmaceutical composition comprises Compound I, wherein at least 95% of Compound I is Compound I Material E. In one embodiment, a pharmaceutical composition comprises Compound I, wherein at least 95% of Compound I is Compound I Material F.

In one embodiment, a pharmaceutical composition comprises Compound I, wherein at least 97% of Compound I is in a form as described herein. In one embodiment, a pharmaceutical composition comprises Compound I, wherein at least 97% of Compound I is Compound I Material A. In one embodiment, a pharmaceutical composition comprises Compound I, wherein at least 97% of Compound I is Compound I Material B. In one embodiment, a pharmaceutical composition comprises Compound I, wherein at least 97% of Compound I is Compound I Material C. In one embodiment, a pharmaceutical composition comprises Compound I, wherein at least 97% of Compound I is Compound I Material D. In one embodiment, a pharmaceutical composition comprises Compound I, wherein at least 97% of Compound I is Compound I Material E. In one embodiment, a pharmaceutical composition comprises Compound I, wherein at least 97% of Compound I is Compound I Material F.

In one embodiment, a pharmaceutical composition comprises Compound I, wherein at least 99% of Compound I is in a form as described herein. In one embodiment, a pharmaceutical composition comprises Compound I, wherein at least 99% of Compound I is Compound I Material A. In one embodiment, a pharmaceutical composition comprises Compound I, wherein at least 99% of Compound I is Compound I Material B. In one embodiment, a pharmaceutical composition comprises Compound I, wherein at least 99% of Compound I is Compound I Material C. In one embodiment, a pharmaceutical composition comprises Compound I, wherein at least 99% of Compound I is Compound I Material D. In one embodiment, a pharmaceutical composition comprises Compound I, wherein at least 99% of Compound I is Compound I Material E. In one embodiment, a pharmaceutical composition comprises Compound I, wherein at least 99% of Compound I is Compound I Material F.

Some embodiments are directed to a pharmaceutical composition comprising a sodium salt of Compound I in a form as described herein. In one embodiment, a pharmaceutical composition comprises Compound I sodium, wherein at least 75% of Compound I sodium is compound I sodium Pattern A. In one embodiment, a pharmaceutical composition comprises Compound I sodium, wherein at least 80% of Compound I sodium is Compound I sodium Pattern A. In one embodiment, a pharmaceutical composition comprises Compound I sodium, wherein at least 85% of Compound I sodium is Compound I sodium Pattern A. In one embodiment, a pharmaceutical composition comprised Compound I sodium, wherein at least 90% of Compound I sodium is Compound I sodium Pattern A. In one embodiment, a pharmaceutical composition comprises Compound I sodium, wherein at least 95% of Compound I sodium is Compound I sodium Pattern A. In one embodiment, a pharmaceutical composition comprised Compound I sodium, wherein at least 97% of Compound I sodium is Compound I sodium Pattern A. In one embodiment, a pharmaceutical composition comprises Compound I sodium, wherein at least 99% of Compound I sodium is Compound I sodium Pattern A.

In one embodiment, a pharmaceutical composition comprises Compound I sodium, wherein at least 75% of Compound I sodium is compound I sodium Form B. In one embodiment, a pharmaceutical composition comprises Compound I sodium, wherein at least 80% of Compound I sodium is Compound I sodium Form B. In one embodiment, a pharmaceutical composition comprises Compound I sodium, wherein at least 85% of Compound I sodium is Compound I sodium Form B. In one embodiment, a pharmaceutical composition comprised Compound I sodium, wherein at least 90% of Compound I sodium is Compound I sodium Form B. In one embodiment, a pharmaceutical composition comprises Compound I sodium, wherein at least 95% of Compound I sodium is Compound I sodium Form B. In one embodiment, a pharmaceutical composition comprised Compound I sodium, wherein at least 97% of Compound I sodium is Compound I sodium Form B. In one embodiment, a pharmaceutical composition comprises Compound I sodium, wherein at least 99% of Compound I sodium is Compound I sodium Form B.

In one embodiment, a pharmaceutical composition comprises Compound I sodium, wherein at least 75% of Compound I sodium is compound I sodium Pattern C. In one embodiment, a pharmaceutical composition comprises Compound I sodium, wherein at least 80% of Compound I sodium is Compound I sodium Pattern C. In one embodiment, a pharmaceutical composition comprises Compound I sodium, wherein at least 85% of Compound I sodium is Compound I sodium Pattern C. In one embodiment, a pharmaceutical composition comprised Compound I sodium, wherein at least 90% of Compound I sodium is Compound I sodium Pattern C. In one embodiment, a pharmaceutical composition comprises Compound I sodium, wherein at least 95% of Compound I sodium is Compound I sodium Pattern C. In one embodiment, a pharmaceutical composition comprised Compound I sodium, wherein at least 97% of Compound I sodium is Compound I sodium Pattern C. In one embodiment, a pharmaceutical composition comprises Compound I sodium, wherein at least 99% of Compound I sodium is Compound I sodium Pattern C.

In one embodiment, a pharmaceutical composition comprises Compound I sodium, wherein at least 75% of Compound I sodium is compound I sodium Form E. In one embodiment, a pharmaceutical composition comprises Compound I sodium, wherein at least 80% of Compound I sodium is Compound I sodium Form E. In one embodiment, a pharmaceutical composition comprises Compound I sodium, wherein at least 85% of Compound I sodium is Compound I sodium Form E. In one embodiment, a pharmaceutical composition comprised Compound I sodium, wherein at least 90% of Compound I sodium is Compound I sodium Form E. In one embodiment, a pharmaceutical composition comprises Compound I sodium, wherein at least 95% of Compound I sodium is Compound I sodium Form E. In one embodiment, a pharmaceutical composition comprised Compound I sodium, wherein at least 97% of Compound I sodium is Compound I sodium Form E. In one embodiment, a pharmaceutical composition comprises Compound I sodium, wherein at least 99% of Compound I sodium is Compound I sodium Form E.

Some embodiments are directed to a pharmaceutical composition comprising a sodium salt of Compound I in a mesophase form as described herein. In one embodiment, a pharmaceutical composition comprised Compound I sodium, wherein at least 75% of Compound I sodium is in a mesophase form as described herein. In one embodiment, a pharmaceutical composition comprised Compound I sodium, wherein at least 80% of Compound I sodium is in a mesophase form as described herein. In one embodiment, a pharmaceutical composition comprised Compound I sodium, wherein at least 85% of Compound I sodium is in a mesophase form as described herein. In one embodiment, a pharmaceutical composition comprised Compound I sodium, wherein at least 90% of Compound I sodium is in a mesophase form as described herein. In one embodiment, a pharmaceutical composition comprised Compound I sodium, wherein at least 95% of Compound I sodium is in a mesophase form as described herein. In one embodiment, a pharmaceutical composition comprised Compound I sodium, wherein at least 97% of Compound I sodium is in a mesophase form as described herein. In one embodiment, a pharmaceutical composition comprised Compound I sodium, wherein at least 99% of Compound I sodium is in a mesophase form as described herein.

Some embodiments are directed to a pharmaceutical composition comprising a sodium salt of Compound I in an amorphous form as described herein. In one embodiment, a pharmaceutical composition comprised Compound I sodium, wherein at least 75% of Compound I sodium is in an amorphous form as described herein. In one embodiment, a pharmaceutical composition comprised Compound I sodium, wherein at least 80% of Compound I sodium is in a an amorphous form as described herein. In one embodiment, a pharmaceutical composition comprised Compound I sodium, wherein at least 85% of Compound I sodium is in an amorphous form as described herein. In one embodiment, a pharmaceutical composition comprised Compound I sodium, wherein at least 90% of Compound I sodium is in an amorphous form as described herein. In one embodiment, a pharmaceutical composition comprised Compound I sodium, wherein at least 95% of Compound I sodium is in an amorphous form as described herein. In one embodiment, a pharmaceutical composition comprised Compound I sodium, wherein at least 97% of Compound I sodium is an amorphous form as described herein. In one embodiment, a pharmaceutical composition comprised Compound I sodium, wherein at least 99% of Compound I sodium is in an amorphous form as described herein.

Some embodiments are directed to pharmaceutical compositions comprising one or more pharmaceutically acceptable carriers and a therapeutically effective amount of a compound selected from: Compound I Material A, Compound I Material B, Compound I Material C, Compound I Material D, Compound I Material E, Compound I Form F, Compound I arginine Material A, Compound I benzathine Form A, Compound I diethylamine Material A, Compound I ethanolamine Material A, Compound I ethylenediamine Materials A+B, Compound I lysine Material A, Compound I meglumine Material A, Compound I potassium Material A, Compound I tromethamine Form A, Compound I sodium Pattern A, Compound I sodium Form B, Compound I sodium Pattern C, Compound I sodium Form E, Compound I sodium mesophase, and Compound I sodium amorphous.

Some embodiments are directed to pharmaceutical compositions comprising one or more pharmaceutically acceptable carriers and a therapeutically effective amount of Compound I sodium Form B.

Pharmaceutical compositions described herein may be presented in single or multiple doses. Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21st edition, Lippincott, Williams and Wilkins, Philadelphia, Pa., 2005 (hereby incorporated by reference herein).

The compounds as described herein (e.g., the solid forms of Compound I or salts/co-crystals thereof) can be administered by different routes including intravenous, intraperitoneal, subcutaneous, intramuscular, oral, transmucosal, rectal, transdermal, or inhalant. In some embodiments, the compounds as described herein can be administered by oral administration. For oral administration, for example, the compounds can be formulated into conventional oral dosage forms such as capsules, tablets, and liquid preparations such as syrups, elixirs, and concentrated drops.

For inhalants, compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the disclosure may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the compounds described herein with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds described herein may be formulated in sterile liquid solutions, such as in physiologically compatible buffers or solutions, such as saline solution, Hank's solution, or Ringer's solution. In addition, the compounds described herein may be formulated in solid form and re-dissolved or suspended immediately prior to use. Lyophilized forms can also be produced.

Administration of the compound described herein can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than C12). In one embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The compounds described herein may also be used in combination with other therapies, drugs, medical procedures, etc. for treating the same disease. In some embodiments, such combination use includes administration of one or more other therapies, drugs, or medical procedures at different times (e.g., within a short time, such as within hours (e.g., 1, 2, 3, 4-24 hours), or within a longer time (e.g., 1-2 days, 2-4 days, 4-7 days, 1-4 weeks)) than a compound described herein, or at the same time as a compound described herein. In some embodiments, use in combination includes use with at least one other therapy, drug or medical procedure that is administered once or infrequently, such as surgery, along with a compound described herein administered within a short time or longer time before or after the other therapy, drug or procedure. In some embodiments, use in combination includes delivery of a compound described herein and one or more other drug therapeutics by the same route or different routes of administration. In some embodiments, a compound described herein and one or more other drug therapeutics may be delivered together in any formulation by the same route of administration, including formulations where the compounds and other drug therapeutic(s) are chemically linked in such a way that they maintain their therapeutic activity when administered. In some embodiments, the other drug therapeutic(s) may be co-administered with a compound described herein. In some embodiments, co-administration includes administration of co-formulations or formulations of chemically joined compounds, or administration of two or more compounds in separate formulations within a short time of each other (e.g., within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapeutics delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components. In some embodiments, the compounds as disclosed herein may be used in adjuvant or neoadjuvant therapy in combination with other therapies or therapeutic agents as described herein. In some embodiments involving combination use, dosage may be modified for one or more of the compounds of the present disclosure or other therapeutics used in combination, e.g., reduction in the amount dosed relative to a compound or therapy used alone, by methods well known to those of ordinary skill in the art. Exemplary combination therapies are discussed below.

4. Methods of Use

Kynurenine-3-monooxygenase (KMO) is an enzyme in the tryptophan degradation pathway that catalyzes the conversion of kynurenine (KYN) into 3-hydroxykynurenine (3-HK), which is further degraded to the excitotoxic NMDA receptor agonist QUIN (3-hydroxyanthranilate oxygenase). 3-OH—KYN and QUIN act synergistically, i.e. 3-OH—KYN significantly potentiates the excitotoxic actions of QUIN. KMO expression increases in inflammatory conditions or after immune stimulation. For instance, 3-OH—KYN, the product of its activity, accumulates in the brain of vitamin B-6 deficient neonatal rats and it causes cytotoxicity when added to neuronal cells in primary cultures or when locally injected into the brain. Recently, it was reported that relatively low concentrations (nanomolar) of 3-OH—KYN may cause apoptotic cell death of neurons in primary neuronal cultures.

It was also recently demonstrated that KMO activity is particularly elevated in the iris-ciliary body and that neoformed 3-OH—KYN is secreted into the fluid of the lens. An excessive accumulation of 3-OH—KYN in the lens may cause cataracts.

QUIN is an agonist of a subgroup of NMDA receptors, and when directly injected into brain areas, destroys most neuronal cell bodies sparing fibers en passant and neuronal terminals. QUIN is a relatively poor agonist of the NMDA receptor complex containing either NR2C or NR2D subunits, while it interacts with relatively high affinity with the NMDA receptor complex containing NR2A and NR2B subunits. The neurotoxicity profile found after intrastriatal injection of QUIN resembles that found in the basal nuclei of Huntington's disease patients: while most of the intrinsic striatal neurons are destroyed, NADH-diaphorase-staining neurons (which are now considered able to express nitric oxide synthetase) and neurons containing neuropeptide Y seem to be spared together with axon terminals and fiber en passant.

In models of inflammatory neurological disorders such as experimental allergic encephalitis, bacterial and viral infections, forebrain global ischemia or spinal trauma, brain QUIN levels are extremely elevated. This increased brain QUIN concentration could be due to either an elevated circulating concentration of the excitotoxin or to an increased de novo synthesis in activated microglia or in infiltrating macrophages. In retrovirus-infected macaques, it has been proposed that most of the increased content of brain QUIN (approximately 98%) is due to local production. In fact, a robust increase in the activities of IDO, KMO and kynureninase has been found in areas of brain inflammation.

Elevation of KYNA in brain can have effects in cognitive disorders and disorders arising from, or influenced by, changes in the levels of the neurotransmitters glutamate, dopamine, or Ach (such as Alzheimer's, MCI, PD, schizophrenia, HD, OCD, Tourette's).

Accordingly, the present disclosure provides, in some embodiments, a method for treating a subject suffering from or at risk of a disease or condition mediated by (or at least in part by) kynurenine 3-mono-oxygenase (KMO) activity, where the method includes administering to the subject in need thereof a therapeutically effective amount of at least one compound described herein (e.g., any one or more solid forms of Compound I or salts/co-crystals thereof) or a pharmaceutical composition thereof. In other embodiments, provided is the use of a compound described herein (e.g., any one or more solid forms of Compound I or salts/co-crystals thereof) or a pharmaceutical composition thereof for the treatment of a disease or condition mediated by (or at least in part by) kynurenine 3-mono-oxygenase (KMO) activity. In yet other embodiments, provided is a compound described herein or a pharmaceutical composition thereof for the manufacture of a medicament for treating a disease or condition mediated by (or at least in part by) kynurenine 3-mono-oxygenase (KMO) activity.

The present disclosure also provides, in some embodiments, a method for treating a neurodegenerative pathology mediated by (or at least in part by) KMO activity in a subject in need thereof, the method comprising administering to the subject a therapeutically effective amount of at least one at least one compound described herein or a pharmaceutical composition thereof. In other embodiments, provided is the use of a compound described herein or a pharmaceutical composition thereof for the treatment of a neurodegenerative pathology mediated by (or at least in part by) KMO activity. In yet other embodiments, provided is the use of a compound described herein or a pharmaceutical composition thereof for the manufacture of a medicament for treating a neurodegenerative pathology mediated by (or at least in part by) KMO activity.

The present disclosure also provides, in some embodiments, a method for treating Huntington's disease in a subject in need thereof, the method comprising administering to the subject a therapeutically effective amount of at least one at least one compound described herein or a pharmaceutical composition thereof. In other embodiments, provided is the use of a compound described herein or a pharmaceutical composition thereof for the treatment of Huntington's disease. In yet other embodiments, provided is the use of a compound described herein or a pharmaceutical composition thereof for the manufacture of a medicament for treating Huntington's disease. In some embodiments, the compound for use in treating Huntington's disease is Compound I in any one or more solid forms of Compound I or salts/co-crystals thereof or a pharmaceutical composition thereof described herein.

The present disclosure additionally provides, in some embodiments, a method for treating a disease or condition mediated by (or at least in part by) the presence 3-OH—KYN, QUIN and/or KYNA, the method comprising administering to the subject a therapeutically effective amount of at least one at least one compound described herein (e.g., any one or more solid forms of Compound I or salts/co-crystals thereof) or a pharmaceutical composition thereof. In other embodiments, provided is use of a compound described herein or a pharmaceutical composition thereof for the treatment of a disease or condition mediated by (or at least in part by) the presence 3-OH—KYN, QUIN and/or KYNA. In yet other embodiments, provided is use of a compound described herein or a pharmaceutical composition thereof for the manufacture of a medicament for treating a disease or condition mediated by (or at least in part by) the presence 3-OH—KYN, QUIN and/or KYNA.

The present disclosure further provides, in some embodiments, a method for treating a degenerative or inflammatory condition in which an (i) increased synthesis in the brain of QUIN or 3-OH—KYN or (ii) an increased release of GLU are involved and which may cause neuronal damage, where the method comprises administering to the subject a therapeutically effective amount of at least one at least one compound described herein (e.g., any one or more solid forms of Compound I or salts/co-crystals thereof) or a pharmaceutical composition thereof. In other embodiments, provided is use of a compound described herein or a pharmaceutical composition thereof for the treatment of a degenerative or inflammatory condition in which an (i) increased synthesis in the brain of QUIN or 3-OH—KYN or (ii) an increased release of GLU are involved and which may cause neuronal damage. In yet other embodiments, provided is use of a compound described herein or a pharmaceutical composition thereof for the manufacture of a medicament for treating of a degenerative or inflammatory condition in which an (i) increased synthesis in the brain of QUIN or 3-OH—KYN or (ii) an increased release of GLU are involved and which may cause neuronal damage.

The term "treatment" or "treating" refers to an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival. In some embodiments, inhibiting the disease means reducing a clinical marker of the disease.

The term "inhibition" indicates a significant decrease in the baseline activity of a biological activity or process. For instance, "inhibition of KMO activity" refers to a decrease in KMO activity as a direct or indirect response to the presence of at least one compound described herein (e.g., any one or more solid forms of Compound I or salts/co-crystals thereof), relative to the activity of KMO in the absence of the at least one compound. The decrease in activity may be due to the direct interaction of a compound described herein with KMO, or due to the interaction of a compound described herein with one or more other factors that in turn affect KMO activity. For example, the presence of a compound described herein may decrease KMO activity by directly binding to the KMO, by causing (directly or indirectly) another factor to decrease KMO activity, or by (directly or indirectly) decreasing the amount of KMO present in the cell or organism. Inhibition of KMO activity may additionally refer to an observable inhibition of 3-HK and QUIN production in a standard assay such as the assay described below. In some embodiments, the inhibition of KMO activity also refers to an observable increase in the production of KYNA.

The term "KMO activity" includes activation, redistribution, reorganization, or capping of one or more various KMO membrane-associated proteins (such as those receptors found in the mitochondria), or binding sites can undergo redistribution and capping that can initiate signal transduction. KMO activity also can modulate the availability of kynurenine, which can affect the synthesis or production of QUIN, KYNA, anthranilic acid, and/or 3-HK.

The term "prevention" or "preventing" refers to any treatment of a disease or condition that causes the clinical symptoms of the disease or condition not to develop. Compounds as described herein may, in some embodiments, be administered to a subject (including a human) who is at risk or has a family history of the disease or condition.

The term "administering" refers to oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "modulating" or "modulate" refers to an effect of altering a biological activity, especially a biological activity associated with a particular biomolecule such as kynurenine 3-mono-oxygenase (KMO). For example, an agonist or antagonist of a particular biomolecule modulates the activity of that biomolecule, e.g., an enzyme, by either increasing (e.g., agonist, activator), or decreasing (e.g., antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

A disease or condition mediated by kynurenine 3-monooxygenase (KMO) activity" refers to a disease or condition in which the biological function of KMO, including any mutations thereof, affects the development, course, and/or symptoms of the disease or condition, and/or in which modulation of the KMO alters the development, course, and/or symptoms of the disease or condition. The KMO mediated disease or condition includes a disease or condition for which inhibition provides a therapeutic benefit, e.g., wherein treatment with KMO inhibitor(s), including one or more solid, crystalline or polymorphs of Compound I as described herein, provides a therapeutic benefit to the subject suffering from or at risk of the disease or condition.

The term "therapeutically effective amount" or "effective amount" of a compound described herein means an amount sufficient to effect treatment when administered to a subject, or to provide a therapeutic benefit such as amelioration of symptoms or slowing of disease progression. The therapeutically effective amount may vary depending on the subject, disease or condition being treated, the weight and age of the subject, the severity of the disease or condition, and the manner of administering, which can readily be determined by a medical practitioner. In some embodiments, the therapeutically effective amount of a compound described herein may be an amount sufficient to decrease the symptoms of a disease responsive to inhibition of KMO activity and modulation of kynurenine pathway metabolites (such as kynurenine, kynurenic acid, anthranilic acid, 3-OH-kynurenine, 3-OH anthranilic acid, or quinolinic acid). In some embodiments, the therapeutically effective amount of a compound described herein may be sufficient to inhibit, treat the symptoms of, or reduce the signs or side effects of, a neurodegenerative pathway or disease. In some embodiments, the therapeutically effective amount of a compound described herein may be an amount sufficient to prevent a significant increase or significantly reduce the level of neuronal cell death. In some embodiments, the therapeutically effective amount of a compound described herein may be an amount sufficient to prevent a significant increase or significantly reduce the level of QUIN associated with neuronal cell death. In some embodiments, the therapeutically effective amount of a compound described herein may be an amount sufficient to effect an increase in the level of KYNA associated with neuronal cell health. In some embodiments, the therapeutically effective amount of a compound described herein may be an amount sufficient to increase the anticonvulsant and neuroprotective properties associated with lowered levels of QUIN and increased levels of KYNA. In some embodiments, the therapeutically effective amount of a compound described herein may be an amount sufficient to modulate an inflammatory process in the body, including but not limited to inflammation in the brain, spinal cord, and peripheral nervous system, or meninges. In some embodiments, the therapeutically effective amount of a compound described herein may be an amount sufficient to modulate the production of cytokines responsible for mounting an effective immune response (such as IL-1 beta or TNF-alpha) or an amount sufficient to affect monocyte/macrophage pro-inflammatory activity in the periphery or in the brain in conditions where the blood-brain barrier is compromised, such as in multiple sclerosis). In some embodiments, the therapeutically effective amount of a compound described herein may be an amount sufficient to modulate Huntington's disease, a pathology arising therefrom, or a symptom thereof.

In some embodiments, diseases or conditions disclosed herein, such as those mediated at least in part by KMO and/or the presence of 3-OH—KYN, QUIN and/or KYNA, include a neurodegenerative pathology. In some embodiments, the diseases or conditions disclosed herein include, but are not limited to, Huntington's disease and other polyglutamine disorders such as spinocerebellar ataxias neurodegenerative diseases, psychiatric or neurological diseases or disorders, Alzheimer's disease, Parkinson's disease, amyotrophic lateral sclerosis, Creutzfeldt-Jacob disease, trauma-induced neurodegeneration, high-pressure neurological syndrome, dystonia, olivopontocerebellar atrophy, amyotrophic lateral sclerosis, multiple sclerosis, epilepsy, consequences of stroke, cerebral ischemia, ischemic disorders including stroke (focal ischemia), hypoxia, multi-infarct dementia, consequences of cerebral trauma or damage, damage to the spinal cord, dementia such as senile dementia and AIDS-dementia complex, AIDS-induced encephalopathy, other infection related encephalopathy, viral or bacterial meningitis, infectious diseases caused by viral, bacterial and other parasites, for example, general central nervous system (CNS) infections such as viral, bacterial or parasites, for example, poliomyelitis, Lyme disease (Borrelia burgdorferi infection) septic shock, and malaria, cancers, cancers with cerebral localization, hepatic encephalopathy, systemic lupus, analgesia and opiate withdrawal symptoms, feeding behavior, psychiatric disorders such as insomnia, depression, schizophrenia, severe deficit in working memory, severe deficit in long term memory storage, decrease in cognition, severe deficit in attention, severe deficit in executive functioning, slowness in information processing, slowness in neural activity, anxiety, generalized anxiety disorders, panic anxiety, obsessive compulsive disorders, social phobia, performance anxiety, post-traumatic stress disorder, acute stress reaction, adjustment reaction, separation anxiety disorder, alcohol withdrawal anxiety, depressive disorders, disorders of the developing or aged brain, diabetes, and complications thereof, Tourette's syndrome, Fragile X syndrome, autism spectrum disorders, disorders that cause severe and pervasive impairment in thinking feeling, language and the ability to relate to others, mood disorders, psychological disorders characterized by abnormalities of emotional state, such as without limitation, bipolar disorder, unipolar depression, major depression, endogenous depression, involutional depression, reactive depression, psychotic depression, depression caused by underlying medical conditions, depressive disorders, cyclothymic disorders, dysthymic disorders, mood disorders due to general medical condition, mood disorders not otherwise specified and substance-induced mood disorders, acute necrotizing pancreatitis, HIV-related disorders, AIDS (disease), analgesia, aseptic meningitis, brain disease, for example, Gilles de la Tourette syndrome, Asperger syndrome, Rett syndrome, pervasive developmental disorders, aging-related brain disease, and developmental brain disease, burnout syndrome, carbon monoxide poisoning, cardiac arrest or insufficiency and hemorrhagic shock (global brain ischemia), cataract formation and aging of the eye, central nervous system disease, cerebrovascular disease, chronic fatigue syndrome, chronic stress, cognitive disorders, convulsive disorders, such as variants of Grand mal and petit mal epilepsy and Partial Complex Epilepsy, diabetes mellitus, disease of the nervous system (e.g., dyskinesia, L-DOPA induced movement disorders, drug addiction, pain and cataract), drug dependence, drug withdrawal, feeding disorders, Guillain Barre-Syndrome and other neuropathies, hepatic encephalopathy, immune disease, immunity disorders and therapeutic treatment aimed at modifying biological responses (for instance administrations of interferons or interleukins), inflammation (systemic inflammatory response syndrome), inflammatory disorders of the central and/or peripheral nervous system, Injury (trauma, polytrauma), mental and behavioral disorders, metabolic disease, pain disease, or disorder selected from a group of inflammatory pain, neuropathic pain or migraine, allodynia, hyperalgesia pain, phantom pain, neuropathic pain related to diabetic neuropathy, multiple organ failure, near drowning, necrosis, neoplasms of the brain, neoplastic disorders including lymphomas and other malignant blood disorders, nervous system disease, nicotine addiction and other addictive disorders including alcoholism, cannabis, benzodiazepine, barbiturate, morphine and cocaine dependence, change in appetite, sleep disorders, changes in sleep patterns, lack of energy, fatigue, low self-esteem, self-reproach inappropriate guilt, frequent thoughts of death or suicide, plans or attempts to commit suicide, feelings of hopelessness and worthlessness, psychomotor agitation or retardation, diminished capacity for thinking, concentration, or decisiveness, pain, post-traumatic stress disorder, sepsis, spinal cord disease, spinocerebellar ataxia, systemic lupus erythematosus, traumatic damage to the brain and spinal cord, and tremor syndromes and different movement disorders (dyskinesia), poor balance, bradykinesias, rigidity, tremor, change in speech, loss of facial expression, micrographia, difficulty swallowing, drooling, dementia, confusion, fear, sexual dysfunction, language impairment, impairment in decision making, violent outbursts, aggression, hallucination, apathy, and impairment in abstract thinking.

Such diseases or conditions include, for example, cardiovascular diseases, which refers to diseases and disorders of the heart and circulatory system. These diseases are often associated with dyslipoproteinemias and/or dyslipidemias. Cardiovascular diseases include but are not limited to cardiomegaly, atherosclerosis, myocardial infarction, and congestive heart failure, coronary heart disease, hypertension and hypotension.

Other such diseases or conditions include hyperproliferative diseases of benign or malignant behavior, in which cells of various tissues and organs exhibit aberrant patterns of growth, proliferation, migration, signaling, senescence, and death. Generally hyperproliferative disease refers to diseases and disorders associated with, the uncontrolled proliferation of cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, Age-related Macular Degeneration and various retinopathies, as well as the proliferation of ECs and smooth muscle cells that cause restenosis as a consequence of stenting in the treatment of atherosclerosis. Hyperproliferative disorders involving fibroblasts (i.e., fibrogenesis) include but are not limited to disorders of excessive scaring (i.e., fibrosis) such as Age-related Macular Degeneration, cardiac remodeling and failure associated with myocardial infarction, excessive wound healing such as commonly occurs as a consequence of surgery or injury, keloids, and fibroid tumors and stenting.

Additional diseases or conditions include transplant rejection (suppression of T-cells) and graft vs host disease, chronic kidney disease, systemic inflammatory disorders, brain inflammatory disorders including malaria and African trypanosomiasis, stroke, and pneumococcal meningitis.

In some embodiments, the disease or condition is a neurodegenerative disease.

In some embodiments, the disease or condition is acute necrotizing pancreatitis, disorders of the developing or aged brain, psychiatric disorders, Alzheimer's disease, inflammation, cancer, schizophrenia, neurodegenerative disease, or transplant rejection.

In some embodiments, the disease or condition is Huntington's disease, a memory and/or cognitive impairment associated with Huntington's disease, Parkinson's disease, a memory and/or cognitive impairment associated with Parkinson's disease, Alzheimer's disease, dementia, epilepsy, or multiple sclerosis. In one embodiment, the disease or condition is Huntington's disease or a memory and/or cognitive impairment associated with Huntington's disease. In one embodiment, the disease or condition is Parkinson's disease or a memory and/or cognitive impairment associated with Parkinson's disease. In one embodiment, the disease or condition is Alzheimer's disease. In one embodiment, the disease or condition is dementia. In one embodiment, the disease or condition is epilepsy. In one embodiment, the disease or condition is multiple sclerosis.

In some embodiment, the disease or condition is an HIV-related disorder. HIV is the virus that causes Acquired Immunodeficiency Syndrome (AIDS), which is the most advanced stage of HIV infection. HIV destroys the CD4(+) T lymphocytes (CD4(+) cells) of the immune system, leaving the body vulnerable to life-threatening infections and cancers. HIV is a retrovirus that occurs as two types: HIV-1 and HIV-2. Both types are transmitted through direct contact with HIV-infected body fluids, such as blood, semen, and genital secretions, or from an HIV-infected mother to her child during pregnancy, birth, or breastfeeding (through breast milk). HIV-1 can be classified into four groups: M Group, N Group, O Group, and P Group. Viruses within each group can then be further classified by subtype. For example, the HIV-1 M group includes at least nine subtypes: A1, A2, B, C, D, F1, F2, G, H, J, and K. HIV-2 infection is endemic to West Africa. It generally takes longer to progress to symptomatic HIV/AIDS and has a lower mortality rate than HIV-1 infection.

In some embodiments, the disease or condition is HIV-1, HIV-1 M group, HIV-1 M group subtype A1, HIV-1 M group subtype A2, HIV-1 M group subtype B, HIV-1 M group subtype C, HIV-1 M group subtype D, HIV-1 M group subtype F1, HIV-1 M group subtype F2, HIV-1 M group subtype G, HIV-1 M group subtype H, HIV-1 M group subtype J, HIV-1 M group subtype K, HIV-1 N Group, HIV-1l Group, HIV-1 P Group, or HIV-2. In some embodiments, the disease or condition is HIV-1. In one embodiment, the disease or condition is HIV-1 M group. In one embodiment, the disease or condition s HIV-1 M group subtype A1. In one embodiment, the disease or condition is HIV-1 M group subtype A2. In one embodiment, the disease or condition is HIV-1 M group subtype B. In one embodiment, the disease or condition is HIV-1 M group subtype C. In one embodiment, the disease or condition is HIV-1 M group subtype D. In one embodiment, the disease or condition is HIV-1 M group subtype F1. In one embodiment, the disease or condition is HIV-1 M group subtype F2. In one embodiment, the disease or condition is HIV-1 M group subtype G. In one embodiment, the disease or condition is HIV-1 M group subtype H. In one embodiment, the disease or condition is HIV-1 M group subtype J. In one embodiment, the disease or condition is HIV-1 M group subtype K. In one embodiment, the disease or condition is HIV-1 N Group. In one embodiment, the disease or condition is HIV-1 O Group. In one embodiment, the disease or condition is HIV-1 P Group. In some embodiments, the HIV is HIV-2.

HIV enters the central nervous system (CNS) early in the course of the infection and causes several important CNS conditions over the course of the disease, such as HIV encephalopathy and AIDS dementia complex. As part of the acute HIV syndrome during seroconversion, patients may experience HIV encephalopathy. HIV-associated progressive encephalopathy (HPE) is a syndrome complex with cognitive, motor, and behavioral features seen in children. Prior to the advent of highly active antiretroviral therapy (HAART), dementia was a common source of morbidity and mortality in HIV-infected patients. It was usually observed in the late stages of AIDS, when CD4(+) lymphocyte counts fall below 200 cells/mL, and was seen in up to 50% of patients prior to their deaths. In 1986, the term AIDS dementia complex (ADC) was introduced to describe a unique constellation of neurobehavioral findings. HIV associated neurocognitive disorder (HAND) encompasses a hierarchy of progressively more severe patterns of neurological involvement. It can range from asymptomatic neurocognitive impairment (ANI) to minor neurocognitive disorder (MND) to more severe HIV-associated dementia (HAD) (also called AIDS dementia complex [ADC] or HIV encephalopathy). ADC is considered a single entity with a broad and varied spectrum of clinical manifestations and severity. ADC is characterized by cognitive, motor, and behavioral features in adults, usually those with advanced AIDS. With the advent of HAART, a less severe dysfunction, minor cognitive motor disorder (MCMD), has become more common than ADC. The overall psychosocial and emotional burden on the family and friends of patients with HIV dementia is tremendous, far beyond that of a cognitively intact patient with AIDS. Patients with cognitive difficulties have problems with compliance and adherence to their medication regimen. Because of their neuropsychiatric problems, these patients are likely to be less inhibited and are more prone to HIV-related risk behavior (e.g., unprotected intercourse), and they therefore pose a greater risk of transmission of the virus. In addition to HIV itself, other causes of neurologic complications in HIV-infected individuals include opportunistic infections, tumors, and antiretroviral drugs. Other neurologic complications that arise from primary HIV infection include vacuolar myelopathy, peripheral neuropathies, and polymyositis.

In some embodiments, diseases or conditions disclosed herein may include Human Immunodeficiency Virus (HIV)-related disorders. Accordingly, in some embodiments, a therapeutically effective amount of a compound described herein may be amount sufficient to treat the symptoms of an HIV-related disorder. In some embodiments, a therapeutically effective amount of a compound described herein may be an amount sufficient to reduce the signs or side effects of an HIV-related disorder. In some embodiments, a therapeutically effective amount of a compound described herein may be an amount sufficient to prevent a significant increase or significantly reduce the level of HIV-related neuronal cell death. In some embodiments, a therapeutically effective amount of a compound described herein may be an amount sufficient to prevent a significant increase or significantly reduce the level of QUIN associated with HIV-related neuronal cell death. In some embodiments, a therapeutically effective amount of a compound described herein may be an amount sufficient to effect an increase in the level of KYNA associated with neuronal cell health in an HIV-infected patient. In some embodiments, a therapeutically effective amount of a compound described herein an amount sufficient to increase the anticonvulsant and neuroprotective properties associated with lowered levels of QUIN and increased levels of KYNA in an HIV-infected patient. In some embodiments, a therapeutically effective amount of a compound described herein may be an amount sufficient to modulate an inflammatory process in an HIV-infected patient, including but not limited to inflammation in the brain, spinal cord, and peripheral nervous system, or meninges. In methods described herein for adjunctively treating an HIV-related disorder, a therapeutically effective amount of a compound described herein may also be an amount sufficient, when administered to a patient, to detectably slow the progression of the HIV-related disorder, or prevent the patient to whom the composition is given from presenting symptoms of the HIV-related disorder. In some methods described herein for treating an HIV-related disorder, a therapeutically effective amount of a compound described herein may also be an amount sufficient to produce a detectable decrease in the level of HIV-related neuronal cell death. For example, in some embodiments, a therapeutically effective amount of a compound described herein may be an amount sufficient to significantly decrease the level of HIV-related neuronal death by effecting a detectable decrease in the amount of QUIN, and an increase in the amount of kynurenine, KYNA, or anthranilic acid.

In some embodiments, the HIV-related disorder is an opportunistic infection selected from: candidiasis, coccidioidomycosis, cryptococcosis, cryptosporidiosis, cytomegalovirus, herpes simplex virus, herpes zoster, histoplasmosis, isosporiasis, mycobacterium avium complex, pneumocystis pneumonia, bacterial pneumonia, progressive multifocal leukoencephalopathy salmonella, toxoplasmosis, and tuberculosis.

In some embodiments, the HIV-related disorder is an AIDS-related cancer selected from: cervical cancer, Kaposi sarcoma, and lymphomas.

In some embodiments, the HIV-related disorder is an AIDS-defining illnesses selected from: candidiasis of the esophagus, bronchi, trachea, or lungs, invasive cervical cancer, disseminated or extrapulmonary coccidioidomycosis, extrapulmonary cryptococcosis, chronic intestinal cryptosporidiosis, cytomegalovirus disease (other than liver, spleen, or nodes), cytomegalovirus retinitis with loss of vision, HIV related-encephalopathy, herpes simplex (with chronic ulcers, bronchitis, pneumonitis, or esophagitis), disseminated or extrapulmonary histoplasmosis, chronic intestinal isosporiasis, Kaposi sarcoma, Burkitt's lymphoma, immunoblastic lymphoma, primary lymphoma of brain, disseminated or extrapulmonary mycobacterium avium complex or M. kansasii, pulmonary or extrapulmonary mycobacterium tuberculosis, disseminated or extrapulmonary mycobacterium species, pneumocystis jiroveci pneumonia, recurrent pneumonia, progressive multifocal leukoencephalopathy, recurrent salmonella septicemia, toxoplasmosis of brain, and wasting syndrome due to HIV.

In some embodiments, the HIV-related disorder is a neurological disorder. In some embodiments, the neurological disorder is selected from: AIDS dementia complex, AIDS-induced encephalopathy, HIV encephalopathy, HIV-associated progressive encephalopathy, HIV-associated neurocognitive disorder, asymptomatic neurocognitive impairment, minor neurocognitive disorder, HIV-associated dementia, minor cognitive motor disorder, vacuolar myelopathy, peripheral neuropathies, and polymyositis. In one embodiment, the neurological disorder is AIDS dementia complex. In one embodiment, the neurological disorder is AIDS-induced encephalopathy. In one embodiment, the neurological disorder is HIV encephalopathy. In one embodiment, the neurological disorder is HIV-associated progressive encephalopathy. In one embodiment, the neurological disorder is HIV-associated neurocognitive disorder. In one embodiment, the neurological disorder is asymptomatic neurocognitive impairment. In one embodiment, the neurological disorder is minor neurocognitive disorder. In one embodiment, the neurological disorder is minor cognitive motor disorder. In one embodiment, the neurological disorder is vacuolar myelopathy. In one embodiment, the neurological disorder is peripheral neuropathy. In one embodiment, the neurological disorder is polymyositis.

5. Combination Therapy

Patients treated for diseases mediated by KMO may benefit from combination drug treatment. Accordingly, in some embodiments a compound described herein (e.g., any one or more solid forms of Compound I or salts/co-crystals thereof) a compound described herein (e.g., any one or more solid forms of Compound I or salts/co-crystals thereof) may be combined with one or more additional therapeutic agents.

In one embodiment, a compound described herein (e.g., any one or more solid forms of Compound I or salts/co-crystals thereof) as described herein may be administered sequentially with the additional therapeutic agent(s). Sequential administration or administered sequentially means that the form of Compound I as described herein and the additional therapeutic agent(s) are administered with a time separation of a few seconds, several minutes, hours, days, or weeks. In one embodiment, the time separation may correspond to about 30 seconds or less, about 15 minutes or less, about 30 minutes or less, about 60 minutes or less, about 1 day, about 2 days, about 3 days, about 4 days, about 5 days, about 6 days, about 7 days, about 2 weeks, about 3 weeks, about 4 weeks, about 5 weeks, about 6 weeks, about 7 weeks, or about 8 weeks. When administered sequentially, the form of Compound I as described herein and the additional therapeutic agent(s) may be administered in two or more administrations, and contained in separate compositions or dosage forms, which may be contained in the same or different package or packages.

In one embodiment, a compound described herein (e.g., any one or more solid forms of Compound I or salts/co-crystals thereof) may be administered simultaneously with the additional therapeutic agent(s). Simultaneous administration or administered simultaneously means that the form of Compound I as described herein and the additional therapeutic agent(s) are administered with a time separation of no more than a few minutes or seconds, e.g., no more than about 15 minutes, about 10 minutes, about 5 minutes, or 1 minute. When administered simultaneously, the form of Compound I as described herein and the additional therapeutic agent(s) may be in separate compositions or dosage forms, or the same composition or dosage form.

In one embodiment, a compound described herein (e.g., any one or more solid forms of Compound I or salts/co-crystals thereof) may be combined with one or more additional therapeutic agents in a unitary dosage form (for example for oral administration). In one embodiment, a form of Compound I as described herein may and the one or more additional therapeutic agents may be separate dosage forms.

In some embodiments, a composition includes a compound described herein (e.g., any one or more solid forms of Compound I or salts/co-crystals thereof) along with one or more compounds that are therapeutically effective for the same disease indication, wherein the compounds have a synergistic effect on the disease indication. For instance, in one embodiment, the composition includes any one or more compound(s) as described herein effective in treating a particular disease or condition mediated at least in part by KMO and one or more additional therapeutic agents that are also effective in treating the same disease or condition mediated at least in part by KMO, further wherein the compounds are synergistically effective in treating said disease or condition. A "synergistic effect" may encompass a more than additive effect of two or more agents compared to their individual effects.

In some embodiments, a compound described herein (e.g., any one or more solid forms of Compound I or salts/co-crystals thereof) can be administered in combination with at least another additional agent having activity for treatment of Huntington's disease, including memory and/or cognitive impairment associated with Huntington's disease. In one such embodiment, the additional therapeutic agent may be Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, or Risperidone.

In some embodiments, a compound described herein (e.g., any one or more solid forms of Compound I or salts/co-crystals thereof) can be administered in combination with at least another additional agent having activity for treatment of Parkinson's disease, including treating memory and/or cognitive impairment associated with Parkinson's disease. In one such embodiment, the additional therapeutic agent herein may be Levodopa, Parlodel, Permax, Mirapex, Tasmar, Contan, Kemadin, Artane, or Cogentin.

In some embodiments, a compound described herein (e.g., any one or more solid forms of Compound I or salts/co-crystals thereof) can be administered in combination with at least another additional agent having activity for treatment of Alzheimer's disease. In one such embodiment, the additional therapeutic agent may be Reminyl, Cognex, Aricept, Exelon, Akatinol, Neotropin, Eldepryl, Estrogen or Cliquinol.

In some embodiments, a compound described herein (e.g., any one or more solid forms of Compound I or salts/co-crystals thereof) can be administered in combination with at least another additional agent having activity for treatment of dementia. In one such embodiment, this additional therapeutic agent may be Thioridazine, Haloperidol, Risperidone, Cognex, Aricept, or Exelon.

In some embodiments, a compound described herein (e.g., any one or more solid forms of Compound I or salts/co-crystals thereof) can be administered in combination with at least another additional agent having activity for treatment of epilepsy. In one such embodiment, the additional therapeutic agent may be Dilantin, Luminol, Tegretol, Depakote, Depakene, Zarontin, Neurontin, Barbita, Solfeton, or Felbatol.

In some embodiments, a compound described herein (e.g., any one or more solid forms of Compound I or salts/co-crystals thereof) can be administered in combination with at least another additional agent having activity for treatment of multiple sclerosis. In one such embodiment, the additional therapeutic agent may be Detrol, Ditropan XL, OxyContin, Betaseron, Avonex, Azothioprine, Methotrexate, or Copaxone.

In some embodiments, a compound described herein (e.g., any one or more solid forms of Compound I or salts/co-crystals thereof) can be administered in combination with an antiviral agent for treatment of an HIV-related disorder.

HIV drugs/agents are classified into six drug classes on the basis of how each drug interferes with the HIV life cycle. These six classes include the nucleoside/nucleotide reverse transcriptase inhibitors (NRTIs), non-nucleoside reverse transcriptase inhibitors (NNRTIs), protease inhibitors (PIs), fusion inhibitors, CCR5 antagonists, and integrase strand transfer inhibitors (INSTIs). HIV uses reverse transcriptase (RT) to convert its RNA into DNA (reverse transcription). Blocking RT and reverse transcription prevents HIV from replicating. NRTIs lack a 3' hydroxyl group and are metabolically activated by host cellular kinases to their corresponding 5'-triphosphate forms, which are subsequently incorporated into DNA by HIV reverse transcriptase (RT) and which act as chain terminators of DNA synthesis. Examples of NRTIs include amdoxovir, Combivir®, Emtriva®, Epivir®, Epzicom®, Retrovir®, tenofovir alafenamide fumarate, Trizivir®, Truvada®, Videx®, Videx® EC, Viread®, Zerit®, and Ziagen®. NNRTIs are noncompetitive inhibitors of DNA polymerization, binding to a hydrophobic pocket in RT near the polymerase active site. Examples of NRTIs include Edurant®, Intelence®, lersivirine, Rescriptor®, Sustiva®, Viramune®, and Viramune® XR. After transcription in the nucleus, viral mRNA enters the cytoplasm and uses the host's cellular machinery to manufacture virus proteins. The viral components then gather at the cell membrane and immature viruses bud off the cell. Core proteins are produced as part of long polypeptides, which must be cut into smaller fragments by the enzyme protease in order to form mature, functional proteins. PIs bind to the site where protein cutting occurs, and so prevent the enzyme from releasing the individual core proteins. In this way the new viral particles are unable to mature or become infectious. Examples of PIs include Aptivus®, Crixivan®, Invirase®, Kaletra®, Lexiva®, Norvir®, Prezista®, Reyataz®, and Viracept®. Fusion inhibitors block the HIV envelope from merging with the host cell membrane (fusion), which prevents HIV from entering the host cell. Examples of fusion inhibitors include Fuzeon®. CCR5 antagonists block the CCR5 receptor on the surface of certain immune cells, such as CD4+ cells, which prevents HIV from entering the cell. Examples of CCR5 antagonists include cenicriviroc and Selzentry®. INSTIs block integrase, an enzyme HIV uses to insert (integrate) its viral DNA into the DNA of the host cell. Blocking integrase prevents HIV from replicating. Examples of INSTIs include Isentress®, Tivicay®, and Elvitegravir®. Multi-class combination drugs include Atripla® (efavirenz+tenofovir+emtricitabine), Complera® (rilpivirine+tenofovir+emtricitabine), Stribild® (elvitegravir+cobicistat+tenofovir+emtricitabine), and Trii™ (dolutegravir+abacavir+lamivudine). Recommended antiretroviral therapy (ART) regimens for the treatment of HIV involve using a combination of three or more antiretroviral (ARV) drugs from at least two different HIV drug classes. The current standard of care for HIV/AIDS in the developed world is highly active antiretroviral therapy (HAART) therapy, usually a combination of two reverse transcriptase inhibitors and a protease inhibitor. Class-sparing regimens purposefully exclude all ARV drugs from a specific drug class to save specific ARV drugs for future use in case a regimen needs to be changed because of toxicity or drug resistance. A class-sparing regimen may also be used to avoid adverse effects associated with a specific drug class. Certain HIV ART regimens include a pharmacokinetic enhancer that increases the level of certain ARVs in the blood and make them more effective. Examples of pharmacokinetic enhancers include Cobicistat®, a component of the approved fixed-dose combination tablet Stribild®; ritonavir, a PI that improves the pharmacokinetic (PK) profiles of concomitant PIs; and SPI-452. Experimental immune-based HIV therapies include, Aralen®, DermaVir®, interleukin-7, lexgenleucel-T, Plaquenil®, Proleukin®, and SB-728-T. Entry inhibitors are a class of ARVs that include fusion inhibitors, CCR5 antagonists, and glycosidase inhibitors. Maturation inhibitors are a class of ARVs that target the gag polyprotein precursor, the main structural protein responsible for assembly and budding of virion particles during maturation.

In some embodiments, the antiviral agent administered in combination with a compound described herein (e.g., any one or more solid forms of Compound I or salts/co-crystals thereof) is selected from: entry inhibitors, fusion inhibitors, glycosidase inhibitors, CCR5 antagonists, immune-based therapies, integrase inhibitors, maturation inhibitors, multi-class combination drugs, non-nucleoside reverse transcriptase inhibitors, nucleoside/nucleotide reverse transcriptase inhibitors, pharmacokinetic enhancers, and protease inhibitors, and combinations thereof.

In some embodiments, the antiviral agent is selected from: nucleoside/nucleotide reverse transcriptase inhibitors, non-nucleoside reverse transcriptase inhibitors, protease inhibitors, fusion inhibitors, CCR5 antagonists, and integrase strand transfer inhibitors, and combinations thereof.

In some embodiments, the antiviral agent is selected from: amdoxovir, Aptivus®, Aralen®, Atripla®, cenicriviroc, Cobicistat®, Combivir®, Complera®, Crixivan®, DermaVir®, Edurant®, elvitegravir, Emtriva®, Epivir®, Epzicom®, Fuzeon®, ibalizumab, Intelence®, interleukin-7, Invirase®, Isentress®, Kaletra®, lersivirine, lexgenleucel-T, Lexiva®, Norvir®, Plaquenil®, Proleukin®, Prezista®, PRO 140, Rescriptor®, Retrovir®, Reyataz®, SB-728-T, Selzentry®, SPI-452, Stribild®, Sustiva®, tenofovir alafenamide fumarate, Tivicay®, Trii™ Trizivir®, Truvada®, Videx®, Videx® EC, Viracept®, Viramune®, Viramune® XR, Viread®, Zerit®, and Ziagen®, and combinations thereof.

In some embodiments, the antiviral agent is HAART.

6. Dosages

The specific dose level of a compound described herein (e.g., any one or more solid forms of Compound I or salts/co-crystals thereof), when administered alone or in one of the prescribed combinations, for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. In some embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein (e.g., any one or more solid forms of Compound I or salts/co-crystals thereof) administered per dose or per day. Daily dosage of a compound of Table 1 may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application (e.g., any one or more solid forms of Compound I or salts/co-crystals thereof) or the compositions thereof may be administered once, twice, three, four, or more times daily, using any suitable mode described above.

In a particular embodiment, the method comprises administering to the subject an initial daily dose of about 1 to 800 mg of a compound described herein (e.g., any one or more solid forms of Compound I or salts/co-crystals thereof) and increasing the dose by increments until clinical efficacy is achieved. Increments of about 5, 10, 25, 50, or 100 mg can be used to increase the dose. The dosage can be increased daily, every other day, twice per week, or once per week.

7. Kits

Provided herein are also kits that include one or more compounds described herein (e.g., any one or more solid forms of Compound I or salts/co-crystals thereof) or a pharmaceutical composition thereof, and suitable packaging. In one embodiment, a kit further includes instructions for use. In one aspect, a kit includes one or more compounds described herein, or a pharmaceutical composition thereof, and a label and/or instructions for use of the compound(s) in the treatment of the indications, including the diseases or conditions, described herein.

Provided herein are also articles of manufacture that include a compound described (e.g., any one or more solid forms of Compound I or salts/co-crystals thereof) or a pharmaceutical composition thereof in a suitable container. The container may be a vial, jar, ampoule, preloaded syringe, and intravenous bag.

EXAMPLES

1. Synthetic Example

The sodium salt of Compound I can be prepared according to the following synthetic procedures.

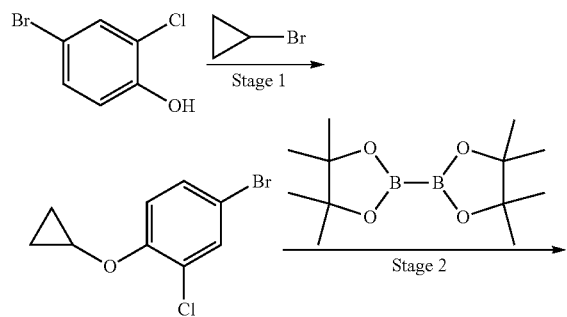

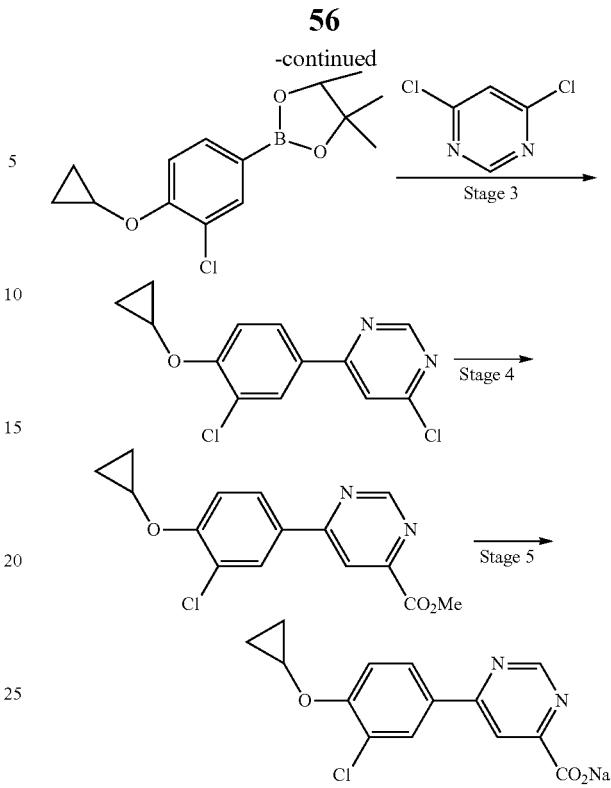

Stage 1

A 20-L, high pressure reactor was charged with 4-bromo-2-chlorophenol (750 g, 3.62 moles), cesium carbonate (3180 g, 9.76 moles, 2.7 equiv), and dimethyl acetamide (11.25 L). Bromocyclopropane (1750 g, 1159 mL, 14.48 moles, 4 equiv) was then added in a single charge (no exotherm on addition). The pressure reactor was closed and heated at 130-135° C. and held at this temperature for 48 h when deemed complete by HPLC analysis.

The reaction mixture was cooled to 25° C. and was combined with 300 g batch for workup. The combined batches were transferred via vacuum to a 50-L reactor containing chilled water (5° C., 15.75 L), and methyl tert-butyl ether (MTBE, 17.85 L) and stirred for 5 min. The MTBE layer was separated, and the aqueous phase was extracted with MTBE (2×5.25 L). The combined organic extracts were washed with 50% brine solution (5.25 L), followed by brine (5.25 L). The organics were dried over anhydrous $MgSO_4$ (4 kg), filtered with the aid of Celite, then concentrated via rotary evaporation to provide the title compound as an orange oil (1195 g, 95%). This material was used without purification in the next step.

Stage 2

A 30-L reactor equipped with a heating mantle was charged with 4-bromo-2-chloro-1-cyclopropoxybenzene (1195 g, 94.6 wt %, 4.57 moles), bis-(pinacolato)diboron (1392 g, 5.48 moles, 1.2 equiv), potassium acetate (1345 g, 13.72 moles, 3.0 equiv), and DMSO (12 L). The batch was degassed using a vacuum/nitrogen release method prior to the addition of $Pd(dppf)Cl_2$ (149 g, 183 mmol, 4 mol %). The reaction mixture was brought to an internal temperature of 75-80° C. and stirred for 3 h when deemed complete by HPLC analysis. The batch was cooled to 20-25° C. and transferred via vacuum to a 100-L reactor containing EtOAc (18 L) and water (14.4 L). Two phases were separated and the aqueous phase was extracted with EtOAc (2×6 L). The combined organic phases were washed with 50% brine solution (2×8 L) causing emulsions that required filtration through Celite to achieve phase separation. The rich organic was washed with brine and dried over anhydrous $MgSO_4$ (3 kg) and filtered with the aid of Celite. Concentration via rotary evaporation provided the crude title compound as a dark brown semi solid. The crude material was dissolved in DCM (2.5 L) and concentrated in the presence of silica gel to a powder. The mixture was then loaded onto a 10" diameter column packed with 10 kg of silica gel and eluted with 1-2 psi air pressure using an eluent gradient from 100% heptanes to 20% EtOAc in heptanes to provide the title compound as a pale yellow solid (1019 g, 76%).

Stage 3

A 30-L reactor equipped with a heating mantle was charged with 2-(3-chloro4-cyclopropoxyphenyl)-4,4,5,5-tetramethyl-1,3,2-dioxaborolane (1100 g, 3.47 moles), 4,6-dichloropyrimidine (732 g, 4.8 moles, 1.4 equiv), 1,4-dioxane (13.2 L), and 2 M aqueous $K_2CO_3$ solution (4.95 L, 9.88 moles, 2.85 equiv). The batch was degassed using a vacuum/nitrogen release method prior to the addition of $Pd(PPh_3)_4$ (284 g, 243 mmol, 7 mol %). The reaction mixture was brought to an internal temperature of 87-90° C. and stirred for 3 h when deemed complete by HPLC analysis. The batch was cooled to 20-25° C., transferred via vacuum to a 20-L rotary evaporator, and concentrated to a residue. The residue was re-dissolved in DCM (11 L) and washed with water (11 L) causing emulsions that required filtration through Celite to achieve phase separation. The rich organic was washed with brine (5 L), dried over anhydrous $MgSO_4$ (3 kg), filtered with the aid of Celite, and partially concentrated. When the pot volume was approximately 2 L, 2 kg of silica gel was added and the mixture was concentrated to a powder. The mixture was then loaded onto a 10" diameter column packed with 10 kg of silica gel and eluted with 1-2 psi air pressure using an eluent gradient from 100% heptanes to 20% EtOAc in heptanes to provide the title compound as a pale yellow solid (705 g, 71%).

Stage 4

A 20-L Hastalloy pressure vessel was charged with 4-chloro-6-(3-chloro-4-cyclopropoxyphenyl)pyrimidine (705 g, 2.50 moles), $Pd(dppf)Cl_2$ (82 g, 100 mmol, 4 mol %), triethylamine (549 mL, 3.96 moles, 1.58 equiv), and methanol (10.5 L). The vessel was vacuum purged and pressurized three times with 80 psi carbon monoxide gas. The reaction mixture was warmed to 50° C. and the pressure was adjusted to maintain 80 psi. The reaction mixture was stirred at this temperature and pressure for 12 h when deemed complete by HPLC analysis. The reaction vessel was cooled and the carbon monoxide atmosphere was replaced with argon. The contents were transferred to a 20-L rotary evaporator and methanol was removed and swapped with EtOAc, maintaining ≈5 vol during the solvent exchange. To this was added EtOAc (14 L) and rich organic solution was transferred to a 30-L reactor and washed with water (triethylamine hydrochloride had precipitated partially at this point), causing emulsions that required filtration to achieve phase separation. The rich organic was washed with brine (5 L), dried over anhydrous $MgSO_4$ (2 kg), filtered with the aid of Celite, and partially concentrated. When the pot volume was approximately 2 L, 2 kg of silica gel was added and the mixture was concentrated to a powder. The mixture was then loaded onto a 10" diameter column packed with 10 kg of silica gel and eluted with 1-2 psi air pressure using an eluent gradient from 30% heptanes to 100% EtOAc to provide the title compound as a pale yellow solid (470 g, 62%).

Stage 5

A 50-L, jacketed reactor was charged with methyl 6-(3-chloro-4-propoxyphenyl)pyrimidine-4-carboxylate (2080 g, 2080 g, 6.83 moles) and IPA (72.8 L). The batch was heated up to 50-55° C. and added aqueous sodium hydroxide (2 M, 3.65 L, 7.3 moles, 1.07 equiv) while maintaining a temperature of 50-55° C. The resulting mixture was stirred for 3 h when deemed complete by HPLC analysis. The reaction mixture was cooled to 20-25° C. and the batch hold at same temperature for 12-18 h. The precipitated solids were filtered on an 18" Hastalloy Nutsche filter. The cake was washed with IPA (2×2 bed vol) and tray was dried at 65-70° C. under vacuum to give the title compound as an off-white solid (1980 g, 93%).

The resulting product may be further purified as follows. The resulting product was converted to the corresponding methyl ester according to the following procedure: Acetyl chloride (527 g, 6.75 moles) was added cautiously to cold (0-5° C.) methanol (8.4 L). The exotherm was controlled by rate of addition such that the internal temperature was kept below 20° C. This mixture was stirred at 20-22° C. for 15 minutes when the resulting product (703.2 g, 2.25 moles) was added in portions (no exotherm). The resulting suspension was heated to reflux and held at reflux for 3 hours when the solution became clear and TLC analysis showed the absence of starting material. The mixture was cooled to room temperature, and the solution was concentrated to dryness. The crude product was dissolved in DCM (2 L) and concentrated in the presence of silica gel (800 g) to a powder. The powder was loaded on to 5 kg of silica gel and eluted with DCM (35 L). The methyl ester was then eluted from the column using 10% MeOH in DCM. The rich fractions were concentrated to give the methyl ester as a white solid (609.4 g, 85%).

The methyl ester was subsequently hydrolyzed and converted back to the resulting sodium salt according to the techniques described above.

2. Experimental Methods a. Approximate Solubility

A weighed sample was treated with aliquots of the test solvent at room temperature. The mixture was sonicated between additions to facilitate dissolution. Complete dissolution of the test material was determined by visual inspection. Solubility was estimated based on the total solvent used to provide complete dissolution. Some samples were then heated and observed visually for complete dissolution. The actual solubility may be greater than the value calculated because of the use of solvent aliquots that were too large or due to a slow rate of dissolution. The solubility is expressed as "less than" if dissolution did not occur during the experiment. If complete dissolution was achieved as a result of only one aliquot addition, the solubility is expressed as "greater than."

b. Cooling and Slow Cools

Solutions were prepared in the selected solvent or solvent/anti-solvent system. These solutions were chilled below room temperature within a refrigerator for varying lengths of time in an attempt to induce nucleation. The presence or absence of solids was noted. Upon observation of solids, in quantities sufficient for analysis, isolation of material was conduction. If insufficient quantities were present further cooling was performed in a freezer. Samples were either isolated for analysis wet or as dry powders.

c. Fast Evaporation

Solutions were prepared in selected solvents and agitated between aliquot additions to assist in dissolution. Once a mixture reached complete dissolution, as judged by visual observation, the solution was filtered through a 0.2 µm nylon filter and allowed to evaporate at ambient temperature in an uncapped vial or at ambient under nitrogen. The solids that formed were isolated for evaluation.

d. Lyophilization

An attempt to generate amorphous material was conducted by lyophilization from a water/dimethylsulfoxide/Compound I sodium Form B suspension. The suspension was filtered into a flask and frozen in a thin layer within the vessel and placed onto an FTS systems Flexi Dry bench top lyophilization system.

e. Slow Evaporation

Solutions were prepared in selected solvents and agitated between aliquot additions to assist in dissolution. Once a mixture reached complete dissolution, as judged by visual observation, the solution was filtered through a 0.2 µm nylon filter into a vial. The vial opening was covered with foil and pierced to slow the rate of evaporation (compared to unobstructed opening) and allowed to evaporate at ambient. The solids that formed were isolated for evaluation.

f. Slurry

Solutions were prepared by adding enough solids to a given solvent so that excess solids were present. The mixture was then agitated in a sealed vial at either ambient or an elevated temperature. After a given amount of time, the solids were isolated for analysis.

g. Vacuum

Selected materials were dried under reduced pressure for a set time period. Initial stressing was conducted with the in-house vacuum system with absolute pressure readings below <500 mTorr, typically 30 to 50 mTorr (0.030 to 0.05 mm Hg).

h. Single Solvent Crystallization

For single solvent crystallization, as described, e.g., in Table 9A, approximately 30.0-33.0 mg of Compound I sodium Pattern A starting material was placed into glass vials equipped with stir bars and dissolved with a minimum amount of solvents (starting with about a 500 µL increment) at about 70.0° C. (up to about 7.0 mL). When using methanol, about 60.0° C. was used due to low b.p. temperature at 64.7° C. Each hot solution was polish filtered through a 0.45 m syringe filter into a clean preheated vial. After hot filtration, the vials were placed in a refrigerator (about 4.0° C.) without stirring over 24 hours in the fast cooling procedure, or cooled to ambient temperature at a rate of about 20.0° C./hr and allowed to equilibrate with stirring at ambient temperature over 24 hours in the slow cooling procedure. The resulting solids were isolated by vacuum filtration. The samples without precipitation were evaporated to dryness under a gentle stream of nitrogen gas. All obtained solids were analyzed by XRPD to determine the solid form.

i. Binary Solvent Crystallization

For binary solvent crystallization, as described, e.g., in Tables 9B-9C, approximately 29.0-32.0 mg of Compound I sodium Pattern A starting material was placed into glass vials equipped with stir bars and dissolved with a minimum amount of solvents (starting with about a 500 µL increment) at about 70.0° C. (up to about 7.0 mL). Each solution was polish filtered through a 0.45 m syringe filter into a clean preheated vial. After hot filtration, anti-solvent was added drop-wise. The vials were placed in a refrigerator (about 4.0° C.) without stirring over 24 hours in the fast cooling procedure, or cooled to ambient temperature at a rate of about 20.0° C./hr and allowed to equilibrate with stirring at ambient temperature over 24 hours in the slow cooling procedure. The resulting solids were isolated by vacuum filtration. The samples without precipitation were evaporated to dryness under a gentle stream of nitrogen gas. All obtained solids were analyzed by XRPD to determine the solid form.

j. Indexing

Indexing uses a proprietary SSCI software TRIADS™, U.S. Pat. No. 8,576,9850. Indexing is the process of determining the size and shape of the crystallographic unit cell given the peak positions in a diffraction pattern. The term gets its name from the assignment of Miller index labels to individual peaks. XRPD indexing serves several purposes. If all of the peaks in a pattern are indexed by a single unit cell, this is strong evidence that the sample contains a single crystalline phase. Given the indexing solution, the unit cell volume may be calculated directly and can be useful to determine salt stoichiometries or solvation states. Indexing is also a robust description of a crystalline form and provides a concise summary of all available peak positions for that phase at a particular thermodynamic state point.

3. Instrumental Techniques a. PANalytical X'PERT Pro MPD Diffractometer (Transmission Mode)

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-µm-thick films and analyzed in transmission geometry. A beam-stop, short antiscatter extension, antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror.

b. PANalytical X'PERT Pro MPD Diffractometer (Reflection Mode)

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was prepared as a/thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

c. Solution ¹H NMR Spectroscopy

The solution ¹H NMR spectrum was acquired by Spectral Data Services of Champaign, Ill. The residual peak from incompletely deuterated DMSO is at approximately 2.50 ppm. The relatively broad peak at approximately 3.3 ppm is due to water.

d. Differential Scanning Calorimetry (DSC)

DSC was performed using a TA Instrument Q2000 differential scanning calorimeter. Temperature calibration was performed using NIST-traceable indium metal. The sample was placed into an aluminum Tzero crimped DSC pan, covered with a lid, and the weight was accurately recorded. A weighed aluminum pan configured as the sample pan was placed on the reference side of the cell. The sample was heated from 25 to 225° C., at 10° C./min.

e. Dynamic Vapor Sorption/Desorption (DVS)

Moisture sorption/desorption data were collected on a VTI SGA-100 Vapor Sorption Analyzer. NaCl and PVP were used as calibration standards. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

f. Thermal Gravimetric Analysis (TGA)

TG analyses were performed using a TA Instruments Discovery thermogravimetric analyzer. Temperature calibration was performed using nickel and Alumel™. Each sample was placed in an aluminum pan. The sample was hermetically sealed, the lid pierced, then inserted into the TG furnace. The furnace was heated under nitrogen. The ramp rate for each thermogram was 10° C./min.

g. High Performance Liquid Chromatography (HPLC)

HPLC conditions for analyzing samples were as follows:

TABLE 1

| HPLC Conditions | |
|---|---|
| System | Agilent 1100 Series HPLC |
| Column | Agilent Eclipse XDB C18, (SN: USK H026080) 4.6 × 150 mm, 5.0 μm |
| Column temperature | 30.0° C. |
| Auto sampler temp | Ambient |
| Flow rate | 1.0 mL/min |
| Injection volume | 5.0 μL |
| Run time | 26 minutes |
| Detection | 26 minutes |

4. Solid Forms of Compound I (Free Acid)

Solid forms of Compound I free acid were prepared at a gram scale from a starting material comprising Compound I sodium Pattern A, which was prepared as described herein. Two methods were used to prepare the solid forms of Compound I free acid: (1) an aqueous slurry of the sodium salt was reacted with HCl and the free acid was extracted with ethyl acetate (EtOAc), and (2) the free acid was precipitated directly from an aqueous solution of the sodium salt with the addition of HCl. Of these methods, the second method utilizing aqueous precipitation procedure was preferred and was used to generate the free acid for further studies, such as the salt/co-crystal screen described in section 4 below. The solid forms of Compound I free acid observed from the aforementioned first and second methods are summarized in Tables 2 and 3, respectively. Particular crystalline forms of Compound I free acid are further described in section 3.1-3.6 below.

TABLE 2

Free Acid Generation from Compound I Sodium Pattern A, EtOAc Extraction

| Method/Description[1] | Observation[2] | Form |
|---|---|---|
| 1. Compound I sodium Pattern A dissolved in water, 10 mg/mL<br>2. added molar equivalent of HCl<br>3. EtOAc extraction<br>4. filtered aqueous phase<br>5. dried organic phase (MgSO₄) rotary evaporated, vacuum dried | 1. solids remained<br>2. precipitation<br>3. solids in aqueous phase<br>4. solids retained<br>5. sheets of material, fines, birefringent | C |
| 1. Compound I sodium Pattern A dissolved in water, 10 mg/mL<br>2. added molar equivalent of HCl<br>3. EtOAc extraction<br>4. filtered aqueous phase and retained solids slurried in water | — | D + peaks |
| 1. Compound I sodium Pattern A dissolved in water, 10 mg/mL<br>2. added molar equivalent of HCl<br>3. EtOAc extraction<br>4. filtered aqueous phase and bulk dried in vacuum oven at 86° C. | solids, NB | A + F + peaks |
| 1. Compound I sodium Pattern A dissolved in water, 10 mg/mL<br>2. added molar equivalent of HCl<br>3. EtOAc extraction<br>4. filtered aqueous phase and retained solids: rinsed portion with water | <4 mg/mL solubility observed | not analyzed |
| 1. Compound I sodium Pattern A dissolved in water, 10 mg/mL<br>2. added molar equivalent of HCl<br>3. EtOAc extraction<br>4. filtered aqueous phase and rinsed residual solids from flask with ether, post rotary evaporation process | fines, birefringent | C |

TABLE 2-continued

Free Acid Generation from Compound I Sodium Pattern A, EtOAc Extraction

| Method/Description[1] | Observation[2] | Form |
|---|---|---|
| 1. Compound I sodium Pattern A dissolved in water, 10 mg/mL<br>2. added molar equivalent of HCl<br>3. EtOAc extraction<br>4. filtered aqueous phase, isolated the resulting filtrate | gelled then nucleated, fines, birefringent | B |

[1]Times are approximate.
[2]B = birefringent and NB = no birefringence when observed by polarized light microscopy.

TABLE 3

Free Acid Generation from Compound I Sodium Pattern A, H$_2$O Procedure

| Method/Description[1] | Observation[2] | Results |
|---|---|---|
| 1. Compound I sodium Pattern A dissolved in water with heat (5 mg/mL), treated with 1.2 molar equivalents of HCl<br>2. rinsed with water | 1. precipitation-<br>2. fine aciculars, birefringent | A indexed |
| 1. Compound I sodium Pattern A dissolved in water at 45° C., overnight<br>2. contacted with charcoal, filtered, added 1.2 molar eq. of HCl<br>3. 10 minute slurry<br>4. rinsed with water, briefly dried under N$_2$<br>5. vacuum dried, 83° C. | 1. almost complete dissolution, limited blade like solids<br>2. solution after charcoal/filtration, precipitation with acid addition<br>3. fine aciculars, B<br>4. damp solids<br>5. solids, fine aciculars, B | A + F |
| blade like solids isolated from step 1 directly above | blade like morphology, cleaved on smooth planes, NB material dissolved in DMSO | — |
| 1. Compound I sodium Pattern A dissolved in water at 45° C., overnight<br>2. contacted with charcoal, filtered, added 1.2 molar eq. of HCl<br>3. 10 minute slurry<br>4. rinsed with water, briefly dried under N$_2$ | wet solids | D indexed |
| 1. Compound I sodium Pattern A dissolved in water heated<br>2. filtered 0.2 pm filter<br>3. 1.2 molar eq. of HCl added, slurry, overnight, ambient<br>4. filtered rinsed with water<br>5. vacuum dried, 65° C. | 1. limited solids remained<br>2. solids removed<br>3. slurry<br>4. solids<br>5. solids | A + F |
| filter paper from step 4 directly above retained | solids | — |
| 1. Compound I sodium Pattern A dissolved in water at 45° C., overnight<br>2. contacted with charcoal, filtered, added 1.2 molar eq. of HCl<br>3. 10 minute slurry<br>4. rinsed with water, briefly dried under N2<br>5. heated resulting solids to 83° C. under vaccum<br>6. heated resulting solids at 160° C. | solids melted and recrystallized | E |
| 1. Compound I sodium Pattern A dissolved in water at 45° C., overnight<br>2. contacted with charcoal, filtered, added 1.2 molar eq. of HCl<br>3. 10 minute slurry<br>4. rinsed with water, briefly dried under N2<br>5. heated resulting solids at 125° C. | solids | A + F |

[1]Times are approximate.
[2]B = birefringent and NB = no birefringence when observed by polarized light microscopy.

4.1 Compound I Material A

Figure 2:
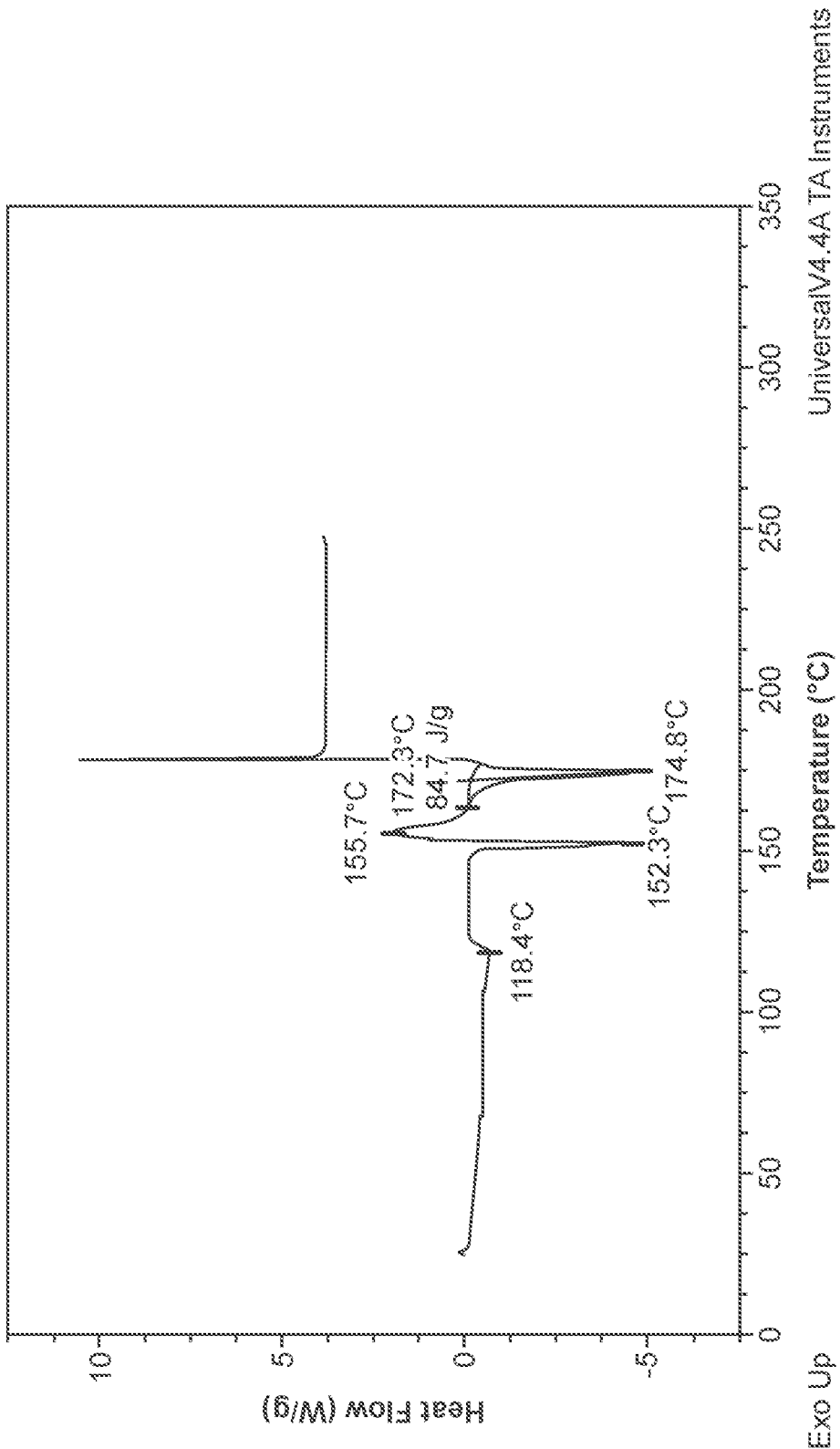
FIG. 2 is a differential scanning calorimeter (DSC) curve of Compound I Material A.
Figure 3:
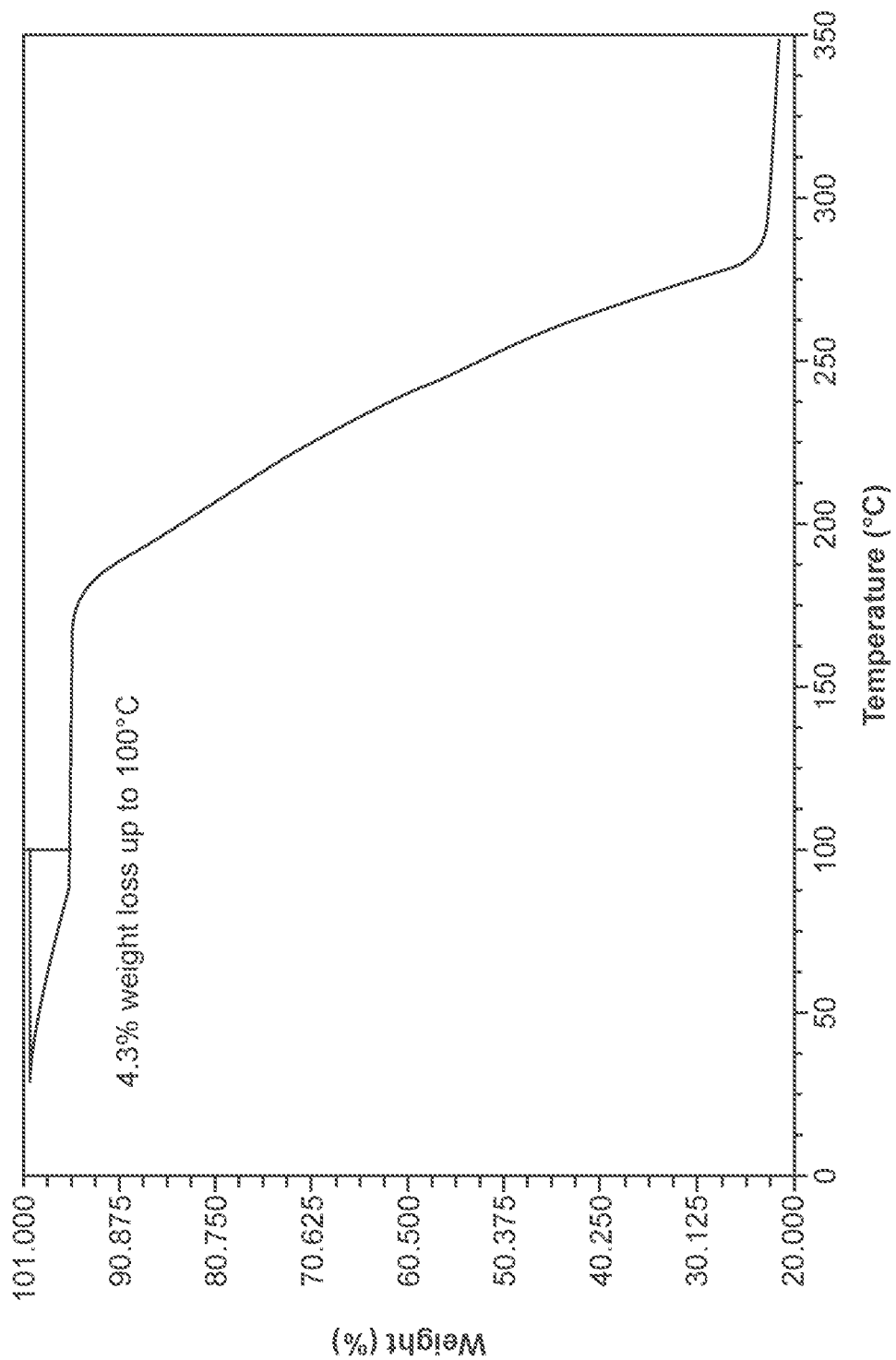
FIG. 3 is a thermogravimetric analysis (TGA) of Compound I Material A.

Compound I Material A is crystalline as determined via XRPD analysis (FIG. 1). Compound I Material A can be characterized by an X-ray powder diffractogram comprising the following peaks: 10.79, 25.92, and 27.18°2θ±0.2°2θ. The DSC curve for Compound I Material A shows an endotherm with onset at about 172° C., additional endotherms with peaks at about 118° C. and about 152° C., as well as an exotherm with a peak at about 156° C. (FIG. 2). TGA analysis shows a weight loss of about 4.3% up to about 100° C. (FIG. 3).

Compound I Material A was formed via isolation from a starting material comprising Compound I sodium Pattern A. Compound I sodium Pattern A (about 5 mg/mL) was dissolved in water and heated. The resulting mixture was treated with about 1.2 molar equivalents of HCl, and Compound I Material A precipitated therefrom.

4.2 Compound I Material B

Figure 4:
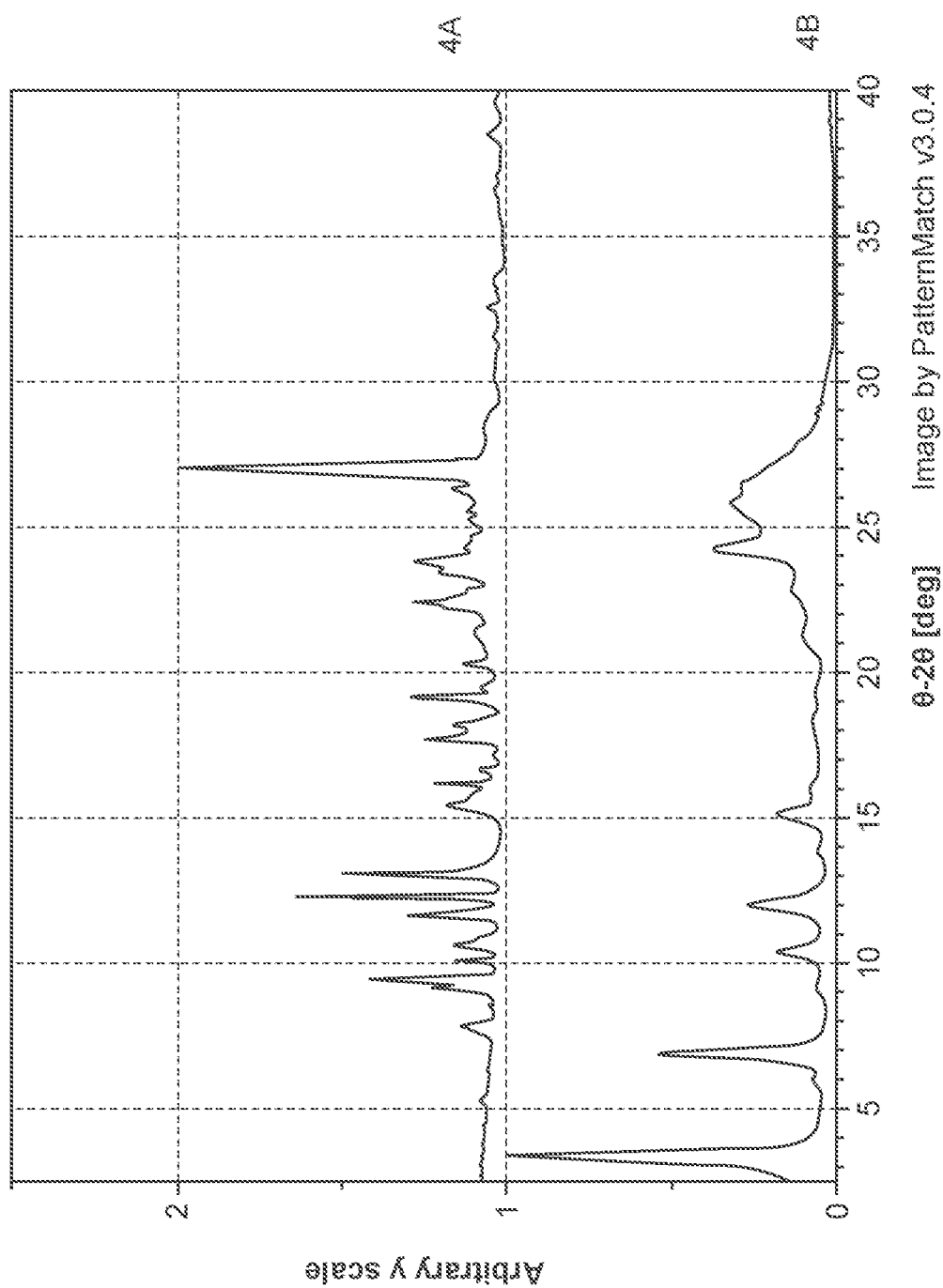
FIG. 4 are X-ray powder diffractograms of Compound I Material B (4A) and Compound I Material C (4B).

Compound I Material B is crystalline as determined via XRPD analysis (FIG. 4A). Compound I Material B can be characterized by an X-ray powder diffractogram comprising the following peaks: 9.42, 12.28, and 27.03°2θ±0.2°2θ.

Compound I Material B was formed via isolation from a starting material comprising Compound I sodium Pattern A. Compound I sodium Pattern A (about 10 mg/mL) was dissolved in water, subsequently reacted with HCl, and extracted with ethyl acetate (EtOAc). The aqueous phase was filtered, and Compound I Material B nucleated from the diethyl ether filtrate.

4.3 Compound I Material C

Compound I Material C is crystalline as determined via XRPD analysis (FIG. 4B). Compound I Material C can be characterized by an X-ray powder diffractogram comprising the following peaks: 3.40, 6.88, and 11.99°2θ±0.2°2θ.

Compound I Material C was formed via isolation from a starting material comprising Compound I sodium Pattern A. Compound I sodium Pattern A (about 10 mg/mL) was dissolved in water, subsequently reacted with HCl, and extracted with ethyl acetate (EtOAc). The aqueous phase was filtered, and the organic phase was dried (e.g., using $MgSO_4$), rotary evaporated and vacuum dried, thereby forming Compound I Material C.

4.4 Compound I Material D

Figure 5:
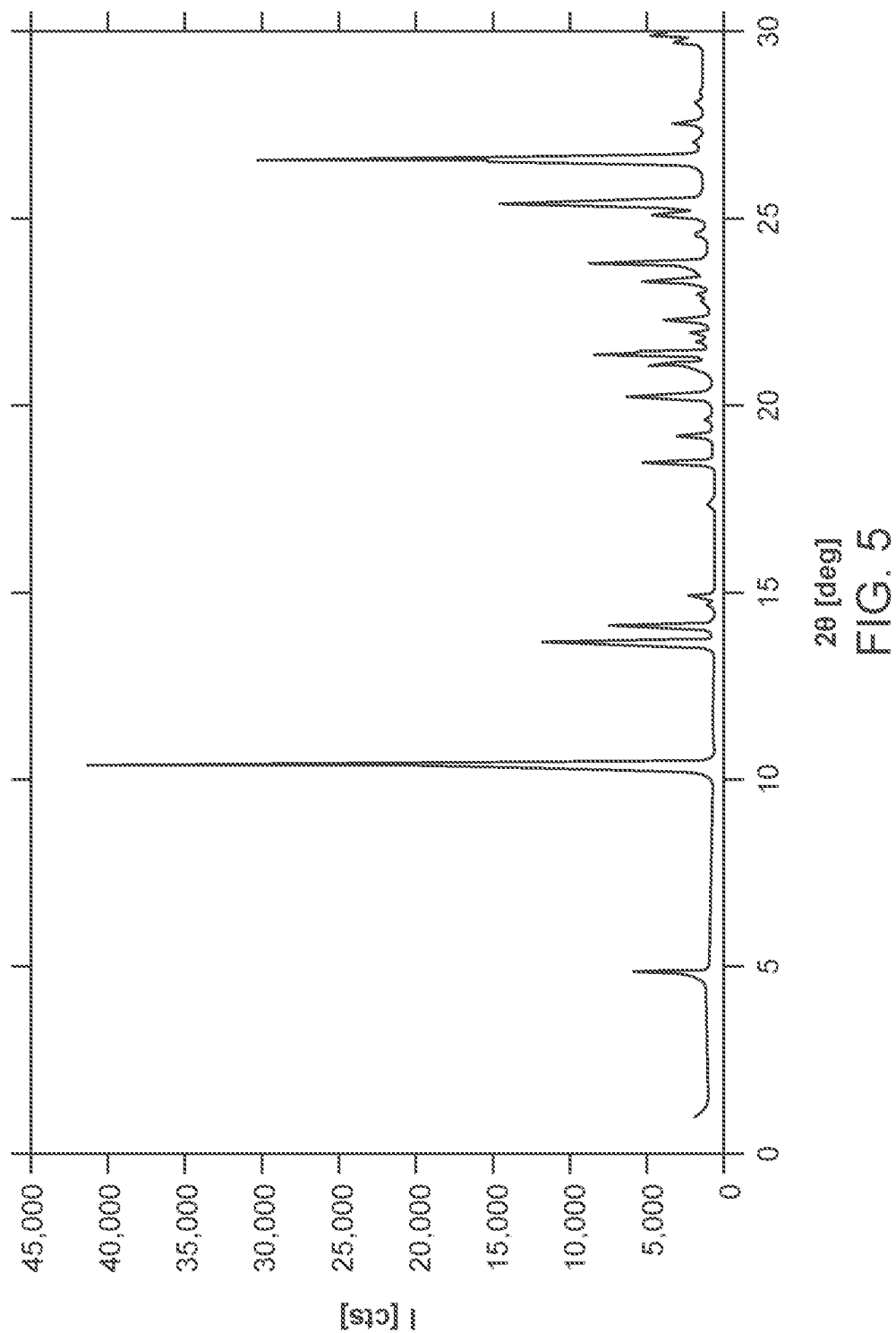
FIG. 5 is an X-ray powder diffractogram of Compound I Material D.

Compound I Material D is crystalline as determined via XRPD analysis (FIG. 5, 6A). Compound I Material D can be characterized by an X-ray powder diffractogram comprising the following peaks: 10.42, 23.80, and 26.59°2θ±0.2°2θ.

Compound I Material D was formed via isolation from a starting material comprising Compound I sodium Pattern A. Compound I sodium Pattern A was dissolved in water and heated at about 45° C. overnight. The mixture was treated with about 1.2 molar equivalents of HCl, and the resulting solids were rinsed with water and briefly dried under $N_2$ to form Compound I Material D.

4.5 Compound I Material E

Figure 6:
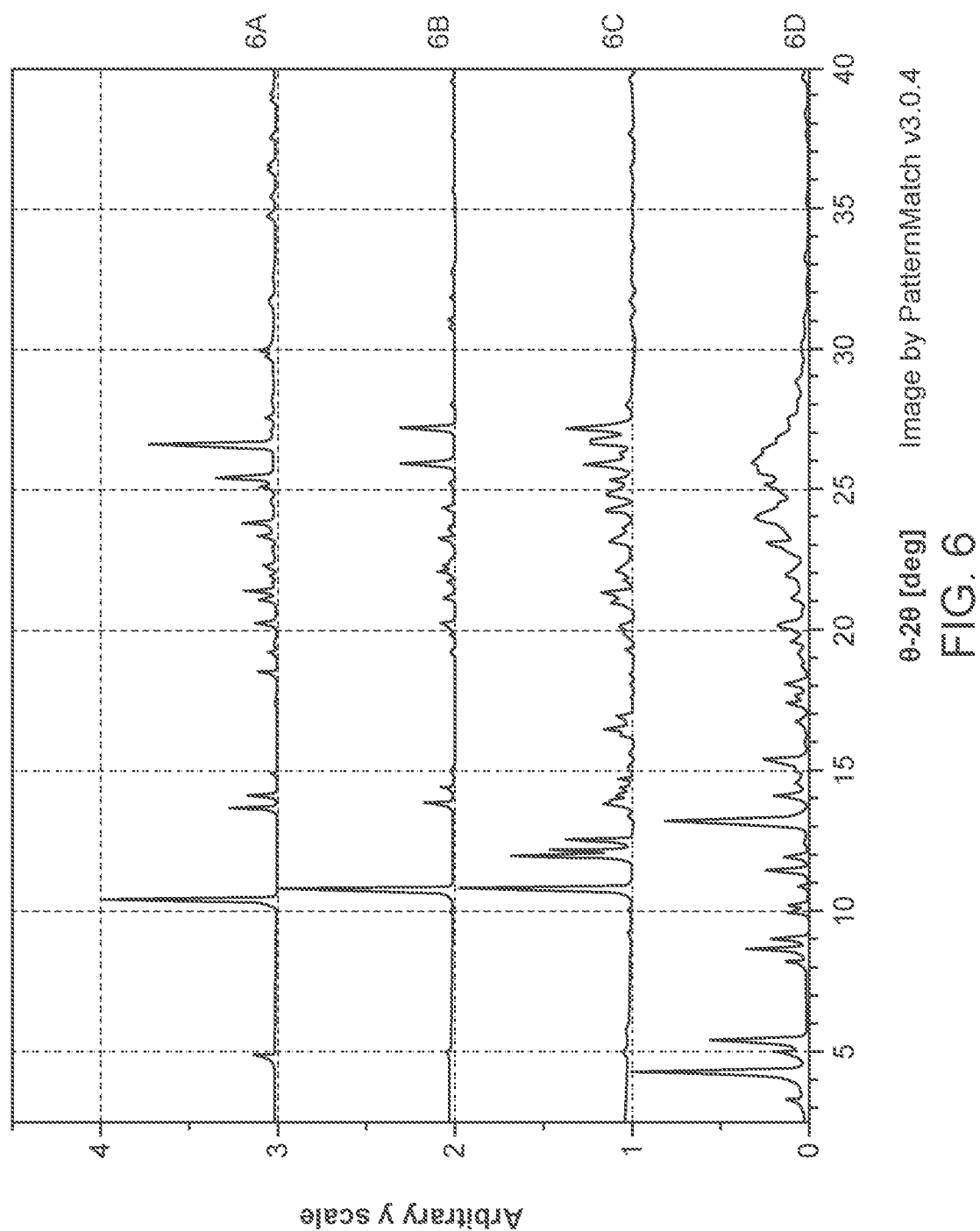
FIG. 6 are X-ray powder diffractograms of Compound I Material D (6A), Compound I Material A (6B), Compound I Material A+F (6C), and Compound I Material E (6D).

Compound I Material E is crystalline as determined via XRPD analysis (FIG. 6D). Compound I Material E can be characterized by an X-ray powder diffractogram comprising the following peaks: 4.31, 5.42, and 13.21°2θ±0.2°2θ.

Compound I Material E was formed via isolation from a starting material comprising Compound I sodium Pattern A. Compound I sodium Pattern A was dissolved in water and heated at about 45° C. overnight. The mixture was treated with about 1.2 molar equivalents of HCl, thereby forming a slurry that was stirred, e.g., overnight. The resulting solids were isolated by filtration, rinsed with water, and dried under $N_2$ to initially form Compound I Material D. The solids were further vacuum dried at about 83° C., and recrystallized at about 160° C. to form Compound I Material E.

4.6 Compound I Material F

Compound I Material F is crystalline as determined via XRPD analysis (FIG. 6C). Compound I Material F can be characterized by an X-ray powder diffractogram comprising the following peaks: 11.97, 12.53, and 26.75°2θ±0.2°2θ.

Compound I Material F was formed via isolation from a starting material comprising Compound I sodium Pattern A. Compound I sodium Pattern A was dissolved in water and heated at about 45° C. overnight. The mixture was treated with about 1.2 molar equivalents of HCl, thereby forming a slurry that was stirred, e.g., overnight. The resulting solids were isolated by filtration, rinsed with water, and dried under $N_2$ to initially form Compound I Material D. The solids were further vacuum dried at about 83° C. to form Compound I Material F.

5. Salt/Co-Crystal Screen of Compound I

A salt/co-crystal screen of Compound I free acid, prepared as described herein, was implemented with various counterions. The salt/co-crystal screen generally involved in the direct addition of a solution containing approximately a molar equivalent of the counterion to free acid in solution or suspension. Materials were harvested if immediate precipitation of sufficient quantity occurred or additional steps such as, but not limited to, cooling, anti-solvent addition, and/or slurrying were performed to induce crystallization. The resulting products were qualitatively evaluated for crystallinity by PLM or XRPD. Materials exhibiting unique XRPD patterns were analyzed by solution 1H NMR spectroscopy to confirm composition/stoichiometry as well as evaluate the amount of solvent present and ensure that chemical degradation has not occurred. DSC and TGA were also used to evaluate the thermal behavior of the material and determine whether the material is anhydrous or solvated. Indexing solutions were able to be determined for the benzathine, diethanolamine, and tromethamine salts.

The formation of observed salts/co-crystals of Compound I are summarized in Table 4, and further described in sections 4.1-4.11 below.

TABLE 4

| Salt/Co-crystals of Compound I | | | |
| --- | --- | --- | --- |
| Salt | Method[1] | Observation[2] | Results |
| DL-arginine | 1. Compound I free acid Materials A + F in ACN<br>2. 1 molar eq. of guest in water added, sonicated<br>3. added ACN and sonicated<br>4. sub sample on slide<br>5. aciculars from slide added to bulk, slurried, 4 days, filtered | 1. solution<br>2. precipitates, clumping<br>3. no clumping in solution<br>4. aciculars form from solution<br>5. poor recovery | DL-arginine A |
| benzathine | 1. Compound I free acid Material C in MeOH<br>2. molar equivalent of guest added, stored | 1. slurry<br>2. solution-oil droplets<br>3. sheets of blades and diamond morphology, B, | Benzathine A + peaks |

TABLE 4-continued

Salt/Co-crystals of Compound I

| Salt | Method[1] | Observation[2] | Results |
|---|---|---|---|
| | ambient overnight<br>3. evaporation<br>4. MeOH rinse, dried under $N_2$ | single crystals and oil droplets<br>4. singles show conversion | |
| | 1. Compound I free acid Materials A + F in ACN<br>2. 4 molar eq. of guest added<br>3. stored ambient overnight<br>4. filtered, dried under $N_2$ | 1. faint haze<br>2. increase in turbidity then cleared<br>3. rosettes of thin blades, B<br>4. — | Benzathine A |
| calcium | 1. Compound I free acid Materials A + F in ACN<br>2. molar eq. of $Ca(OH)_2$ in 4:1 $H_2O$/ACN (slurry) added<br>3. sub sample on slide<br>4. sub sample added to bulk, slurry overnight, ambient filtered, briefly $N_2$ dried | 1. solution<br>2. suspension flocculent<br>3. irregular masses and acicula's forming<br>4. aciculars and irregular masses | Free Acid D + broad peaks likely associated with calcium salt formation |
| | Filtrate from step 4 | nucleation of fine aciculars, B | Free Acid A + Free Acid D not analyzed |
| choline | 1. Compound I free acid Material C in EtOH<br>2. molar equivalent of guest added<br>3. treated with ether<br>4. freezer overnight<br>5. fast evaporation | 1. few solids<br>2. cleared then hazy, oil droplet<br>3. clear<br>4. no changes<br>5. oily residue and fine acicular, B, mesophase, solids flow with pressure | |
| diethylamine | 1. Compound I free acid Materials A + F in ACN<br>2. 1.1 molar eq. of guest added, sonicated<br>3. left overnight, filtered | 1. solution<br>2. precipitation in ~2 minutes blades, B<br>3. fines and blades, B | Diethylamine A |
| Diethanolamine | 1. Compound I free acid Materials A + F in ACN<br>2. 1.1 molar eq. of guest added, shook and sonicated<br>3. left overnight, filtered | 1. solution<br>2. precipitation clumped, fine blades/sheets, B<br>3. hexagonal flake and fines, B | Diethanolamine A |
| | 1. Compound I free acid Materials A + F in CAN filtered<br>2. seeded with Diethanolamine A<br>3. 1 molar eq. of guest added with stirring<br>4. slurried overnight filtered, rinsed with ACN and briefly dried under $N_2$ | 1. solution<br>2. seeds remained<br>3. slowly became hazy<br>4. — | Diethanolamine A |
| ethanolamine | 1. Compound I free acid Materials A + F in MEK<br>2. 1.2 molar eq. of guest added, sonicated<br>3. additional MEK added<br>4. EtOAc added with sonication, left for 1 hr, harvested by filtration and briefly $N_2$ dried | 1. solution<br>2. precipitation slurry, limited fines, B<br>3. bulk sample thick film, NB<br>4. solids, irregular fines, B | Ethanolamine A |
| ethylenediamine | 1. Compound I free acid Materials A + F in MEK<br>2. 1.2 molar eq. of guest added, sonicated<br>3. treated with EtOAc<br>4. after 3 days filtered | 1. solution<br>2. precipitation, irregular, B<br>3. fines, B and emulsion like<br>4. fines, NB | Ethylenediamine A + B |

TABLE 4-continued

Salt/Co-crystals of Compound I

| Salt | Method[1] | Observation[2] | Results |
|------|-----------|----------------|---------|
| | and briefly N$_2$ dried 1. Compound I free acid Materials A + F in ACN, filtered 2. 1 molar eq. of guest added, sonicated 3. seeded with ethylenediamine A+B, slurried, 5 days 4. filtered and briefly N$_2$ dried | 1. solution 2. precipitation, NB material 3. — 4. fines, NB | Ethylenediamine B + A |
| glycine | 1. Compound I free acid Materials A + F in ACN 2. 1 molar eq. of guest in 1:1 ACN/H$_2$O sonicated 3. filtered and dried briefly under N$_2$ | 1. solution 2. precipitation forming, slowly fine aciculars and blades, B 3. — | Free Acid A + Free Acid D + glycine |
| DL-lysine | 1. Compound I free acid Materials A + F in ACN 2. 1 molar eq. of guest in water added, sonicated 3. ambient, 4 days, filtered, briefly dried under N$_2$ | 1. solution 2. precipitated clumped, fines forming, B turning white 3. — | DL-lysine A |
| meglumine | 1. Compound I free acid Materials A + F in ACN 2. a slurry of 1 molar eq. of guest in ACN added with sonication 3. slurried overnight, filtered 4. reanalyzed sample 7 days later | 1. solution 2. turbidity change 3. fines, B 4. signs of change | Meglumine A + meglumine Meglumine A shifts + meglummine |
| potassium | 1. Compound I free acid Materials A + F in ACN 2. 1 molar eq. of guest rinsed in heptane added, sonicated 3. slurried, 5 days, filtered | 1. solution 2. precipitation gel 3. — | Potassium A |
| tromethamine | 1. Compound I free acid Materials A + F in ACN 2. a slurry of 1 molar eq. of guest in 4:3 MeOH/ACN added 3. additional CAN added, stored in freezer overnight 4. warmed to ambient 5. filtered, and briefly N$_2$ dried | 1. solution 2. limited blades, B 3. limited solids 4. nucleation 5. solids, fines and thin flake, B | Tromethamine A |
| sodium | 1. Compound I free acid Materials A + F in ACN 2. 1 molar eq. of guest in H$_2$O/ACN added 3. slurried overnight, filtered | 1. solution 2. precipitation gel like and flocculent, fines B 3. fine aciculars, NB | Sodium B |

[1]Times are approximate.
[2]B = birefringent and NB = no birefringence when observed by polarized light microscopy.

5.1 Compound I Arginine Material A

Figure 7:
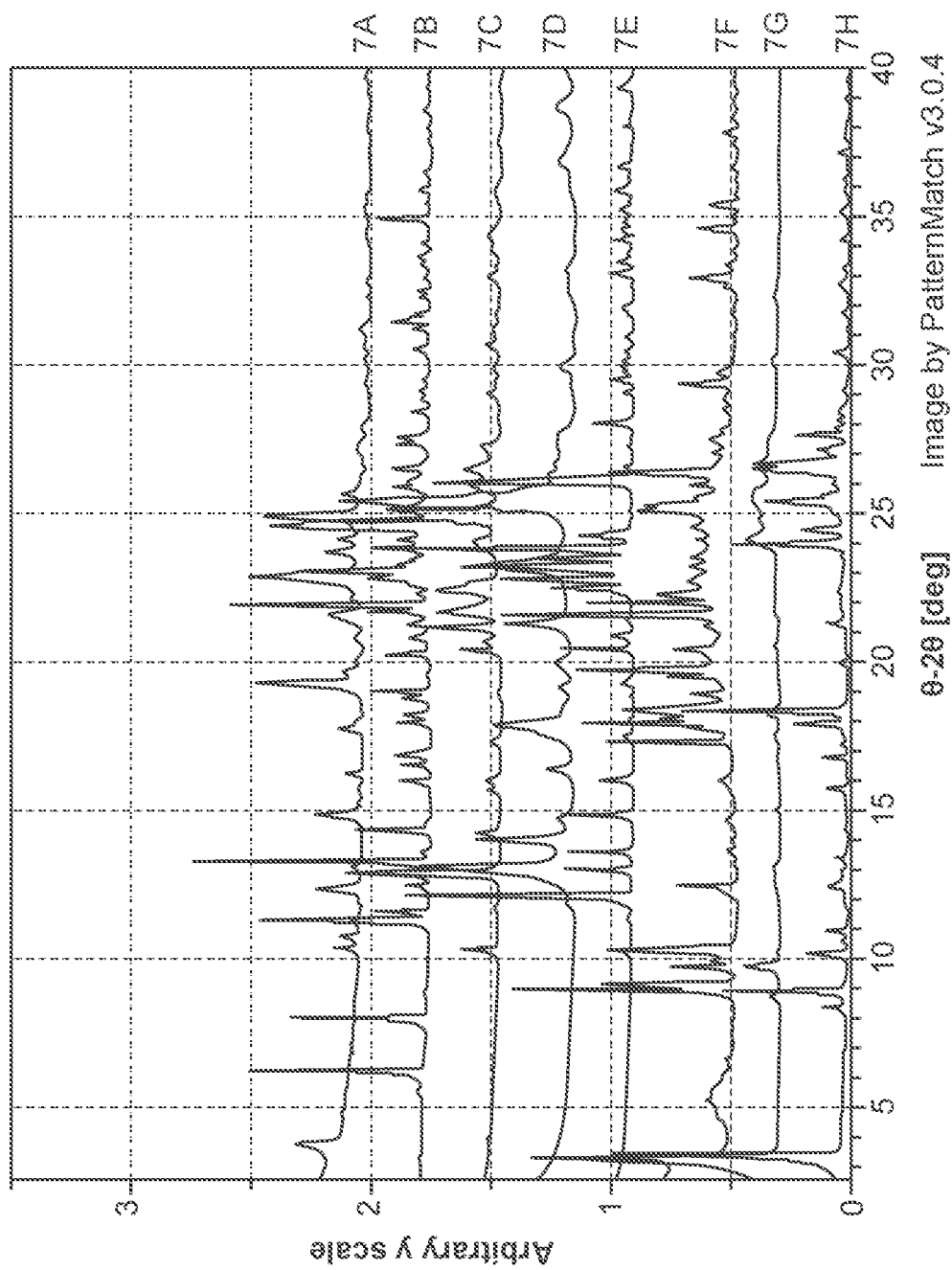
FIG. 7 are X-ray powder diffractograms of Compound I arginine Material A (7A), Compound I diethylamine Material A (7B), Compound I ethanolamine Material A (7C), Compound I ethylenediamine Materials A+B (7D), Compound I lysine Material A (7E), Compound I meglumine Material A (7F), Compound I potassium Material A (7G), and Compound I sodium Form B (7H).

Compound I arginine Material A was formed as described in Table 4, in one embodiment. Compound I arginine Material A is crystalline as determined via XRPD analysis (FIG. 7A). Compound I arginine Material A can be characterized by an X-ray powder diffractogram comprising the following peaks: 3.75, 19.25, and 22.86°2θ±0.2°2θ.

5.2 Compound I Benzathine Material A

Figure 8:
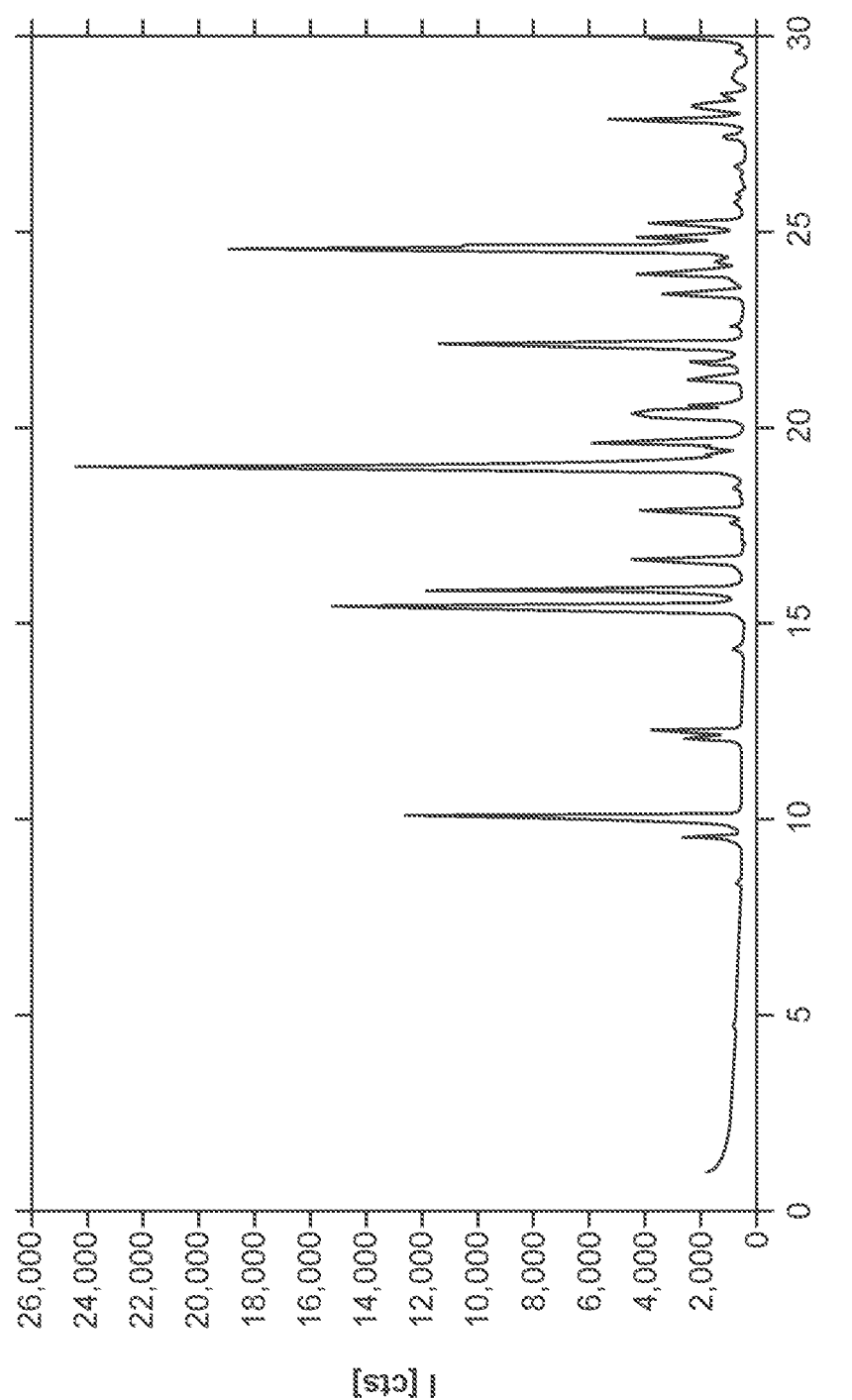
FIG. 8 is an X-ray powder diffractogram of Compound I benzathine Material A.
Figure 9:
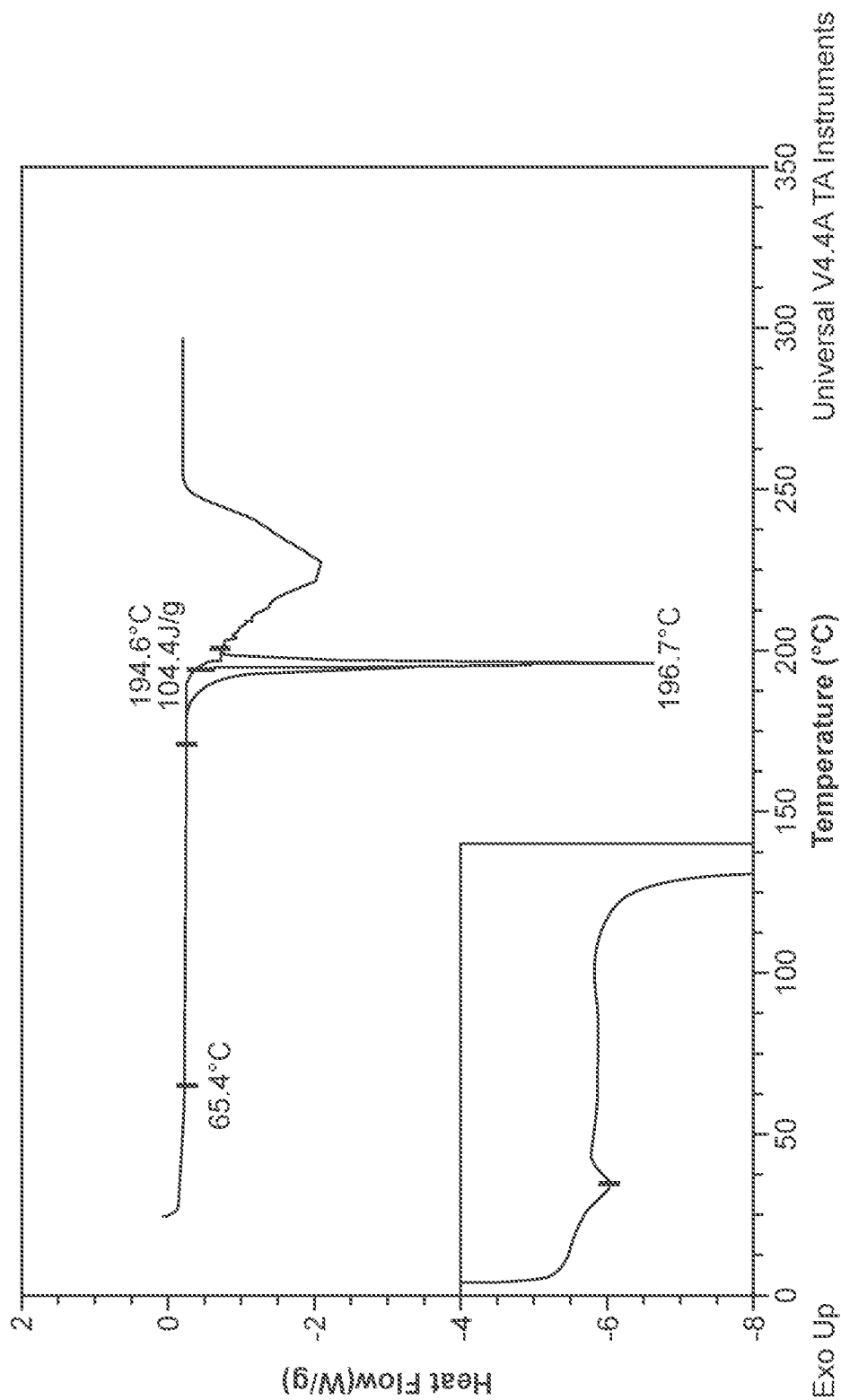
FIG. 9 is a differential scanning calorimeter (DSC) curve of Compound I benzathine Material A.
Figure 10:
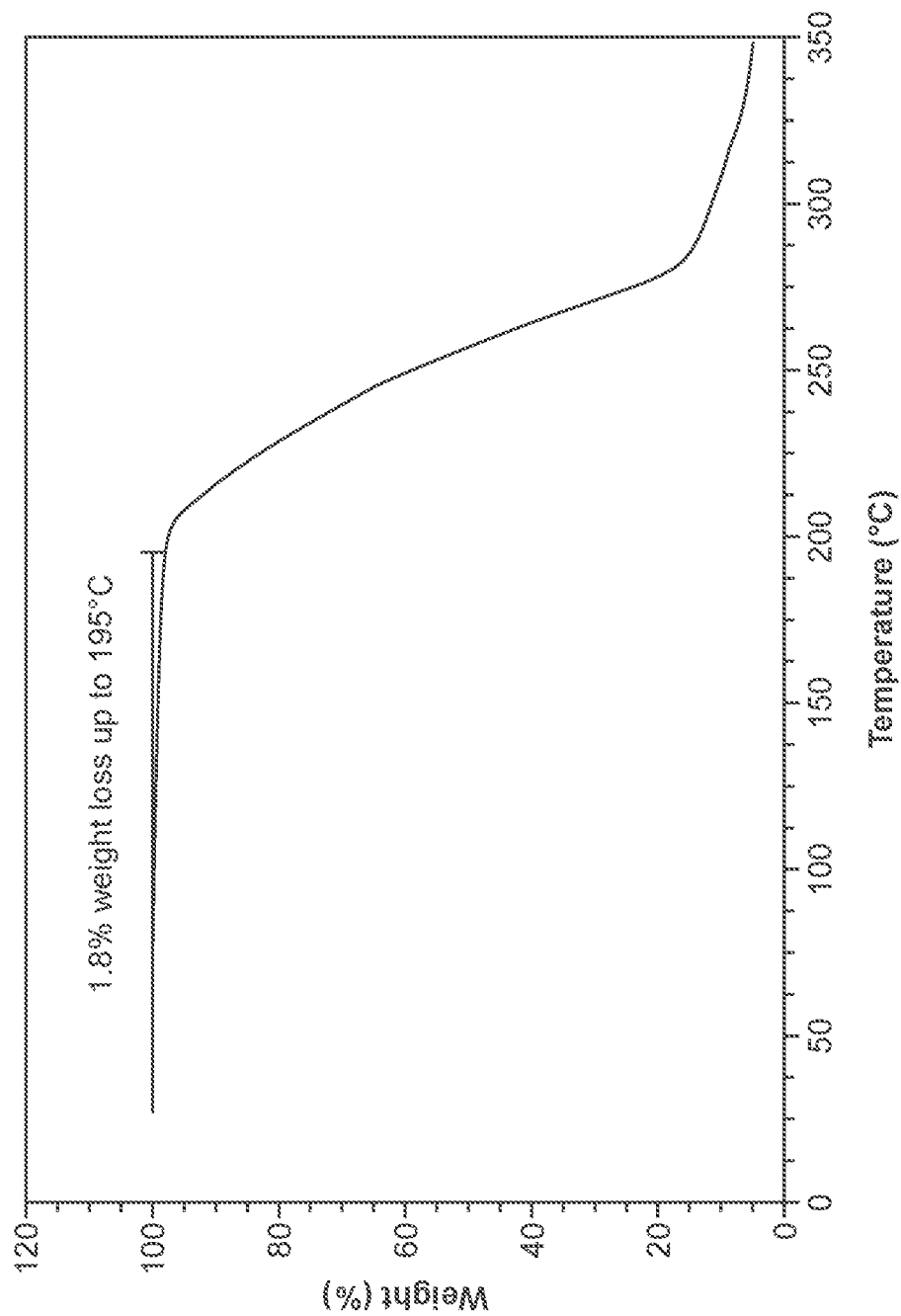
FIG. 10 is a thermogravimetric analysis (TGA) of Compound I benzathine Material A.

Compound I benzathine Material A is formed as described in Table 4, in one embodiment. Compound I benzathine Material A is crystalline as determined via XRPD analysis (FIG. 8). Compound I benzathine Material A can be characterized by an X-ray powder diffractogram comprising the following peaks: 10.07, 19.04, and 24.58°2θ±0.2°2θ. The DSC curve for Compound I benzathine Material A shows an endotherm with onset at about 195° C., and an additional endotherm with a peak at about 65° C. (FIG. 9). TGA analysis of Compound I benzathine Material A shows a weight loss of about 1.8% up to about 195° C. (FIG. 10).

5.3 Compound I Diethanolamine Form A

Figure 11:
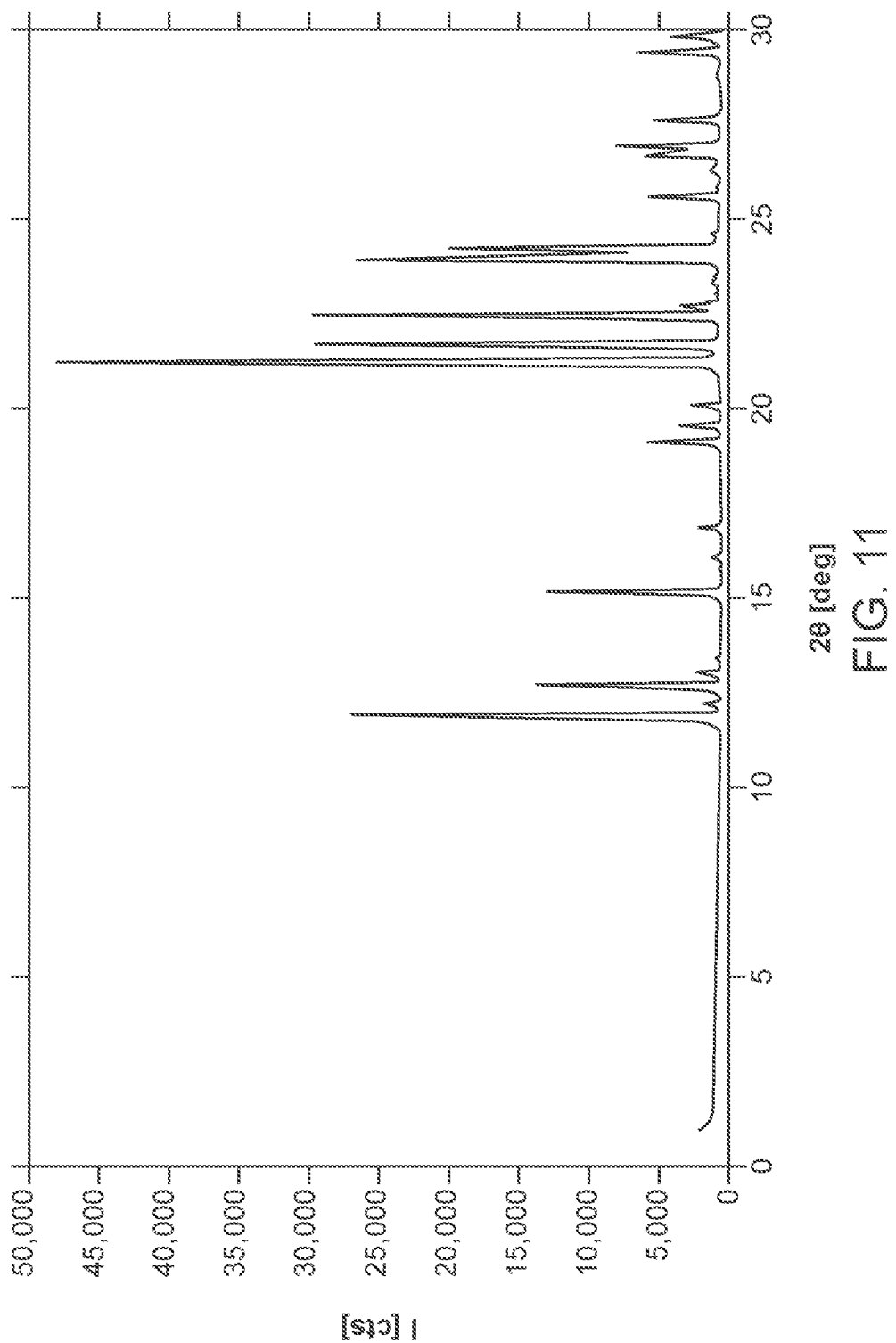
FIG. 11 is an X-ray powder diffractogram of Compound I diethanolamine Form A.
Figure 12:
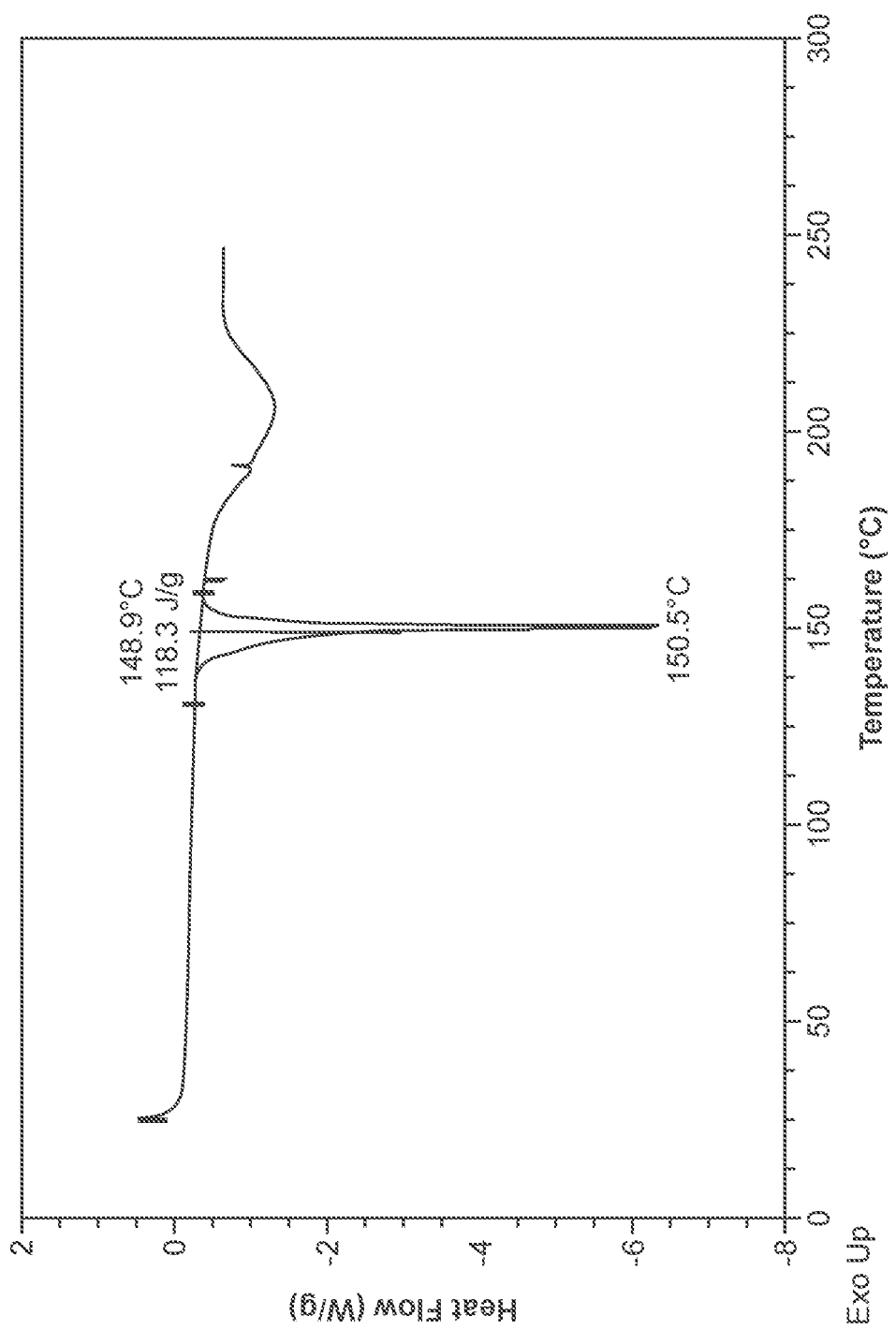
FIG. 12 is a differential scanning calorimeter (DSC) curve of Compound I diethanolamine Form A.
Figure 13:
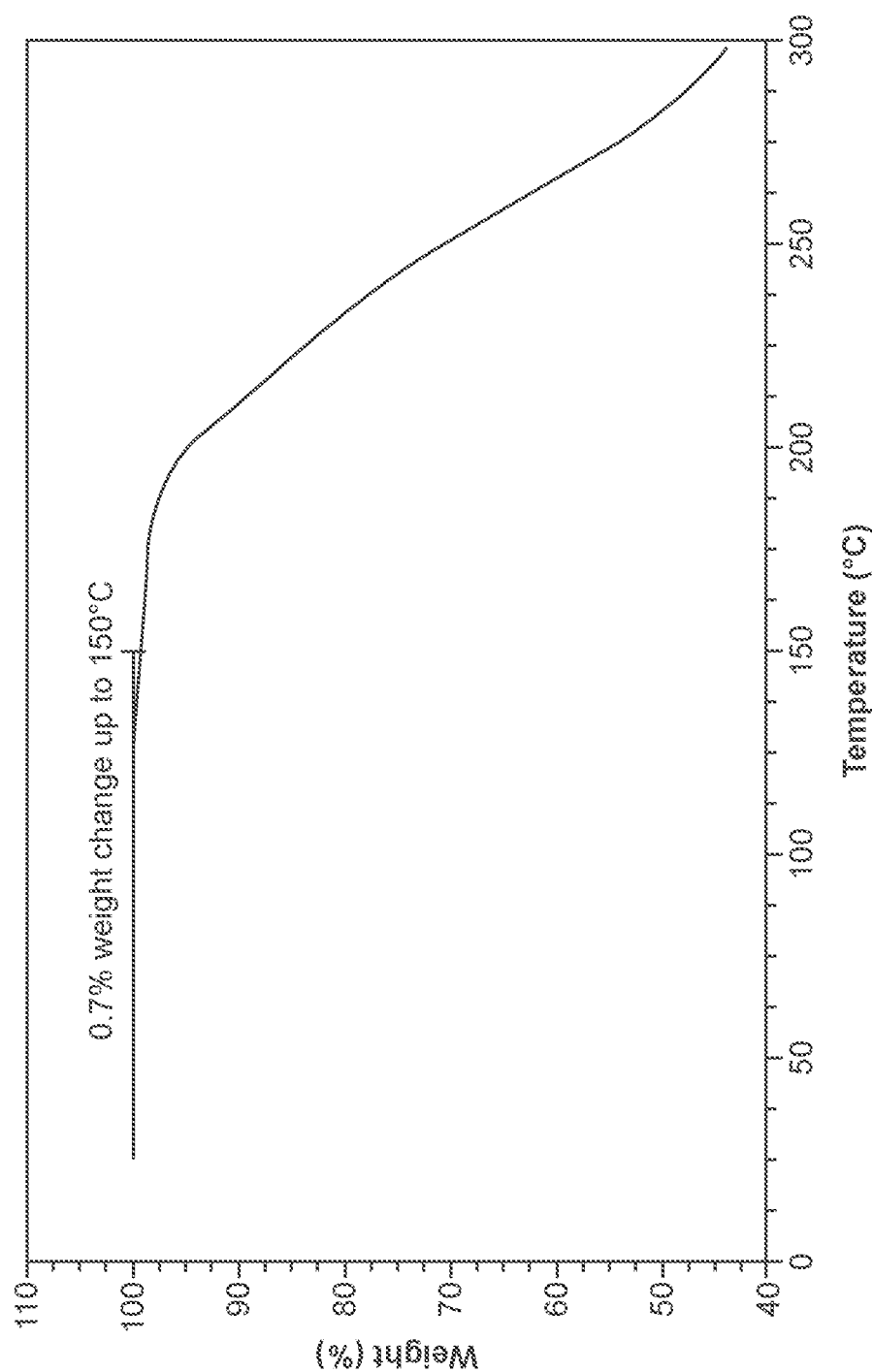
FIG. 13 is a thermogravimetric analysis (TGA) of Compound I diethanolamine Form A.

Compound I diethanolamine Form A is formed as described in Table 4, in one embodiment. Compound I diethanolamine Form A is crystalline as determined via XRPD analysis (FIG. 11). Compound I diethanolamine Form A can be characterized by an X-ray powder diffractogram comprising the following peaks: 11.90, 21.25, and 23.96°2θ±0.2°2θ. The DSC curve for Compound I diethanolamine Form A shows an endotherm with onset at about 149° C. (FIG. 12). TGA analysis of Compound I diethanolamine Form A shows a weight loss of about 0.7% up to about 150° C. (FIG. 13).

Compound I diethanolamine Form A was determined to be not hygroscopic by DVS analysis (FIG. 14), as said form gained or lost negligible weight through the sorption and desorption cycle. Moreover, the Compound I diethanolamine Form A material recovered from the DVS analysis was substantially the same as the starting material by XRPD, suggesting that phase change did not occur.

5.4 Compound I Diethylamine Material A

Figure 15:
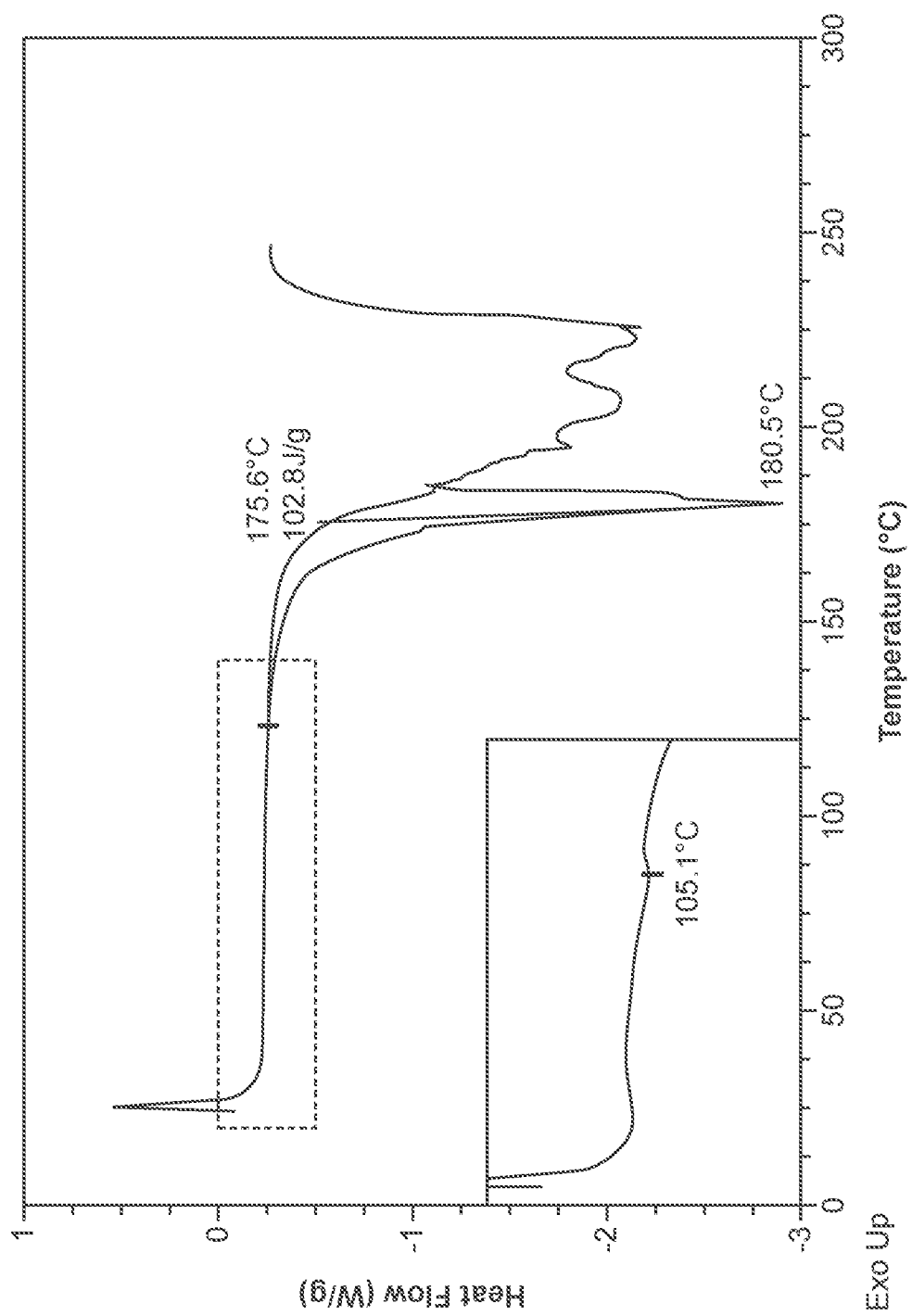
FIG. 15 is a differential scanning calorimeter (DSC) curve of Compound I diethylamine Material A.
Figure 16:
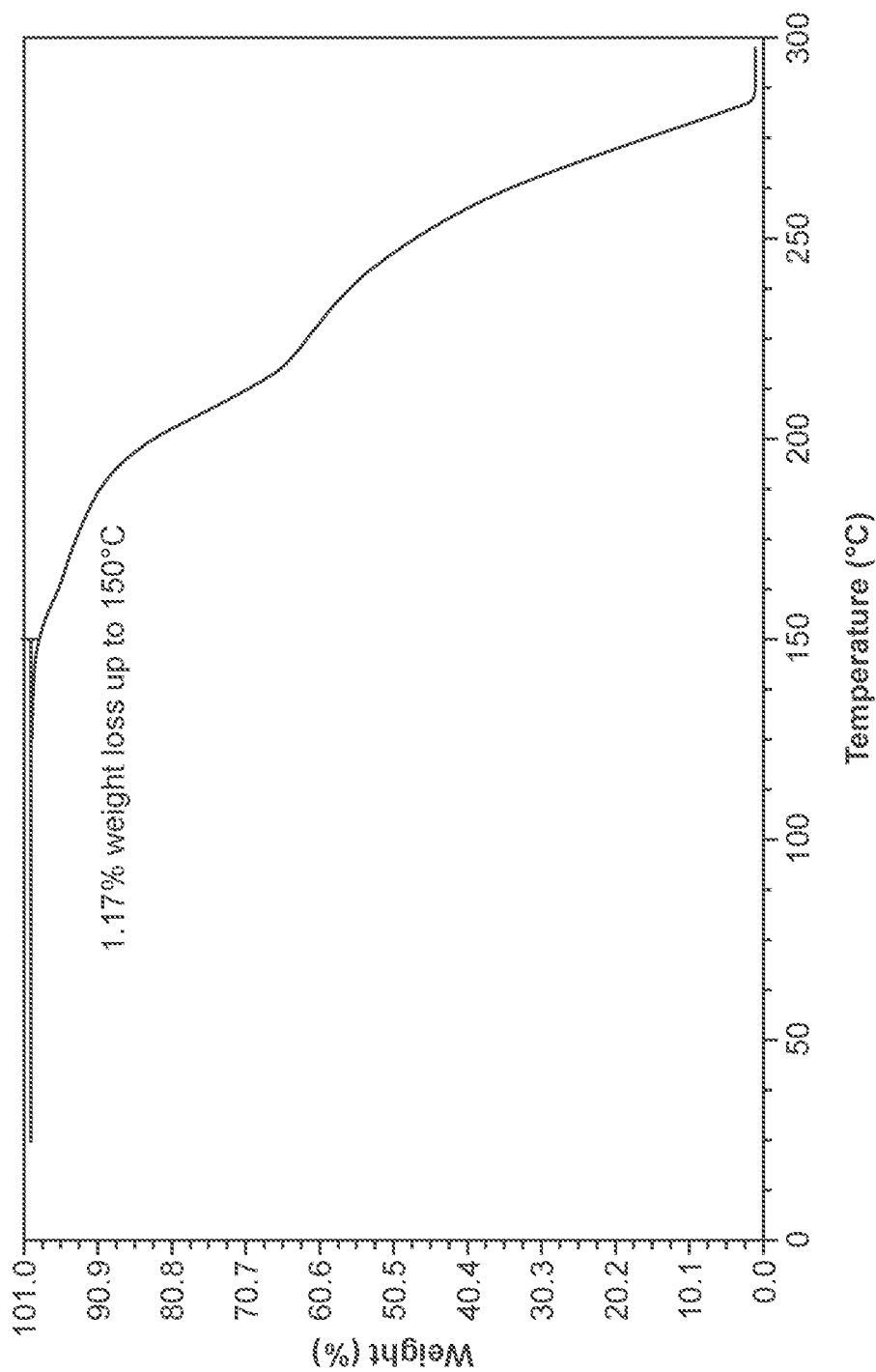
FIG. 16 is a thermogravimetric analysis (TGA) of Compound I diethylamine Material A.

Compound I diethylamine Material A is formed as described in Table 4, in one embodiment. Compound I diethylamine Material A is crystalline as determined via XRPD analysis (FIG. 7B). Compound I diethylamine Material A can be characterized by an X-ray powder diffractogram comprising the following peaks: 6.21, 11.30, and 13.25°2θ±0.2°2θ. The DSC curve for Compound I diethylamine Material A shows an endotherm with onset at about 176° C., and an additional endotherm with a peak at about 105° C. (FIG. 15). TGA analysis of Compound I diethylamine Material A shows a weight loss of about 1.2% up to about 150° C. (FIG. 16).

Compound I diethylamine Material A was found to be hygroscopic by DVS analysis (FIG. 17), with nearly a 2 wt % gain observed, the majority of which occurred above 35% RH. Compound I diethylamine Material A did not reach equilibrium weight at the higher humidity steps, indicating that addition weight gains are possible. Compound I diethylamine Material A returned to its starting weight below 35% RH, and the Compound I diethylamine Material A material recovered from the DVS analysis was substantially the same as the starting material by XRPD suggesting that a phase change did not occur.

5.5 Compound I Ethanolamine Material A

Figure 18:
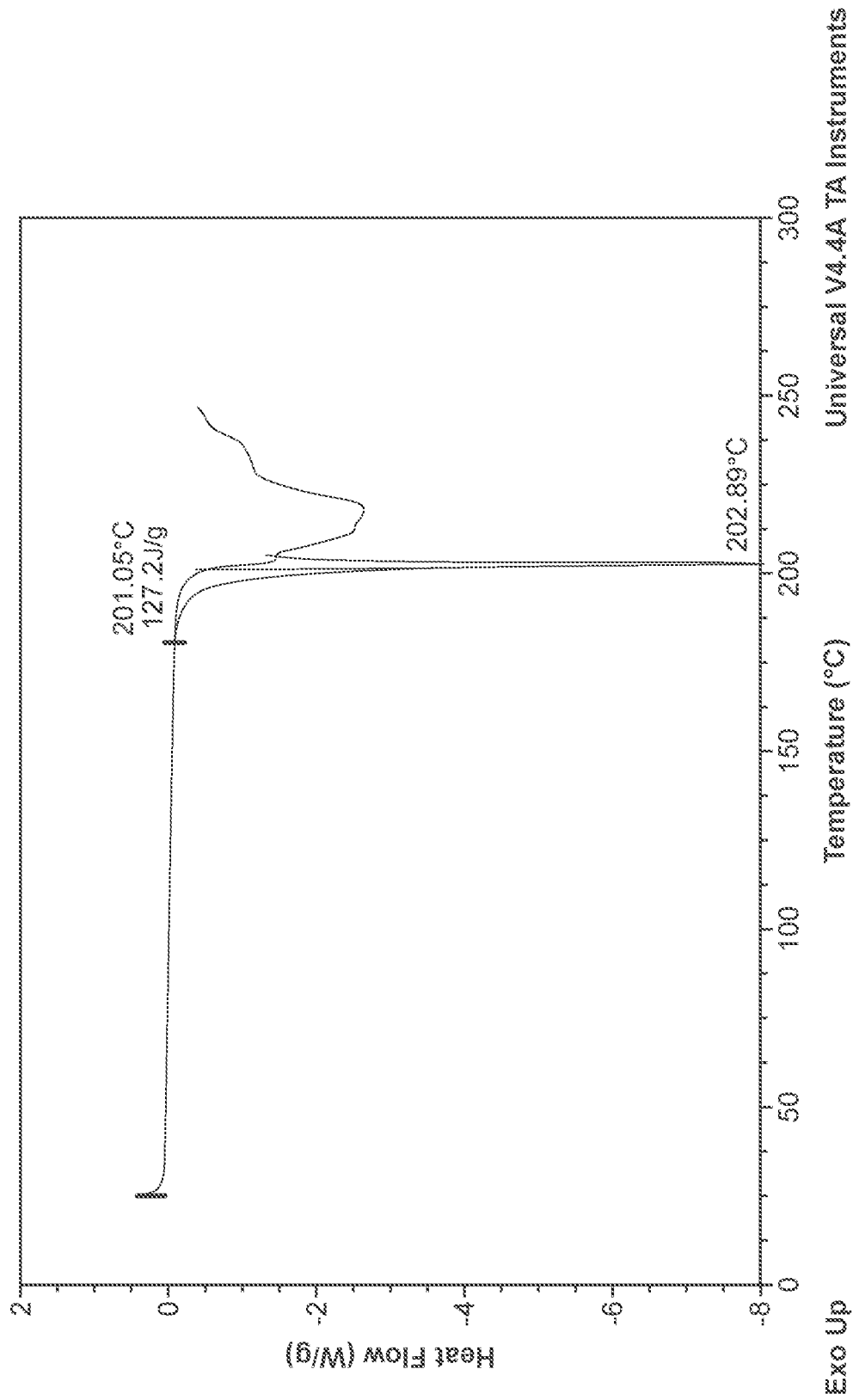
FIG. 18 is a differential scanning calorimeter (DSC) curve of Compound I ethanolamine Form A.
Figure 19:
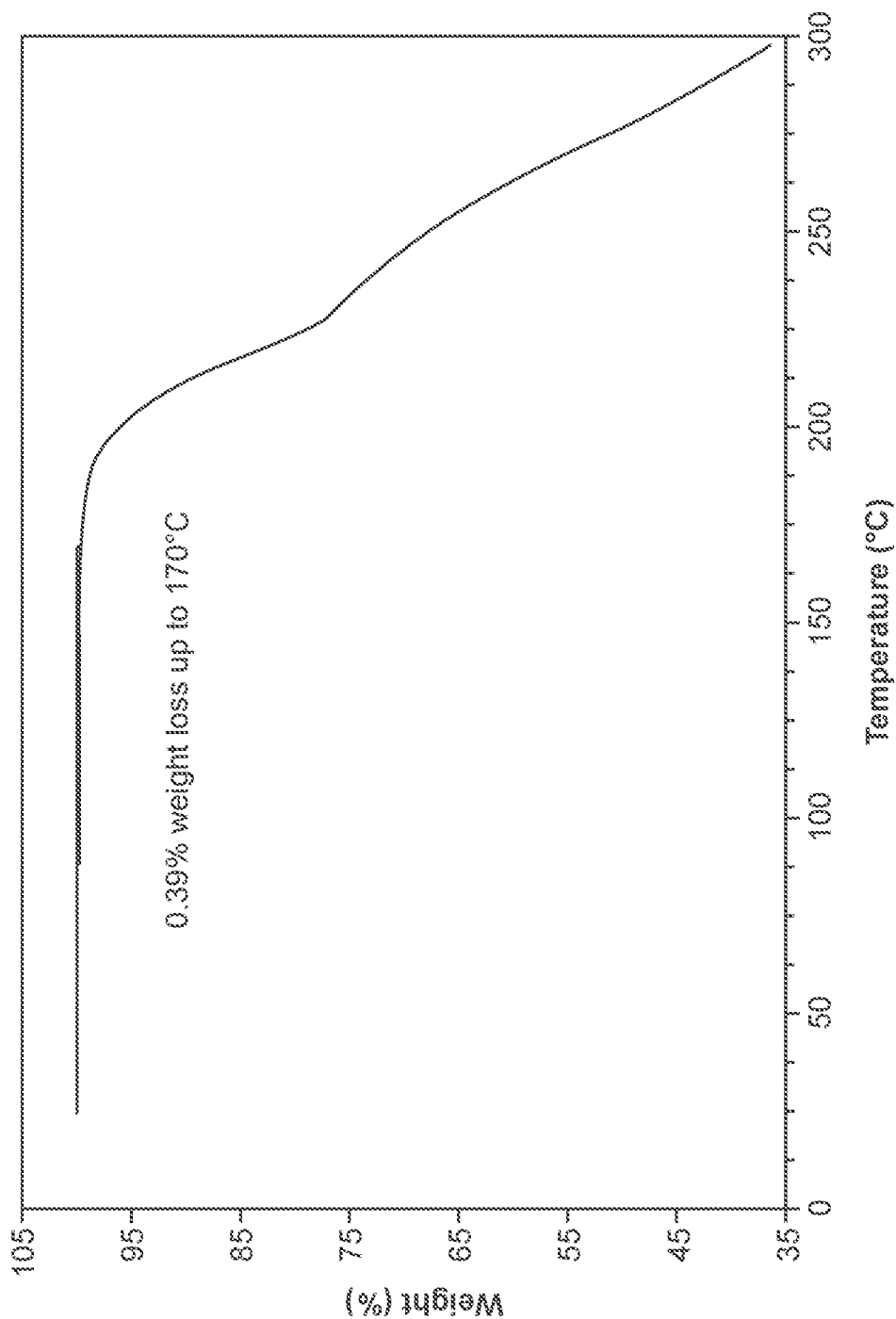
FIG. 19 is a thermogravimetric analysis (TGA) of Compound I ethanolamine Form A.

Compound I ethanolamine Material A is formed as described in Table 4, in one embodiment. Compound I ethanolamine Material A is crystalline as determined via XRPD analysis (FIG. 7C). Compound I ethanolamine Material A can be characterized by an X-ray powder diffractogram comprising the following peaks: 12.86, 21.14, and 24.95°2θ±0.2°2θ. The DSC curve for Compound I ethanolamine Material A shows an endotherm with onset at about 201° C. (FIG. 18). TGA analysis of Compound I ethanolamine Material A shows a weight loss of about 0.39% up to about 170° C. (FIG. 19).

5.6 Compound I Ethylenediamine Materials A+B

Figure 20:
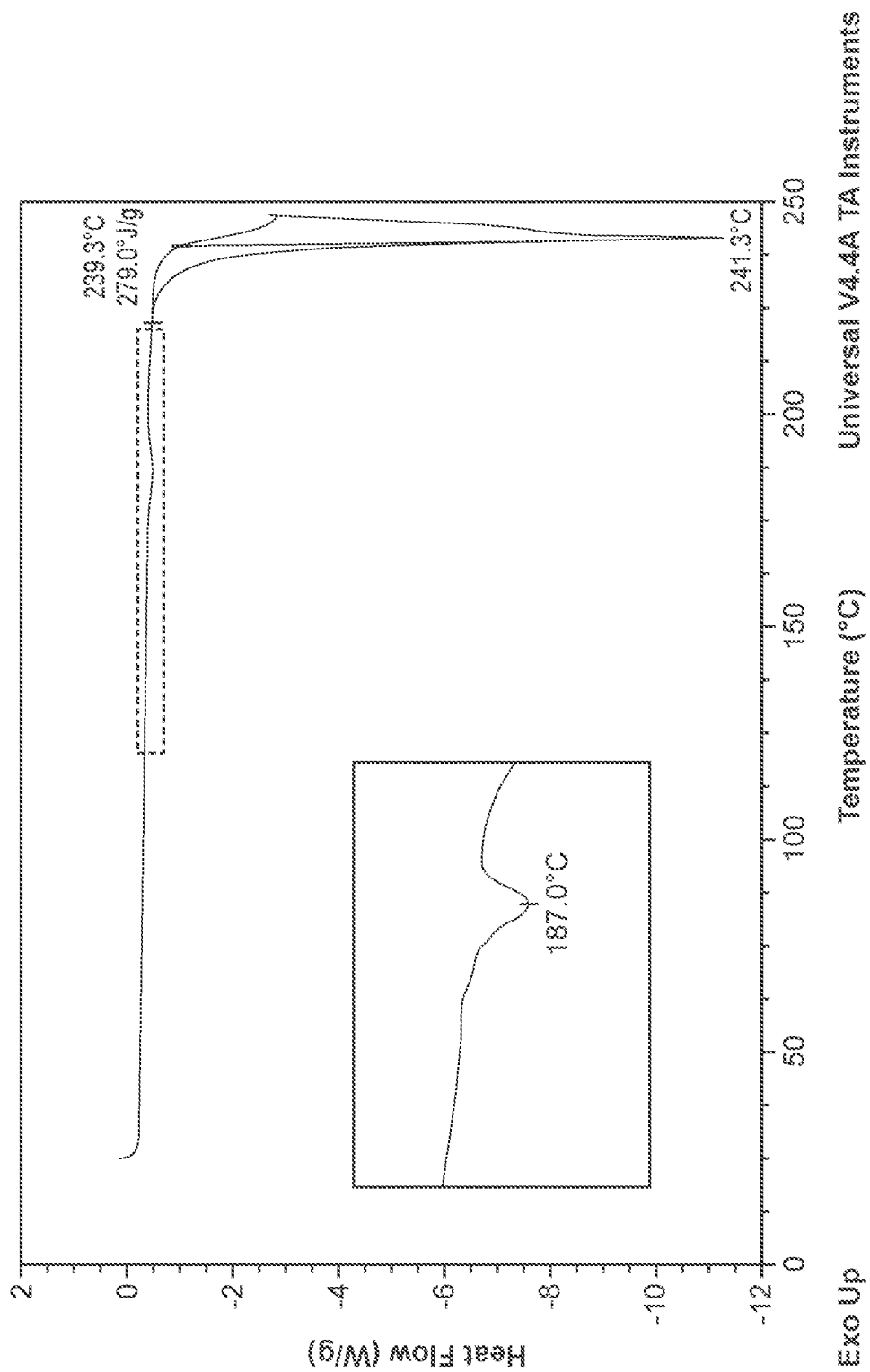
FIG. 20 is a differential scanning calorimeter (DSC) curve of Compound I ethylenediamine Materials A+B.
Figure 21:
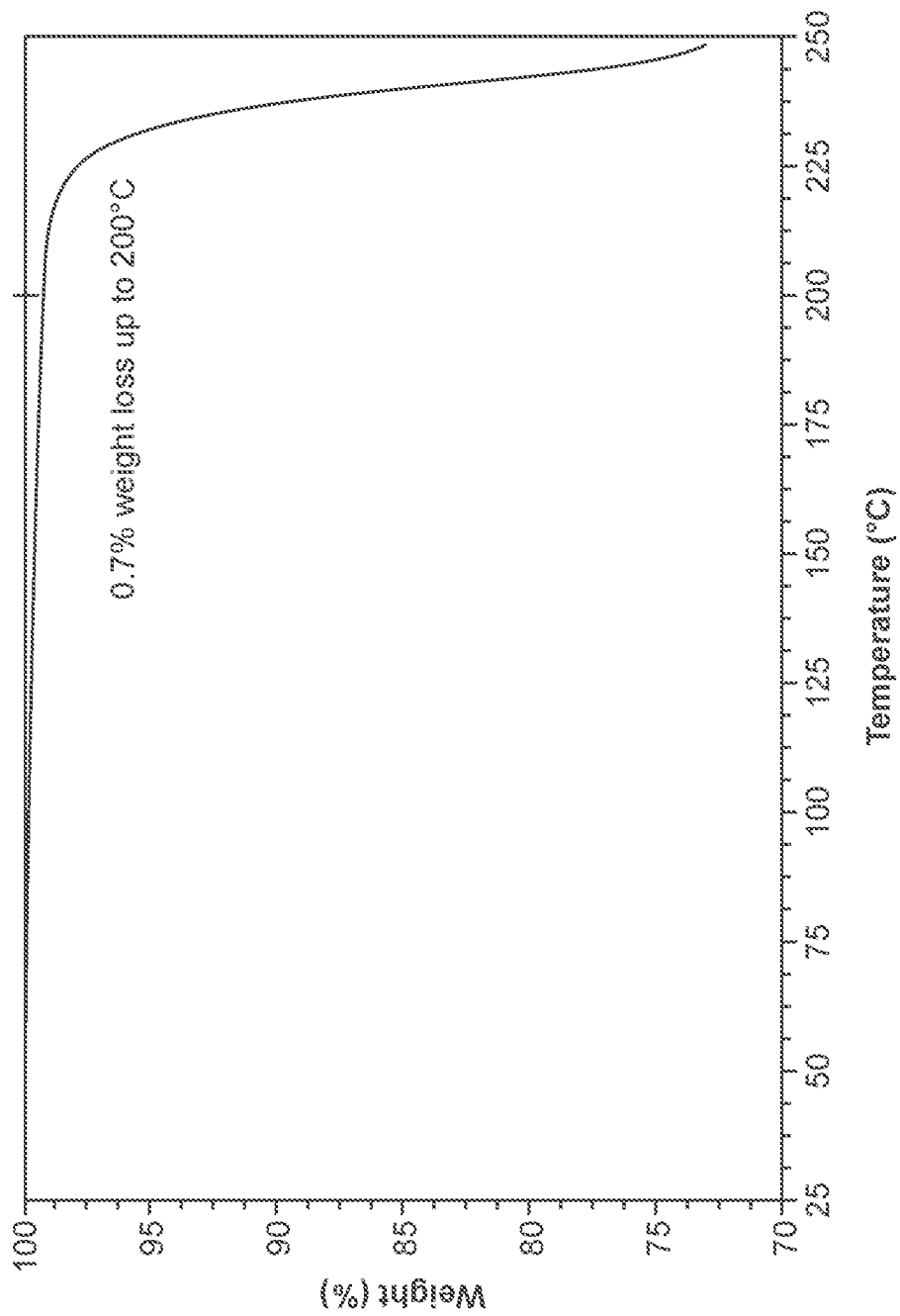
FIG. 21 is a thermogravimetric analysis (TGA) of Compound I ethylenediamine Materials A+B.

Compound I ethylenediamine Materials A+B is formed as described in Table 4, in one embodiment. Compound I ethylenediamine Materials A+B comprise a mixture of crystalline phases as determined via XRPD analysis (FIG. 7D). Compound I ethylenediamine Materials A+B can be characterized by an X-ray powder diffractogram comprising the following peaks: 13.03, 17.85, and 25.40°2θ±0.2°2θ. The DSC curve for Compound I ethylenediamine Materials A+B shows an endotherm with onset at about 239° C., and an additional endotherm with a peak at about 187° C. (FIG. 20). TGA analysis of Compound I ethylenediamine Materials A+B shows a weight loss of about 0.7% up to about 200° C. (FIG. 21).

5.7 Compound I Lysine Material A

Figure 22:
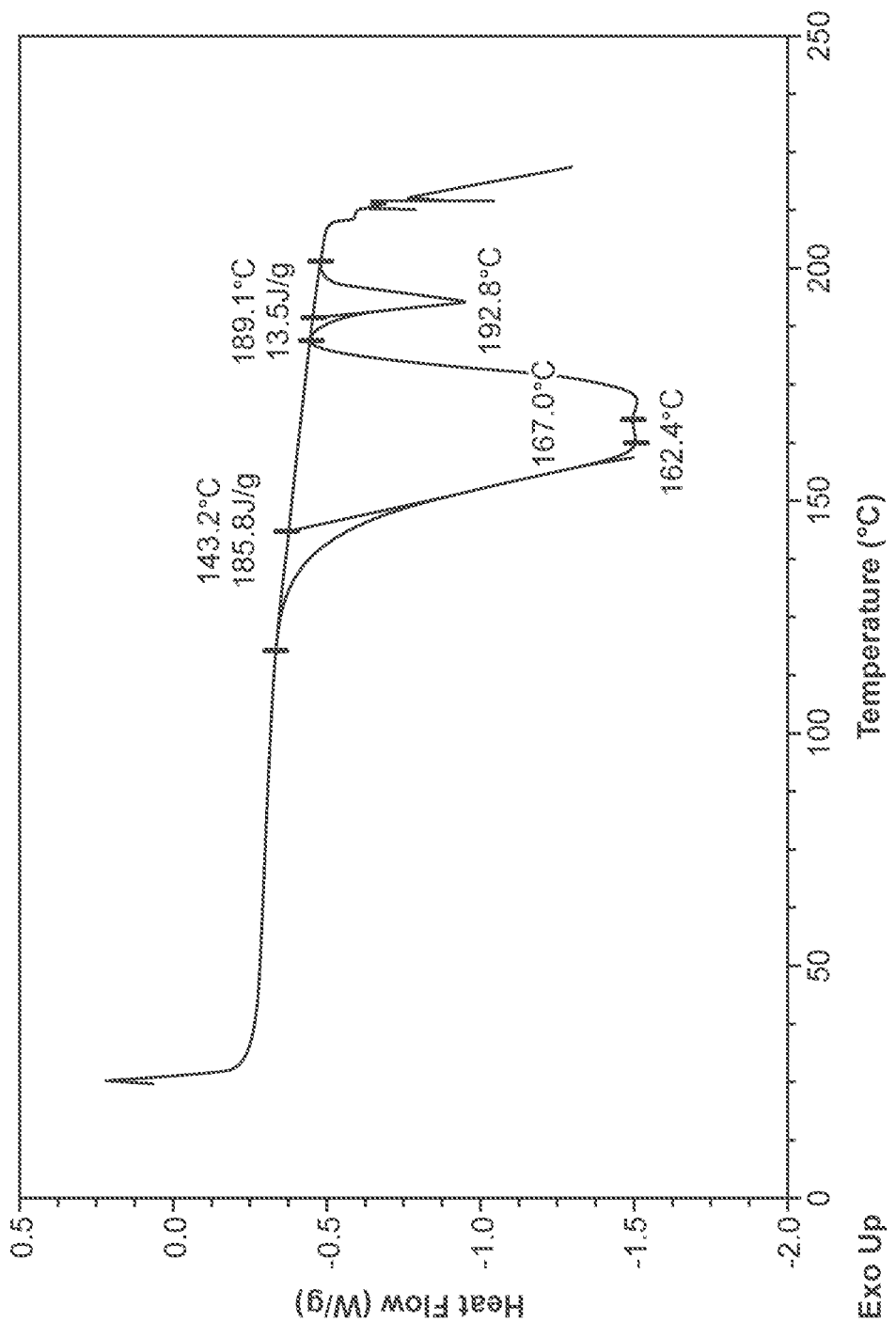
FIG. 22 is a differential scanning calorimeter (DSC) curve of Compound I lysine Material A.
Figure 23:
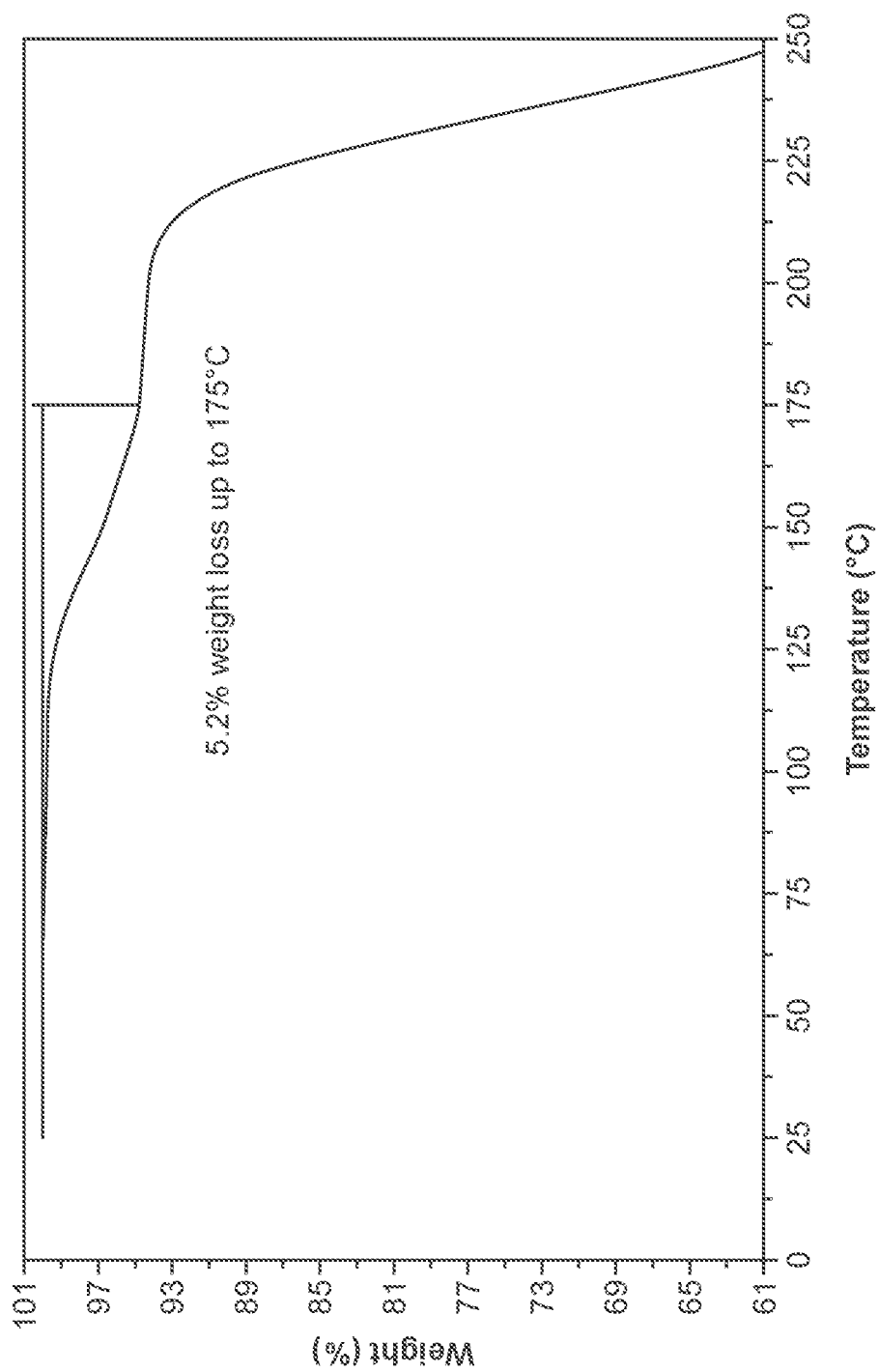
FIG. 23 is a thermogravimetric analysis (TGA) of Compound I lysine Material A.

Compound I lysine Material A is formed as described in Table 4, in one embodiment. Compound I lysine Material A is crystalline as determined via XRPD analysis (FIG. 7E). Compound I lysine Material A can be characterized by an X-ray powder diffractogram comprising the following peaks: 12.09, 23.82, and 26.00°2θ±0.2°2θ. The DSC curve for Compound I lysine Material A shows endotherms with onsets at about 189° C. and about 143° C., and an exotherm with a peak at about 167° C. (FIG. 22). TGA analysis of Compound I lysine Material A shows a weight loss of about 5.2% up to about 175° C. (FIG. 23).

5.8 Compound I Meglumine Material A

Figure 24:
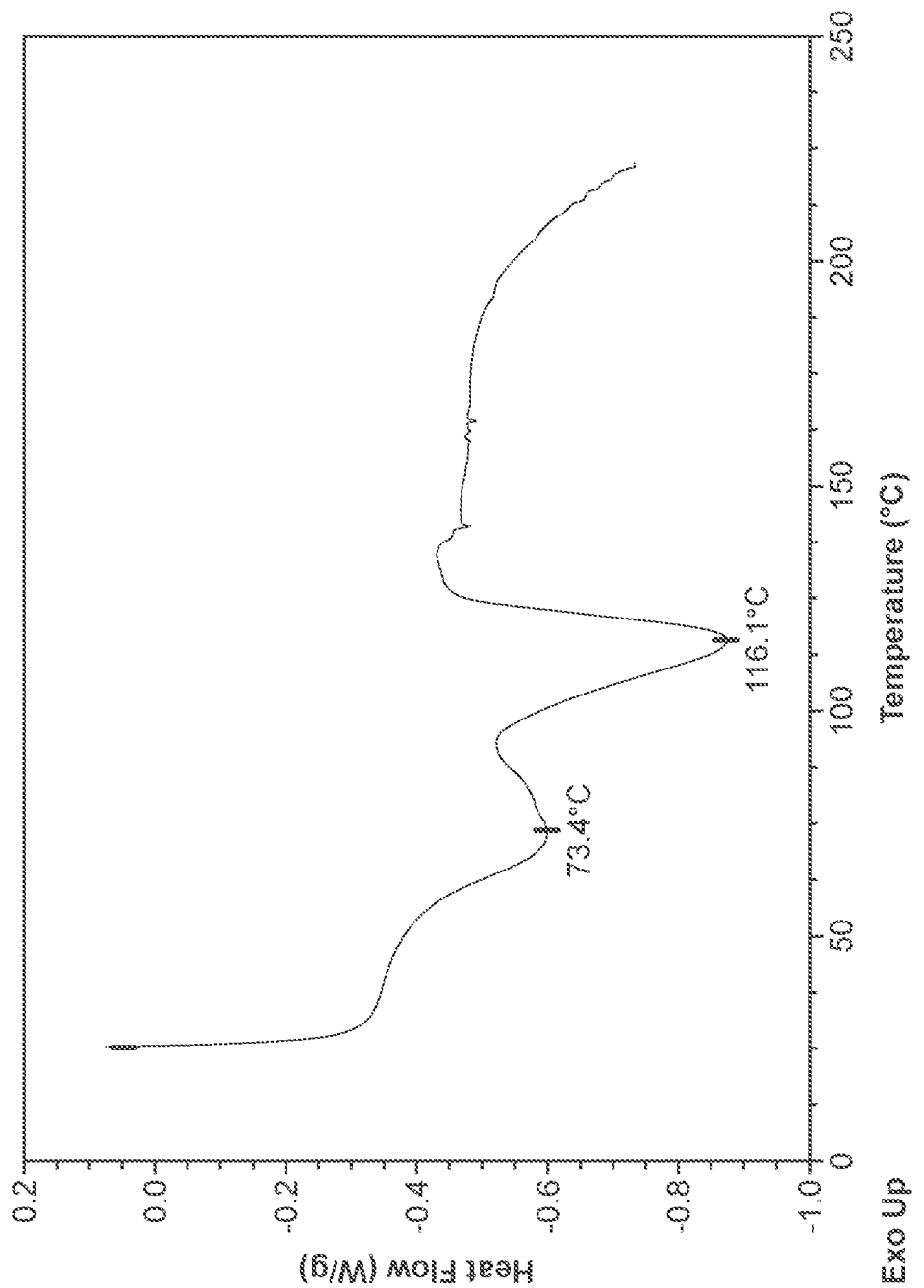
FIG. 24 is a differential scanning calorimeter (DSC) curve of Compound I meglumine Material A.
Figure 25:
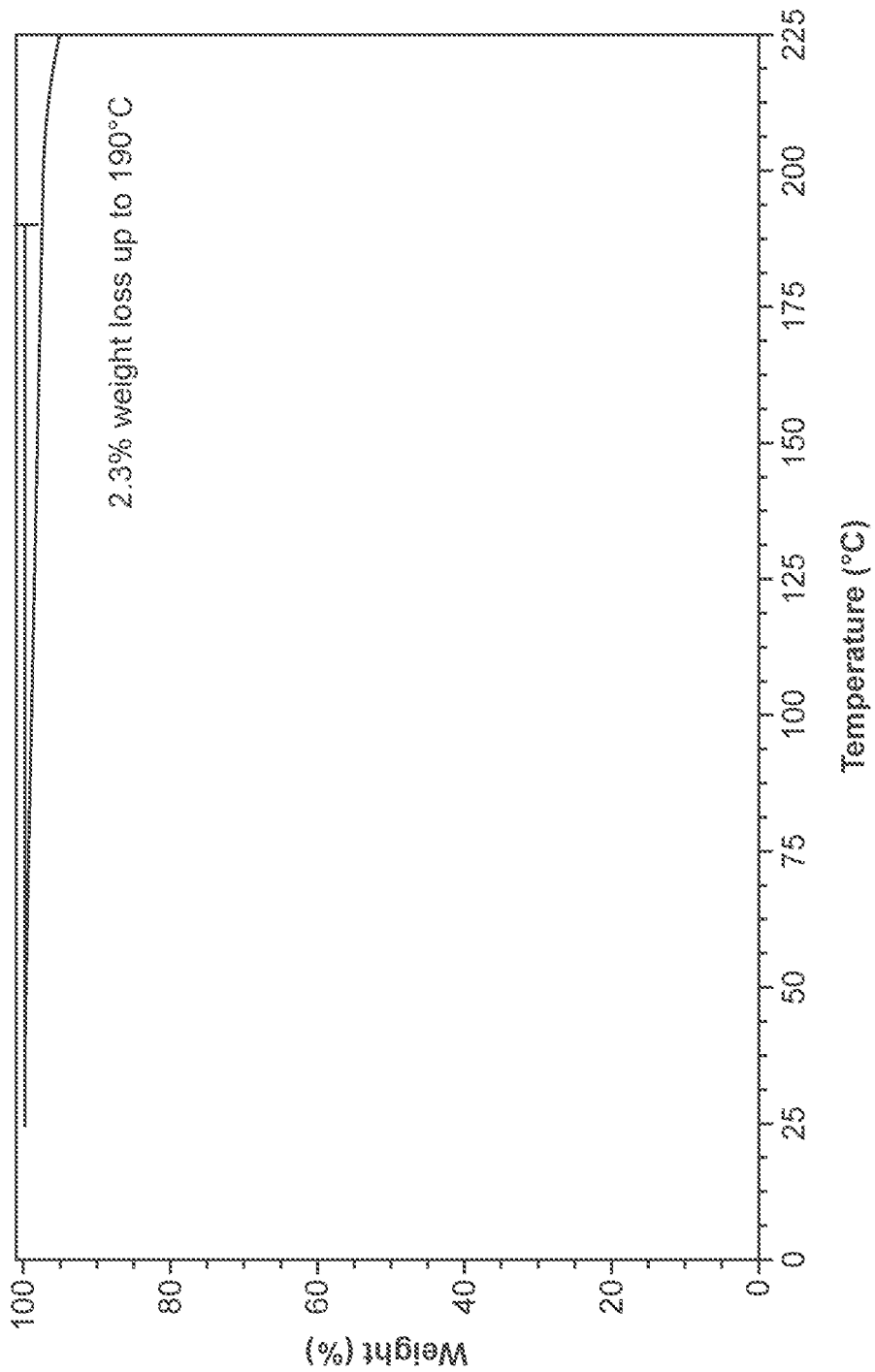
FIG. 25 is a thermogravimetric analysis (TGA) of Compound I meglumine Material A.

Compound I meglumine Material A is formed as described in Table 4, in one embodiment. Compound I meglumine Material A is crystalline as determined via XRPD analysis (FIG. 7F). Compound I meglumine Material A can be characterized by an X-ray powder diffractogram comprising the following peaks: 3.27, 9.14, and 18.38°2θ±0.2°2θ. The DSC curve for Compound I meglumine Material A shows endotherms with peaks at about 116° C. and about 73° C. (FIG. 24). TGA analysis of Compound I meglumine Material A shows a weight loss of about 2.3% up to about 190° C. (FIG. 25).

5.9 Compound I Potassium Material A

Figure 26:
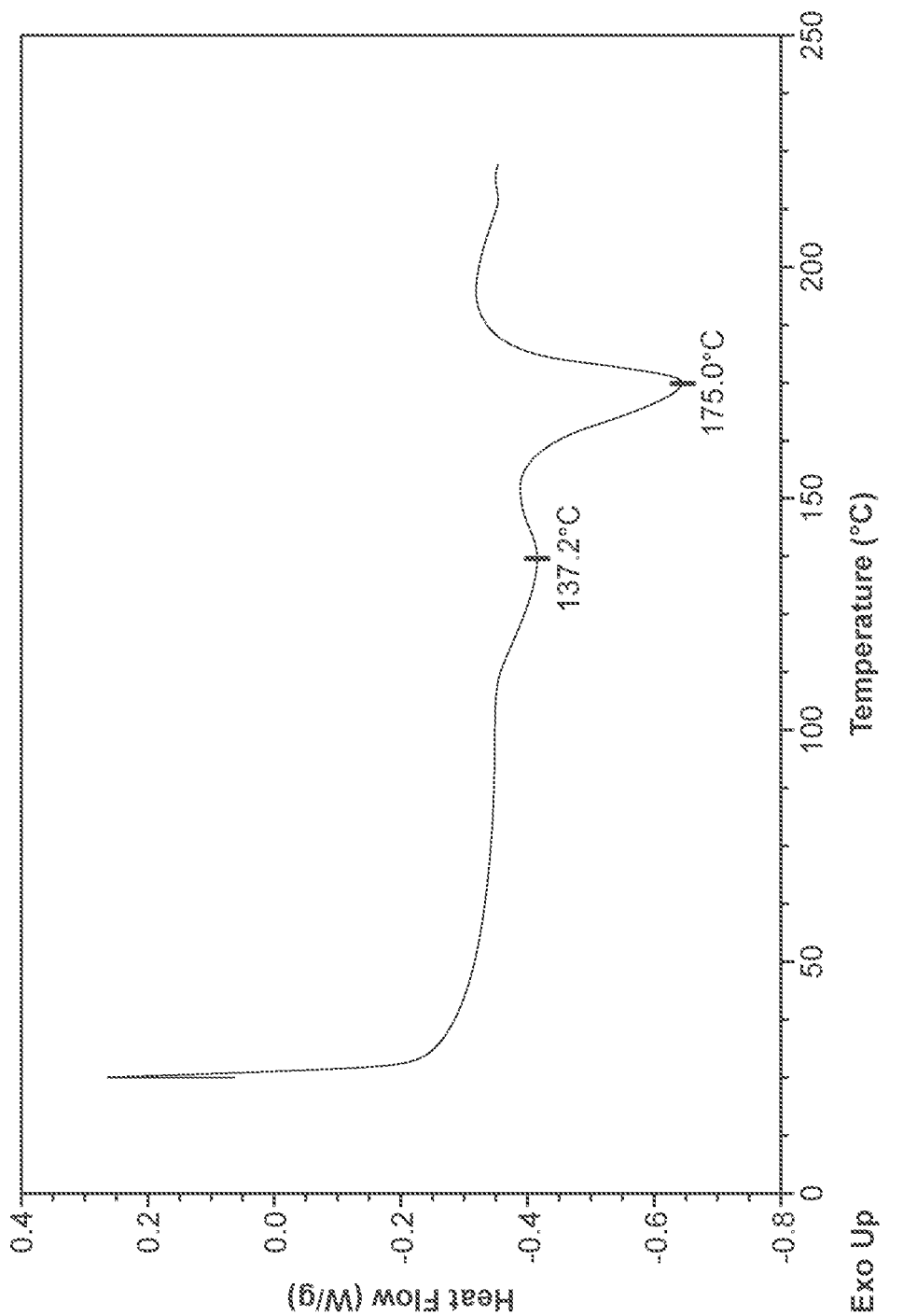
FIG. 26 is a differential scanning calorimeter (DSC) curve of Compound I potassium Material A.
Figure 27:
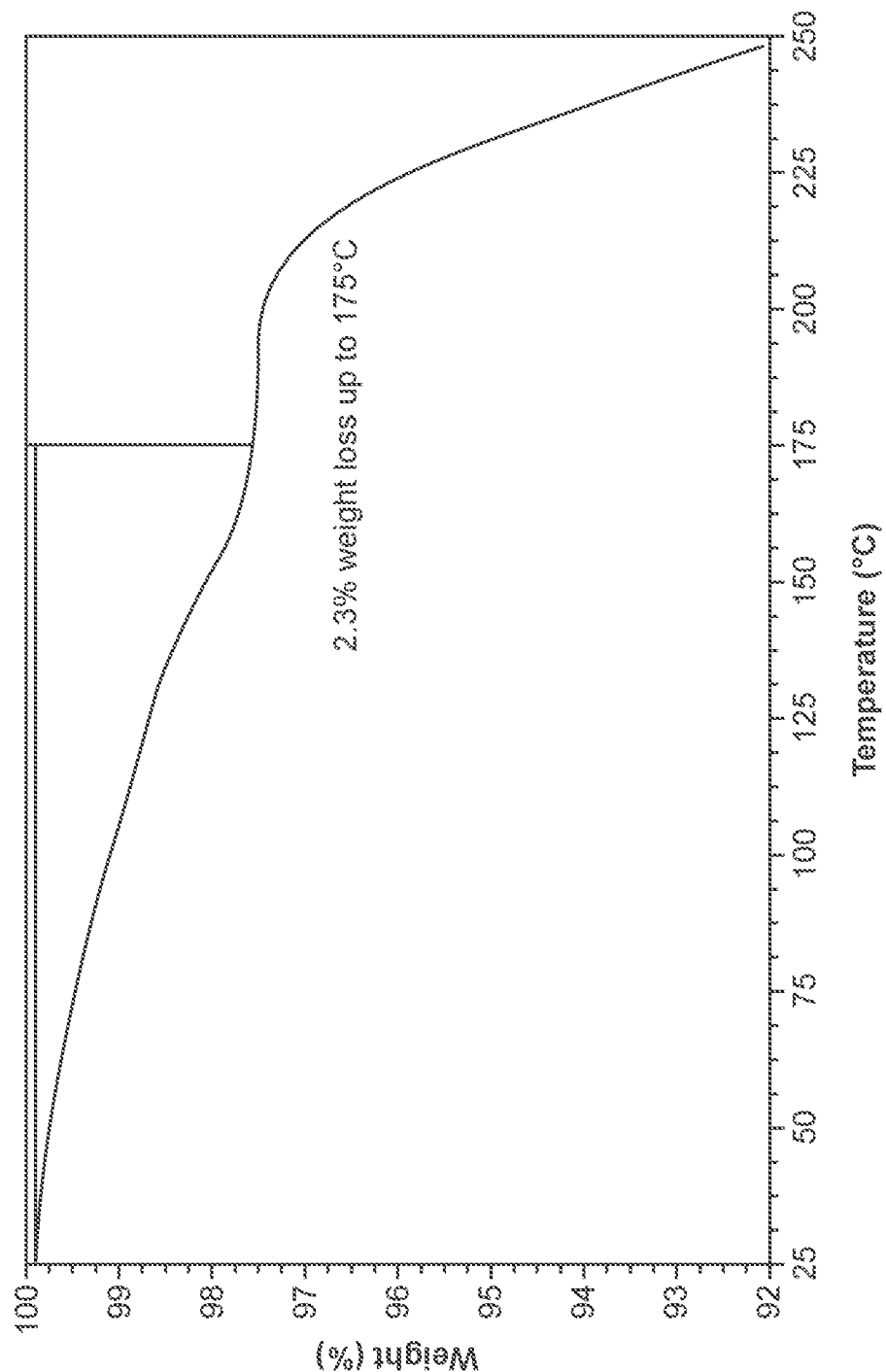
FIG. 27 is a thermogravimetric analysis (TGA) of Compound I potassium Material A.

Compound I potassium Material A is formed as described in Table 4, in one embodiment. Compound I potassium Material A is crystalline as determined via XRPD analysis (FIG. 7G). Compound I potassium Material A can be characterized by an X-ray powder diffractogram comprising the following peaks: 3.22, 9.71, and 24.13°2θ±0.2°2θ. The DSC curve for Compound I potassium Material A shows endotherms with peaks at about 175° C. and about 137° C. (FIG. 26). TGA analysis of Compound I potassium Material A shows a weight loss of about 2.3% up to about 175° C. (FIG. 27).

5.10 Compound I Tromethamine Form A

Figure 28:
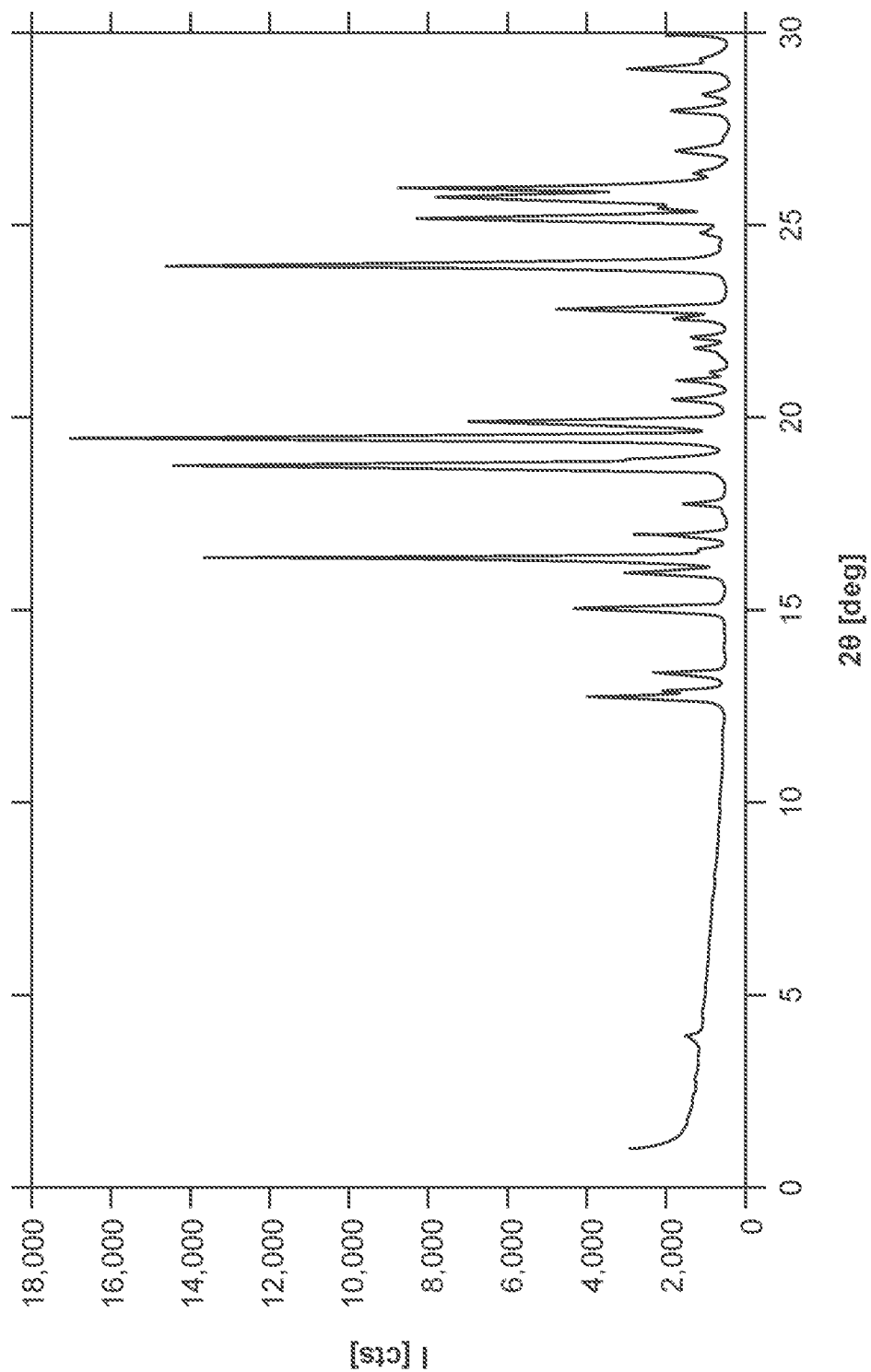
FIG. 28 is an X-ray powder diffractogram of Compound I tromethamine Form A.
Figure 29:
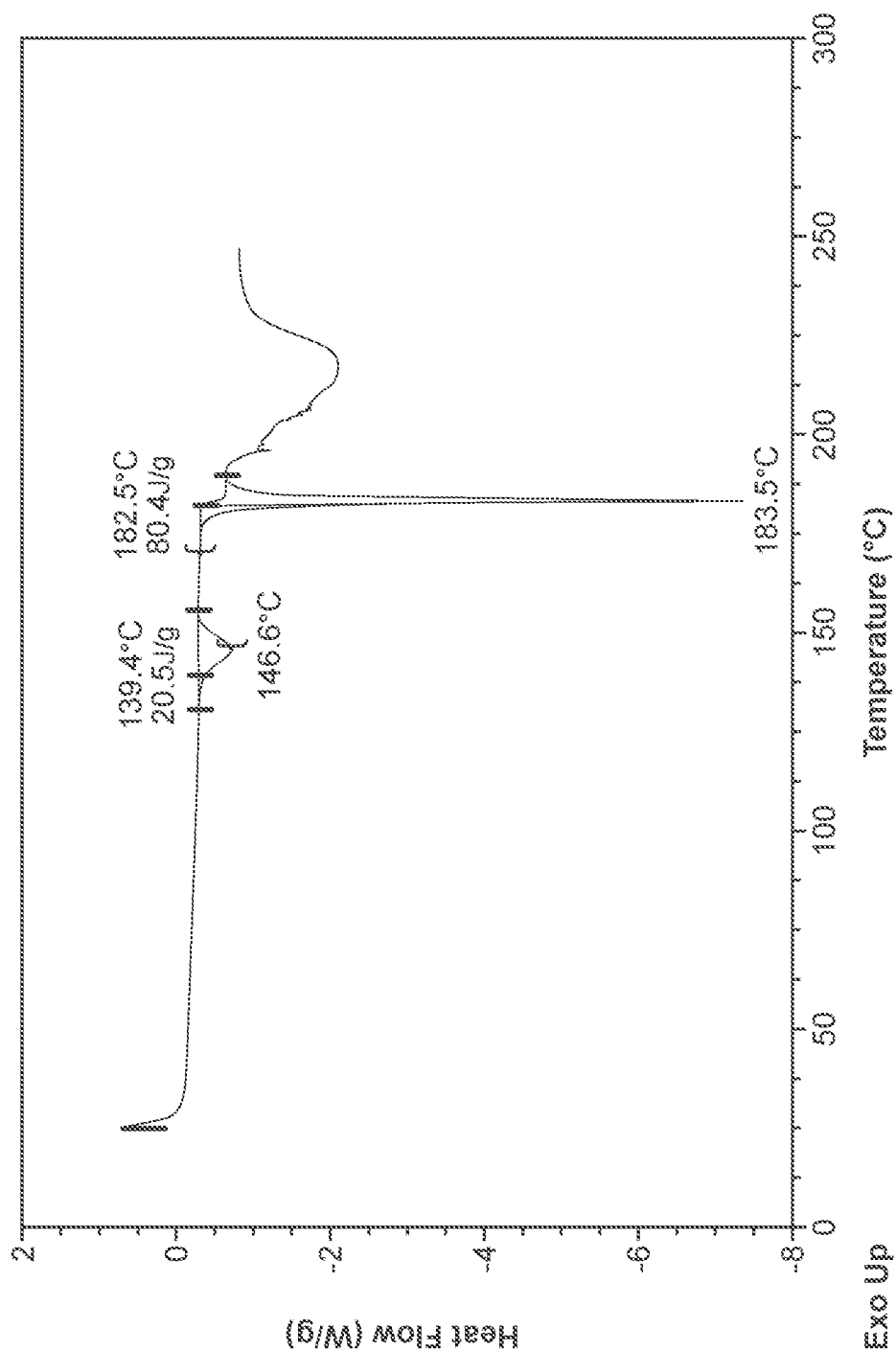
FIG. 29 is a differential scanning calorimeter (DSC) curve of Compound I tromethamine Form A.
Figure 30:
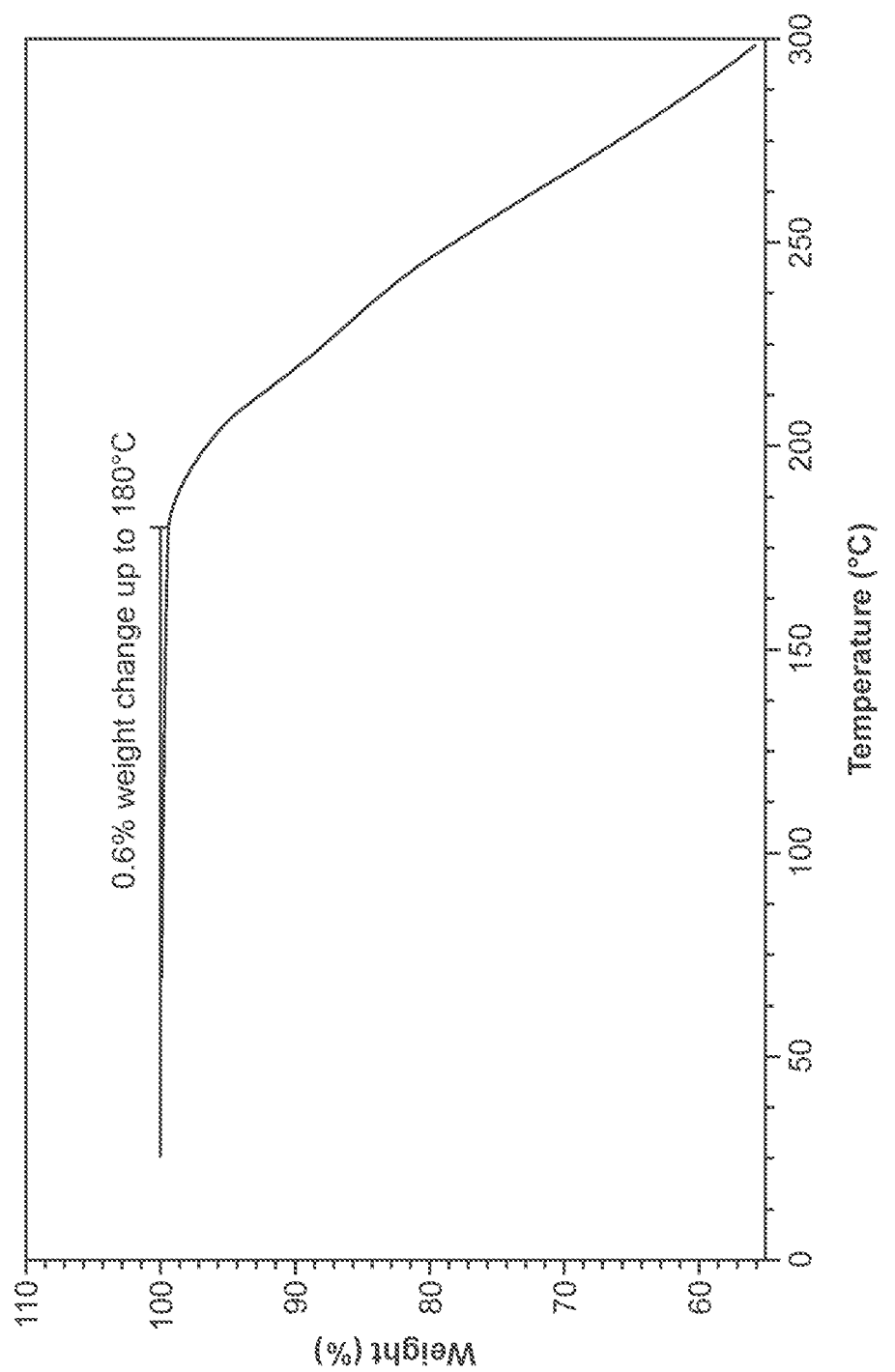
FIG. 30 is a thermogravimetric analysis (TGA) of Compound I tromethamine Form A.

Compound I tromethamine Form A is formed as described in Table 4, in one embodiment. Compound I tromethamine Form A is crystalline as determined via XRPD analysis (FIG. 28). Compound I tromethamine Form A can be characterized by an X-ray powder diffractogram comprising the following peaks: 16.38, 19.49, and 23.98°2θ±0.2°2θ. The DSC curve for Compound I tromethamine Form A shows endotherms with onsets about 183° C. and about 139° C. (FIG. 29). TGA analysis of Compound I tromethamine Form A shows a weight loss of about 0.6% up to about 180° C. (FIG. 30).

Compound I tromethamine Form A was determined to be not hygroscopic by DVS analysis (FIG. 31), as said form gained or lost negligible weight through the sorption and desorption cycle. Moreover, the Compound I tromethamine Form A material recovered from the DVS analysis was substantially the same as the starting material by XRPD, suggesting that phase change did not occur.

5.11 Compound I Sodium Form B

Compound I sodium Form B is formed as described in Tables 4 or 11, in one embodiment. Compound I sodium Form B may also be recrystallized as described in Table 10, in one embodiment.

Figure 37:
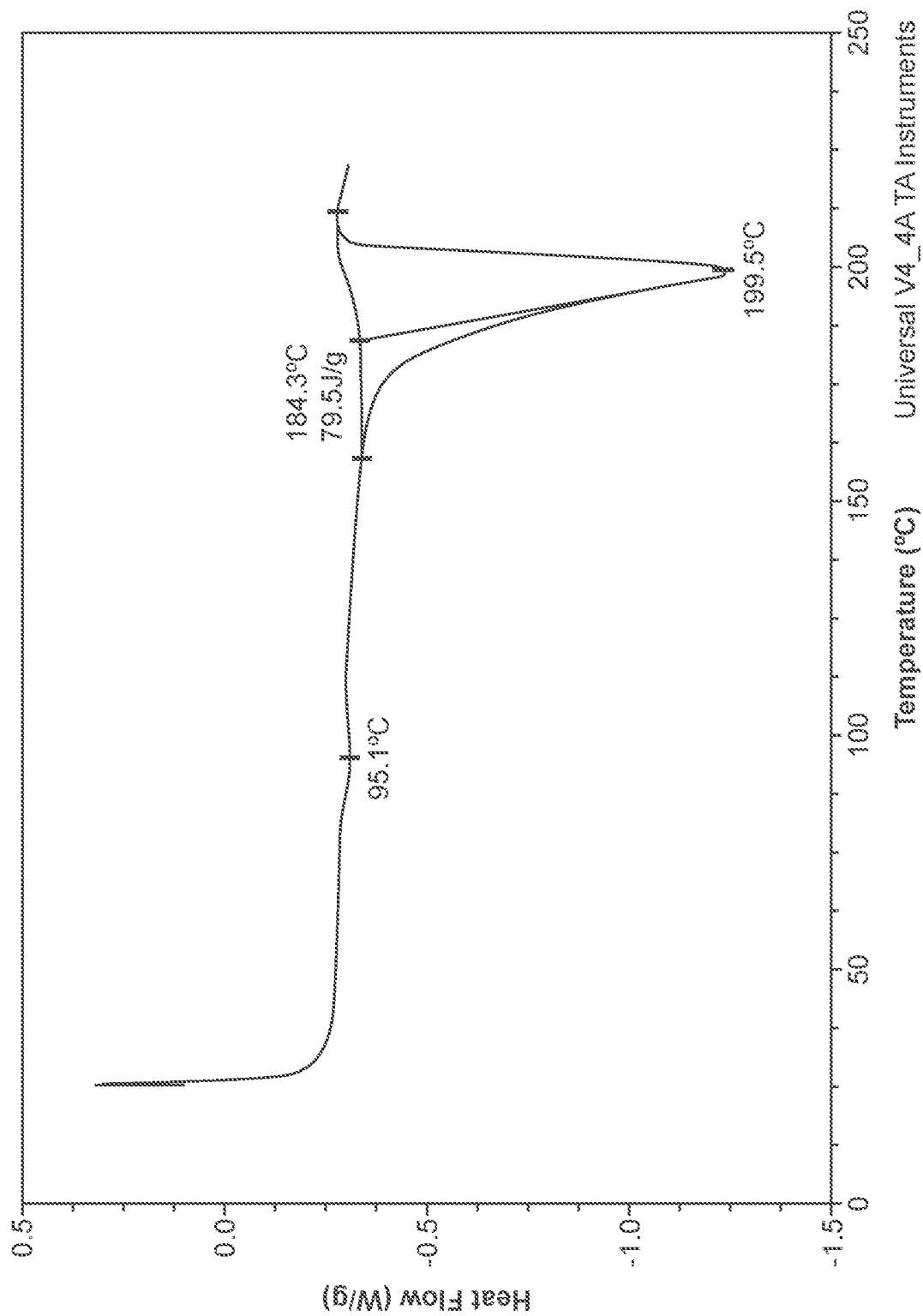
FIG. 37 is a differential scanning calorimeter (DSC) curve of Compound I sodium Form B.
Figure 38:
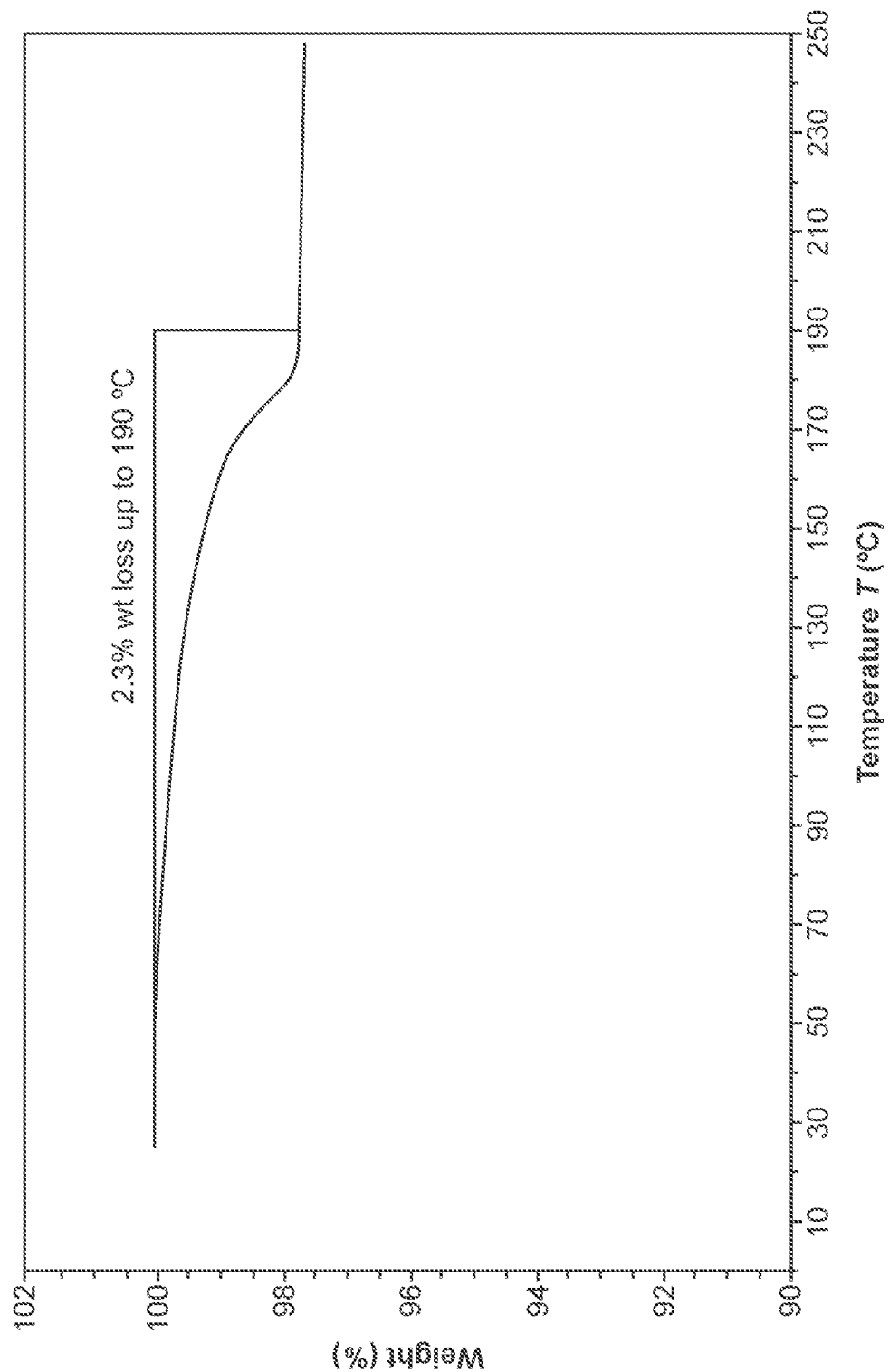
FIG. 38 is a thermogravimetric analysis (TGA) of Compound I sodium Form B.

Compound I sodium Form B is crystalline as determined via XRPD analysis (FIGS. 7H, 36). Compound I sodium Form B can be characterized by an X-ray powder diffractogram comprising the following peaks: 3.36, 8.90, and 18.30°2θ±0.2°2θ. The DSC curve for Compound I sodium Form B shows an endotherm with an onset about 184° C., and an additional endotherm with a peak at 95° C. (FIG. 37). TGA analysis of Compound I sodium Form B shows a weight loss of about 2.3% up to about 190° C., with the majority of the loss occurring above about 150° C. (FIG. 38).

Compound I sodium Form B was found to be hygroscopic by DVS analysis (FIG. 39), with nearly a 5 wt % gain observed. However, the majority of the weight gain occurred above 85% RH. Compound I sodium Form B did not reach equilibrium weight at the higher humidity steps, indicating that addition weight gains are possible. Compound I sodium Form B returned to its starting weight below 35% RH, and the Compound I sodium I Form B material recovered from the DVS analysis was substantially the same as the starting material by XRPD suggesting that a phase change did not occur.

In slurry experiments, Compound I sodium Form B was found to be stable for about at least seven days in IPA and acetone (see section 8/Table 13 below). Further, the relativity stability of Compound I sodium Form B in organic solvents indicated that Compound I sodium Pattern A is not a hydrated form.

No chemical and physical form changes were observed for Compound I sodium Form B after storing the material at elevated temperatures (about 60° C. and about 78° C., e.g., as discussed in section 9/Tables 15 and 16 below).

6. Deliquescence of Salts/Co-Crystals of Compound I

The salts identified from the salt/co-crystal screen of Compound I (see section 4 above) were assessed visually for deliquescence during exposure to 75% RH at ambient temperature (Table 5). The salts did not appear to deliquesce within the 3 day exposure. The materials from these experiments were recovered and re-analyzed by XRPD to determine if changes in solid form occurred. No changes by XRPD were observed indicating that all ten putative salts were physically stable under the conditions evaluated.

TABLE 5

Deliquescence of Salts/Co-crystals of Compound I

| Material | Observation | Result |
|---|---|---|
| DL-Arginine A | no deliquescence | Arginine A minus peaks |
| Benzathine A | no deliquescence | Benzathine A |
| Diethanolamine A | no deliquescence | Diethanolamine A |
| Diethylamine A | no deliquescence | Diethylamine A |
| Ethanolamine A | no deliquescence | Ethanolamine A |
| Ethylenediamine B + A | no deliquescence | Ethylenediamine B + A |
| DL-Lysine A | no deliquescence | DL-Lysine A |
| Potassium A | no deliquescence | Potassium A |
| Sodium B | no deliquescence | Sodium B |
| Tromethamine A | no deliquescence | Tromethamine A |

7. Aqueous Solubility of Salts/Co-Crystals of Compound I

With the exception of Compound I Arginine Material A (a low yield did not provide enough material to evaluate further), the aqueous solubility of the of the salts identified from the salt/co-crystal screen of Compound I (see section 4 above) was estimated visually using a solvent addition method (Table 6). Four of the salt candidates provided adequate aqueous solubility or better: Compound I sodium Form B exhibited 4 mg/mL, Compound I diethylamine Material A exhibited nearly 30 mg/mL, Compound I tromethamine Form A exhibited nearly 134 mg/mL, and Compound I diethanolamine Form A was above 260 mg/mL. A small quantity of solids did nucleate from the solutions used for the solubility assessment of Compound I diethylamine Material A and Compound I tromethamine Form A; however, the quantity of solids was not sufficient to suggest that disproportionation occurred.

TABLE 6

Aqueous Solubility of Salts/Co-crystals of Compound I

| Material | Solubility (mg/mL) | Observation |
|---|---|---|
| Benzathine A | <7 | significant amount of solids remained |
| Diethanolamine A | >25 | no nucleation from solution |
|  | >264 | collected for solubility only |
| Diethylamine A | >30 | solution had minor nucleation |
| Ethanolamine A | <4 | — |
| Ethylenediamine B + A | <10 | significant amount of solids remained |
| DL-Lysine A | <4 | minimal solids |
| Potassium A | <4 | limited solids, added more solids |
| Sodium B | 4 | wispy aciculars formed, added more solids |
| Tromethamine A | >134 | solution: minor nucleation |

Solids remaining from the aqueous solubility assessment of Compound I benzathine Form A, Compound I ethylenediamine Materials A+B, Compound I potassium Material A, and Compound I sodium Form B were recovered from the mother liquor and reevaluated by XRPD for changes in solid form or for disproportionation (Table 7). Compound I benzathine Form A and Compound I sodium Form B remained unchanged by XRPD. Compound I ethylenediamine A+B disproportionated, as peaks similar to those observed for Compound I free acid Material C were observed. Compound I potassium Material A converted to a new material but only a few broad peaks were observed.

TABLE 7

XRPD Analysis of Remaining Solids from Aqueous Solubility Assessments

| Material | Result |
|---|---|
| Benzathine A | Benzathine A |
| Ethylenediamine B + A | Ethylenediamine B + Free Acid C |
| Potassium A | broad reflections |
| Sodium B | Sodium B |

8. Stable Form Screen of Compound I Sodium Salt

A further polymorph screen was implemented to assess the various crystalline forms of the sodium salt of Compound I. Compound I sodium Pattern A or Compound I sodium Form B was provided as the starting material for the polymorph screen. The solubility of Compound I sodium Pattern A and Compound I sodium Form B in various solvents and/or binary solvent systems are provided in Tables 8 and 9, respectively.

TABLE 8

Solubility of Compound I Sodium Pattern A

| Solvent | Temp | Solubility |
|---|---|---|
| Water | 60° C. | 10.0-20.0 mg/mL |
| MeOH |  | 5-6.7 mg/mL |
| EtOH |  | <1.3 mg/mL |
| IPA |  | <1.1 mg/mL |
| BuOH |  | <1.2 mg/mL |

TABLE 8-continued

Solubility of Compound I Sodium Pattern A

| Solvent | Temp | Solubility |
|---|---|---|
| ACN | | <1.2 mg/mL |
| THF | | <1.3 mg/mL |
| 2-MeTHF | | <1.1 mg/mL |
| EtOAc | | <1.1 mg/mL |
| IPAc | | <1.1 mg/mL |
| Acetone | | <1.3 mg/mL |
| MEK | | <1.3 mg/mL |
| MIBK | | <1.2 mg/mL |
| DCM | | <1.3 mg/mL |
| Toluene | | <1.1 mg/mL |
| MTBE | | <1.1 mg/mL |
| Heptane | | <1.2 mg/mL |
| c-Hexane | | <1.2 mg/mL |
| DMSO | | 7.5-11.3 mg/mL |
| DMF | | 5.8-7.7 mg/mL |
| NMP | | 10.3-20.5 mg/mL |

TABLE 9

Solubility of Compound I Sodium Form B

| Solvent | Temp | Solubility |
|---|---|---|
| Acetone | ambient | <2 mg/mL |
| Acetonitrile | | <2 mg/mL |
| Ethanol | | <2 mg/mL |
| Isopropanol | | <2 mg/mL |
| Methanol | | 6 mg/mL loading |
| Water | | 6 mg/mL loading |
| | | 2 mg/mL loading |
| Acetone | 55° C. | <2 mg/mL |
| Acetonitrile | | <2 mg/mL |
| Ethanol | | <2 mg/mL |
| Isopropanol | | <2 mg/mL |
| Acetone/water, 94:6 v/v | ambient | <2 mg/mL |
| Acetonitrile/water, 83:17 v/v | | 2 mg/mL |
| Ethanol/water, 88:12 v/v | | ~2 mg/mL |
| Isopropanol/water, 91:9 v/v | | <2 mg/mL |
| Acetone/water, 94:6 v/v | 55° C. | <2 mg/mL |
| Ethanol/water, 88:12 v/v | | ~2 mg/mL |
| Isopropanol/water, 91:9 v/v | | <2 mg/mL |

Solid forms of the sodium salt of Compound I were prepared using Compound I sodium Form A (Tables 10A-10C), Compound I sodium Form B (Table 11), or Compound I free acid (Material F or Material D, Table 12). It is of note that Compound I Material F was prepared from Compound I sodium Form B in a process involving: (i) dissolving Compound I sodium Form B in water, (ii) treating the solution with activated carbon, (iii) adding about 1.3 molar equivalents of HCl to the solution; (iv) isolating the resulting solids via filtration, and (v) rinsing the solids with water followed by drying the solid at about 50° C. in vacuum overnight. Compound I Material D was prepared from Compound I sodium Form B in a process involving: (i) dissolving Compound I sodium Form B in water heated to reflux, (ii) cooling the solution to about 85° C., (iii) filtering the solution through a 0.2 μm filter, (iv) adding about 1 molar equivalent of HCl to the solution, (v) isolating the resulting solids via filtration, and (vi) rinsing the solid with water.

The resulting forms of the sodium salt of Compound I as prepared by the processes in Tables 10A/B/C-12 are further described in sections 7.1-7.8.

TABLE 10A

Single Solvent Crystallization of Compound I Sodium Pattern A

| Cmpd. I Sodium Pattern A (mg) | Solvent | Vol (mL) | Temp (° C.) | Cooling | Precipitation/Isolation | XRPD |
|---|---|---|---|---|---|---|
| 31.7 | Water | 2.5 | 70 | Fast (refrigerated 4° C.) | Precipitate, filtered | A |
| 31.6 | MeOH | 6.0 | 60 | | Scratched, evaporated | Amorphous |
| 31.4 | DMSO | 2.5 | 70 | | Solution, insufficient for filtration | Amorphous |
| 31.7 | DMF | 4.5 | 70 | | Solution, insufficient for filtration | Amorphous |
| 30.0 | NMP | 4.0 | 70 | | Solution, insufficient for filtration | Amorphous |
| 31.7 | Water | 2.5 | 70 | Slow (20° C./hr) | Precipitate, filtered | A |
| 31.6 | MeOH | 6.0 | 60 | | Precipitate, filtered | A |
| 31.5 | DMSO | 2.5 | 70 | | Solution, insufficient for filtration | Amorphous |
| 32.9 | DMF | 4.5 | 70 | | Solution, insufficient for filtration | Amorphous |
| 30.2 | NMP | 4.0 | 70 | | Solution, insufficient for filtration | Not analyzed |

TABLE 10B

Binary Solvent Crystallization of Compound I Sodium Pattern A in Water (2.5 mL)

| Cmpd. I Sodium Pattern A (mg) | Solvent | Vol (mL) | Temp (° C.) | Cooling | Precipitation/Isolation | XRPD |
|---|---|---|---|---|---|---|
| 29.2 | MeOH | 5.0 | 70.0 | Fast cooing (refrigerated 4° C.) | Scratched, evaporated | A |
| 31.6 | EtOH | 5.0 | 70.0 | | Scratched, evaporated | A |
| 31.9 | IPA | 5.0 | 70.0 | | Scratched, evaporated | A |
| 30.8 | ACN | 5.0 | 70.0 | | Scratched, evaporated | A |
| 31.6 | THF | 5.0 | 70.0 | | Scratched, evaporated | A |
| 30.5 | Acetone | 5.0 | 70.0 | | Scratched, evaporated | A |
| 31.4 | DMSO | 5.0 | 70.0 | | Scratched, evaporated | B |
| 30.9 | DMF | 5.0 | 70.0 | | Scratched, evaporated | Amorphous |
| 30.3 | MeOH | 5.0 | 70.0 | Slow cooling (20° C./hr) | Scratched, evaporated | A |
| 31.5 | EtOH | 5.0 | 70.0 | | Scratched, evaporated | A |
| 31.2 | IPA | 5.0 | 70.0 | | Scratched, evaporated | A |
| 31.2 | ACN | 5.0 | 70.0 | | Scratched, evaporated | A |
| 30.8 | THF | 5.0 | 70.0 | | Scratched, evaporated | A |
| 30.6 | Acetone | 5.0 | 70.0 | | Scratched, evaporated | A |
| 31.3 | DMSO | 5.0 | 70.0 | | Scratched, evaporated | Amorphous |
| 32.1 | DMF | 5.0 | 70.0 | | Scratched, evaporated | Amorphous |

TABLE 10C

Binary Solvent Crystallization of Comp. I Sodium Pattern A in DMSO (2.0 mL)

| Solvent | Vol (mL) | Temp (° C.) | Cooling | Precipitation/Isolation | XRPD |
|---|---|---|---|---|---|
| Water | 4.0 | 70.0 | Fast cooling (refrigerated at 4° C. 24 hrs) | Solution, scratched, evaporated | B |
| MeOH | 4.0 | 70.0 | | Solution, scratched, evaporated | B |
| EtOH | 4.0 | 70.0 | | Gel, evaporated | B |
| IPA | 3.4 | 70.0 | | Gel, evaporated | B |
| BuOH | 4.0 | 70.0 | | Gel, evaporated | Amorphous |
| ACN | 0.5 | 70.0 | | Gel, evaporated | B |
| THF | 4.0 | 70.0 | | Gel, evaporated | Amorphous |
| EtOAc | 2.0 | 70.0 | | Solution, evaporated | B |
| Acetone | 1.0 | 70.0 | | Gel, evaporated | B |
| MEK | 2.5 | 70.0 | | Gel, evaporated | B |
| DCM | 1.0 | 70.0 | | Gel, evaporated | B |
| Toluene | 4.0 | 70.0 | | Gel, evaporated | B |
| MTBE | 2.0 | 70.0 | | | B |
| Water | 4.0 | 70.0 | Slow cooling (20° C./hr) | Solution, scratched, evaporated | |
| MeOH | 4.0 | 70.0 | | Solution, scratched, evaporated | |
| EtOH | 4.0 | 70.0 | | Solution, scratched, evaporated | |
| IPA | 3.4 | 70.0 | | Solution, evaporated | B |
| BuOH | 4.0 | 70.0 | | Solution, evaporated | Amorphous |
| ACN | 0.5 | 70.0 | | Solution, evaporated | Amorphous |
| THF | 4.0 | 70.0 | | Gel, evaporated | Amorphous |
| EtOAc | 2.0 | 70.0 | | Gel, evaporated | Amorphous |
| Acetone | 1.0 | 70.0 | | Solution, evaporated | Amorphous |
| MEK | 2.5 | 70.0 | | Gel, evaporated | Amorphous |
| DCM | 1.0 | 70.0 | | Solution, evaporated | Amorphous |
| Toluene | 4.0 | 70.0 | | Gel, evaporated | Amorphous |
| MTBE | 2.0 | 70.0 | | Gel, evaporated | Amorphous |

TABLE 11

Polymorph Form Screen of Compound I Sodium Form B

| Solvent | Method[a] | Observation[b] | Results |
|---|---|---|---|
| acetone | slurry, ambient, 2 weeks | fines, B | Form B |
| ACN | slurry, ambient, 2 weeks | fines, B | Form B |
| | slurry, 55° C., 19 days | fines, B, wet cake | Form B |
| DMSO | 1. slurry, ambient, 3 days 2. treated with IPE slurry, 1 week | 1. gel, B 2. irregular masses, B | Form B |
| IPA | slurry, 47° C., 4 days | fines, B | — |
| | slurry, 55° C., 7 days | — | Form B |
| HFIPA | fast evaporation | film, B | diffuse scatter |
| | 1. slow cool, 75° C. 2. warmed to ambient 3. treated with heptane 4. acetone added until single phase 5. evaporated | 1. froze in freezer 2. solution 3. two phase system 4. turbid formed gel plug 5. aggregated, wispy, B | Form B |
| | slurry, ambient, 1 day | solids dissolved, solids added, sample turned to paste on same day, waxy, B | diffuse scatter |

TABLE 11-continued

Polymorph Form Screen of Compound I Sodium Form B

| Solvent | Method[a] | Observation[b] | Results |
|---|---|---|---|
| | The above slurry was isolated and dried under $N_2$ with stirring | brittle after drying | diffuse scatter + Form B |
| MeOH | cooling of solution | flocculent, B limited insufficient for analysis | — |
| | fast evaporation | two distinct zones of nucleation, upper film, cracked pale, B lower level aggregates composed of wispy solids, B, some film | Form B + Form E |
| | slow evaporation | gel/film and areas of wispy solids, film, B | Form E + Form B |
| | slurry, ambient, 2 weeks | solids, NB | Pattern C + peaks |
| | slurry, ambient 1 day sub sample of slurry noted directly above (Pattern C + peaks) | wet cake, clump/paste, B | disordered |
| | 1. slurry, 80° C. seeds of Pattern C + peaks 2. cooled to ambient, slurry 4 days | 1. initial fines, solids clumped after seeding, upon heating increased in thickness 2. fines, B wet cake | Pattern C + peaks |
| MeOH | slurry, 67° C., 1 day | irregular clumps, B | Form B |
| MEK | slurry, 67° C., 1 day | — | Form B |
| TFE | fast evaporation (sub sample of slurry leading to diffuse scatter) | white to pale yellow film, B | diffuse scatter |
| | slurry, ambient, 2 weeks | fines, B, damp | Form B |
| | slurry, 75° C., 2 days | thin gel with striations, B, irregular feathered blades, B | diffuse scatter |
| | slurry, ambient, 2 weeks | fines, B | Form B |
| toluene | fast evaporation of above filtrate | fines, B | Form B |
| $H_2O$ | rinse of solids | — | Form B |
| | cooling of solution 1. refrigerated, 3 days 2. freezer 3. thawed 4. fast evaporation | 1. solution, readily formed "suds" 2. frozen 3. limited irregular masses of thin film B 4. film, irregular flakes, B | Form E |
| | 1. slow cool from 100° C. 2. vacuum dried ambient | 1. thick plug of solids, fines B 2. NB | Pattern A |
| | residual solution from glassware used to form Pattern A directly above | rapid nucleation, film gel like, B. | Form E |
| | slurry, ambient, 10 days | fines, B | Form E |
| IPA/ acetic acid 80:10 v/v | 1. dissolved in acetic acid then added IPA 2. slurry, ambient, 7 days 3. evaporated | 1. gel plug formed, flowed when agitated, irregular masses, B 2. opaque gel, B 3. fines, B | diffuse scatter |
| Acetone/water 94:6 v/v | slurry, 55° C., overnight | — | Form B |
| Acetone/ water 50:50 v/v | slurry, 75° C, 4 days | solids stuck to stir bar above solution, aggregates of wispy solids, B | Form B + Form E |
| | cooling of saturated solution from slurry directly above | fines, B | Form E |
| EtOH/ water 88:12 v/v | cooling of saturated solution | fines aciculars/wispy forming rosettes and aggregates, B | Form B |
| | filtrate from solution directly above | — | Form E |
| EtOH/ water 15:2 v/v | 1. slow cool, 68° C. 2. warmed to ambient and seeded with Compound I sodium Form B | 1. formed gel plug upon cooling in freezer 2. gel dissipated, clear solution 3. solids present | Pattern F |

TABLE 11-continued

Polymorph Form Screen of Compound I Sodium Form B

| Solvent | Method[a] | Observation[b] | Results |
|---|---|---|---|
| | 3. refrigerated<br>4. filtered | 4. fine wispy solids aggregated, B | |
| | filtrate from directly above (used to prepare Pattern F) | — | Form E |
| IPA/water 91:9 v/v slurry, 55° C., overnight | | — | Form B |

[a]Times and temperatures are approximate.
[b]B = birefringent and NB = no birefringence when observed by polarized light microscopy

TABLE 12

Solid Forms of Compound I Sodium Salt from Compound I Free Acid

| Method/Description[a] | Observation[b] | Results |
|---|---|---|
| 1. suspension of Compound I Material F in ACN heated to 65° C., 200 RPM<br>2. molar eq. of NaOH, in water added drop wise<br>3. heat turned off, cooled<br>4. filtered and dried for 2 hours in a 50° C. vacuum oven | 1. slightly hazy<br>2. precipitates formed during addition and remained after ½ volume addition<br>3. turbidity increased<br>4. solids | diffuse scatter + NaOH peaks |
| 1. filtrate from directly above treated with NaOH water solution until pH of solution tested basic<br>2. filtered, water rinse of solids | 1. round gelatinous clumps formed, flowed when pressed, B (mesophase)<br>2. solids left damp | Form E |
| 1. suspension of Compound I Material D dissolved in ACN and heated to 35° C., 200 RPM<br>2. heating discontinued<br>3. molar eq. of NaOH, in water added drop wise<br>4. slurry, ambient, 3 days<br>5. filtered, dried under N$_2$ for 10 min. hours in | 1. clear solution<br>2. —<br>3. precipitation formed upon contact<br>4. fine aciculars, slurry, B<br>5. — | Form B |
| 1. suspension of Na$_2$CO$_3$ (molar equivalent) in DMF added to Compound I Material F<br>2. 75° C. slurry, same day<br>3. 75° C. slurry after 3days, filtered and dried under N$_2$ | 1. free acid readily dissolved<br>2. slurry with unreacted base<br>3. fine aciculars, B | Form B |
| 1. sub sample from directly above isolated at step 2 and filtered through a 0.2 μm NYL filter<br>2. treated with DCM, refrigerated 3 days<br>3. stored in freezer<br>4. fast evaporation | 1. solution<br>2. thick gel with few aggregated crystalline material<br>3. no significant changes<br>4. limited solids, fines, B | Form B |
| same sub sample from above isolated at step 2 treated with water, stored at ambient | solution | — |
| same sub sample from above isolated at step 2, filtered through a .2 μm NYL filter and treated with water drop wise, stored at ambient | fines, B formed briefly then dissolved, irregular NB material precipitated | — |

[a]Times and temperatures are approximate.
[b]B = birefringent and NB = no birefringence when observed by polarized light microscopy.

8.1 Compound I Sodium Pattern A

Compound I sodium Pattern A was formed as described in Table 12, in one embodiment. Compound I sodium Pattern A may also be recrystallized ad described in Table 9A, in one embodiment.

Figure 32:
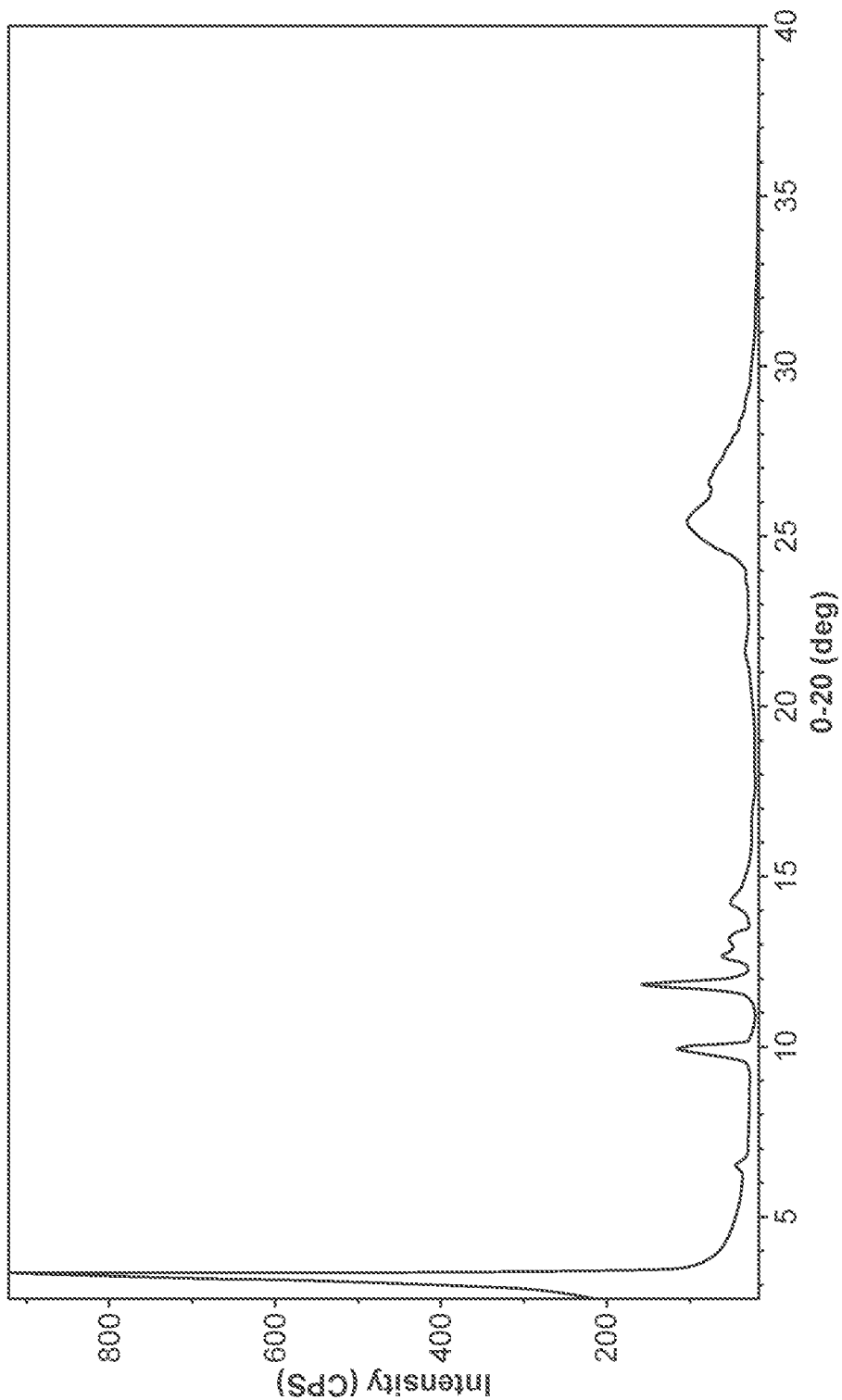
FIG. 32 is an X-ray powder diffractogram of Compound I sodium Material A.
Figure 33:
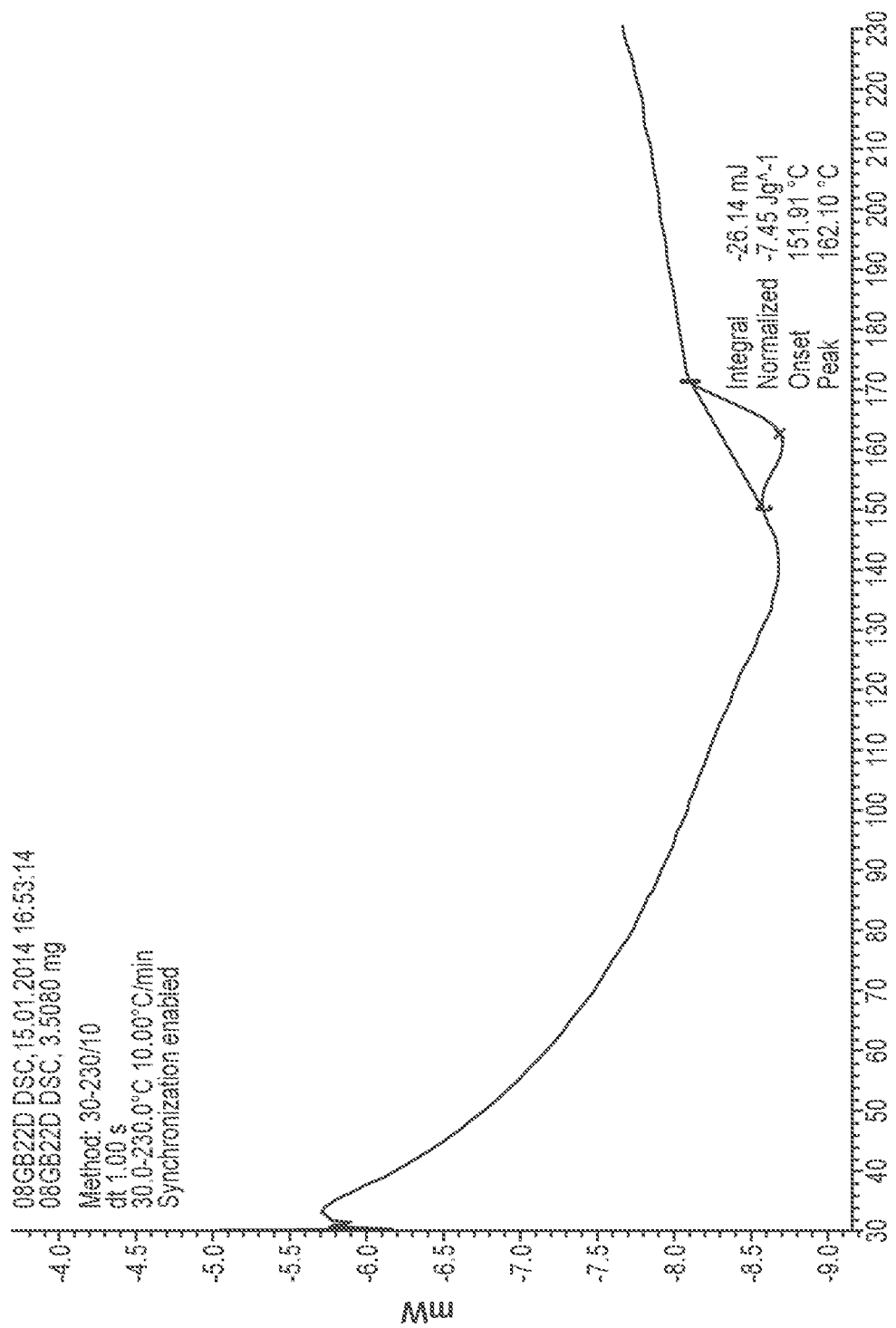
FIG. 33 is a differential scanning calorimeter (DSC) curve of Compound I sodium Material A.
Figure 34:
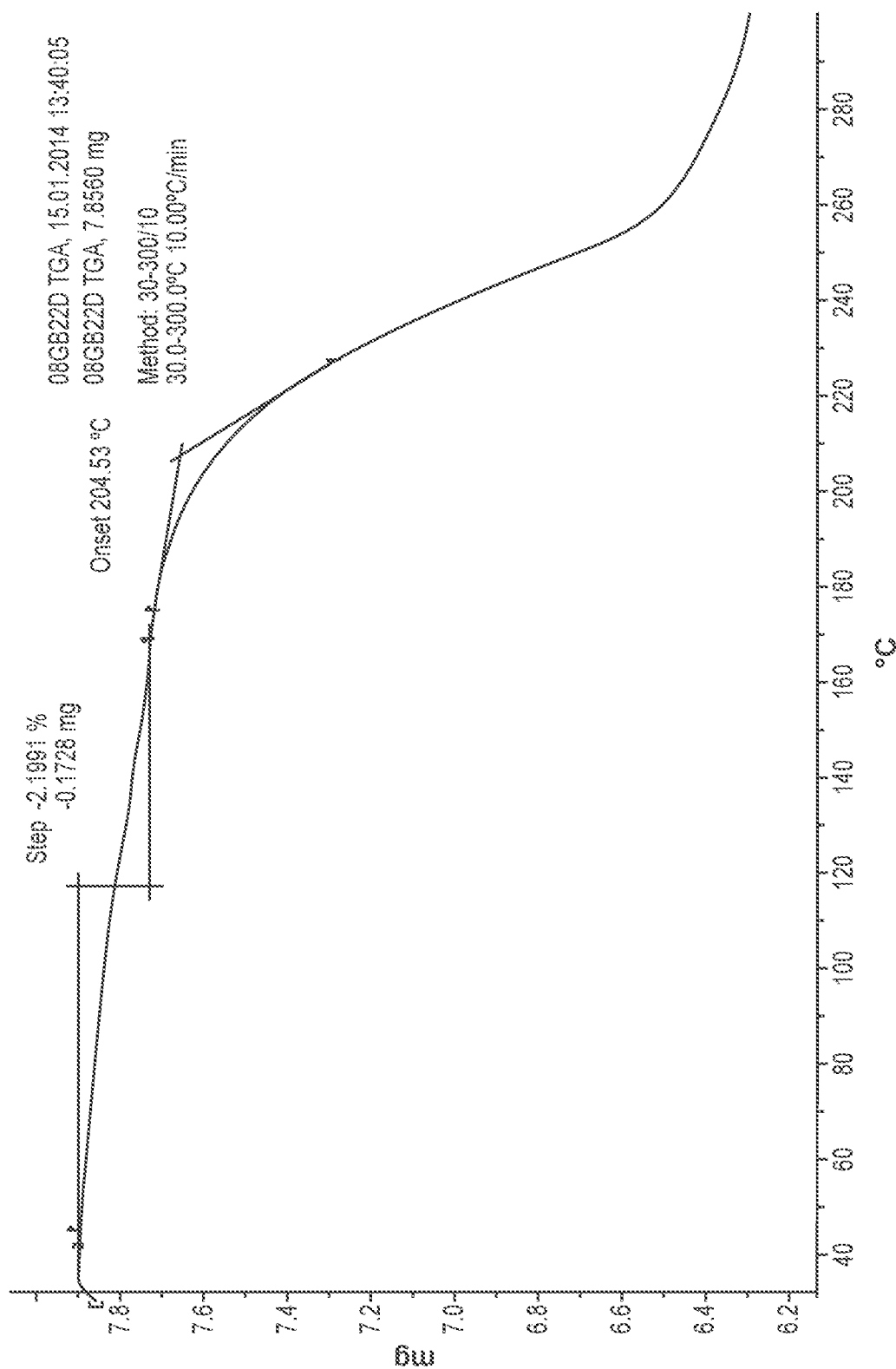
FIG. 34 is a thermogravimetric analysis (TGA) of Compound I sodium Material A.

Compound I sodium Pattern A is crystalline as determined via XRPD analysis (FIG. 32). Compound I sodium Pattern A can be characterized by an X-ray powder diffractogram comprising the following peaks: 3.35, 10.11, and 13.31°2θ±0.2°2θ. The DSC curve for Compound I sodium Pattern A shows a single endotherm with onset at about 152° C. (FIG. 33). TGA analysis of Compound I sodium Pattern A shows a weight loss 2.2% up at about 40-170° C. (attributed to loss of water), followed by onset of decomposition at about 204.5° C. (FIG. 34).

Figure 35:
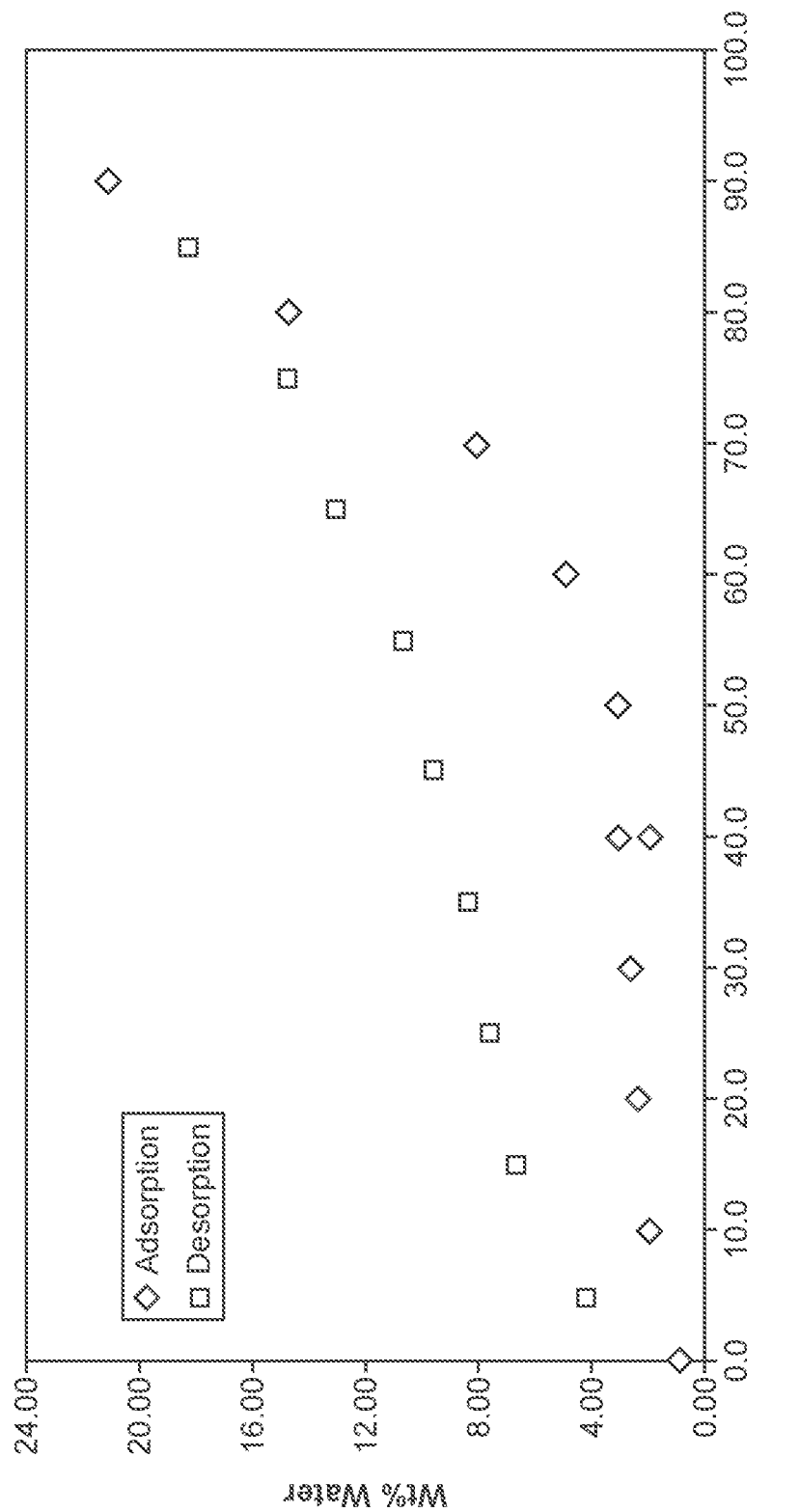
FIG. 35 is a dynamic vapor sorption (DVS) curve of Compound I sodium Material A.

DVS analysis of Compound I sodium Pattern A shows weight gains of about 4.9% at 60% RH and about 21.2% at 90% RH, indicating that the material is hygroscopic (FIG. 35). Compound I sodium Pattern A, while hygroscopic, did not show any indications of deliquescence. Compound I sodium Pattern A material recovered from the DVS analysis was substantially the same as the starting material as analyzed by XRPD suggesting that a phase change did not occur.

In slurry experiments, Compound I sodium Pattern A was found to be stable as a single form for about five days in water, toluene, DCM and MEK (see section 8 and Table 13 below). Further, the relativity stability of Compound I sodium Pattern A in organic solvents indicated that Compound I sodium Pattern A is not a hydrated form.

No chemical and physical form changes were observed for Compound I Pattern A after storing the material at elevated temperature (about 60° C.) (see section 9/Table 15 below).

Compound I sodium Pattern A converted to Compound I sodium Form B when triturated in acetone or isopropanol, or rehydrated to Compound I Form E in solvent systems comprises high water activity. This suggests that Compound I sodium Pattern A is metastable relative to Compound I sodium Form B at least at the conditions evaluated.

8.2 Compound I Sodium Form B

The XRPD pattern, DSC curve, and TGA and DVS analyses of Compound I sodium Form B were described, e.g., in section 4.11 above. Likewise, the formation of Compound I sodium Form B may be found in section 4.11, as well as in Tables 4, 10A-10C, 11, and 12.

Compound I sodium Form B was found to be the most thermodynamically stable anhydrate form of the sodium salt of Compound I sodium. XRPD patterns consistent Compound I sodium Form B were observed from slurry experiments performed up to 75° C. (at low water activities). Further, Compound I sodium Patterns A, C and D were found to convert to Compound I sodium Form B when triturated in various solvent systems. These results are consistent with Compound I sodium Form B being the most stable form at least at the conditions evaluated.

8.3 Compound I Sodium Pattern C

Figure 40:
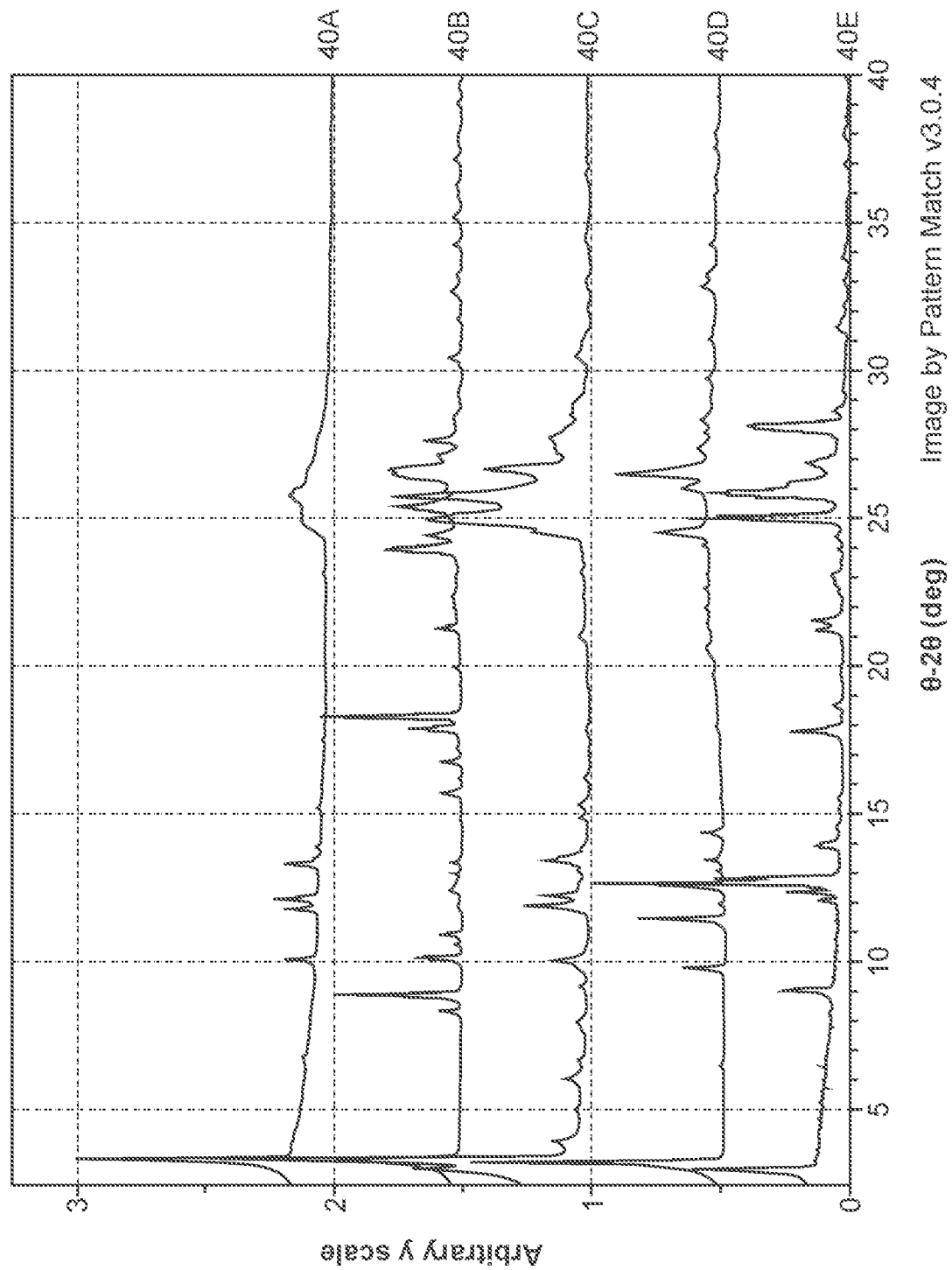
FIG. 40 are X-ray powder diffractograms of Compound I sodium Material A (40A), Compound I sodium Form B (40B), Compound I sodium Pattern C (40C), Compound I sodium Form E (40D), and Compound I sodium Pattern F (40E).
Figure 41:
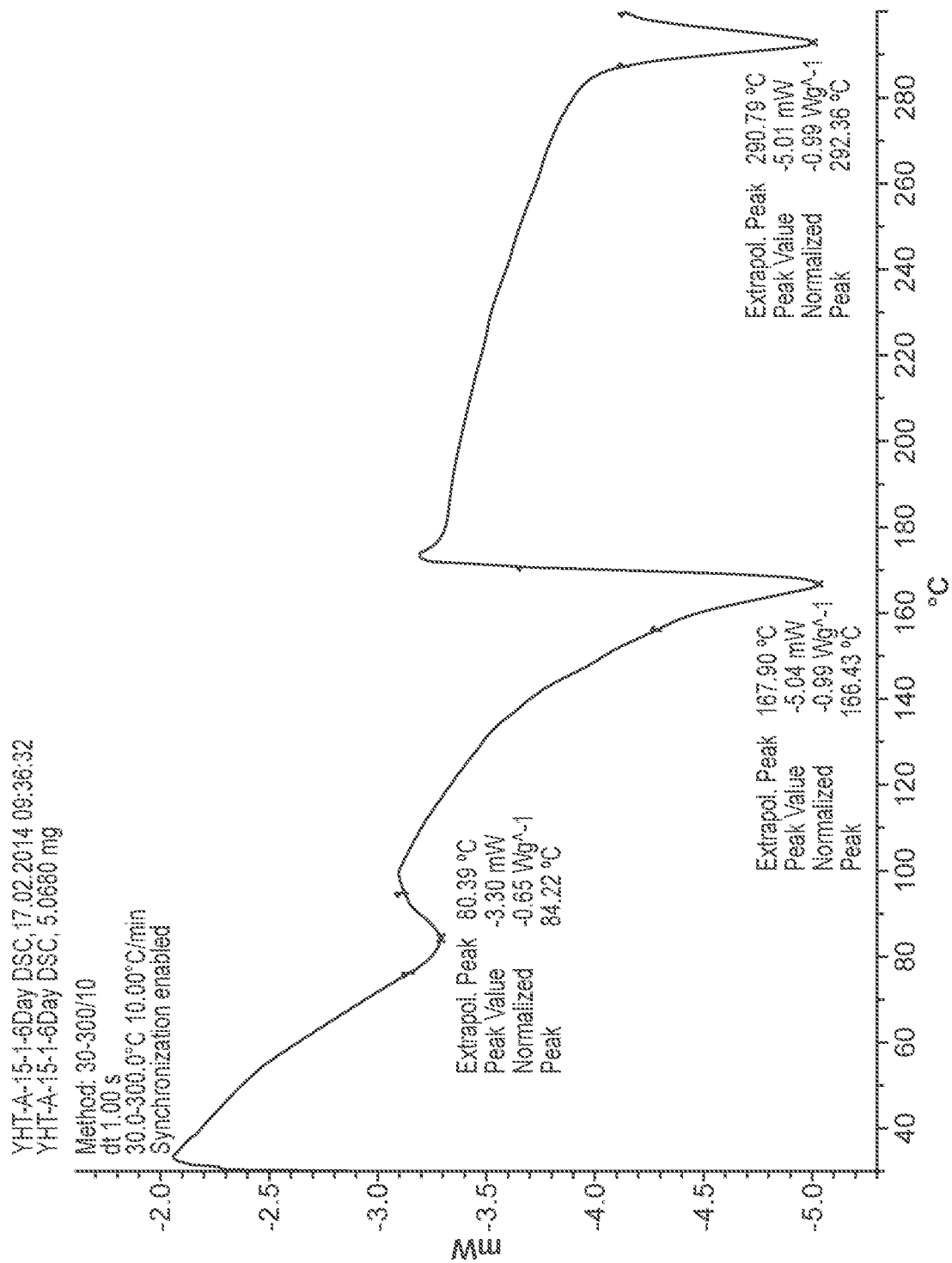
FIG. 41 is a differential scanning calorimeter (DSC) curve of Compound I sodium Pattern C.
Figure 42:
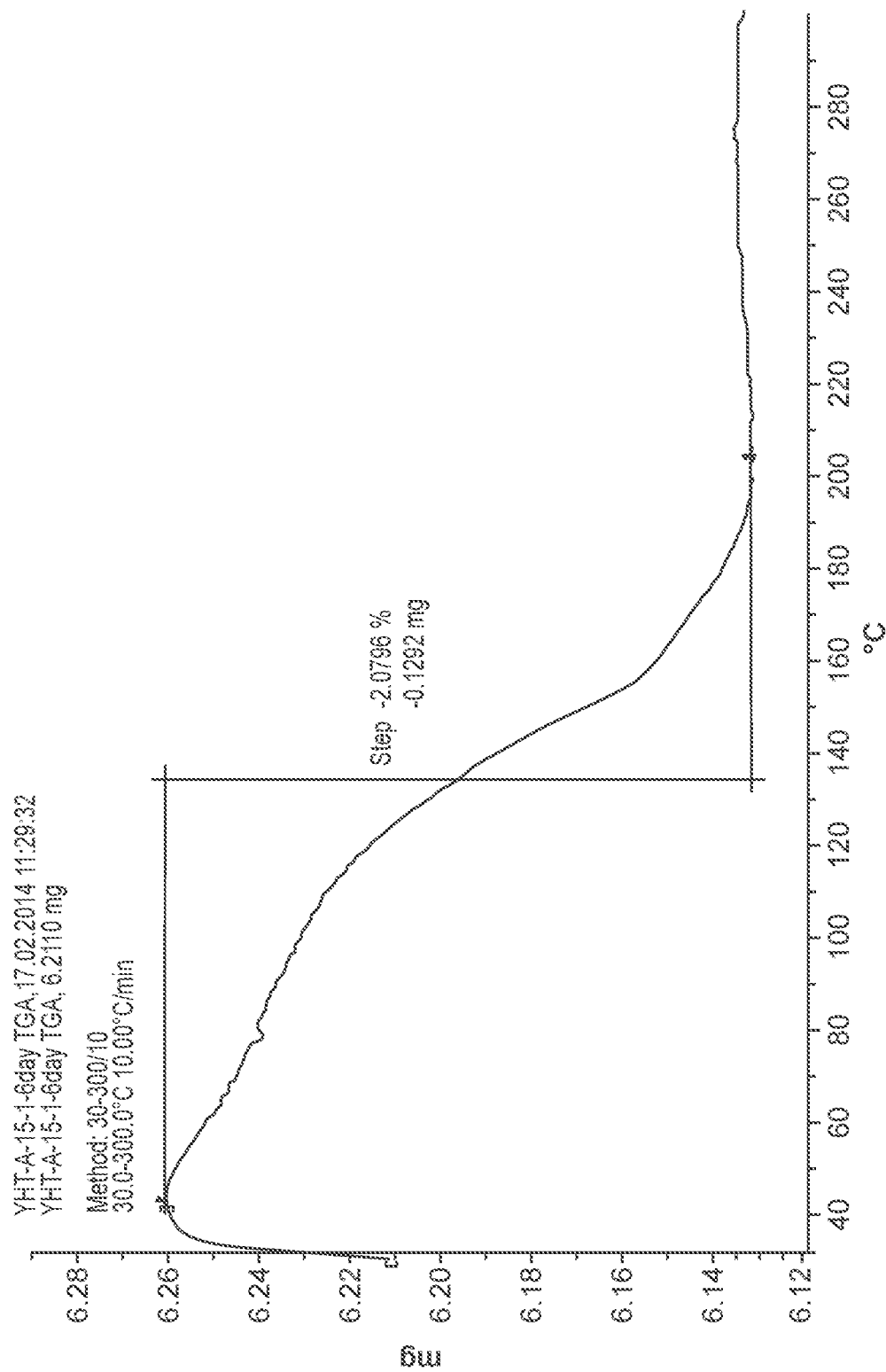
FIG. 42 is a thermogravimetric analysis (TGA) of Compound I sodium Pattern C.

Compound I sodium Pattern C was formed as described in Table 11, in one embodiment. Compound I sodium Pattern C is crystalline as determined via XRPD analysis (FIG. 40C). Compound I sodium Pattern C can be characterized by an X-ray powder diffractogram comprising the following peaks: 3.31, 11.89, and 25.75°2θ±0.2°2θ. The DSC curve for Compound I sodium Pattern C shows endotherms with peaks at about 84° C. (likely due to loss of water), about 166° C. (melt) and about 292° C. (FIG. 41). TGA analysis of Compound I sodium Pattern C shows a weight loss 2.08% up to about 200° C. (FIG. 42).

Figure 43:
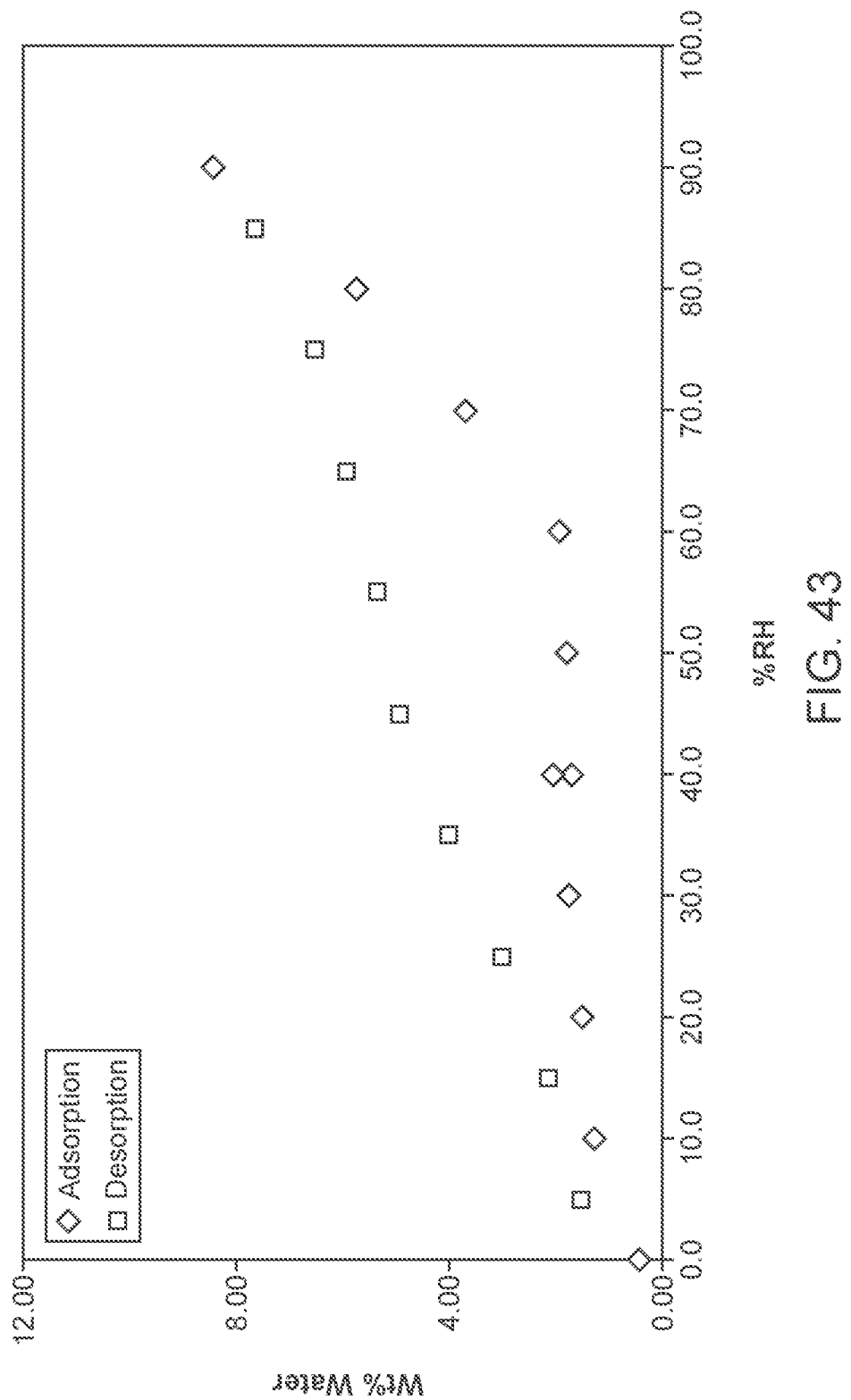
FIG. 43 is an dynamic vapor sorption (DVS) curve of Compound I sodium Pattern C.

DVS analysis of Compound I sodium Pattern C shows weight gains of about 1.9% at 60% RH, and about 8.4% at 90% RH, indicating that the material is slightly hygroscopic (FIG. 43). Compound I sodium I Pattern C material recovered from the DVS analysis was substantially the same as the starting material as analyzed by XRPD suggesting that a phase change did not occur.

In slurry experiments, Compound I sodium Pattern C was found to be stable for about 10 days in methanol (see section 8/Table 13 below).

Compound I sodium Pattern C converted to Compound I sodium Form B in single form and competitive form slurry experiments in acetone and IPA. Additionally, Compound I sodium Pattern C was found to covert to Compound I sodium Form E when triturated in solvent systems with high water activity. These results suggest that Compound I sodium Pattern C is not stable at least at the conditions evaluated.

No chemical and physical form changes were observed for Compound I Pattern C after storing the material at elevated temperature (about 60° C.) (see section 9/Table 15 below).

8.4 Compound I Sodium Pattern D

Compound I sodium Pattern D was formed by combining Compound I sodium Pattern A (about 100 mg) with water (about 2.0 mL) to form a slurry, stirring the slurry for about 10 days at room temperature or for about 48 hours at about 60° C., and isolating the resulting solids.

Figure 44:
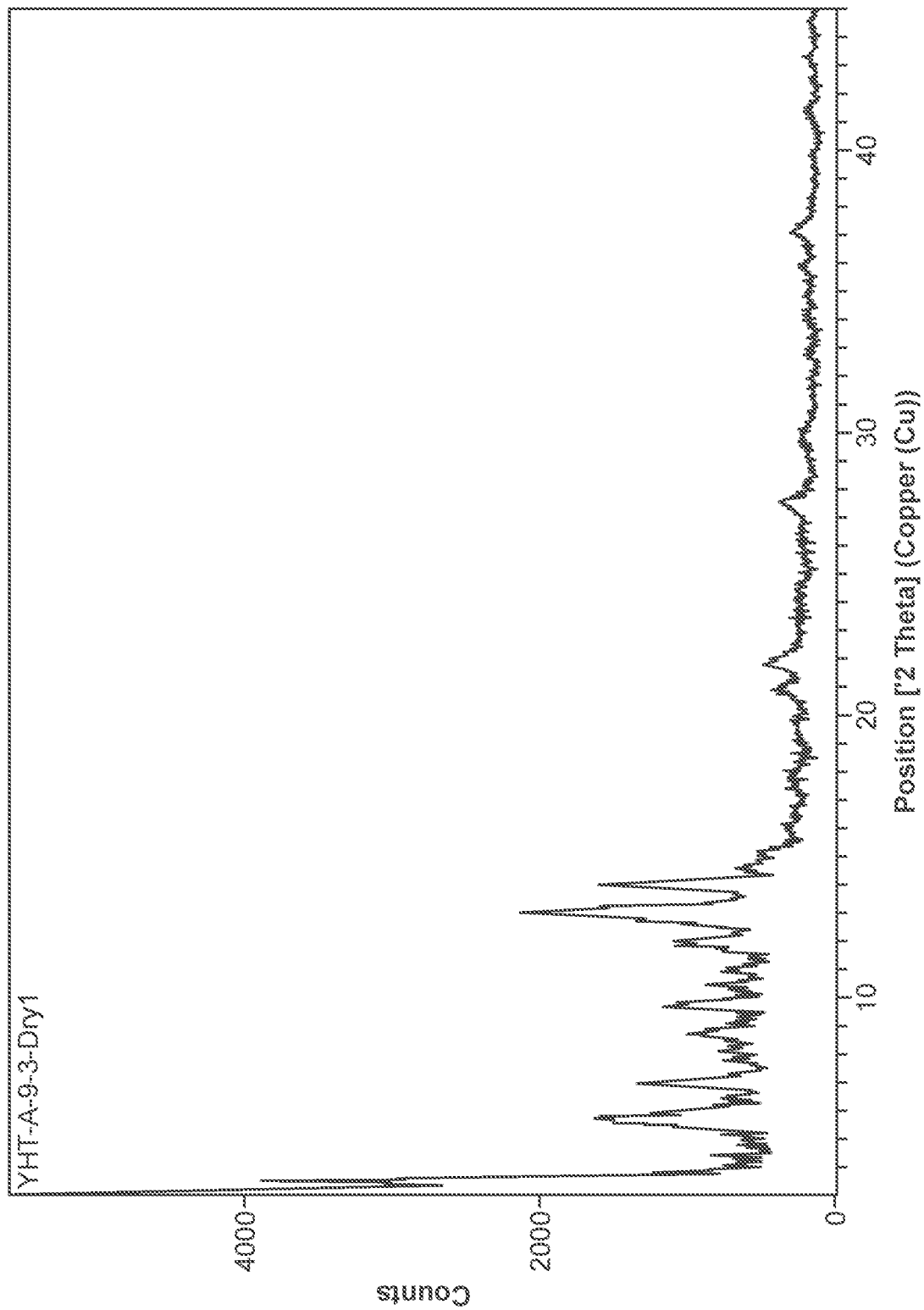
FIG. 44 is an X-ray powder diffractogram of Compound I sodium Pattern D.
Figure 45:
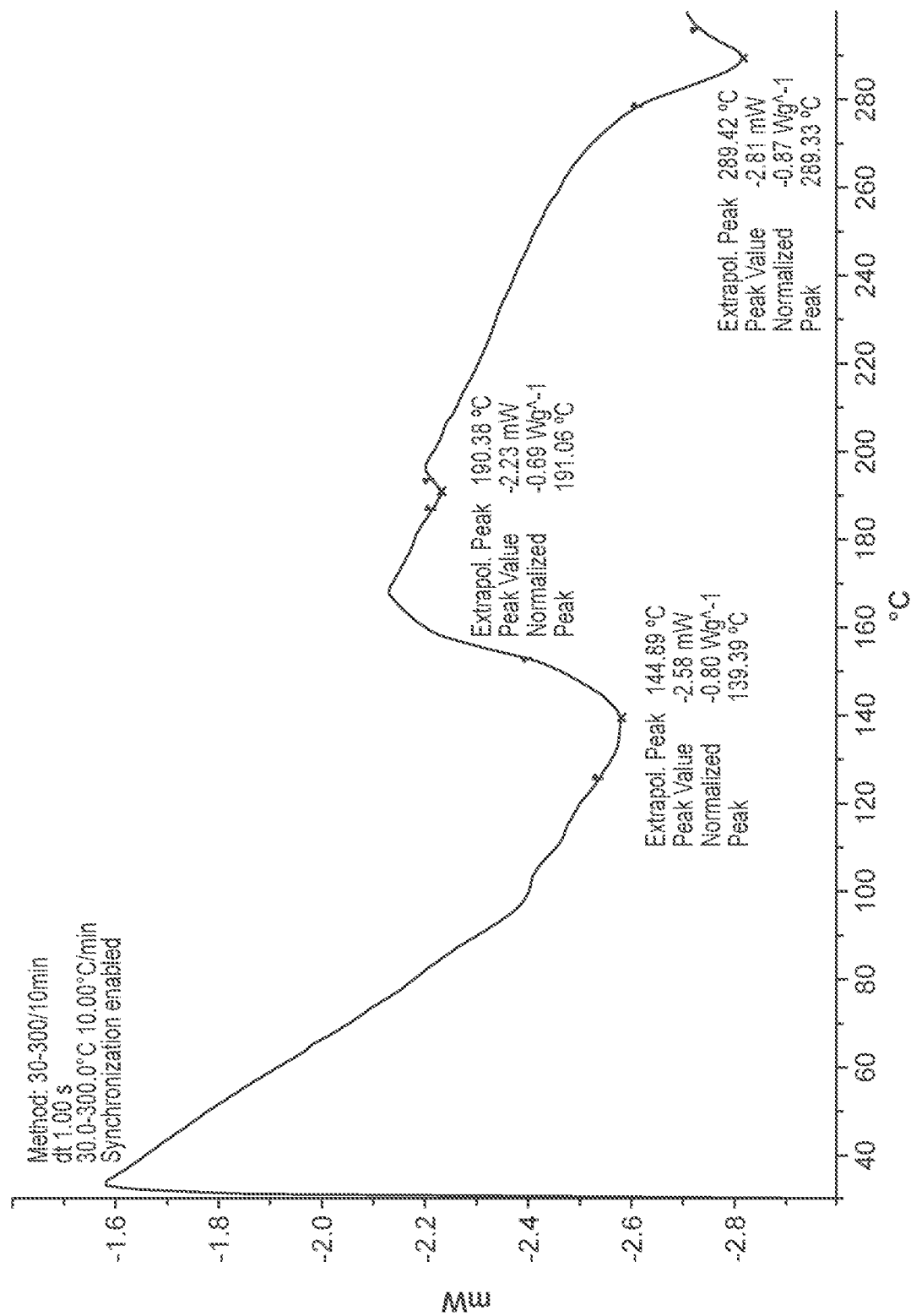
FIG. 45 is a differential scanning calorimeter (DSC) curve of Compound I sodium Pattern D.
Figure 46:
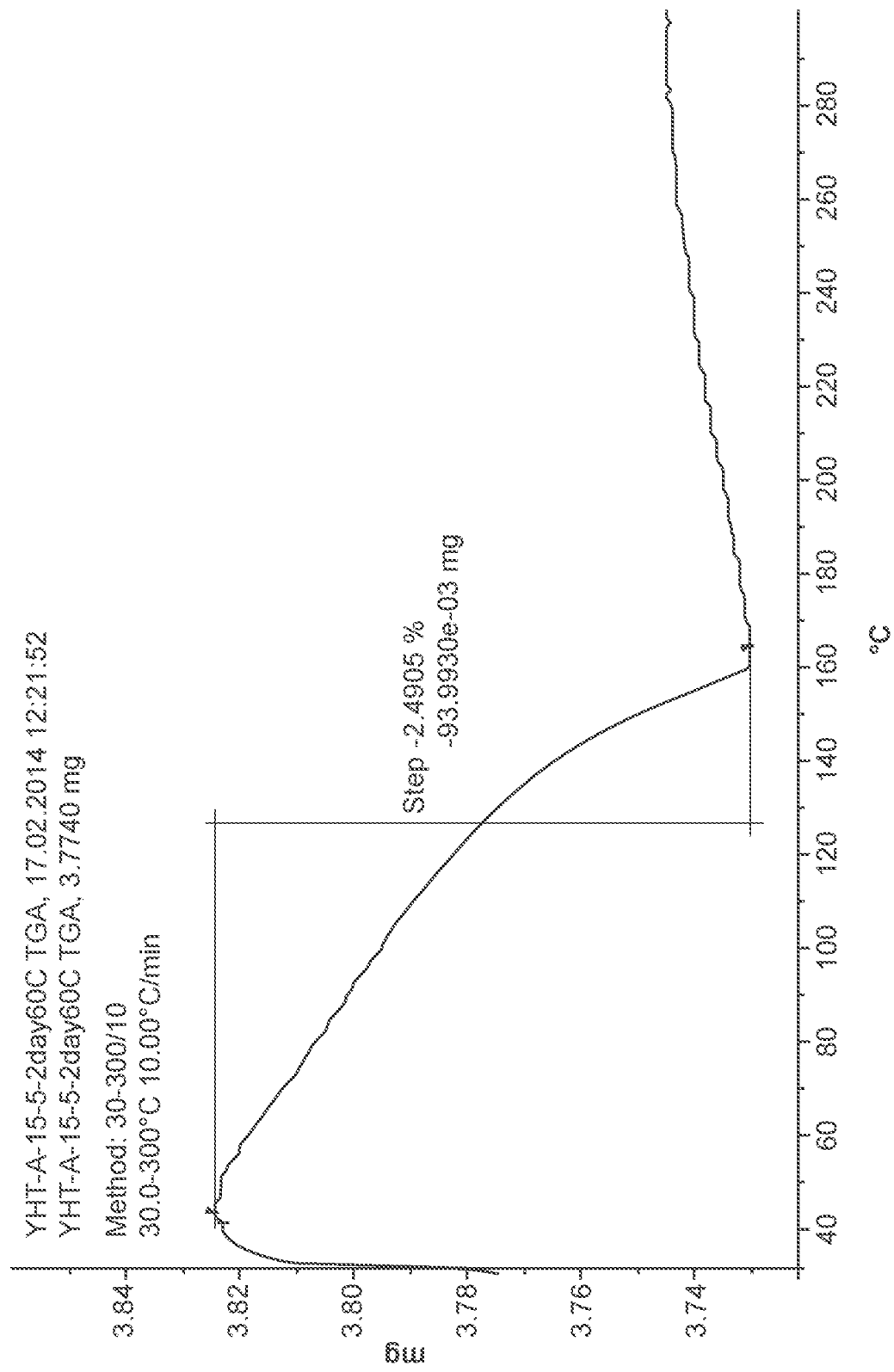
FIG. 46 is a thermogravimetric analysis (TGA) of Compound I sodium Pattern D.

Compound I sodium Pattern D is crystalline as determined via XRPD analysis (FIG. 44). Compound I sodium Pattern D can be characterized by an X-ray powder diffractogram comprising the following peaks: 3.05, 5.75, and 13.09°2θ±0.2°2θ. The DSC curve for Compound I sodium Pattern D shows endotherms with peaks at about 139° C., about 191° C., and about 289° C. (FIG. 45). TGA analysis of Compound I sodium Pattern D shows a weight loss 2.5% before about 160° C. (FIG. 46).

Compound I sodium Pattern D converted to Compound I sodium Form B in a single form slurry in acetone. Compound I sodium Pattern D also converted to Compound I sodium Form B in competitive slurry experiments in acetone and isopropyl alcohol, and to Compound I sodium Form B in water. These results suggest that Compound I sodium Pattern D is not stable at least at the conditions evaluated.

No chemical and physical form changes were observed for Compound I Pattern D after storing the material at elevated temperature (about 60° C.) (see section 9/Table 15 below).

8.5 Compound I Sodium Form E

Figure 47:
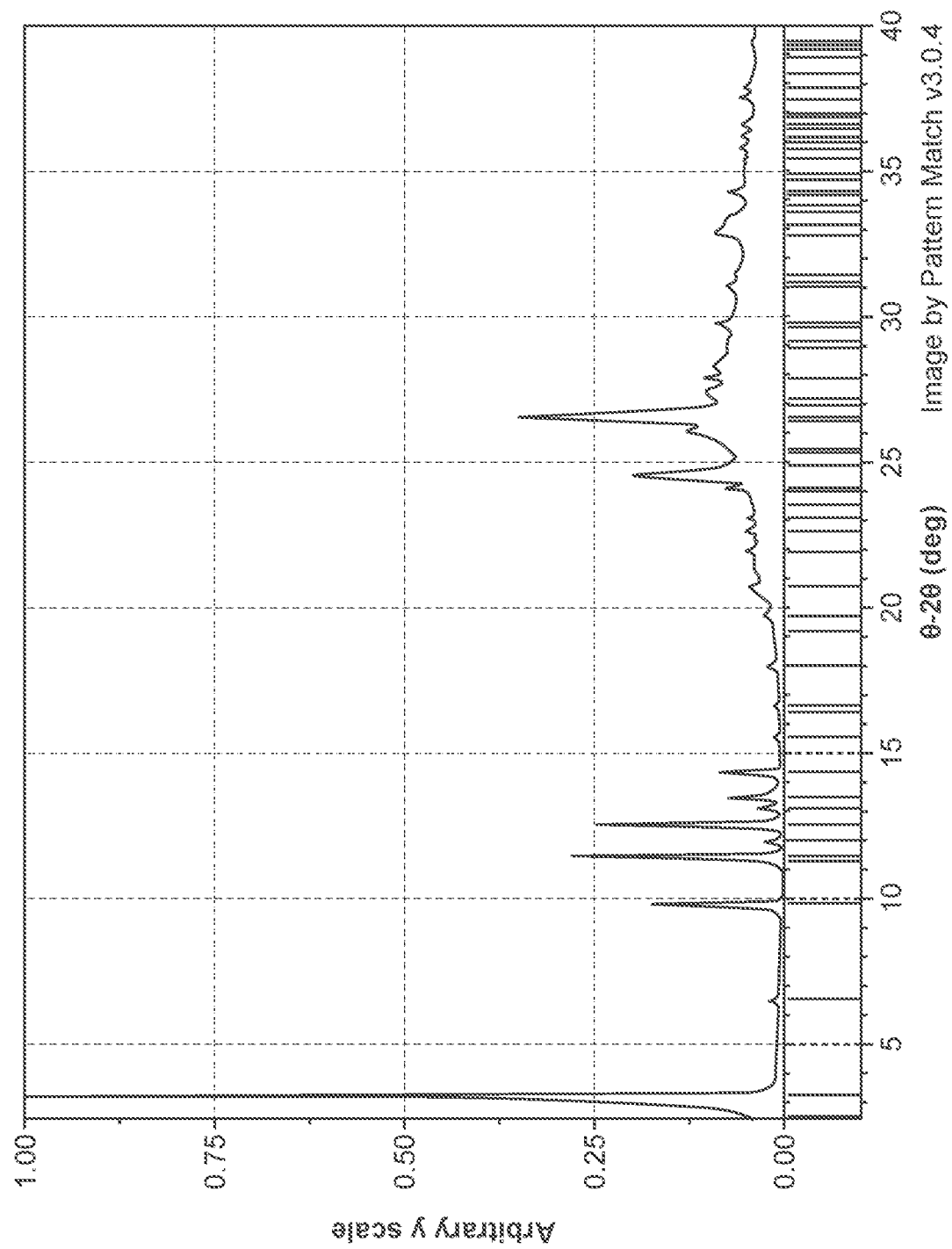
FIG. 47 is an X-ray powder diffractogram of Compound I sodium Form E.
Figure 48:
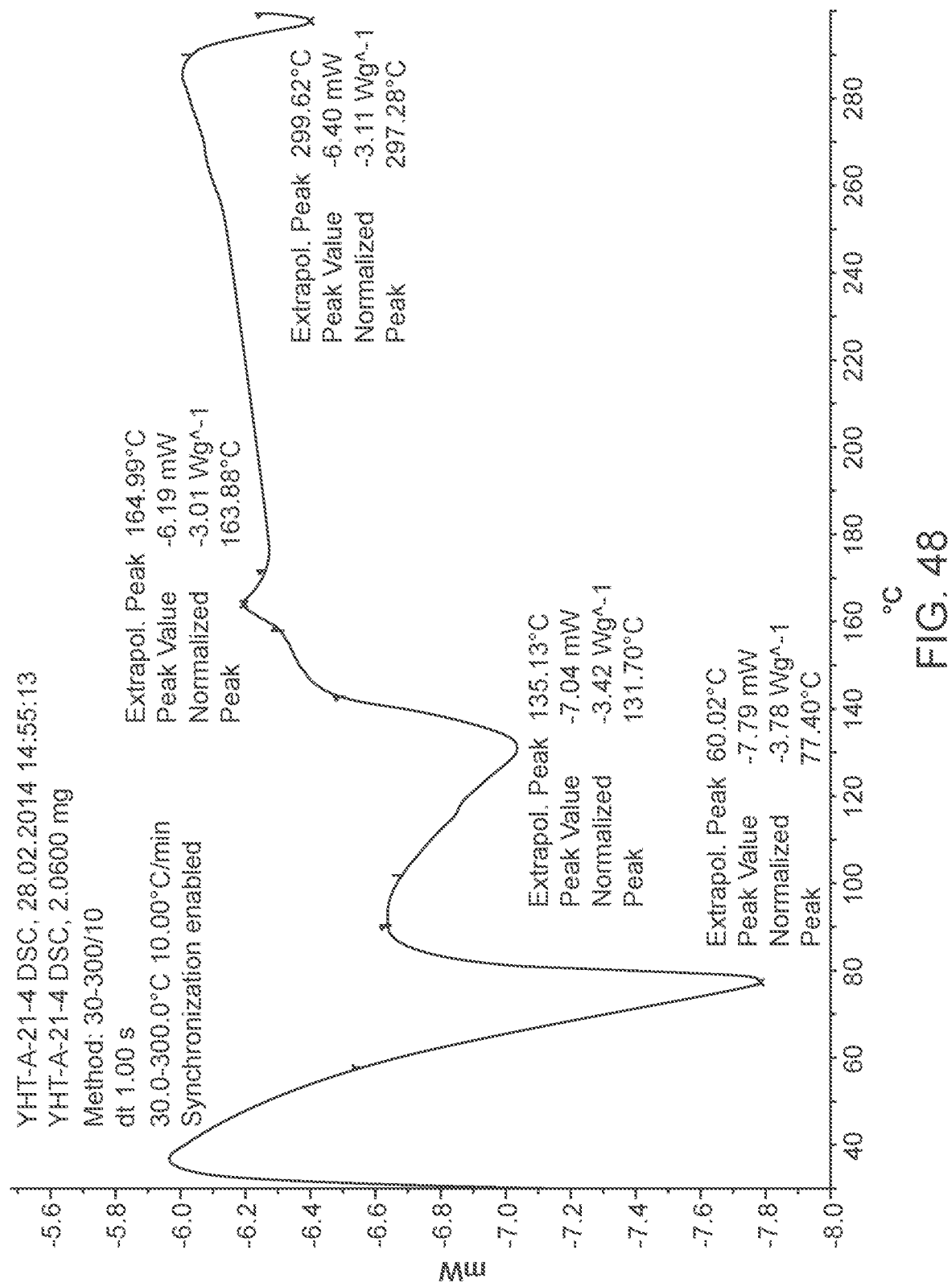
FIG. 48 is a differential scanning calorimeter (DSC) curve of Compound I sodium Form E.
Figure 49:
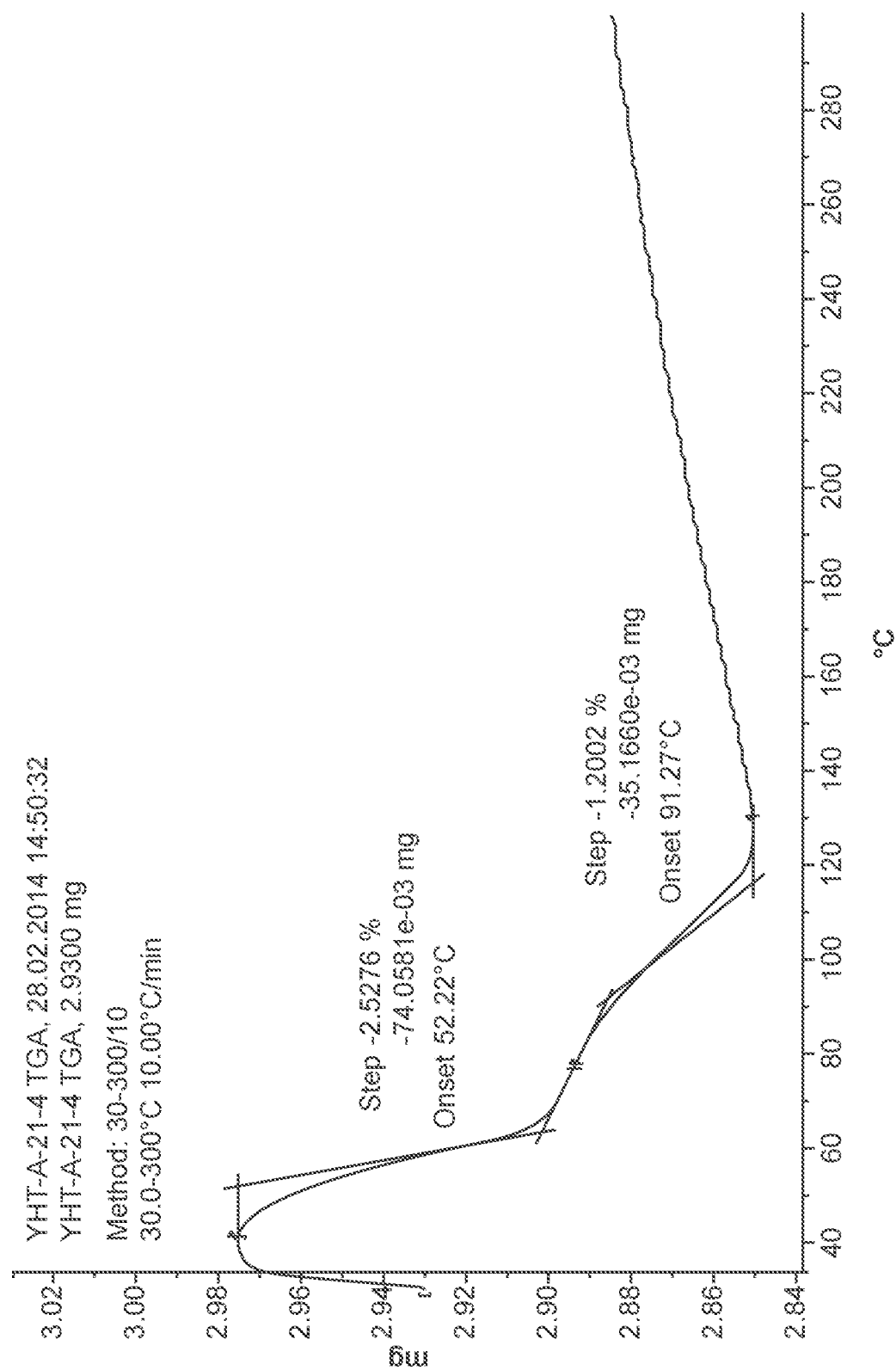
FIG. 49 is a thermogravimetric analysis (TGA) of Compound I sodium Form E.

Compound I sodium Form E was formed as described in Tables 11 and 12, in one embodiment. Compound I sodium Form E is crystalline as determined via XRPD analysis (FIG. 47). Compound I sodium Form E can be characterized by an X-ray powder diffractogram comprising the following peaks: 3.25, 11.47, and 26.51°2θ±0.2°2θ. The DSC curve for Compound I sodium Form E shows endotherms with peaks at about 77° C., about 132° C., and about 297° C., as well as an exotherm with a peak at about 164° C. (FIG. 48). TGA analysis of Compound I sodium Form E shows a weight loss 2.5% before about 80° C., and about 1.2% before about 130° C. (FIG. 49).

Compound I sodium Form E converted to Compound I sodium Form B in a competitive slurry experiment in acetone and water. Compound I sodium Form E also converted to air upon drying in air or exposure to vacuum at ambient temperatures.

8.6 Compound I Sodium Pattern F

Figure 50:
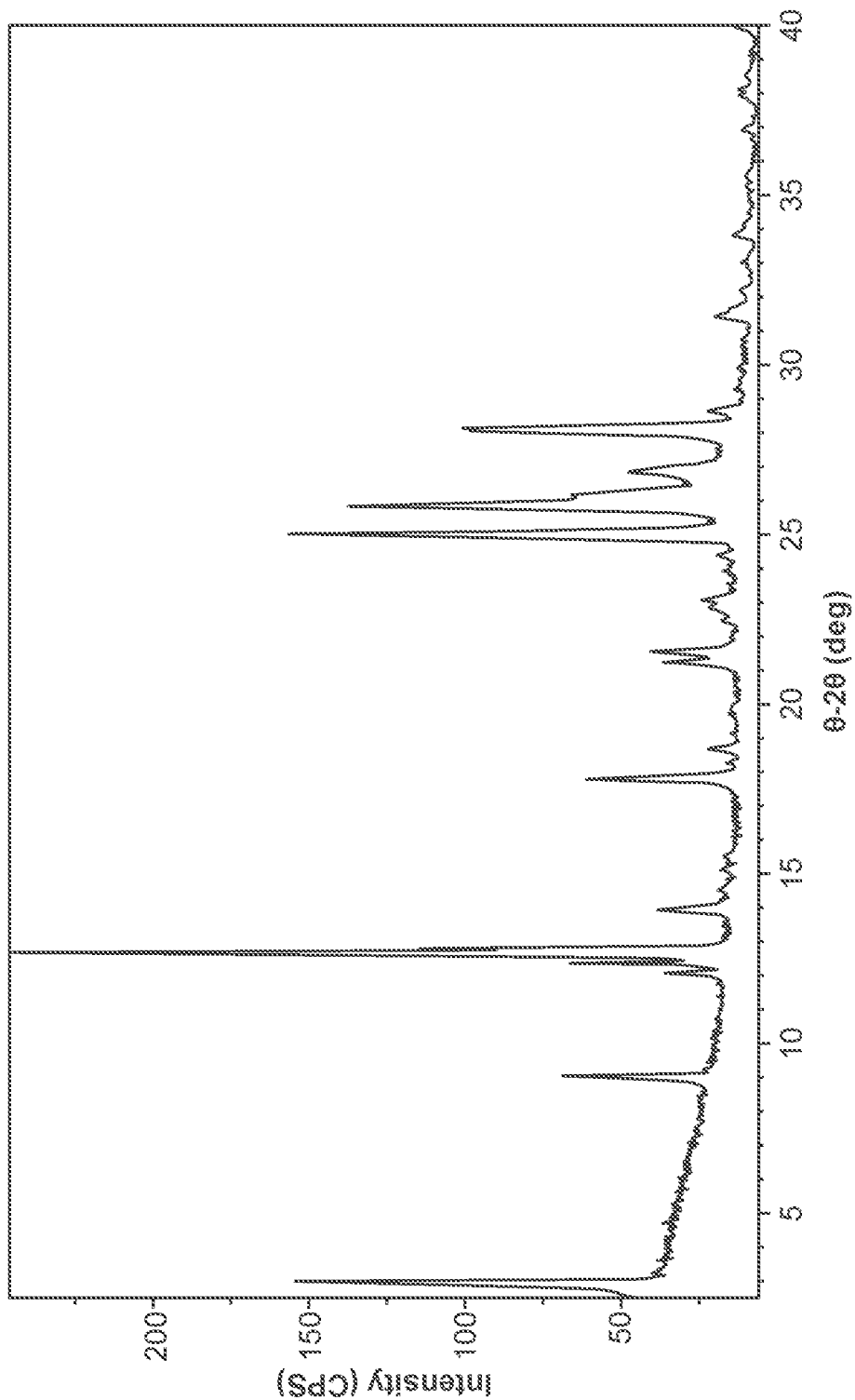
FIG. 50 is an X-ray powder diffractogram of Compound I sodium Pattern F.

Compound I sodium Pattern F was formed as described in Table 11, in one embodiment. Compound I sodium Pattern F is crystalline as determined via XRPD analysis (FIG. 50). Compound I sodium Pattern F can be characterized by an X-ray powder diffractogram comprising the following peaks: 12.67, 25.02, and 28.10°2θ±0.2°2θ. Exposure of Compound I sodium Pattern F to ambient for about 1 day caused the material to become disordered.

8.7 Compound I Sodium Mesophases

Figure 51:
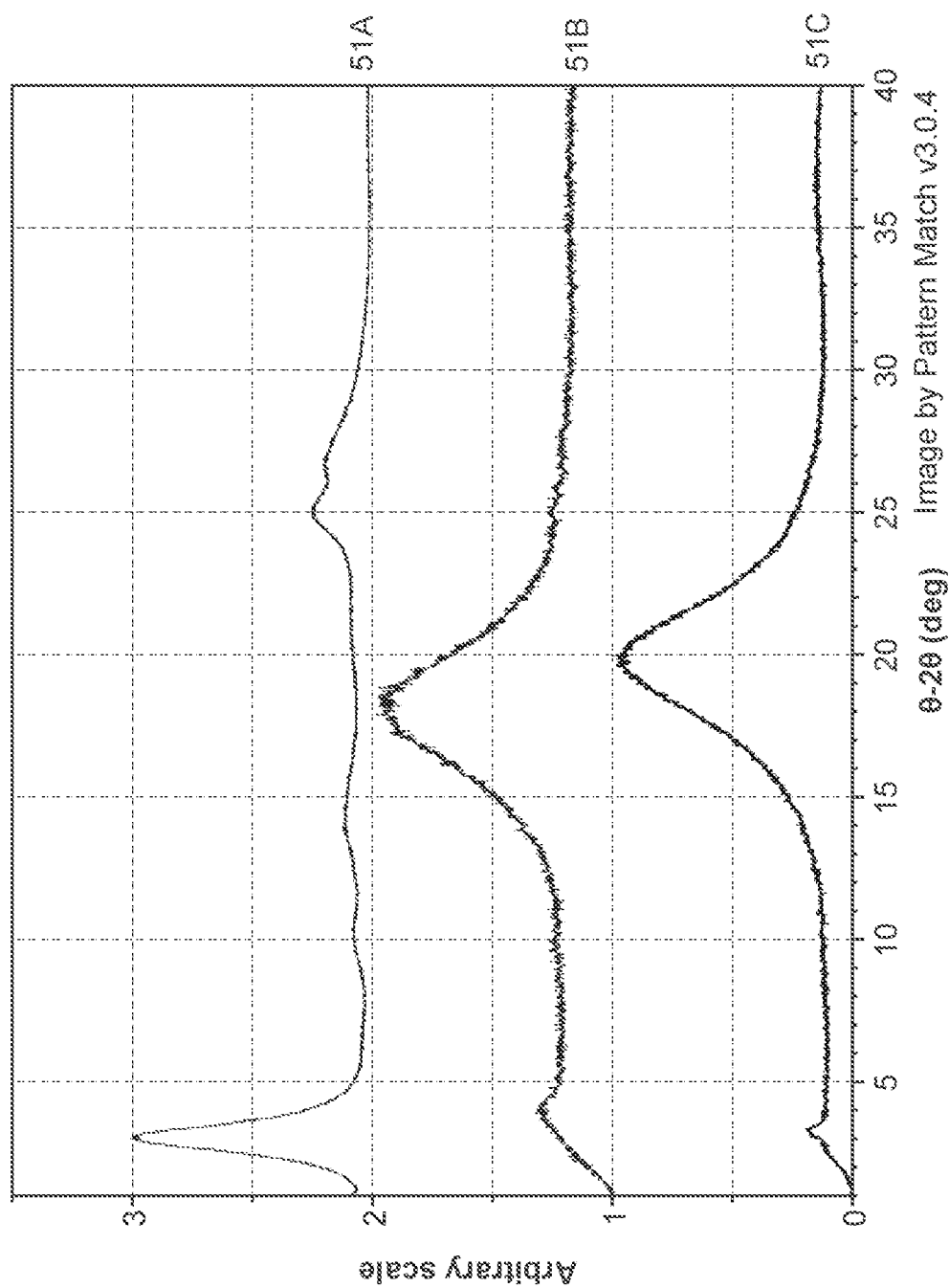
FIG. 51 are X-ray powder diffractogram of Compound I sodium mesophase Pattern A (51A), Pattern B (51B), and Pattern C (51C).

Several ordered phases of Compound I sodium were found to exhibit optical birefringence, indicating that lyotropic mesophases were formed. FIG. 51 provides the XRPD patterns for Compound I sodium mesophase Patterns A-C formed via HFIPA generation, a HFIPA slurry, and TFE slurry at about 75° C., respectively.

Figure 53:
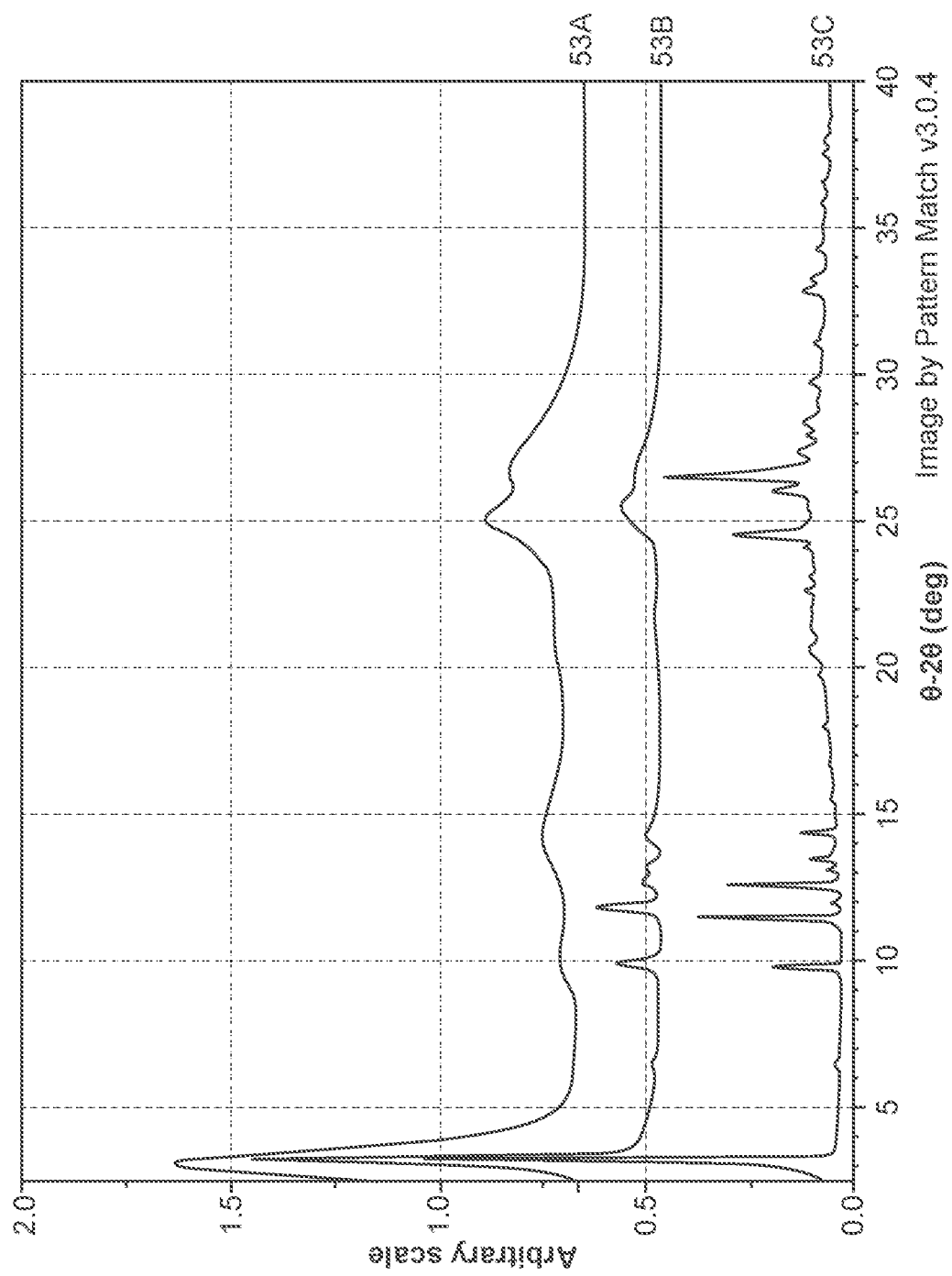
FIG. 53 is an X-ray powder diffractogram of Compound I mesophase Pattern A (53A), Compound I sodium pattern A obtained from an elevated temperature experiment in water (with exposure to vacuum) (53B), and Compound I sodium Form E obtained from an aqueous slurry at room temperature (53C).

FIG. 53 provides a comparison between the XRPD patterns of the Compound I sodium mesophase Pattern A, Compound I sodium pattern A obtained from an elevated temperature experiment in water (with exposure to vacuum), and Compound I sodium Form E obtained from an aqueous slurry at room temperature. As shown in FIG. 53, several regions of diffuse scattering (top pattern) caused by some degree of alignment or long-range order start to exhibit periodic order in all three dimensions, evidenced by sharper peaks (middle and bottom patterns, respectively), as the material behaves more like a crystalline solid. The XRPD patterns of FIG. 53 suggests that the materials described therein are likely related but with slight differences in periodic order.

8.8 Compound I Sodium Amorphous

Compound I sodium amorphous was formed by lyophilizing a 4:1 v/v water/DMSO solution. Compound I sodium amorphous is characterized by an XRPD pattern as substantially shown in FIG. 52. Compound I sodium amorphous converts to Compound I sodium Form B when heated to about 150° C.

9. Slurry Experiments

The formation and stability of solid forms of the sodium salt of Compound I was further evaluated via slurry experiments. The slurries were formed by combining Compound I sodium Pattern A and a solvent, and allowing the slurry to equilibrate at room temperature. If a free flowing slurry was not achieved, an additional amount of the respective solvent was added before the room temperature equilibration step. All slurries were isolated via centrifuge filtration after five days and twelve days of equilibration. The solids were analyzed by XRPD to check for pattern conversion (Table 13).

TABLE 13

Slurry Experiments of Compound I Sodium Pattern A

| Solvent | Solvent Vol (mL) | Method | Time point (5 days) XRPD | Time point (12 days, wet) XRPD | Time point (12 days, dry) XRPD |
|---|---|---|---|---|---|
| Water | 2.0 | Aliquot | A | E | A |
| MeOH | 2.0 | solvent | C | C | C |
| EtOH | 3.0 | into | Amorphous | D | D |
| IPA | 2.0 | Compound I | B | B | B |
| ACN | 2.0 | sodium | N/A | Amorphous | Amorphous |
| THF | 2.0 | Pattern A | Amorphous | Amorphous | Amorphous |
| EtOAc | 2.0 | starting | Amorphous | B | B |
| Acetone | 2.0 | material | B | B | B |
| Toluene | 3.0 | and stir | A | A | A |
| DCM | 3.0 | at room | A | Low crystallinity | Low crystallinity |
| MEK | 3.0 | temp. | A | B | B |

N/A Low quantity, insufficient for XRPD analysis.

Competitive slurry experiments were also conducted to evaluate form stability of the solid forms of the sodium salt of Compound I. Slurries were prepared by combining Compound I sodium Pattern A, Form B, Pattern C and Pattern D with a solvent, allowing the slurry to equilibrate with stirring at room temperature. The slurries were analyzed at three day and ten day time points, filtered, and analyzed by XRPD (Table 14).

TABLE 14

Competitive Slurry Experiments of Compound I Sodium Pattern A, Form B, Pattern C, and Pattern D in various solvents

| Parent Materials | Solvent | Vol. (mL) | Temp (° C.) | Time point (3 days) XRPD | Time point (10 days) XRPD |
|---|---|---|---|---|---|
| Compound I sodium Pattern A Compound I sodium Form B Compound I sodium Pattern C Compound I sodium Pattern D | Acetone | 1.5 | 25.0 | B | B |
| Compound I sodium Pattern A Compound I sodium Form B Compound I sodium Pattern C Compound I sodium Pattern D | IPA | 1.5 | 25.0 | B | B |
| Compound I sodium Pattern A Compound I sodium Form B Compound I sodium Pattern C Compound I sodium Pattern D | Water | 1.5 | 25.0 | A | E[1] |

[1] XRPD analysis showed that Compound I sodium Pattern E converted to Compound I sodium Pattern A after exposure to ambient lab condition for 24 hours.

10. Stability of Compound I Sodium Pattern a, C, and D and Form B at Elevated Temperatures The stability of Compound I sodium Patterns A, C, and D and Form B, at about 60° C. was evaluated. These forms were weighed into vials covered with a Kimwipe tissue and stored in an oven at 60° C. and ambient pressure. After three days and ten days of exposure, the solids were analyzed by XRPD to check for form conversion. The filtrate was analyzed by HPLC for purity assessment.

TABLE 15

Stability of Compound I Sodium Patterns A, C, and D and Form E at 60° C.

| Parent Material | Temp (° C.) | Time point (3 days) XRPD | Time point (10 days) XRPD | Patent Material HPLC (% AUC) | HPLC (% AUC) |
|---|---|---|---|---|---|
| Compound I sodium Pattern A | 60 | A | A | >99.9 | >99.9 |
| Compound I sodium Form B | 60 | B[1] | B[2] | >99.9 | >99.9 |
| Compound I sodium Pattern C | 60 | C[3] | C | >99.9 | >99.9 |
| Compound I sodium Pattern D | 60 | D | D | >99.9 | >99.9 |

[1]Additional peaks at 27.3, 28.3, 28.8, 42.1; missing peak at 8.4 [2θ]
[2]Missing peaks at 8.3, 27.3 [2θ]
[3]Additional peak at 9.7 [2θ]

The stability of Compound I sodium Form B was further evaluated at additional elevated temperatures (about 65° C., 78° C., 175° C., and 205° C.) was evaluated, with the results described in Table 16.

TABLE 16

Stability of Compound I Sodium Form E at 65° C., 78° C., 175° C. and 175° C.

| Method[a] | Observation[b] | Results |
|---|---|---|
| 65° C. | 1. clumps collapsed and expelled solvent, fines, B | Form B |
| 1. after 20 min | | |
| 2. after 50 min | 2. solids, NB | |
| 78° C., 18 days | fines, B | Form B |
| under N$_2$: heat to 175° C. then cooled to 150° C., held for 10 minutes | solids | Form B + peaks |
| 205° C., briefly | fines, B | Form B + peaks |

[a]Times are approximate.
[b]B = birefringent and NB = no birefringence when observed by polarized light microscopy.

12. Water Activity Interconversion Slurries

The effect of water activity ($a_w$) on the hydration state of Compound I sodium Form B was investigated through competitive water activity trituration experiments (slurries) in various aqueous solvent mixtures. The resulting solid phase was characterized by XRPD (Table 16). The experiments establish the physically stable form at various $a_w$.

Water activity is related to relative humidity in that RH %=$a_w$×100. Therefore, it is possible to directly relate the stability of an anhydrous/hydrate system in slurry experiments to solid state stability. Slurry technique at controlled water activities provides an accurate method of rapidly predicting the physically stable form in anhydrous/hydrate systems. This method is particularly valuable when relatively slow kinetics of conversion in the solid state prevents reaching true equilibrium in a reasonable timeframe, since solvent-mediated transformation accelerates the conversion process.

As shown in Table 17, Compound I sodium Form B is stable at and below 0.86 $a_w$, while Compound I sodium Form E is more favored at 0.91 $a_w$ and above.

TABLE 17

Water Activity of Compound I Sodium Form B

| Water Activity Solvent System (% v/v) | Time[a] | Observation[b] | Results |
|---|---|---|---|
| 0.98 $a_w$ 90:10 $H_2O$/Acetone | 6 days | solids, opaque, NB wet cake | Form E |
| 0.91 $a_w$ 50:50 $H_2O$/Acetone | 1 day | no solvent remained, solids damp, irregular clumps of material with wispy material, B | Form E |
| 0.86 $a_w$ 70:30 $H_2O$/MeOH | 6 days | fines, B, wet cake | Form B |
| 0.70 $a_w$ 50:50 $H_2O$/DMF | 6 days | fines, B, wet cake | Form B |
| 0.58 $a_w$ 6:94 $H_2O$/Acetone | 6 days | off white fines, opaque, NB wet cake | Form B |
| 0.50 $a_w$ 30:70 $H_2O$/DMF | 6 days | off white fines, B wet cake | Form B |
| 0.39 $a_w$ 15:85 $H_2O$/MeOH | 6 days | opaque white fines, NB wet cake | Form B |
| 0.33 $a_w$ 16:84 $H_2O$/DMF | 6 days | white fines, B wet cake | Form B |

[a] Times are approximate.
[b] B = birefringent and NB = no birefringence when observed by polarized light microscopy.

12. Gelling Behavior

The gelling behavior during the formation of Compound I sodium Form B was evaluated using different starting materials (Table 17). Isopropanol was used as the crystallization solvent for these experiments since it is often used in contemporary crystallization procedures at large scale.

Once formed, Compound I sodium Form B does not appear to gel when added to isopropanol. Conversely, gelling is observed when starting with Compound I X-ray amorphous; however, Compound I sodium Form B eventually crystallized from the gel after sonication was applied and with an additional three days of stirring.

Attempts to crystallize Compound I sodium Form B through the formation thereof from Compound I free acid also generated thick gels (Table 17); however, seeding with Compound I sodium Form B prior to the addition of sodium hydroxide provided a final crystalline product that was easier to filter than the product generated without seeding.

The gelling behavior of Compound I sodium Form B formed from a methyl ester of Compound I of structure:

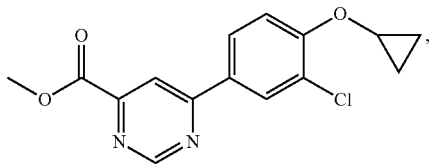 [SMILES: COC(=O)c1cc(-c2ccc(OC3CC3)c(Cl)c2)ncn1]

was also evaluated (Table 17). The methyl ester of Compound I may be characterized by the XRPD pattern as substantially shown in Figure XX. The formation of Compound I sodium Form B from the methyl ester of Compound I produced gel-like agglomerates; however, the bulk of the sample remained fluid and a uniform viscous gel was not observed. Crystalline material was detected within the first 1.5 hours after the addition of sodium hydroxide. Crystallizing Form B of the sodium salt from the conversion of the ester precursor appears to provide a scalable process that avoids the gelling behavior observed from other methods.

TABLE 17

Gelling Behavior During the Formation of Compound I Sodium Form B ins Isopropanol

| Starting Material | Method/Description | Observation | Results |
|---|---|---|---|
| Compound I Sodium Form B | 1. suspension of Compound I Sodium Form B in IPA (58 mg in 3 mL)<br>2. 0.242 mL of water added<br>3. slurry, ambient, 3 days<br>4. filtered | 1. slurry<br>2. no changes<br>3. slurry<br>4. fines, B | Form B |
| Compound I sodium amorphous | 1. addition of IPA to X-ray amorphous sodium salt sample followed by sonication<br>2. stirring, ambient, 3 days | 1. gel forming<br>2. fines acicular, B | Form B |
| Compound I free acid Material A + F | 1. suspension of Compound I free acid in IPA (58 mg in 3 mL)<br>2. molar equivalent of NaOH added 0.242 mL (33 mg/mL NaOH/water)<br>3. slurry, ambient, 3 days<br>4. filtered, rinsed with IPA, and dried under $N_2$ | 1. slight turbidity<br>2. turbidity increased, sample gelled<br>3. thick slurry<br>4. fines, B | Form E + Form B |

TABLE 17-continued

Gelling Behavior During the Formation of Compound I Sodium Form B ins Isopropanol

| Starting Material | Method/Description | Observation | Results |
|---|---|---|---|
| Compound I free acid Material A + F | 1. suspension of Compound I free acid in IPA (58 mg in 3 mL)<br>2. seeded with Compound I sodium Form B<br>3. molar equivalent of NaOH added 0.242 mL (33 mg/mL NaOH/water)<br>4. slurry, ambient, 3 days<br>5. filtered, rinsed with IPA, and dried under $N_2$ | 1. faint turbidity<br>2. —<br>3. turbidity increased, sample gelled<br>4. thick slurry<br>5. filtered quicker than non-seeded, fines, B | Form B |
| Methyl ester of Compound I | 1. solution of the methyl ester of Compound I in IPA (58 mg in 10 mL of IPA, heated)<br>2. molar equivalent of NaOH added 0.227 mL (33 mg/mL NaOH/water)<br>3. 3 hr slurry @ 55° C., ambient slurry overnight | 1. did not dissolve at ambient, clear by 35° C.<br>2. slowly became turbid with gel clumps forming<br>3. turbidity increasing, fines, B first 1.5 hrs, slurry following day | Form B |

What is claimed is:

1. A pharmaceutical composition comprising a pharmaceutically acceptable carrier and at least about 85% w/w of a sodium salt of Compound I:

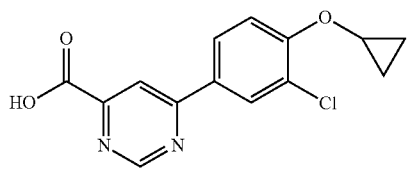

having a crystalline form characterized by an X-ray powder diffractogram comprising peaks at 3.36, 8.90, and 18.30°2θ±0.2°2θ, as determined on a diffractometer using Cu-Kα radiation (Compound I Sodium Form B).

2. The pharmaceutical composition of claim 1, wherein the crystalline form is further characterized by one or more peaks at 10.15, 23.93, and 26.66°2θ±0.2°2θ.

3. The pharmaceutical composition of claim 1, wherein the crystalline form is characterized by a differential scanning calorimetry curve comprising an endotherm with onset at about 184° C.

4. The pharmaceutical composition of claim 1, comprising at least about 95% w/w of Compound I Sodium Form B.

5. The pharmaceutical composition of claim 1, further comprising another therapeutic agent.

6. A method of treating a disease or condition mediated by Kynurenine 3-mono-oxygenase activity in a subject in need of such a treatment which method comprises administering to the subject a therapeutically effective amount of the pharmaceutical composition of claim 1.

7. The method of claim 6, wherein the disease or condition is:

spinocerebellar ataxia, Alzheimer's disease, Parkinson's disease, amyotrophic lateral sclerosis, Creutzfeldt-Jakob disease, trauma-induced neurodegeneration, high-pressure neurological syndrome, dystonia, olivopontocerebellar atrophy, amyotrophic lateral sclerosis, multiple sclerosis, epilepsy, consequences of stroke, cerebral ischemia, an ischemic disorder, hypoxia, multi-infarct dementia, a consequence of cerebral trauma or damage, damage to the spinal cord, senile dementia, AIDS-dementia complex, AIDS-induced encephalopathy, other infection related encephalopathy, viral or bacterial meningitis, a general central nervous system (CNS) infection, poliomyelitis, Lyme disease (Borrelia burgdorferi infection), septic shock, malaria, cancer with cerebral localization, hepatic encephalopathy, systemic lupus, analgesia, an opiate withdrawal symptom, feeding behavior, psychiatric disorder, insomnia, depression, schizophrenia, severe deficit in working memory, severe deficit in long term memory storage, decreased cognition, severe deficit in attention, severe deficit in executive functioning, slowness in information processing, slowness in neural activity, a generalized anxiety disorder, panic anxiety, obsessive compulsive disorder, social phobia, performance anxiety, post-traumatic stress disorder, acute stress reaction, adjustment reaction, separation anxiety disorder, alcohol withdrawal anxiety, a disorder of the developing or aged brain, diabetes, Tourette's syndrome, Fragile X syndrome, autism spectrum disorder, bipolar disorder, unipolar depression, major depression, endogenous depression, involutional depression, reactive depression, psychotic depression, depression caused by an underlying medical condition, cyclothymic disorder, dysthymic disorder, mood disorder due to a general medical condition, substance-induced mood disorder, acute necrotizing pancreatitis, HIV-related disorder, AIDS, aseptic meningitis, brain disease, Gilles de la Tourette syndrome, Asperger syndrome, Rett syndrome, a pervasive developmental disorder, aging-related brain disease, developmental brain disease, burnout syndrome, carbon monoxide poisoning, cardiac arrest or insufficiency and hemorrhagic shock, cataract formation, aging of the eye, central nervous system disease, cerebrovascular disease, chronic fatigue syndrome, chronic stress, variants of Grand mal and petit mal epilepsy and Partial Complex Epilepsy, diabetes mellitus, dyskinesia, L-DOPA induced movement disorders, drug addiction, pain and cataract, drug dependence, drug withdrawal, feeding disorder, Guillain Barre-Syndrome, hepatic encephalopathy, an inflammatory disorder of the central or peripheral nervous system, inflammatory pain, neuropathic pain, migraine, allodynia, hyperalgesia pain, phantom pain, neuropathic pain related to diabetic neuropathy, multiple organ failure, near drowning, necrosis, neoplasms of the brain, nicotine addiction, alcoholism, cannabis addiction, benzodiazepine addiction, barbiturate addiction, morphine addiction, cocaine dependence, change in appetite, a sleep disorder, changes in sleep pattern, lack of energy, fatigue, low self-esteem, self-reproach inappropriate guilt, frequent thoughts of death or suicide, plans or attempts to commit suicide, feelings of hopelessness and worthlessness, psychomotor agitation or retardation, diminished capacity for thinking, concentration, or decisiveness, sepsis, spinal cord disease, systemic lupus erythematosus, traumatic damage to the brain and spinal cord, tremor syndrome and different movement disorder, poor balance, bradykinesia, rigidity, tremor, change in speech, loss of facial expression, micrographia, difficulty swallowing, drooling, dementia, confusion, fear, sexual dysfunction, language impairment, impairment in decision making, violent outbursts, aggression, hallucination, apathy, impairment in abstract thinking, cardiovascular disease, dyslipoproteinemia, dyslipidemias, cardiomegaly, atherosclerosis, myocardial infarction, congestive heart failure, coronary heart disease, hypertension, hypotension, benign hyperproliferative disease, malignant hyperproliferative disease, angiomas, endometriosis, obesity, Age-related Macular Degeneration, retinopathy, proliferation of endothelial cells and smooth muscle cells that cause restenosis as a consequence of stenting in the treatment of atherosclerosis, a hyperproliferative disorder involving fibroblasts, cardiac remodeling and failure associated with myocardial infarction, excessive wound healing, transplant rejection, graft versus host disease, chronic kidney disease, systemic inflammatory disorder, brain inflammatory disorder, or pneumococcal meningitis.

8. The method of claim 6, wherein the disease or condition is acute necrotizing pancreatitis, a disorder of the developing or aged brain, psychiatric disorder, Alzheimer's disease, inflammation, cancer, schizophrenia, neurodegenerative disease, or transplant rejection.

9. The method of claim 6, wherein the disease or condition is a neurodegenerative disease.

10. The method of claim 6, wherein the disease or condition is Huntington's disease.

* * * * *